United States Patent
Flanders et al.

(10) Patent No.: US 12,320,022 B2
(45) Date of Patent: Jun. 3, 2025

(54) SYSTEM AND METHOD FOR CARBON DIOXIDE REACTOR CONTROL

(71) Applicant: Twelve Benefit Corporation, Berkeley, CA (US)

(72) Inventors: Nicholas H. Flanders, San Francisco, CA (US); Kendra P. Kuhl, Oakland, CA (US); Etosha R. Cave, Berkeley, CA (US); Sichao Ma, Dublin, CA (US); Ziyang Huo, Moraga, CA (US); Carter S. Haines, Berkeley, CA (US); Timothy A. Bekkedahl, Sunnyvale, CA (US); Kathryn L. Corp, Berkeley, CA (US); Ashley D. Mishra, Danville, CA (US); Edward Izett, Berkeley, CA (US)

(73) Assignee: Twelve Benefit Corporation, Berkeley, CA (US)

( * ) Notice: Subject to any disclaimer, the term of this patent is extended or adjusted under 35 U.S.C. 154(b) by 228 days.

(21) Appl. No.: 17/444,356

(22) Filed: Aug. 3, 2021

(65) Prior Publication Data
US 2022/0136119 A1    May 5, 2022

Related U.S. Application Data

(63) Continuation-in-part of application No. 16/254,255, filed on Jan. 22, 2019, now Pat. No. 11,512,403.
(Continued)

(51) Int. Cl.
*C25B 9/00* (2021.01)
*B01D 53/14* (2006.01)
(Continued)

(52) U.S. Cl.
CPC ........ *C25B 15/081* (2021.01); *B01D 53/1475* (2013.01); *B01D 53/1493* (2013.01);
(Continued)

(58) Field of Classification Search
CPC ....... C25B 15/081; C25B 15/083; C25B 3/03; C25B 3/26; C25B 9/23
See application file for complete search history.

(56) References Cited

U.S. PATENT DOCUMENTS

| 2,650,245 A | 8/1953 | Boaden et al. |
| 3,755,099 A | 8/1973 | Haupin |

(Continued)

FOREIGN PATENT DOCUMENTS

| CA | 2950294 C | 7/2022 |
| CN | 101981744 A | 2/2011 |

(Continued)

OTHER PUBLICATIONS

Adabi, et al., "High-performing Commercial Fe—N—C Cathode Electrocatalyst for Anion-exchange Membrane Fuel Cells," Nature Energy, 2021, pp. 1-10.
(Continued)

*Primary Examiner* — Zulmariam Mendez
(74) *Attorney, Agent, or Firm* — Weaver Austin Villeneuve & Sampson LLP

(57) ABSTRACT

A system optionally including a carbon oxide reactor. A method for carbon oxide reactor control, optionally including selecting carbon oxide reactor aspects based on a desired output composition, running a carbon oxide reactor under controlled process conditions to produce a desired output composition, and/or altering the process conditions to alter the output composition.

32 Claims, 41 Drawing Sheets

Related U.S. Application Data

(60) Provisional application No. 63/060,583, filed on Aug. 3, 2020, provisional application No. 62/685,771, filed on Jun. 15, 2018, provisional application No. 62/619,996, filed on Jan. 22, 2018, provisional application No. 62/620,109, filed on Jan. 22, 2018.

(51) Int. Cl.

| | | |
|---|---|---|
| *B01D 53/18* | (2006.01) | |
| *B01D 53/22* | (2006.01) | |
| *B01J 20/08* | (2006.01) | |
| *B01J 20/10* | (2006.01) | |
| *B01J 20/20* | (2006.01) | |
| *B01J 20/34* | (2006.01) | |
| *C01B 3/34* | (2006.01) | |
| *C01B 3/50* | (2006.01) | |
| *C07C 1/04* | (2006.01) | |
| *C07C 4/02* | (2006.01) | |
| *C12M 1/00* | (2006.01) | |
| *C12P 5/02* | (2006.01) | |
| *C12P 7/06* | (2006.01) | |
| *C12P 7/16* | (2006.01) | |
| *C12P 7/52* | (2006.01) | |
| *C12P 7/54* | (2006.01) | |
| *C25B 1/23* | (2021.01) | |
| *C25B 3/03* | (2021.01) | |
| *C25B 3/26* | (2021.01) | |
| *C25B 9/23* | (2021.01) | |
| *C25B 13/08* | (2006.01) | |
| *C25B 15/08* | (2006.01) | |

(52) U.S. Cl.
CPC ............ *B01D 53/18* (2013.01); *B01D 53/229* (2013.01); *B01J 20/08* (2013.01); *B01J 20/10* (2013.01); *B01J 20/20* (2013.01); *B01J 20/3483* (2013.01); *C01B 3/34* (2013.01); *C01B 3/503* (2013.01); *C07C 1/0485* (2013.01); *C07C 4/02* (2013.01); *C12M 43/00* (2013.01); *C12P 5/023* (2013.01); *C12P 7/06* (2013.01); *C12P 7/16* (2013.01); *C12P 7/52* (2013.01); *C12P 7/54* (2013.01); *C25B 1/23* (2021.01); *C25B 3/03* (2021.01); *C25B 3/26* (2021.01); *C25B 9/23* (2021.01); *C25B 13/08* (2013.01); *C25B 15/083* (2021.01); *B01D 2252/30* (2013.01); *B01J 2220/42* (2013.01); *C01B 2203/0216* (2013.01); *C01B 2203/0405* (2013.01); *C01B 2203/062* (2013.01)

(56) References Cited

U.S. PATENT DOCUMENTS

| | | | |
|---|---|---|---|
| 4,042,496 | A | 8/1977 | Tsushima et al. |
| 4,089,758 | A | 5/1978 | McAloon |
| 4,116,889 | A | 9/1978 | Chlanda et al. |
| 4,176,215 | A | 11/1979 | Molnar et al. |
| 4,253,900 | A | 3/1981 | Dege et al. |
| 4,355,116 | A | 10/1982 | Lee et al. |
| 4,609,440 | A | 9/1986 | Frese et al. |
| 4,761,207 | A | 8/1988 | Stewart, Jr. et al. |
| 4,766,161 | A | 8/1988 | Chlanda et al. |
| 4,828,941 | A | 5/1989 | Sterzel |
| 4,921,586 | A | 5/1990 | Molter |
| 5,039,389 | A | 8/1991 | McMichael |
| 5,601,937 | A | 2/1997 | Isenberg |
| 5,992,008 | A | 11/1999 | Kindler |
| 6,358,651 | B1 | 3/2002 | Chen et al. |
| 7,605,293 | B2 | 10/2009 | Olah et al. |
| 7,608,356 | B2 | 10/2009 | Risen et al. |
| 7,704,369 | B2 | 4/2010 | Olah et al. |
| 7,883,817 | B2 | 2/2011 | Hori et al. |
| 8,075,746 | B2 | 12/2011 | Hartvigsen et al. |
| 8,131,859 | B2 | 3/2012 | Fujii et al. |
| 8,137,859 | B2 | 3/2012 | Shin et al. |
| 8,268,026 | B2 | 9/2012 | Norbeck et al. |
| 8,277,631 | B2 | 10/2012 | Eastman et al. |
| 8,366,902 | B2 | 2/2013 | Hawkes et al. |
| 8,535,502 | B2 | 9/2013 | Littau et al. |
| 8,592,633 | B2 | 11/2013 | Cole et al. |
| 8,652,104 | B2 | 2/2014 | Goral et al. |
| 8,652,704 | B2 | 2/2014 | Sano et al. |
| 8,658,016 | B2 | 2/2014 | Lakkaraju et al. |
| 8,721,866 | B2 | 5/2014 | Sivasankar et al. |
| 8,741,244 | B2 | 6/2014 | Jones |
| 8,778,156 | B2 | 7/2014 | Eisaman et al. |
| 8,845,875 | B2 | 9/2014 | Teamey et al. |
| 8,845,878 | B2 | 9/2014 | Cole et al. |
| 8,956,990 | B2 | 2/2015 | Masel et al. |
| 9,012,345 | B2 | 4/2015 | Masel et al. |
| 9,108,894 | B1 * | 8/2015 | Foody .................... C10L 1/023 |
| 9,145,615 | B2 | 9/2015 | Zhai et al. |
| 9,181,625 | B2 | 11/2015 | Masel et al. |
| 9,193,593 | B2 | 11/2015 | Masel et al. |
| 9,238,598 | B2 | 1/2016 | Hammad et al. |
| 9,370,773 | B2 | 6/2016 | Masel et al. |
| 9,464,359 | B2 | 10/2016 | Masel et al. |
| 9,481,939 | B2 | 11/2016 | Masel et al. |
| 9,486,771 | B2 | 11/2016 | Lane et al. |
| 9,555,367 | B2 | 1/2017 | Masel et al. |
| 9,566,574 | B2 | 2/2017 | Masel et al. |
| 9,580,824 | B2 | 2/2017 | Masel et al. |
| 9,586,181 | B2 | 3/2017 | Eisaman et al. |
| 9,631,284 | B2 | 4/2017 | Braun et al. |
| 9,914,683 | B2 | 3/2018 | Eisaman |
| 9,920,437 | B2 | 3/2018 | Reytier et al. |
| 9,937,471 | B1 | 4/2018 | Eisaman |
| 10,280,378 | B2 | 5/2019 | Masel |
| 10,329,676 | B2 | 6/2019 | Kaczur et al. |
| 10,648,091 | B2 | 5/2020 | Kuhl et al. |
| 10,822,709 | B2 | 11/2020 | Kulh et al. |
| 10,975,480 | B2 | 4/2021 | Masel |
| 10,975,481 | B2 | 4/2021 | Guo et al. |
| 11,142,832 | B2 | 10/2021 | O'Brien et al. |
| 11,512,403 | B2 | 11/2022 | Kuhl et al. |
| 11,680,328 | B2 | 6/2023 | Huo et al. |
| 11,939,284 | B2 | 3/2024 | Stevic |
| 2003/0059658 | A1 | 3/2003 | Kohler et al. |
| 2005/0147859 | A1 | 7/2005 | Kiefer et al. |
| 2005/0239912 | A1 | 10/2005 | Archella et al. |
| 2006/0016685 | A1 | 1/2006 | Hawkins et al. |
| 2006/0211777 | A1 | 9/2006 | Severinsky |
| 2008/0283411 | A1 | 11/2008 | Eastman et al. |
| 2008/0318093 | A1 | 12/2008 | Lee et al. |
| 2009/0014336 | A1 | 1/2009 | Olah et al. |
| 2009/0117436 | A1 | 5/2009 | Choi et al. |
| 2009/0155102 | A1 | 6/2009 | Park et al. |
| 2010/0137457 | A1 | 6/2010 | Kaplan |
| 2010/0159347 | A1 | 6/2010 | Choi et al. |
| 2010/0273087 | A1 | 10/2010 | Choi et al. |
| 2010/0324256 | A1 | 12/2010 | Ooms et al. |
| 2011/0206566 | A1 | 8/2011 | Stoots et al. |
| 2012/0171583 | A1 | 7/2012 | Bocarsly et al. |
| 2012/0228150 | A1 | 9/2012 | Kang et al. |
| 2012/0252091 | A1 | 10/2012 | Rasmussen et al. |
| 2012/0328942 | A1 | 12/2012 | Thomas-Alyea et al. |
| 2013/0105304 | A1 | 5/2013 | Kaczur et al. |
| 2013/0118911 | A1 | 5/2013 | Sivasankar et al. |
| 2013/0345325 | A1 | 12/2013 | Lecomte et al. |
| 2014/0027303 | A1 | 1/2014 | Cole et al. |
| 2014/0034506 | A1 | 2/2014 | Teamey et al. |
| 2014/0093799 | A1 | 4/2014 | Masel et al. |
| 2014/0151240 | A1 | 6/2014 | Bedell et al. |
| 2014/0206894 | A1 | 7/2014 | Cole et al. |
| 2014/0206896 | A1 | 7/2014 | Sivasankar et al. |
| 2015/0010804 | A1 | 1/2015 | Laramie et al. |
| 2015/0030888 | A1 | 1/2015 | Popat et al. |
| 2015/0057458 | A1 | 2/2015 | Schjodt et al. |
| 2015/0064602 | A1 | 3/2015 | Lee et al. |

(56) References Cited

U.S. PATENT DOCUMENTS

| | | |
|---|---|---|
| 2015/0217266 A1 | 8/2015 | Sherwood |
| 2015/0232999 A1 | 8/2015 | Busskamp et al. |
| 2015/0329979 A1 | 11/2015 | Reytier et al. |
| 2016/0017503 A1 | 1/2016 | Kaczur et al. |
| 2016/0032787 A1 | 2/2016 | Hong et al. |
| 2016/0107154 A1 | 4/2016 | Masel et al. |
| 2016/0152905 A1 | 6/2016 | Kelfkens et al. |
| 2016/0161869 A1 | 6/2016 | Avneri et al. |
| 2016/0194766 A1 | 7/2016 | Eastman et al. |
| 2016/0369688 A1 | 12/2016 | Hamad et al. |
| 2017/0037522 A1 | 2/2017 | Kaczur et al. |
| 2017/0183789 A1 | 6/2017 | Matthews et al. |
| 2017/0218404 A1* | 8/2017 | Simpson .......... C12P 7/065 |
| 2017/0021334 A1 | 11/2017 | Kulh et al. |
| 2017/0321333 A1 | 11/2017 | Kuhl et al. |
| 2017/0321334 A1 | 11/2017 | Kuhl et al. |
| 2017/0328239 A1 | 11/2017 | Fleischer et al. |
| 2018/0057950 A1 | 3/2018 | Co et al. |
| 2018/0086984 A1 | 3/2018 | Chen et al. |
| 2018/0086985 A1 | 3/2018 | von Olshausen et al. |
| 2018/0127668 A1 | 5/2018 | Masel |
| 2018/0171495 A1* | 6/2018 | Masel .......... B01J 31/08 |
| 2018/0194632 A1 | 7/2018 | Jakobsson et al. |
| 2018/0257057 A1 | 9/2018 | Motoshige et al. |
| 2018/0264429 A1 | 9/2018 | Sugano et al. |
| 2018/0265440 A1 | 9/2018 | Kudo et al. |
| 2019/0016594 A1 | 1/2019 | Singh et al. |
| 2019/0032228 A1 | 1/2019 | Krause et al. |
| 2019/0036143 A1 | 1/2019 | Yan et al. |
| 2019/0062931 A1 | 2/2019 | Stark et al. |
| 2019/0093241 A1 | 3/2019 | Baldauf et al. |
| 2019/0127865 A1 | 5/2019 | Li et al. |
| 2019/0134570 A1 | 5/2019 | Pintauro et al. |
| 2019/0211463 A1 | 7/2019 | Masel |
| 2019/0226103 A1 | 7/2019 | Kuhl et al. |
| 2019/0233350 A1 | 8/2019 | Sankaranarayanan et al. |
| 2019/0359894 A1 | 11/2019 | Heidel et al. |
| 2019/0360005 A1* | 11/2019 | Baldauf .......... C12P 7/04 |
| 2019/0376190 A1 | 12/2019 | O'Brien et al. |
| 2020/0095124 A1 | 3/2020 | Rueger |
| 2020/0153013 A1 | 5/2020 | Herrmann et al. |
| 2020/0208278 A1 | 7/2020 | Li et al. |
| 2020/0240023 A1 | 7/2020 | Cave et al. |
| 2020/0308718 A1 | 10/2020 | Patru et al. |
| 2020/0376479 A1 | 12/2020 | Masel |
| 2021/0002775 A1 | 1/2021 | Matsumoto et al. |
| 2021/0031137 A1 | 2/2021 | Goetheer et al. |
| 2021/0047743 A1 | 2/2021 | Goetheer et al. |
| 2021/0123146 A1 | 4/2021 | Berlinguette et al. |
| 2021/0164116 A1 | 6/2021 | Kuhl et al. |
| 2021/0207275 A1 | 7/2021 | Huo et al. |
| 2021/0285111 A1 | 9/2021 | Fernández Sanchis et al. |
| 2021/0381116 A1 | 12/2021 | Kashi et al. |
| 2021/0387139 A1 | 12/2021 | Voskian et al. |
| 2021/0395908 A1 | 12/2021 | Kuhl et al. |
| 2022/0119636 A1 | 4/2022 | Wang et al. |
| 2022/0119641 A1 | 4/2022 | Wang et al. |
| 2022/0152556 A1 | 5/2022 | Hoshino |
| 2022/0153656 A1 | 5/2022 | Flanders et al. |
| 2022/0227684 A1 | 7/2022 | Hashimoto |
| 2022/0227701 A1 | 7/2022 | Bulan et al. |
| 2022/0235479 A1 | 7/2022 | Scheiff et al. |
| 2022/0246966 A1 | 8/2022 | Brown |
| 2023/0041781 A1 | 2/2023 | Okuno et al. |
| 2023/0175088 A1 | 6/2023 | Cintron et al. |
| 2023/0175146 A1 | 6/2023 | Kashi et al. |
| 2023/0202840 A1 | 6/2023 | Flanders et al. |
| 2023/0265572 A1 | 8/2023 | Kuhl et al. |
| 2023/0415104 A1 | 12/2023 | Huo et al. |
| 2023/0417189 A1 | 12/2023 | Ross |
| 2024/0011165 A1 | 1/2024 | Flanders et al. |
| 2024/0051909 A1 | 2/2024 | Stevic |
| 2024/0158928 A1 | 5/2024 | Wu et al. |
| 2024/0174590 A1 | 5/2024 | Stevic |
| 2024/0200208 A1 | 6/2024 | Huo et al. |

FOREIGN PATENT DOCUMENTS

| | | |
|---|---|---|
| CN | 102308028 A | 1/2012 |
| CN | 102978653 A | 3/2013 |
| CN | 106148992 A | 11/2016 |
| CN | 106463743 A | 2/2017 |
| CN | 107180985 A | 9/2017 |
| CN | 107699915 A | 2/2018 |
| CN | 109921060 A | 6/2019 |
| CN | 112994054 A | 6/2021 |
| DE | 102006012313 A1 | 10/2007 |
| DE | 102007037672 A1 | 2/2009 |
| DE | 102013000255 A1 | 7/2014 |
| DE | 102015201132 A1 | 7/2016 |
| DE | 102015214592 A1 | 2/2017 |
| DE | 102016207420 A1 | 10/2017 |
| EP | 2163294 A | 3/2010 |
| EP | 3378968 | 9/2018 |
| EP | 3434810 A1 | 1/2019 |
| EP | 3626861 A1 | 3/2020 |
| EP | 3670700 A1 | 6/2020 |
| EP | 3126038 B1 | 6/2021 |
| GB | 1269841 A | 4/1972 |
| JP | H06145379 A | 5/1994 |
| JP | 2009540130 A | 11/2009 |
| JP | 2010526214 A | 7/2010 |
| JP | 2014152219 A | 8/2014 |
| JP | 2015054994 A | 3/2015 |
| JP | 2015056315 A | 3/2015 |
| JP | 2015513615 A | 5/2015 |
| JP | 2015513616 A | 5/2015 |
| JP | 2016538420 A | 12/2016 |
| JP | 2017048442 A | 3/2017 |
| JP | 2017053013 A | 3/2017 |
| JP | 2017527701 A | 9/2017 |
| JP | 2019044238 A | 3/2019 |
| JP | 2019205997 A | 12/2019 |
| KR | 100962903 | 6/2010 |
| KR | 20160000940 A | 1/2016 |
| KR | 20190028595 A | 3/2019 |
| WO | WO 2007/041872 A1 | 4/2007 |
| WO | WO-2007108014 A1 | 9/2007 |
| WO | WO2008124538 | 10/2008 |
| WO | WO-2011100581 A1 | 8/2011 |
| WO | WO-2011108546 A1 | 9/2011 |
| WO | WO 2012/006240 A1 | 1/2012 |
| WO | WO-2012050530 A1 | 4/2012 |
| WO | WO 2013/006710 A2 | 1/2013 |
| WO | WO 2013/016447 A2 | 1/2013 |
| WO | WO 2014/018091 A1 | 1/2014 |
| WO | WO 2014/032000 A1 | 2/2014 |
| WO | WO 2014/042781 A2 | 3/2014 |
| WO | WO 2014/043651 A2 | 3/2014 |
| WO | WO 2014/046797 A2 | 3/2014 |
| WO | WO 2014/160529 A1 | 10/2014 |
| WO | WO-2014154253 A1 | 10/2014 |
| WO | WO 2015/035521 A1 | 3/2015 |
| WO | WO-2015184388 A1 | 12/2015 |
| WO | WO 2016/039999 A1 | 3/2016 |
| WO | WO-2016124494 A1 | 8/2016 |
| WO | WO 2017/014635 A1 | 1/2017 |
| WO | WO2017021083 A1 | 2/2017 |
| WO | WO-2017116307 A1 | 7/2017 |
| WO | WO-2017171115 A1 | 10/2017 |
| WO | WO-2018001637 A1 | 1/2018 |
| WO | WO-2018044720 A1 | 3/2018 |
| WO | WO-2019020239 A1 | 1/2019 |
| WO | WO-2019051069 A1 | 3/2019 |
| WO | WO-2019051609 A1 | 3/2019 |
| WO | WO-2019120812 A1 | 6/2019 |
| WO | WO-2019136018 A2 | 7/2019 |
| WO | WO-2019144135 A1 | 7/2019 |
| WO | WO-2019157507 A1 | 8/2019 |
| WO | WO2020057998 A1 | 3/2020 |
| WO | WO-2020125868 A1 | 6/2020 |
| WO | WO-2020157205 A1 | 8/2020 |
| WO | WO-2020245070 A1 | 12/2020 |
| WO | WO-2021108446 A1 | 6/2021 |
| WO | WO-2021252535 A2 | 12/2021 |

(56) References Cited

FOREIGN PATENT DOCUMENTS

| | | |
|---|---|---|
| WO | WO-2022031726 A2 | 2/2022 |
| WO | WO-2022061392 A1 | 3/2022 |
| WO | WO-2022235304 A1 | 11/2022 |
| WO | WO-2023081846 A1 | 5/2023 |
| WO | WO-2023205671 A2 | 10/2023 |
| WO | WO-2023212597 A1 | 11/2023 |

OTHER PUBLICATIONS

AU Office Action dated Sep. 7, 2022, in Application No. AU2019210132.
Balster, J. et al., "Tailoring the Interface Layer of the Bipolar Membrane", Journal of Membrane Science, vol. 365, No. 1-2, Dec. 2010, pp. 389-398.
BR Office Action dated Nov. 28, 2022, in Application No. BR1120200149381 with English translation.
Chen, et al., "Poly(Alkyl-terphenyl Piperidinium) Ionomers and Membranes With an Outstanding Alkaline-membrane Fuel-cell Performance of 2.58 Wcm@2," Fuel Cells Hot Paper, 2021, vol. 60, pp. 7710-7718.
Chen, et al., "Poly(Fluorenyl Aryl Piperidinium) Membranes and Ionomers for Anion Exchange Membrane Fuel Cells," Nature Communications, 2021, vol. 12, pp. 1-12.
CN Office Action dated Jan. 4, 2023, in CN Application No. CN201980021305.1 with English translation.
Digdaya, et al., "A Direct Coupled Electrochemical System for Capture and Conversion of Co2 From Oceanwater," Nature Communications, 2020, vol. 11, pp. 1-10.
EP search report dated Sep. 14, 2021, in application No. EP19741371.9.
Fan, et al., "Poly(Bis-arylimidazoliums) Possessing High Hydroxide Ion Exchange Capacity and High Alkaline Stability," Nature Communications, 2019, vol. 10, pp. 1-10.
Ge, et al., Oxygen Reduction in Alkaline Media: From Mechanisms to Recent Advances of Catalysts, "ACS Catalysis," 2015, vol. 5, pp. 1-97.
Gerhardt, et al., "Along-the-channel Impacts Ofwater Management and Carbon-dioxide Contamination in Hydroxide-exchange-membrane Fuel Cells: a Modeling Study," Journal of the Electrochemical Society, 2019, vol. 166(7), pp. F3180-F3192.
Gu, et al., "Electrochemical Energy Engineering: a New Frontier of Chemical Engineering Innovation," Annual Review of Chemical and Biomolecular Engineering, 2014, vol. 5, pp. 429-454.
Hao, J.H. et al., "Preparation of Solvent-resistant Anion-exchange Membranes", Desalination, Jun. 2000, vol. 129, No. 1, pp. 15-22.
Hassan, N., et al., "Achieving High-Performance and 2000 h Stability in Anion Exchange Membrane Fuel Cells by Manipulating Ionomer Properties and Electrode Optimization," Advanced Energy Materials, 2020, pp. 1-8.
Huang, et al., "Composite Poly(Norbornene) Anion Conducting Membranes for Achieving Durability, water Management and High Power 3.4 W/cm2) in Hydrogen/oxygen Alkaline Fuel Cells," Journal of The Electrochemical Society, 2019, vol. 10, pp. F637-F644.
IN Office Action dated Feb. 16, 2022, in Application No. IN202037034886.
Inaba, et al., "Effects of Carbon Dioxide on the Performance of Anion-exchange Membrane Fuel Cells," Electrochemistry, 2011, vol. 79(5), pp. 322-325.
International Preliminary Report on Patentability and Written opinion dated Jun. 9, 2022 in Application No. PCT/US2020/062080.
International Search Report and Written Opinion dated Feb. 23, 2022, in Application No. PCT/US2021/55902.
International Preliminary Report on Patentability dated Feb. 16, 2023 in PCT Application No. PCT/US2021/044378.
International Preliminary Report on Patentability dated May 4, 2023, in Application No. PCT/US2021/055900.
International Preliminary Report on Patentability dated May 4, 2023, in Application No. PCT/US2021/055902.
International Search Report and Written Opinion dated Apr. 10, 2023 in PCT Application No. PCT/US2022/079335.
International Search Report and Written Opinion dated Feb. 24, 2022, in Application No. PCT/US2021/055900.
International Search Report and Written Opinion dated Feb. 28, 2022, in Application No. PCT/US2021/044378.
International Search Report and Written Opinion dated Mar. 7, 2023 in PCT Application No. PCT/US2022/081034.
International Search Report and Written Opinion issued in PCT Application No. PCT/US2020/062080 on Mar. 16, 2021.
JP Office Action dated Jan. 4, 2023, in Application No. JP2020-561577 with English translation.
JP Office Action dated Jul. 11, 2023 in Application No. JP2023-507462 with English translation.
Keith, et al., "A Process for Capturing Co2 From the Atmosphere," Cell Press, 2018, vol. 2, pp. 1573-1594.
Liew, F. et al., "Gas Fermentation—A Flexible Platform for Commercial Scale Production of Low-Carbon-Fuels and Chemicals from Waste and Renewable Feedstocks", Frontiers in Microbiology, May 11, 2016, vol. 7, No. 694, pp. 1-28.
Lu, et al., "Halloysite-derived Nitrogen Doped Carbon Electrocatalysts for Anion Exchange Membrane Fuel Cells," Journal of Power Sources, 2017, vol. 372, pp. 82-90.
Matz, et al., "Demonstration of Electrochemically-driven Co2 Separation Using Hydroxide Exchange Membranes," Journal of the Electrochemical Society, 2021, vol. 168, pp. 1-12.
Muroyama, et al., "Review—CO2 Separation and Transport via Electrochemical Methods," Journal of the Electrochemical Society, 2020, vol. 167, pp. 1-13.
Peng, et al., "Nitrogen-doped Carbon-coox Nanohybrids: a Precious Metal Free Cathode That Exceeds 1.0 Wcm@2 Peak Power and 100 H Life in Anion-Exchange Membrane Fuel Cells," Angewandte Chemie, 2019, vol. 58(4), pp. 1058-1063.
Peng, et al., "Using Operando Techniques to Understand and Design High Performance and Stable Alkaline Membrane Fuel Cells," Nature Communications, 2020, vol. 11, pp. 1-10.
Sharifian, et al., "Electrochemical Carbon Dioxide Capture to Close the Carbon Cycle," Energy & Environmental Science, 2021, vol. 14, pp. 781-814.
Shi, et al., "Editors' Choice—uncovering the Role of Alkaline Pretreatment for Hydroxide Exchange Membrane Fuel Cells," Journal of the Electrochemical Society, 2020, vol. 167, pp. 1-10.
Shi, L. et al., "A shorted membrane electrochemical cell powered by hydrogen to remove $CO_2$ from the air feed of hydroxide exchange membrane fuel cells", Nature Energy, Mar. 2022, vol. 7, 36 pages.
Shi, X., et al., "Sorbents for the Direct Capture of Co2 From Ambient Air," Angewandte Chemie, 2020, vol. 59(18), pp. 1-25.
Shu, Q., et al., "Electrochemical Regeneration of Spent Alkaline Absorbent from Direct Air Capture," Environmental science & technology, 2020, vol. 54(14), pp. 8990-8998.
U.S. Notice of Allowance dated Sep. 1, 2022 in U.S. Appl. No. 16/254,255.
U.S. Final office Action dated Aug. 21, 2023 in U.S. Appl. No. 17/452,395.
U.S. Final office Action dated Nov. 21, 2022 in U.S. Appl. No. 17/247,036.
U.S. Non-Final office Action dated Jan. 20, 2023 in U.S. Appl. No. 17/452,395.
U.S. Non-Final Office Action dated May 24, 2022, in U.S. Appl. No. 17/247,036.
U.S. Non-Final Office Action dated Oct. 22, 2021, in U.S. Appl. No. 16/254,255.
U.S. Notice of Allowance dated Feb. 10, 2023 in U.S. Appl. No. 17/247,036.
U.S. Notice of Allowance dated Mar. 2, 2023 in U.S. Appl. No. 17/247,036.
U.S. Appl. No. 18/051,944, inventors Kuhl et al., filed on Nov. 2, 2022.
U.S. Appl. No. 18/295,412, inventors Flanders et al., filed on Apr. 4, 2023.
U.S. Appl. No. 18/300,380, inventors Ziyang Huo et al., filed on Apr. 13, 2023.

(56) References Cited

OTHER PUBLICATIONS

U.S. Appl. No. 18/306,928, inventors Kendra P. Kuhl et al., filed on Apr. 25, 2023.
U.S. Appl. No. 18/324,929, inventors Huo Ziyang et al., filed on May 26, 2023.
U.S Restriction requirement dated Aug. 1, 2023 in U.S. Appl. No. 18/324,929.
U.S. Restriction Requirement dated Dec. 15, 2022 in U.S. Appl. No. 17/452,395.
U.S. Restriction requirement dated Jul. 28, 2023, in U.S. Appl. No. 17/451,630.
Voskian, S. et al., "Faradaic electro-swing reactive adsorption for $CO_2$ capture", Energy & Environmental Science, 2019, vol. 12, pp. 3530-3547.
Wang, et al., "Approaches for the preparation of non-linear amphiphilic polymers and their applications to drug delivery", Advanced Drug Delivery Reviews, 2012, vol. 64, pp. 852-865.
Wang, L., et al., "A High Conductivity Ultrathin Anion-exchange Membrane With 500+ H Alkali Stability for Use in Alkaline Membrane Fuel Cells That Can Achieve 2 W $Cm^{-2}$ at 80° C.," Journal of Materials Chemistry A, 2018, vol. 6, pp. 15404-15412.
Wang, L., "Radiation-grafted anion-exchange membranes: the switch from low- to high-density polyethylene leads to remarkably enhanced fuel cell performance," Energy and Environmental Science, 2019, vol. 12, 1575-1579.
Wang, Y., et al., "Synergistic Mn—Co Catalyst Outperforms Pt on High-rate Oxygen Reduction for Alkaline Polymer Electrolyte Fuel Cells," Nature Communications, 2019, vol. 10(1), pp. 1-8.
Woo, J., et al., "Promoting Oxygen Reduction Reaction Activity of Fe-N/C Electrocatalysts by Silica-Coating-Mediated Synthesis for Anion-Exchange Membrane Fuel Cells," Chemistry of Materials, 2018, vol. 30, pp. 6684-6701.
Wurzbacher, J., et al., "Concurrent Separation of Co2 and H2o From Air by a Temperature-vacuum Swing Adsorption/desorption Cycle," Environmental science & technology, 2012, vol. 46(16), pp. 9191-9198.
Xin, L., et al., Carbon Supported Ag Nanoparticles as High Performance Cathode Catalyst for H2/O2 anion exchange membrane fuel cell, Frontiers in Chemistry, 2013, vol. 1(16), pp. 1-5.
Xu, C. et al., Preparation of PVA-GA-CS/PVA-Fe-SA Bipolar Membrane and Its Application in Electro-generation of 2,2-dimethyl-3-hydroxypropionic Acid, Journal of Membrane Science, vol. 307, No. 2, Jan. 2008, pp. 218-224.
Yang, B. et al., "Preparation of a Bipolar Membrane by Photografting Polymerization", Frontiers of Chemistry in China, vol. 3, No. 1, Jan. 2008, pp. 10-13.
Zhan, et al., "Multiarm Star Poly(epsilon-caprolactone) with Hyperbranched Polyamidoamine as Core Capable of Selective Accommodating Cationic or Anionic Guests", Chinese Journal of Polymer Science, 2015. Vol. 33, No. 6, pp. 920-930.
Zhang, J., et al., "Recent Insights on Catalyst Layers for Anion Exchange Membrane Fuel Cells," Advanced Science, 2021, vol. 8(15), pp. 1-26.
Zheng, et al., "Hyperbranched polymers: advances from synthesis to applications", Chemical Society Reviews, 2015, vol. 44, pp. 4091-4130.
Zheng, et al., "Editors' Choice—power-generating Electrochemical Co2 Scrubbing From Air Enabling Practical Aemfc Application," Journal of the Electrochemical Society, 2012, vol. 168, pp. 1-8.
Zheng, Y., et al., Quantifying and Elucidating the Effect of Co2 on the Thermodynamics, Kinetics and Charge Transport of AEMFC, Energy and Environmental Science, 2019, vol. 12, pp. 1-14.
Eisaman, M D., et al., $CO_2$ Separation Using Bipolar Membrane Electrodialysis, Energy and Environmental Science, 2011, vol. 4(4), pp. 1319-1328.
European Office Action dated Sep. 4, 2023 in Application No. EP19741371.9.
Ganji P., et al., "Toward Commercial Carbon Dioxide Electrolysis", Advanced Sustainable Systems, Wiley, US, Jun. 9, 2020, vol. 4(8), 22 Pages.
Gurkan, B., et al., "Quinone Reduction in Ionic Liquids for Electrochemical CO 2 Separation," ACS Sustainable Chemistry & Engineering, Jun. 5, 2015, vol. 3(7), pp. 1394-1405.
International Search Report and Written Opinion dated Jul. 20, 2023, in Application No. PCT/US2023/017576.
International Search Report and Written Opinion dated Nov. 27, 2023 in PCT Application No. PCT/US2023/024184.
International Search Report and Written Opinion dated Sep. 21, 2023, in Application No. PCT/US2023/024371.
Jones J H., "The Cativa Process for the Manufacture Plant of Acetic Acid," Platinum Metals, 2000, vol. 44(3), pp. 94-105.
JP Office Action dated Jan. 16, 2024 in JP Application No. 2023-507462 with English translation.
Kalck, P., et al., "Recent Advances in the Methanol Carbonylation Reaction Into Acetic Acid," Coordination Chemistry Reviews, 2020, vol. 402, 58 pages.
Kang, J S., et al., "Redox-responsive Sorbents and Mediators for Electrochemically Based $Co_2$ Capture," Current Opinion in Green and Sustainable Chemistry, Oct. 1, 2021, vol. 31, p. 100504.
KR Office Action dated Nov. 7, 2023 in KR Application No. 10-2020-7024266, with English Translation.
Kungas R., "Review—Electrochemical CO2 Reduction for CO Production: Comparison of Low- and High-Temperature Electrolysis Technologies," Journal of The Electrochemical Society, 2020, vol. 167, 044508, 12 Pages.
Liu, Y., et al., "Electrochemically Mediated Carbon Dioxide Separation with Quinone Chemistry in Salt-concentrated Aqueous Media," Nature Communications, May 8, 2020, vol. 11(1), pp. 1-11.
Qi J et al., "Selective Methanol Carbonylation to Acetic Acid on Heterogeneous Atomically Dispersed ReO4/SiO2 Catalysts," Journal of the American Chemical Society, 2020, vol. 142(33), pp. 14178-14189.
SA Office Action dated Sep. 26, 2023, in application No. SA522441684 with English Translation.
U.S. Corrected Notice of Allowance dated Sep. 20, 2023, in U.S. Appl. No. 18/328,581.
U.S. Non-Final Office Action dated Dec. 1, 2023 in U.S. Appl. No. 18/295,412.
U.S. Non-Final Office Action dated Jan. 10, 2024 in U.S. Appl. No. 18/495,406.
U.S. Non-Final Office Action dated Nov. 15, 2023 in U.S. Appl. No. 18/324,929.
U.S. Notice of Allowance dated Nov. 8, 2023 in U.S. Appl. No. 18/328,581.
U.S. Appl. No. 18/437,574, inventor Stevic L., filed on Feb. 9, 2024.
U.S. Appl. No. 18/495,406, inventors Wu Y, et al., filed on Oct. 26, 2023.
U.S. Appl. No. 18/509,058, inventors Huo Z, et al., filed on Nov. 14, 2023.
Van Bavel, S., et al., "Integrating $CO_2$ Electrolysis into the Gas-to-Liquids-Power-to-Liquids Process," ACS Energy Letters, Jul. 24, 2020, vol. 5(8), pp. 2597-2601.
Wallace, G G., et al., "Manipulating and Monitoring Biomolecular Interactions with Conducting Electroactive Polymers," Advanced Materials, VCH Publishers, DE, Jul. 4, 2002, vol. 14(13-14), pp. 953-960.
Office Action issued on Apr. 1, 2021, in U.S. Appl. No. 16/254,255.
International Search Report and Written Opinion dated Apr. 30, 2019, for application No. PCT/US19/014586.
Aeshala, L.M. et al., "Effect of solid polymer electrolyte on electrochemical reduction of CO2, Separation and Purification Technology," 94, (2012), pp. 131-137.
Badami, M. "Leakage effects on the performance characteristics of a regenerative blower for the hydrogen recirculation of a PEM fuel cell," Energy Conversion and Management, vol. 55, Mar. 2012, pp. 20-25.
Badami, M., "Theoretical model with experimental validation of a regenerative blower for hydrogen recirculation in a PEM fuel cell system," Energy Conversion and Management, vol. 51, Issue 3, Mar. 2010, pp. 553-560.

(56) References Cited

OTHER PUBLICATIONS

Blaszczyk, J., "In-Situ Anode Recirculation Rate Measurement Method (Draft)," Ogura Industrial Corporation, Ballard Power Systems, Full Cell Seminar & Exposition 2011, Oct. 31-Nov. 3, 2011, 22 pages.
Casebolt, R., et al., "Effect of Electrolyte Composition and Concentration on Pulsed Potential Electrochemical CO2 Reduction," ChemElectroChem, Chemistry Europe, Accepted Manuscript, 25 pp., Dec. 18, 2020.
Delacourt et al., "Design of an Electrochemical Cell Making Syngas (CO+H2) from CO2 and H2O Reduction at Room Temperature," Journal of The Electrochemical Society, 155 (1), (2008), pp. B42-B49.
Endrodi, B., "Multilayer Electrolyzer Stack Converts Carbon Dioxide to Gas Products at High Pressure with Multilayer Electrolyzer Stack Converts Carbon," acs Energy Lett. 2019, 4, 1770-1777.
Hori, Y., "Chapter 48: Co2-reduction, catalyzed by metal electrodes," Handbook of Fuel Cells—Fundamentals, Technology and Applications, vol. 2, Electrocatalysis, 2003. pp. 720-733.
James, B.D., et al. 2017 DOE Hydrogen and Fuel Cells Program Review, Fuel Cell Systems Analysis, Strategic Analysis, Project IDI FC163, Jun. 8, 2017, 34 pages.
Kim, C., et al., "Impact of Pulsed Electrochemical Reduction of $CO_2$ on the formation of $C_{2+}$ Products over Cu," ACS Catal., 2020, 10, 12403-12413.
Kimura, K.W., et al., "Selective Electrochemical CO2 Reduction During Pulsed Potential Stems From Dynamic Interface," ACS Catalysis, ACS Paragon Plus Environment, University of Illinois at Urbana-Champaign, Downloaded from pubs.acs.org on Jun. 30, 2020, 31 pages.
Kriescher, Stefanie M.A. et al., "A membrane electrode assembly for the electrochemical synthesis of hydrocarbons from C02(g) and Ho2(g), Electrochemistry Communications," 50 (2015), pp. 64-68.
Li, et al., "Electrolysis of Co2 to Syngas in Bipolar Membrane-Based Electrochemical Cells," ACS Publications, ACS Energy Letters, 2016, 1, pp. 1149-1153.
Li, et al., "Electrolytic Conversion of Bicarbonate into CO in a Flow Cell," Cell Press, Joule 3, Jun. 19, 2019, pp. 1487-1497.
Sharma, et al., "Electrocatalytic conversion of carbon dioxide to fuels: a review on the interaction between CO2 and the liquid electrolyte," WIREs Energy Environ 2017, 6:e239. doi: 10.1002/wene.239, pp. 1-21.
Spets et al. "Direct Glucose Fuel Cell With Anion Exchange Membrane in the Near Neutral State Electrolyte, International Journal of Electrochemical Science," 7, 11696-11705, Dec. 1, 2012, entire document, http.electrochemsci .org/papers/vol?/71211696 .pdf.
Srinivasan, S. et al., "Advances in Solid Polymer Electrolyte Fuel Cell Technology with Low Platinum Loading Electrodes," Journal of Power Sources, 22 (1988) pp. 359-375.
Verma, et al., "The effect of electrolyte composition on the electroreduction of CO2 to CO on Ag based gas diffusion electrodes," Phys. Chem. Chem. Phys., 2016, 18, pp. 7075-7084.
Xia, Chuan, et al., "Continuous production of pure liquid fuel solutions via electrocatalytic CO2 reduction using solid electrolyte devices," Nature Energy, http://www.nature.com/natureenergy; https://doi.org/10.1038/s41560-019-0451-x(2019).
Xu, Y., et al., "Self-Cleaning CO2 Reduction Systems: Unsteady Electrochemical Forcing Enables Stability," ACS Energy Letters, 2021, 6, pp. 809-815.
Zhu, Wenlei et al., "Monodisperse Au Nanoparticles for Selective Electrocatalytic Reduction of CO2 to CO.Journal of the American Chemical Society," 2013, 135, pp. 16833-16836.
International Preliminary Report on Patentability and Written Opinion dated May 16, 2024 in PCT Application No. PCT/US2022/079335.
International Search Report and Written Opinion dated May 6, 2024 in PCT Application No. PCT/US2022/081209.
International Search Report and Written Opinion dated May 29, 2024 in PCT Application No. PCT/US2023/077221.
U.S. Final Office Action dated Apr. 24, 2024 in U.S. Appl. No. 18/324,929.
U.S. Non-Final Office Action dated Mar. 26, 2024 in U.S. Appl. No. 17/452,395.
U.S. Appl. No. 18/623,555, inventor Cintron E, filed on Apr. 1, 2024.
U.S. Appl. No. 18/636,022, inventors Flanders N.H, et al., filed on Apr. 15, 2024.
JP Office Action dated Sep. 17, 2024 in JP Application No. 2023-507462 with English translation.
Hu L., et al., "A Scalable Membrane Electrode Assembly Architecture for Efficient Electrochemical Conversion of CO2 to Formic Acid," Nature Communications, 2023, vol. 14 (7605), pp. 1-11.
Hu L., et al., "A Scalable Membrane Electrode Assembly Architecture for Efficient Electrochemical Conversion of CO2 to Formic Acid," Supporting Information, pp. 1-15. (2023).
International Preliminary Report on Patentability and Written Opinion dated Jun. 20, 2024 in PCT Application No. PCT/US2022/081034.
International Preliminary Report on Patentability and Written Opinion dated Jun. 20, 2024 in PCT Application No. PCT/US2022/081209.
International Search Report and Written Opinion dated Dec. 23, 2024, (Applicant first notified on Dec. 17, 2024) for Application No. PCT/US2024/048988.
International Search Report and Written Opinion dated Jul. 8, 2024 in PCT Application No. PCT/US2024/022685.
Lyons W., et al., "Standard Handbook of Petroleum and Natural Gas Engineering", Ideal Gas Laws, 3rd Edition, 2016, vol. 2, pp. 148-149.
Pang X., et al., "Membrane-free electrochemical CO2 conversion using serially connected porous flow-through electrodes," Cell Press, Joule 6, 2022, pp. 2745-2761.
Pappijn, C., et al., "Challenges and Opportunities of Carbon Capture and Utilization: Electrochemical Conversion of CO2 to Ethylene," Original research, 2020, vol. 8, pp. 1-12.
Rickard J., et al., New Device Architecture Enables Streamlined Production of Formic Acid From CO2 Using Renewable Electricity, News & Feature Stories, pp. 1-4. (2024).
Sabatino F., et al., "Evaluation of a Direct Air Capture Process Combining Wet Scrubbing and Bipolar Membrane Electrodialysis", Industrial & Engineering Chemistry Research, vol. 59(15), 2020, pp. 7007-7020.
Sturman, M., et al., "Process Parameters in the Electrochemical Reduction of Carbon Dioxide to Ethylene," ChemBioEng, 2021, vol. 8(3), pp. 1-41.
Taniguchi I., et al., "Low Energy CO2 Capture by Electrodialysis", Energy Procedia, vol. 114, 2017, pp. 1615-1620.
U.S. Final Office Action dated Jul. 26, 2024 in U.S. Appl. No. 18/495,406.
U.S. Non-Final Office Action dated Jun. 17, 2024 in U.S. Appl. No. 18/623,555.
U.S. Notice of Allowance dated Nov. 20, 2024 in U.S. Appl. No. 17/452,395.
U.S. Appl. No. 18/900,442, inventors Huo Z, et al., filed on Sep. 27, 2024.
U.S. Restriction Requirement dated Dec. 5, 2024 in U.S. Appl. No. 18/509,058.
U.S. Restriction requirement dated Jul. 18, 2024, in U.S. Appl. No. 18/295,412.

\* cited by examiner

SYSTEM AND METHOD FOR CARBON DIOXIDE REACTOR CONTROL

STATEMENT OF GOVERNMENT SUPPORT

This invention was made with Government support under Award Number 1738554 awarded by the National Science Foundation, under Award Numbers DE-SC0015872, DE-SC0017725, DE-SC0018549, and DE-SC0018549 awarded by the Department of Energy Office of Science, under Agreement Numbers FA864920P0616 and FA8649-19-9-9026 awarded by the United States Air Force. The Government has certain rights in the invention.

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in their entireties and for all purposes.

TECHNICAL FIELD

This disclosure relates generally to the carbon oxide reactor field, and more specifically to a new and useful system and method for reactor control in the carbon oxide reactor field.

BACKGROUND

Typical systems and methods for carbon dioxide reactor control focus on maximization of aspects relating to production of carbon monoxide (CO) and/or other carbon-containing products (CCPs), such as maximizing or adjusting ratios of CO to other reactor products (e.g., $CO:H_2$ ratio), CO concentration, and/or total CO output or output rate.

Thus, there is a need in the carbon oxide reactor field to create a new and useful system and method for reactor control.

SUMMARY

Some aspects of this disclosure pertain to systems for producing a polycarbonate polymer. Such systems may be characterized by the following features: (a) a carbon dioxide reduction electrolyzer comprising a membrane electrode assembly, which comprises one or more ion conductive polymer layers and a cathode catalyst for facilitating chemical reduction of carbon dioxide to carbon monoxide; (b) a plurality of intermediate reactors collectively configured to receive carbon monoxide produced by the carbon dioxide reduction electrolyzer and produce one or more intermediate chemicals; and (c) a polycarbonate synthesis reactor configured to receive the one or more intermediate chemicals or one or more derivatives thereof and synthesize polycarbonate polymer.

Certain aspects of this disclosure pertain to methods for producing a polycarbonate polymer. Such methods may be characterized by the following operations: (a) reducing carbon dioxide to carbon monoxide in a carbon dioxide reduction electrolyzer comprising a membrane electrode assembly, which comprises one or more ion conductive polymer layers and a cathode catalyst for facilitating chemical reduction of carbon dioxide to carbon monoxide; (b) reacting carbon monoxide produced by the carbon dioxide reduction electrolyzer in one or more of a plurality of intermediate reactions to produce one or more intermediate chemicals; and (c) synthesizing polycarbonate polymer from the one or more intermediate chemicals or one or more derivatives thereof.

Certain aspects of this disclosure pertain to systems for producing a metal formate. Such systems may be characterized by the following features: (a) a carbon dioxide reduction electrolyzer comprising a membrane electrode assembly, which comprises one or more ion conductive polymer layers and a cathode catalyst for facilitating chemical reduction of carbon dioxide to carbon monoxide; (b) a formate synthesis reactor configured to receive carbon monoxide produced by the carbon dioxide reduction electrolyzer and produce a metal formate; and (c) one or more units configured to separate and/or purify the metal formate produced by the formate synthesis reactor.

Certain aspects of this disclosure pertain to methods for producing a metal formate. Such methods may be characterized by the following operations: (a) reducing carbon dioxide to carbon monoxide in a carbon dioxide reduction electrolyzer comprising a membrane electrode assembly, which comprises one or more ion conductive polymer layers and a cathode catalyst for facilitating chemical reduction of carbon dioxide to carbon monoxide; (b) reacting carbon monoxide produced by the carbon dioxide reduction electrolyzer with a metal hydroxide to produce a metal formate; and (c) separating and/or purifying the metal formate produced in (b).

Certain aspects of this disclosure pertain to systems for producing one or more chemical compounds. Such systems may be characterized by the following features: (a) carbon dioxide capture unit configured to capture carbon dioxide from air and output carbon dioxide at a concentration greater than the concentration of carbon dioxide in air; and (b) a carbon dioxide reduction electrolyzer comprising a membrane electrode assembly, which comprises one or more ion conductive polymer layers and a cathode catalyst for facilitating chemical reduction of the carbon dioxide to a carbon-containing reaction product. The system may be configured to provide carbon dioxide from the carbon dioxide capture unit to the carbon dioxide reduction electrolyzer.

Certain aspects of this disclosure pertain to systems for producing liquid hydrocarbons. Such systems may be characterized by the following features: (a) a carbon dioxide reduction electrolyzer comprising a membrane electrode assembly, which comprises one or more ion conductive polymer layers and a cathode catalyst for facilitating chemical reduction of carbon dioxide to carbon monoxide; and (b) a Fischer Trosch reactor configured to produce a liquid hydrocarbon mixture from carbon monoxide and hydrogen, wherein the system is configured to transport carbon monoxide and hydrogen from the carbon dioxide reduction electrolyzer to the Fischer Tropsch reactor.

Certain aspects of this disclosure pertain to systems for producing one or more chemical compounds. Such systems may be characterized by the following features: (a) a carbon oxide reduction electrolyzer comprising a membrane electrode assembly, which comprises one or more ion conductive polymer layers and a cathode catalyst for facilitating chemical reduction of the carbon oxide to a carbon-containing reaction product; and (b) a gas fermentation reactor configured to receive the carbon-containing reaction product produced by the carbon dioxide reduction electrolyzer and produce the one or more chemical compounds.

These and other features of the disclosure will be described in detail below with reference to associated figures.

DESCRIPTION

Figure 1:
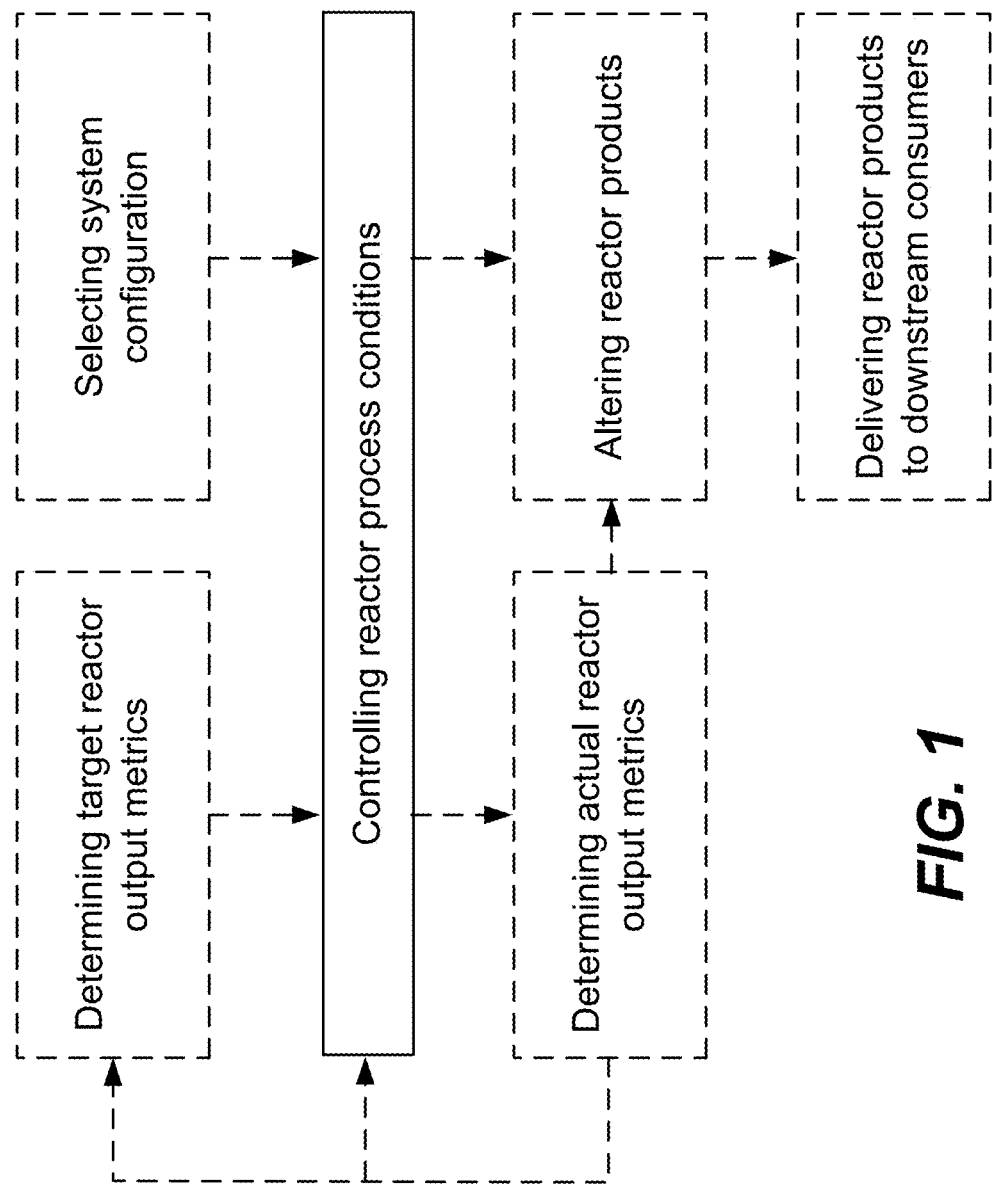
FIG. 1 is a flow chart representation of an embodiment of the method.
Figure 2A:
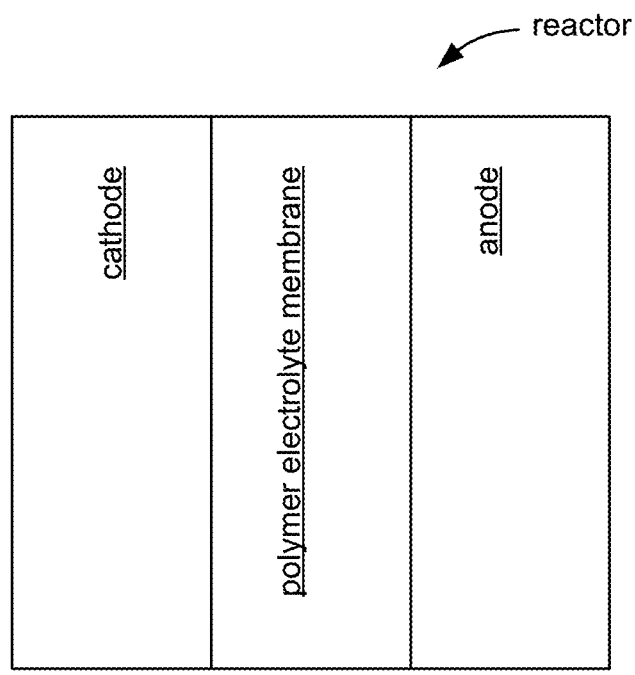
FIGS. 2A-2B are a schematic representation of an embodiment of the system and a variation of the embodiment, respectively.
Figure 2B:
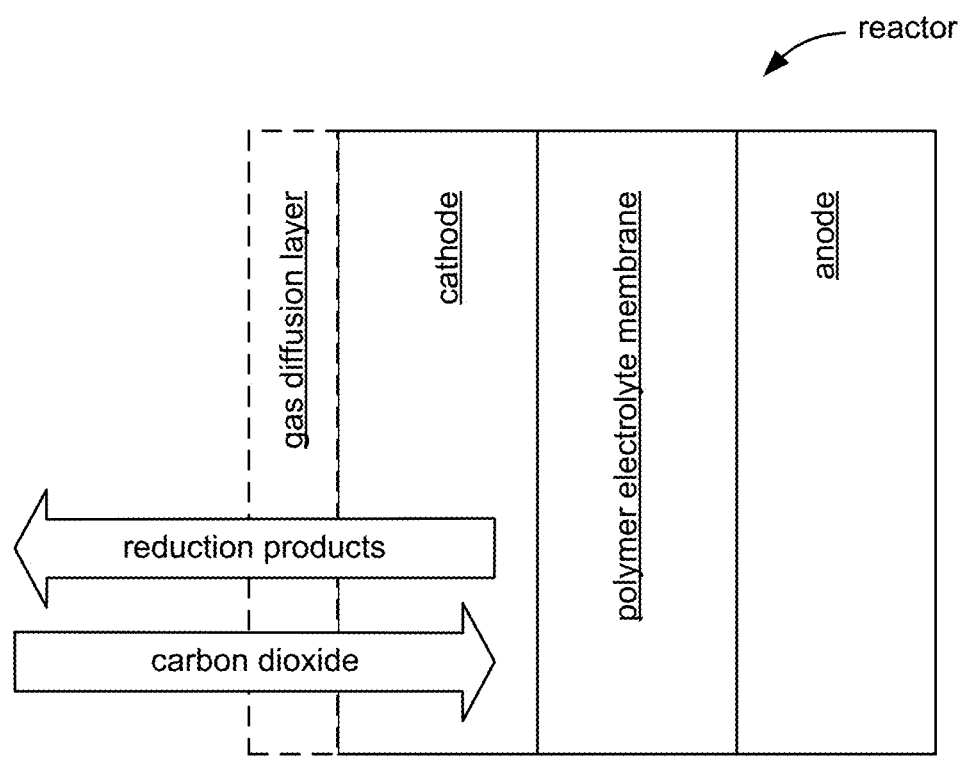
Figure 2C:
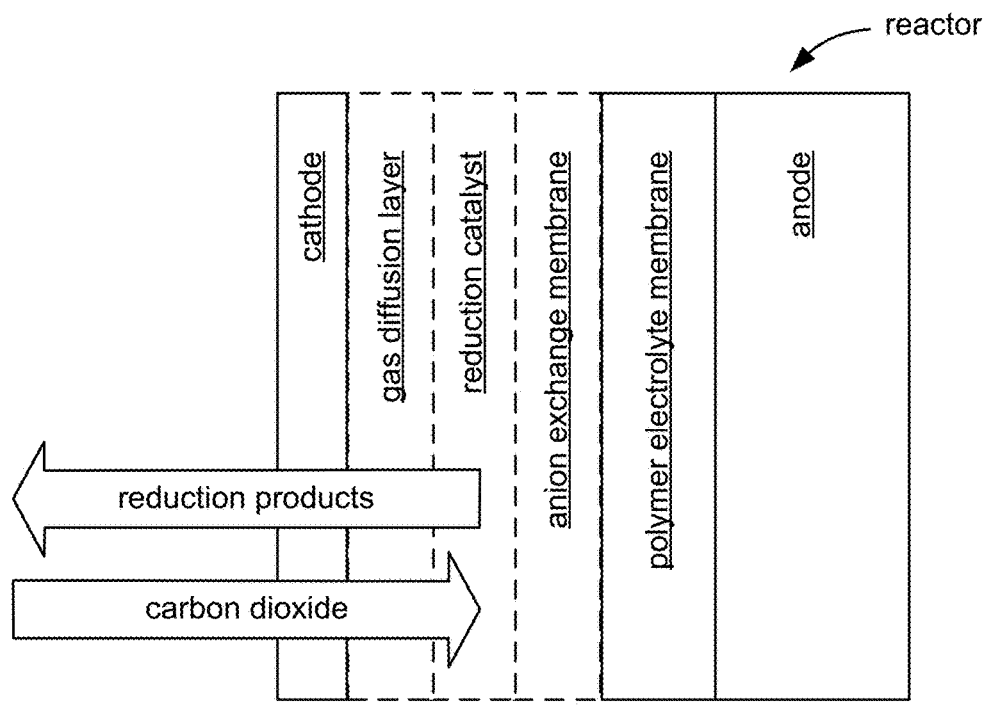
FIGS. 2C-2D are schematic representations of a first and second example, respectively, of the embodiment of the system.
Figure 2D:
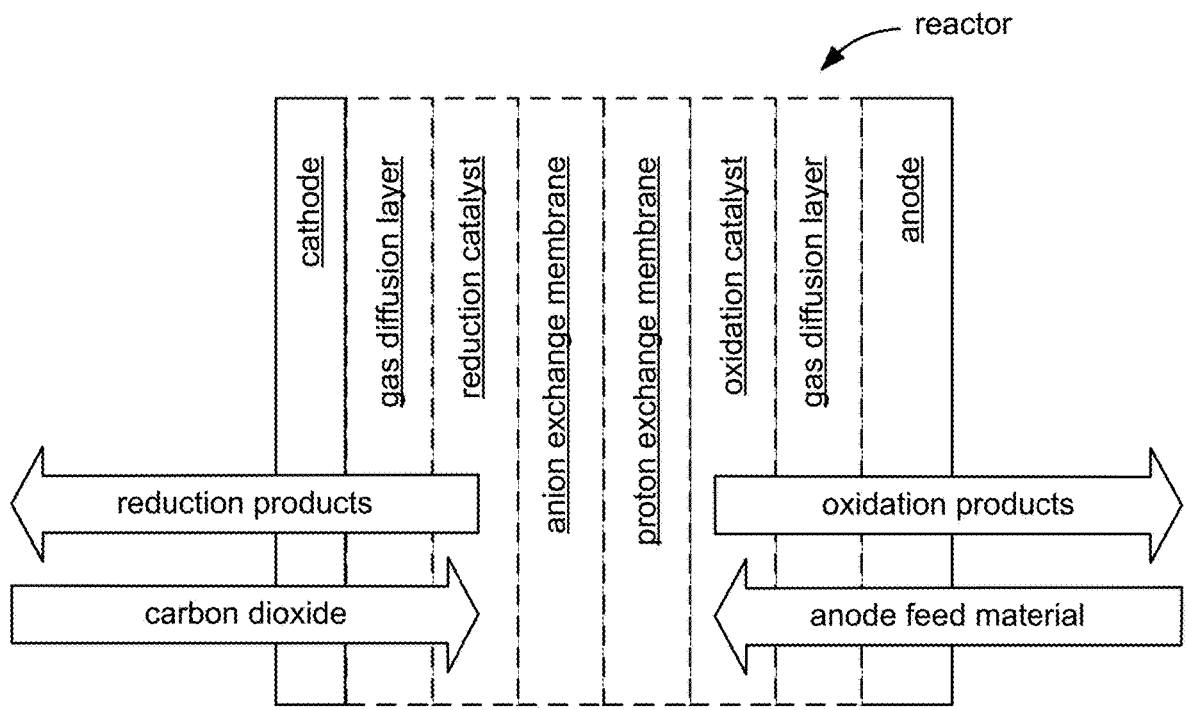

The following description of the preferred embodiments is not intended to limit the disclosure to these embodiments, but rather to enable any person skilled in the art to make and use this disclosure.

1. Overview

A system and/or method for carbon dioxide reactor control may be configured to control aspects of reactor production, such as aspects relating to quantity, concentration, and/or ratios of reactor products. Electrochemical carbon oxide reduction cells may be integrated with any of various other chemical processing systems such as chemical reactors, chemical separation units, purification units, and the like, along with associated sensing and/or control systems. Integrated systems may employ an electrochemical carbon oxide reduction cell and another chemical processing system disposed upstream, downstream, or in parallel with the electrochemical carbon oxide reduction cell.

Examples of carbon oxide reactants include carbon dioxide and carbon monoxide, typically though not necessarily in gaseous form. Other examples of carbon oxide reactant include carbonate ions and compound, and bicarbonate ions and compounds.

Typical systems and methods for carbon dioxide reactor control have focused on maximization of aspects relating to production of carbon monoxide (CO) and/or other carbon-containing products (CCPs) (e.g., carbon-containing species (CCSs)), such as maximizing ratios of CO to other reactor products (e.g., $CO:H_2$ ratio), CO concentration, and/or total CO output or output rate.

However, for some applications, simply maximizing aspect values can be undesirable, and that arbitrary control of such aspects (e.g., dynamic or selective aspect control to meet a value within a range of target aspect values), rather than simple maximization, can be beneficial. For example, it can be desirable to selectively control the $CO:H_2$ ratio of the reactor products (e.g., enabling arbitrary control within a spectrum from the highest $CO:H_2$ ratio possible for a given system and/or process, down to approximately 1:3 $CO:H_2$ or lower). With such control, the reactor output can be more effectively used (e.g., wherein the reactor outputs are directly fed to a subsequent input) for applications such as liquid hydrocarbon production via the Fischer-Tropsch process (e.g., controlling the reactor to produce an approximately 1:2 $CO:H_2$ output ratio), chemical synthesis processes, and/or gas (e.g., syngas) fermentation processes (e.g., bioreactors).

2. System

The system can include a carbon dioxide reactor, such as a reactor that generates carbon-containing products (e.g., CO, alkanes, alcohols, etc.) and/or hydrogen from an input (e.g., an input stream, such as a fluid stream) that includes carbon dioxide. Example carbon oxide electrolyzers are illustrated in FIGS. 2A-2D. The reactor may be configured to accept a gas-phase carbon dioxide input and/or performs the reaction(s) using gas-phase carbon dioxide (e.g., is a gas-phase reactor), but can additionally or alternatively accept liquid-phase carbon dioxide, supercritical fluid-phase carbon dioxide, solid-phase carbon dioxide, and/or any other suitable carbon dioxide input. While the discussion herein focuses on carbon dioxide reactors, in many cases the discussion applies equally to carbon monoxide reactors (e.g., electrochemical carbon monoxide reduction reactors), and carbonate and/or bicarbonate reduction reactors. So, unless otherwise specified or clear from context, reference to carbon dioxide reactors is understood to more generally reference carbon oxide reactors. As indicated, the reactor may an electrolyzer (e.g., electrochemical reactor) such as a gas-phase polymer-electrolyte membrane electrolyzer, but can additionally or alternatively include any other suitable reactors.

The reactor may include one or more: electrodes (e.g., anode, cathode), catalysts (e.g., within and/or adjacent the cathode and/or anode), gas diffusion layers (e.g., adjacent the cathode and/or anode), and/or flow fields (e.g., defined within and/or adjacent the electrodes and/or gas diffusion layers, such as one or more channels defined opposing the cathode across the gas diffusion layer). In some embodiments, the reactor includes a membrane stack or membrane electrode assembly (MEA) having one or more polymer electrolyte membranes (PEMs), providing ionic communication between the anode and cathode of the reactor. In certain embodiments, the reactor includes a membrane stack including: a cathode layer including a reduction catalyst and an ion-conducting polymer; a PEM membrane (e.g., bipolar membrane, monopolar membrane, etc.; membrane including one or more anion conductors such as anion exchange membranes (AEMs), proton and/or cation conductors such as proton exchange membranes, and/or any other suitable ion-conducting polymers; membrane including one or more buffer layers; etc.); and an anode layer including an oxidation catalyst and an ion-conducting polymer. The ion-conducting polymers of each layer can be the same or different ion-conducting polymers.

In some embodiments, one or more of the catalysts (e.g., reduction catalyst, oxidation catalyst) can include catalyst particles (e.g., defining a porous network of particles), such as nanoparticles. One or more of the catalysts can additionally or alternatively include one or more polymer electrolytes, optionally wherein the polymer electrolyte is mixed with the catalyst nanoparticles (e.g., arranged within the porous network, such as loaded into the open regions defined by the porous network). The catalyst nanoparticles can define one or more characteristic sizes (e.g., mean size, median size, minimum size, maximum size, size at a particular percentile of the particle size distribution, etc.), and/or the porous network can define a porosity (e.g., fraction of empty space within the network), density, circuitousness (e.g., characteristic path length per layer thickness, area, and/or volume, such as path through the empty spaces or path along interconnected particles, etc.), and/or any other suitable porous network metrics.

In some configurations, a bipolar MEA has the following stacked arrangement: cathode layer/cathode buffer layer (an anion conducting layer)/cation conductive layer (with may be a PEM)/anode layer. In some implementations, the bipolar MEA has a cathode layer containing an anion conductive polymer and/or an anode layer containing a cation conductive layer. In some implementations, the bipolar MEA has an anode buffer layer, which may contain a cation conductive material, between the cation conductive layer and the anode layer.

In some configurations, a bipolar MEA has the following stacked arrangement: cathode layer/cation conducting layer (with may be a PEM)/anion conductive layer/anode layer. In some applications, a bipolar MEA having this arrangement is configured in a system for reducing a carbonate and/or bicarbonate feedstock such as an aqueous solution of carbonate and/or bicarbonate.

In some configurations, an MEA has the following stacked arrangement: cathode layer/anion conducting layer/anode layer. In some implementations, this MEA has no cation conductive layers between the cathode layer and the anode layer. In some applications, an MEA containing only anion conductive material between the cathode and anode is configured in a system for reducing carbon monoxide feedstock.

In one example ("reactor configuration A"), the system includes: a carbon fiber paper gas diffusion layer (e.g., Sigracet 39BC); a catalyst layer including approximately 20% by weight of approximately 4 nm gold particles on Vulcan carbon and an anion-conducting polymer (e.g., Fumasep FAA-3); a bipolar PEM; and a flow field such as a single, double, triple, or quadruple serpentine flow field or an interdigitated flow field. In a specific example, the electrodes define an area of approximately 25 $cm^2$, but can additionally or alternatively define any other suitable area.

In some embodiments, the reactor includes one or more elements such as described in U.S. patent application Ser. No. 15/586,182, filed 3 May 2017 and titled "Reactor with Advanced Architecture for the Electrochemical Reaction of $CO_2$, CO and Other Chemical Compounds", which is hereby incorporated in its entirety by this reference. However, the reactor can additionally or alternatively include any other suitable elements in any suitable arrangement.

Additional information regarding optional embodiments and/or elements of the system and/or method are provided below, in US Patent Application Publication No. 2017/0321334, filed May 3, 2017, and in U.S. Provisional Patent Application No. 62/939,960, filed Nov. 25, 2019, which are incorporated herein by reference in their entireties.

A carbon oxide reduction reactor may comprise more than one cells or MEAs. The multiple cells or MEAs may be arranged in a stack, electrically connected to one another in series and/or parallel. Unless otherwise indicated, all references herein to a carbon oxide reduction reactor, a carbon oxide electrolyzer, and the like embody single cell electrolyzers and multicell stacks of electrolyzers.

A carbon oxide reduction reactor may obtain carbon oxides from various sources. As mentioned, examples of carbon oxide reactants include carbon dioxide, carbon monoxide, carbonate, and/or bicarbonate. In certain embodiments, a carbonate or bicarbonate is provided in the form of an aqueous solution (e.g., an aqueous solution of potassium bicarbonate) that can be delivered to the cathode of a reduction cell. Carbonates and bicarbonates may be obtained from various sources (e.g., minerals) and/or by various reactions (e.g., reacting carbon dioxide with hydroxide).

A system may optionally include an upstream source of carbon dioxide input, connected to an input of a carbon dioxide reactor of the disclosure, including one or more of: a biogas production system; an ethanol fermentation system such as corn ethanol production system, a beer production system, a wine production system; a natural gas processing system; a cement production system; a blast furnace system, for example a steel blast furnace system, capable of producing blast furnace gas; a coke gas production system; power plant systems, such as petroleum power plant systems, natural gas power plant systems, coal power plant systems; petroleum refinery systems; ethylene production systems; ammonia production systems; hydrogen production systems, such as water-gas shift systems; natural gas processing plants (e.g., Benfield processing); ethylene oxide production systems; aluminum smelting systems; liquified natural gas (LNG) production systems; solid feedstock gasifiers (e.g., municipal solid waste, biomass, or coal feedstocks); reformers (e.g., steam methane reformers, autothermal reformers); systems performing Boudouard reactions; direct air capture (DAC) of carbon dioxide process; atmospheres of planets or moons (e.g., the Martian atmosphere); soil of moons (e.g., the soil of the earth's moon), and/or any other system capable of producing carbon dioxide. An upstream source of carbon dioxide may be connected directly to an input of a carbon dioxide reactor of the disclosure (e.g., serves as the input, such as connected to the reduction catalyst via the cathode flow field and/or gas diffusion layer, etc.) or alternatively the upstream source may be connected to a purification system; a gas compression system; or both a purification system and a gas compression system, in either order; which then connect to an input of a carbon dioxide system of the disclosure. Multiple purification and/or gas compression systems (e.g., scrubbers, etc.) may be employed.

The carbon dioxide, carbon monoxide, or carbonate provided as input to a carbon oxide reduction reactor may, depending on the construction and operating conditions of the reactor, have a range of concentrations. In certain embodiments, carbon dioxide provided to a carbon dioxide reduction reactor has a concentration of at least about 20 mole percent, or at least about 40 mole percent, or at least about 75 mole percent, or at least about 90 mole percent. In certain embodiments, carbon dioxide provided to a carbon dioxide reduction reactor has a concentration of about 40 to 60 mole percent.

An upstream source of water for an electrolytic carbon oxide reduction reactor may come from any of various source and in various forms such as purified tap water, purified sea water, a byproduct of direct air capture of water, optionally with capture of carbon dioxide, combustion processes that may also produce carbon dioxide feedstock, fuel cell byproduct, and the like.

A system may include an input of a downstream system, capable of transforming chemical outputs from a carbon dioxide reactor of the disclosure, connected to an output of a carbon dioxide reactor of the disclosure. As examples, a downstream system of the disclosure may include one or more of: a bioreactor system; a Fischer-Tropsch system; an anaerobic fermentation system; an aerobic fermentation system, a syngas fermentation system; a ketone and/or polyketone production system; a formate production system; a formate ester production system; a formamide production system; a hydroformylation system; a methanol synthesis system; an ethylene polymerization system; a phosgene production system, an isocyanate production system, a polymer (e.g., a polycarbonate, polyethylene terephthalate, or polyurethane) production system, a monoethylene glycol production system, a polyethylene glycol production system, and oxalic acid production system, and/or any other system capable of transforming chemical outputs from a carbon oxide reduction reactor. A carbon dioxide reactor output of the disclosure may be directly connected (e.g., via the cathode flow field and/or gas diffusion layer) to a downstream system, and/or the carbon dioxide reactor output may be connected to a purification system; a gas compression system; or both a purification system and a gas compression system, in either order; which then optionally connect to an input of a downstream system. Multiple purification systems and/or gas compression systems may be employed.

A downstream system may produce carbon dioxide output in addition to other product outputs. A system may further include a connection between a carbon dioxide containing output of a downstream system and an input of a carbon dioxide reactor. The carbon dioxide containing output of a downstream system may be directly connected to an input of a carbon dioxide reactor or alternatively the downstream carbon dioxide containing output may be connected to a purification system; a gas compression system; or both a purification system and a gas compression system, in either order; which then connect to an input of a carbon dioxide reactor of the disclosure. Multiple purification systems and/or gas compression systems may be employed.

A carbon dioxide reactor can make a range of products (for example, methane, ethylene, carbon monoxide (CO), molecular hydrogen ($H_2$), ethanol, formate, formic acid, acetate, acetic acid, propanol, butanol, ethane, methanol) that can be used in downstream systems and processes. Different carbon dioxide reactors (e.g., including different layer stacks, catalysts and/or catalyst layers, PEMs, flow fields, gas diffusion layers, cell compression configurations, and/or any other suitable aspects, etc.) can be used to achieve different reduction products (e.g., product compositions such as HCR); however, different reduction products can additionally or alternatively be achieved by adjusting the operation parameters, and/or be otherwise achieved. Many possible downstream systems and processes release $CO_2$ (examples include bio-utilization of methane, bio-utilization of formic acid or formate, bio-utilization of acetic acid or acetate, Fischer-Tropsch processes, and methanol synthesis). A carbon dioxide recycling system sized appropriately for the specific application can be used in many of these cases to return $CO_2$ from the downstream system output to an input of a carbon dioxide reactor of the disclosure to increase the carbon efficiency of the overall process.

A system may further include a source of electrical energy connected to a carbon dioxide reactor, the source of electrical energy comprising one or more of: a solar electrical energy production system; a wind electrical energy production system; a geothermal electrical energy production system; a fossil fuel electrical energy production system; or any other system capable of electrical energy production.

A system may be employed to store electrical energy in the form of chemical energy. For example, power producers may produce excess power during off-peak usage periods. Systems containing carbon oxide reduction reactors are able to respond quickly to a need to consume excess power. They do not need to warm up to operate, and they can be cycled between power on and power off states without deterioration of carbon dioxide reactors. The ability to respond quickly to power utilization needs allows systems to work well with intermittent sources of power such as solar electrical energy production systems, and wind electrical energy production systems.

An embodiment of a system may include an upstream bioreactor, a carbon dioxide reactor, and an intermittent source of electrical energy. When electrical power is available from solar, or wind, or low off-peak demand, or other sources, a power availability detector may be used to start the carbon dioxide reactor. In addition, the system may boost the output of the upstream bioreactor by, for example, raising the temperature of the upstream bioreactor and increasing the flow of nutrients to the upstream bioreactor. For other upstream carbon dioxide sources, other means may be used as necessary to increase the flow of carbon dioxide to an input of a carbon dioxide reactor of the disclosure.

Any of the systems disclosed herein may include components (e.g., sensors, systems, etc.) to measure conditions, outputs, and inputs in the systems connected to a carbon dioxide reactor. Such components may include chemical property measurement systems such as gas chromatographs, mass spectrometers, infrared spectrometers, visible light spectrometers, and/or ultraviolet light spectrometers; temperature detectors; flow rate measurement sensors; electrical power availability detectors; and/or any other monitoring systems. The monitoring systems can monitor the parameters of the input and/or output streams, the parameters of a component of the input and/or output streams (e.g., the impurity concentration, the carbon dioxide concentration, the product concentration, etc.), and/or monitor any other suitable parameter(s) of the stream.

Any of the systems disclosed herein may include components for responding to conditions measured in systems connected to a carbon dioxide reactor. Such components may include systems for adjusting flow rates, temperatures, power consumption or other system parameters. A system may include one or more carbon dioxide reactors. However, the system can additionally or alternatively include any other suitable elements in any suitable arrangement. In various embodiments, one or more monitoring or sensing components is used in conjunction with a control system including a controller with appropriately programmed or constructed logic (e.g., processors and memory) for determining that one or more operating conditions should be modified and causing such operating condition(s) to be modified. Feedforward and/or feedback control systems may be employed.

3. Method

The method may be implemented using any of the components described above including an electrochemical carbon oxide reduction reactor but can additionally or alternatively be implemented using any other suitable system(s). The method optionally includes running the reactor under controlled process conditions (e.g., as described below in further detail) to produce the desired outputs (e.g., CO, $H_2$, etc.) in the desired ratios (e.g., molecular hydrogen-to-CCP ratio (HCR) and/or CCP-to-molecular hydrogen ratio), and/or altering the process conditions to alter the outputs and/or output ratios (e.g., as shown in FIG. 1).

Running the reactor can include: providing one or more inputs (e.g., gasses, liquids, solids, etc.), such as carbon dioxide, carbon monoxide, a carbon oxide source (e.g., waste gas), and/or water; causing all or some of the inputs to undergo reactions (e.g., by applying a voltage across the device electrodes), thereby generating products; and/or removing the products from the reactor (e.g., as an output gas stream). Such reactions can include, for example, reducing carbon dioxide and/or water to generate products such as CO (and/or other CCPs, such as formic acid, methanol, glyoxal, methane, acetic acid, glycolaldehyde, ethylene glycol, acetaldehyde, ethanol, ethylene, hydroxyacetone, acetone, allyl alcohol, propionaldehyde, n-propanol, etc.), and/or $H_2$. However, running the reactor can additionally or alternatively include causing any other suitable reactions to occur, and/or can additionally or alternatively include any other suitable elements performed in any suitable manner.

The method can include controlling the system to achieve a desired set of process conditions (e.g., aspects), such as process conditions known to result in a desired output metric value (e.g., a desired $CCP:H_2$ ratio, such as a $CO:H_2$ ratio). The method can additionally or alternatively include altering process conditions, such as based on a difference between actual and desired outputs (e.g., to reduce or eliminate the difference). For example, the method can include: imposing an initial set of process conditions; monitoring one or more output metrics (e.g., CCP:$H_2$ ratio); determining that an output metric differs from a target output metric (e.g., is greater than or less than the target); altering one or more process conditions to reduce the output metric difference (e.g., reducing or increasing a process condition value, such as a condition for which the output metric tends to increase or decrease along with an increasing process condition value); and optionally continuing to monitor the output metrics and/or alter the process conditions (e.g., implementing a closed-loop control of the process conditions based on the output metrics).

The method can optionally include determining the target output metric(s), which functions to determine which parameter(s) or aspect(s) to target (e.g., key parameter for a given application or downstream system). One or more target output metrics can be selected for a given process. The target output metric can be: the output metric associated with (e.g., predetermined for, dictated by, etc.) an application (e.g., applications described above, such as Fischer-Tropsch); randomly selected; empirically determined (e.g., through iterative testing and monitoring of downstream application performance); optimized (e.g., based on downstream application operation parameters, reactor operation parameters, etc.); specified by a user; and/or otherwise determined.

The method can optionally include determining the target value for the target output metric, which functions to identify a value (from a range of values) to target. In some variations, the target value can be a maximum or minimum value (e.g., maximum or minimum practically achievable value, theoretical maximum or minimum, etc.). However, the target value can additionally or alternatively not be an extremal value (e.g., can be an intermediate value or range of values between the maximum and minimum). The target value can be: a value associated with the application (e.g., predetermined, pre-associated); randomly selected; empirically determined (e.g., through iterative target value selection, monitoring of downstream application performance, and target value adjustment based on the application performance); optimized (e.g., based on downstream application operation parameters, reactor operation parameters, etc.); or otherwise determined. However, the target value can be any other suitable value and can be determined in any suitable manner.

Under some conditions, the method may achieve carbon dioxide conversion (e.g., CO fractional yield) greater than 95% (e.g., up to 100%), such as wherein the system, run under such conditions, can achieve at least the threshold conversion metric. However, the method can additionally or alternatively include achieving carbon dioxide conversion greater than 50%, 60%, 70%, 80%, 90%; between 10%-100%, such as 10-40, 30-50, 40-60, 50-70, 60-75, 70-85, 80-95, 90-95, 92-98, and/or 95-100%; and/or any other suitable carbon dioxide conversion.

The method optionally includes providing the reactor products (or a subset thereof) to a downstream consumer of the products (e.g., as described above, such as regarding applications of the reactor output; as described below, such as in the example section; etc.). The method can optionally include altering the reactor products after they are produced (e.g., before feeding the altered products to a downstream consumer, etc.). Altering the reactor products can optionally include purifying the products (e.g., removing impurities, such as SON and/or NON, from a reactor output stream). Altering the reactor products can additionally or alternatively include mixing additional gasses (and/or other substances) into a reactor output stream (and/or input stream), such as to achieve a desired output metric. In one variation, if the CO:$H_2$ ratio of the reactor output differs from a desired value, the ratio can be adjusted by mixing the reactor output with other gasses (e.g., substantially pure CO and/or $H_2$; another mixture of CO and $H_2$, such as previously produced and stored outputs of the reactor, the output of a second reactor, outputs and/or waste gasses of other systems, etc.). For example, the CO:$H_2$ ratio of the output stream (and/or gasses in any other portion of the reactor) can be monitored (e.g., continuously during reactor production), and deviations from the desired value can be compensated for by mixing in other gasses (e.g., adding CO and/or a CO-rich mixture to increase the ratio, adding $H_2$ and/or an $H_2$-rich mixture to decrease the ratio). This example may also include altering the process conditions in order to correct the reactor outputs (e.g., as described above regarding closed-loop control). In a second variation, in which an external gas supply (e.g., the outputs and/or waste gasses of one or more other system, such as a steel mill) is fed to a downstream consumer (e.g., a gas fermenter), the reactor products are used to alter the CCP:$H_2$ ratio (e.g., CO:$H_2$ ratio) of the external gas supply (e.g., if the CCP:$H_2$ ratio of the external gas supply differs from a desired value, mixing in the reactor products to achieve the desired value). For example, based on the deviation of the external gas supply from the desired value, the process conditions can be controlled to alter the CO:$H_2$ ratio of the reactor products (e.g., increasing the ratio in response to a CO-poor external gas supply, decreasing the ratio in response to a CO-rich external gas supply), and/or the quantity of reactor product mixed into the external gas supply can be controlled (e.g., to achieve the desired value). However, the reactor output stream can additionally or alternatively be altered in any other suitable manner or can be used without alteration.

In some examples, the method includes determining one or more metrics (e.g., operation metrics) associated with the one or more upstream and/or downstream elements of the system (e.g., downstream reactors, upstream inputs, etc.). Such operation metrics can include, for example: reactor conditions such as temperature, pressure, etc.; downstream reactor and/or upstream source output metrics such as output quantity, composition, purity, etc.; metrics associated with other inputs for the downstream reactor(s), such as input quantity, composition, purity, etc.; reactor efficiency metrics; and/or any other suitable metrics. In such examples, the method may include altering carbon dioxide reactor operation based on the metrics (e.g., to improve and/or maintain operation of the downstream reactor; to improve and/or maintain operation of the carbon dioxide reactor, such as to accommodate changes in the upstream source; to improve and/or maintain a target output metric, such as HCR or reduction product concentration, such as given a varying carbon dioxide source; etc.), such as by altering the HCR of the carbon dioxide reactor output. However, the method can additionally or alternatively include determining any other suitable metrics and/or acting (e.g., based on the metrics) in any other suitable manner.

4. Process Conditions

The process conditions can include, e.g., input carbon dioxide flow rate and/or pressure, input gas hydration, current density, voltage (e.g., maintained between about 1.5 V and 3 V, additionally or alternatively operated at less than about 1.5 V, between about 2 V-2.5 V, between about 2 V-4 V, greater than about 4 V, and/or at any other suitable voltage(s)), and/or temperature. The process conditions can additionally or alternatively include system configurations, such as gas diffusion layer aspects, catalyst aspects, flow field aspects, and/or PEM aspects. However, any other suitable process condition can be controlled or targeted. The process condition can be uncontrolled (e.g., dictated by an upstream system), controlled to meet a target value (e.g., wherein the target value can be determined based on the application receiving the reactor output, the instantaneous or anticipated reactor operation parameters, or otherwise determined), or otherwise determined.

The process conditions may include a pressure (e.g., input gas pressure, reactor pressure, etc.) greater than atmospheric pressure (e.g., within and/or greater than a threshold pressure range, such as about 1-5, about 5-10, about 10-20, about 20-50, about 50-100, about 100-300, about 300-1000, about 1-10, about 5-50, about 10-100, about 20-500, and/or greater than about 1000 atm, about 14-50, about 50-150, about 100-300, about 200-500, about 500-1000, about 750-1500, about 1000-3000, about 3000-10,000, about 10,000-20,000, and/or greater than about 20,000 psi, etc.) and/or greater than pressures typically feasible in electrolyzers other than gas-phase electrolyzers, but can additionally or alternatively include pressures substantially equal to 1 atmosphere, less than about 1 atmosphere, and/or any other suitable pressures. The process conditions may include a temperature (e.g., reactor temperature) greater than typical room temperature (e.g., within and/or greater than a threshold temperature range, such as about 25-50, about 40-60, about 50-100, about 50-75, about 70-100, and/or greater than about 100° C., etc.) and/or greater than temperatures typically feasible in electrolyzers other than gas-phase electrolyzers, but can additionally or alternatively include temperatures substantially equal to room temperature (e.g., about 20-30° C.), less than room temperature, and/or any other suitable temperatures. However, the process conditions can additionally or alternatively include any other suitable process conditions.

A higher carbon dioxide flow rate can lead to increased production of CCPs such as CO (e.g., due to greater availability of carbon dioxide for reduction), and thus an increased $CCP:H_2$ ratio (and correspondingly, lower carbon dioxide flow rate can lead to decreased CCP production and $CCP:H_2$ ratio). In some embodiments, higher carbon dioxide flow rate can also result in reduced carbon dioxide conversion efficiency, thereby diluting the output stream (e.g., syngas output) with unreacted carbon dioxide. For example, carbon dioxide flow rate (e.g., measured at the reactor inlet) can be maintained at one or more values in the range of about 0.1-1000 sccm/cm$^2$ (e.g., about 0.1-1, about 1-10, about 10-100, and/or about 100-1000 sccm/cm$^2$).

In a first specific example of control based on input gas flow rate, reactor configuration A with a triple serpentine flow field is used, reactor pressure is substantially maintained at 120 psi, current density is substantially maintained at 500 mA/cm$^2$, and reactor temperature is substantially maintained at 30° C. In this specific example, substantially pure carbon dioxide gas is input at various flow rates, wherein input flow rates (e.g., measured at the reactor inlet) of 12 sccm/cm$^2$, 20 sccm/cm$^2$, and 40 sccm/cm$^2$ result in $CO:H_2$ ratios of approximately 1:1, 2:1.1, and 4:1, respectively.

In a second specific example of control based on input gas flow rate, reactor configuration A with a serpentine flow field is used, reactor pressure is substantially maintained at 130 psi, and current density is substantially maintained at 500 mA/cm$^2$. In this specific example, substantially pure carbon dioxide gas input at a 40 sccm/cm$^2$ flow rate results in a $CO:H_2$ ratio of approximately 8:2, whereas a 12 sccm/cm$^2$ flow rate results in an approximately 1:1 ratio.

Higher carbon dioxide pressure can lead to increased CCP fractional yield and/or $CCP:H_2$ ratio (and correspondingly, lower carbon dioxide pressure can lead to decreased CCP fractional yield and/or $CCP:H_2$ ratio). First, increased carbon dioxide pressure can result in greater availability of carbon dioxide for reduction, thereby increasing the total production of CCPs. Second, higher pressure at the catalyst can reduce water ingress to the catalyst (e.g., from the cathode), thereby lowering the amount of water available for reduction, which can directly increase the $CCP:H_2$ ratio and/or can reduce competition for catalyst reaction sites and/or reaction energy (e.g., thereby favoring reduction of carbon dioxide). Thus, in some embodiments (e.g., in which high CCP fractional yield and/or $CCP:H_2$ ratio is desired), high reactor pressure (e.g., greater than 100 psi, up to but no greater than a carbon dioxide phase transition pressure, such as a critical pressure of 1070 psi, etc.) may be employed. For example, reactor pressure can be maintained at one or more values in the range of about 1-1100 psi (e.g., about 1-10, about 10-100, about 100-300, about 200-600, and/or about 500-1100 psi), and/or at any other suitable pressure.

In a specific example of control based on reactor pressure, reactor configuration A with a single serpentine flow field is used, substantially pure carbon dioxide gas is input at about 100 sccm/cm$^2$, current density is substantially maintained at about 150 mA/cm$^2$, and reactor temperature is substantially maintained at about 20° C. In this specific example, reactor pressure is substantially maintained at various pressures, wherein reactor pressures of 25, 50, 75, and 100 psi result in $CO:H_2$ ratios of approximately 3:2, 2.4:1, 3:1, and 5:1 and CO fractional yields of approximately 59%, 69%, 75%, and 84%, respectively.

Increasing input gas hydration can lead to increased water reduction (e.g., due to greater availability of water for reduction), and thus to a decreased $CCP:H_2$ ratio. For a substantially pure carbon dioxide input, only small amounts of water reach the catalyst (coming almost exclusively from the cathode side of the reactor), leading to a higher $CCP:H_2$ ratio. In contrast, when hydrated input gas is used, significant amounts of water from the input gas can reach the catalyst and react. For example, input gas hydration (e.g., proportion of water vapor in the input gas) can be maintained at one or more values in the range of 0% (e.g., substantially pure carbon dioxide, substantially unhydrated input gas) to 100% (e.g., 0-1, 1-3, 3-5, 5-7, 7-10, 10-15, 15-25, 25-50, 50-75, and/or 75-100 percent).

In a specific example of control based on input gas hydration, reactor configuration A with a single serpentine flow field is used, current density is substantially maintained at 50 mA/cm$^2$, reactor pressure is substantially maintained at 12 psi, and reactor temperature is substantially maintained at 20° C. In this specific example, carbon dioxide gas with varying amounts of hydration is input at 100 sccm/cm$^2$, wherein pure carbon dioxide input gas results in a $CO:H_2$ ratio of approximately 3:2, input gas with 12.2% hydration results in a $CO:H_2$ ratio of approximately 1:5.67, and intermediate hydration amounts result in $CO:H_2$ ratios between these two values.

Figure 3A:
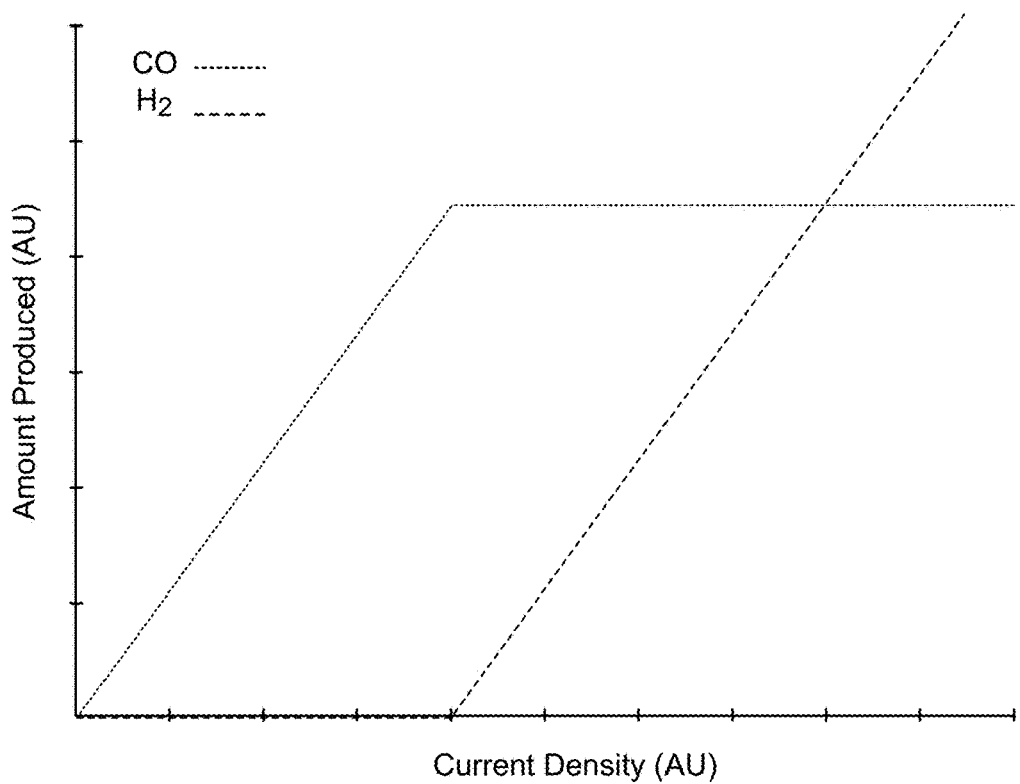
FIGS. 3A-3B are examples of idealized and non-idealized dependence of reactor outputs on current density, respectively.
Figure 3B:
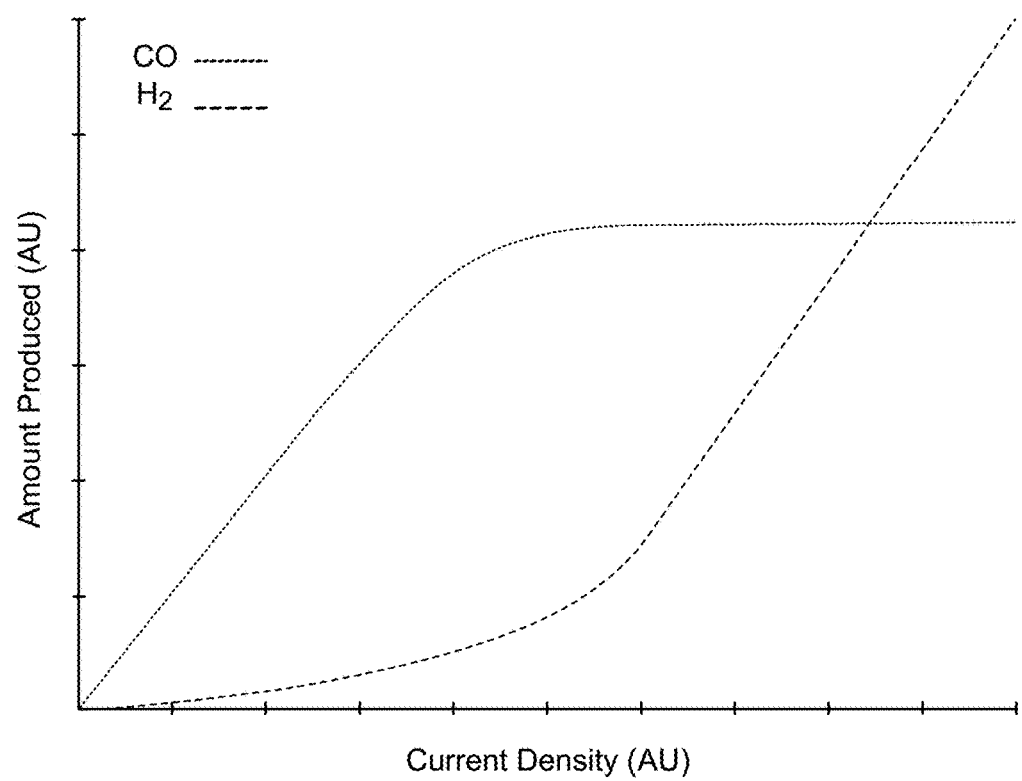

Reactors can exhibit different regimes of CCP and $H_2$ production with respect to current density. In an idealized reactor, at low current densities, no water reduction occurs and all current goes to reducing carbon dioxide, resulting in a substantially linear dependence of CO production on current and substantially no $H_2$ production; whereas at higher current densities, additional current (e.g., above a threshold current at which substantially all carbon dioxide is already being consumed) is used to reduce water, resulting in a substantially linear dependence of $H_2$ production on the additional current and substantially constant CO production (e.g., as shown in FIG. 3A). In many typical reactors, these idealities are loosened, but the two general regimes are still exhibited: CO production increases much faster than $H_2$ production in the low current density regime, then approaches a plateau in the higher current density regime while $H_2$ production increases more rapidly (e.g., as shown in FIG. 3B). The method can include controlling CO and/or $H_2$ production (e.g., controlling $CO:H_2$ ratio) by operating at any or all of a wide range of current densities (e.g., controlling the reactor operation within the low and/or high current density regime, etc.). In some embodiments, the use of gas phase input carbon dioxide can enable relatively high current densities (whereas reactors using aqueous carbon dioxide may be limited to current densities of tens of $mA/cm^2$ or less). For example, the method can include operating at current densities between about 1 $mA/cm^2$ and 100 $A/cm^2$ (e.g., about 1-75 $mA/cm^2$, about 50-100 $mA/cm^2$, about 100-200 $mA/cm^2$, about 200-500 $mA/cm^2$, about 500-1000 $mA/cm^2$, about 50-1000 $mA/cm^2$, about 0.5-10 $A/cm^2$, about 1-2 $A/cm^2$, about 2-5 $A/cm^2$, about 5-10 $A/cm^2$, about 5-100 $A/cm^2$, about 10-20 $A/cm^2$, about 20-50 $A/cm^2$, about 50-100 $A/cm^2$, etc.; at, above, or below a threshold value such as about 50 $mA/cm^2$, about 65 $mA/cm^2$, about 80 $mA/cm^2$, about 90 $mA/cm^2$, about 100 $mA/cm^2$, about 110 $mA/cm^2$, about 120 $mA/cm^2$, about 130 $mA/cm^2$, about 140 $mA/cm^2$, about 150 $mA/cm^2$, about 200 $mA/cm^2$, about 300 $mA/cm^2$, about 500 $mA/cm^2$, about 700 $mA/cm^2$, about 1000 $mA/cm^2$, about 1500 $mA/cm^2$, etc.) and/or at any other suitable current densities.

In some embodiments, increased reactor temperature can result in a reduced $CO:H_2$ ratio (e.g., due to increased ingress of water from the cathode, increased reactivity of water, etc.). The method can include controlling reactor temperature within an operation range, such as a range between a minimum temperature (e.g., a water freezing temperature such as 0° C.) and a maximum temperature (e.g., about 40° C., about 50° C., about 60° C., about 75° C., etc.; a water boiling temperature such as 100° C.), in order to control $CO:H_2$ ratio and/or any other suitable output metrics.

In a specific example of control based on reactor temperature, reactor configuration A with a quadruple serpentine flow field is used, substantially pure carbon dioxide gas is input at 70 $sccm/cm^2$, current density is substantially maintained at 150 $mA/cm^2$, and reactor pressure is substantially maintained at 100 psi. In this specific example, reactor temperature is substantially maintained at various temperatures, wherein reactor temperatures of 26.7, 35, 38.7, and 41.9° C. result in $CO:H_2$ ratios of approximately 1:0.4, 2:1, 1:1.8, and 1:3, respectively.

Characteristics of the gas diffusion layer (GDL) can additionally or alternatively be used to affect CCP and/or $H_2$ production. For example, the GDL hydrophobicity can alter $H_2$ production (e.g., by affecting water transport), wherein a more hydrophilic GDL favors $H_2$ production (thereby reducing the $CCP:H_2$ ratio) and a more hydrophobic GDL inhibits $H_2$ production (thereby increasing the $CCP:H_2$ ratio). Other GDL characteristics, such as thickness and/or pore size, can also be used to alter the reactor output.

Characteristics of the membrane (e.g., polymer electrolyte membrane) can additionally or alternatively be used to affect CCP and/or $H_2$ production. In examples, an anion exchange membrane, which favors CCP production, can be used to achieve high $CCP:H_2$ ratios, a cation exchange membrane, which favors $H_2$ production, can be used to achieve low $CCP:H_2$ ratios, and hybrid membranes (e.g., enabling both anion and cation transport) exhibiting various anion and cation transport characteristics (e.g., mobilities) can be used to achieve various intermediate ratios (e.g., membranes favoring anion transport for higher ratios, membranes favoring cation transport for lower ratios).

Characteristics of the catalysts (e.g., particle size, catalyst species, etc.) can additionally or alternatively be used to affect CCP and/or $H_2$ production. For example, larger catalyst particles can result in poor carbon dioxide transport, thereby inhibiting CCP production and reducing the $CCP:H_2$ ratio, whereas smaller catalyst particles can favor CCP production, thereby increasing the ratio. The relative number of active sites with high turnover frequency for hydrogen evolution ("hydrogen sites") and those with high turnover frequency for carbon dioxide reduction ("carbon dioxide sites") can additionally or alternatively be dependent on catalyst particle size: larger catalyst particles typically have a higher ratio of hydrogen sites to carbon dioxide sites, favoring $H_2$ production, whereas smaller catalyst particles typically have a lower ratio, favoring CO production. The catalyst type (e.g., catalyst species) can additionally or alternatively be used to control the reactor output, such as by employing a mixture of one or more catalyst materials, wherein a first set of catalyst materials (e.g., gold) favor carbon dioxide reduction and a second set of catalyst materials (e.g., platinum) favor water reduction. In examples, a substantially pure gold catalyst can be used to achieve high $CCP:H_2$ ratios, a substantially pure platinum catalyst can be used to achieve low $CCP:H_2$ ratios, and gold-platinum mixtures (e.g., alloyed particles, mixtures of gold particles and platinum particles, etc.) of varying composition can be used to achieve various intermediate ratios (e.g., more gold for higher ratios, more platinum for lower ratios). The catalyst can additionally or alternatively include V, Cr, Mn, Fe, Co, Ni, Cu, Sn, Zr, Nb, Mo, Ru, Rh, Pd, Ag, Cd, Hf, Ta, W, Re, Ir, Hg, Al, Si, In, Ga, Tl, Pb, Bi, Sb, Te, Sm, Tb, Ce, Nd, and/or combinations thereof. The catalyst can additionally or alternatively be associated with (e.g., attached to, supported by, embedded in, adjacent, in contact with, etc.) one or more support structures (e.g., support particles, support matrix, etc.), which may be conductive support structures such as carbon, boron-doped diamond, and/or fluorine-doped tin oxide. However, the catalyst can additionally or alternatively include any other suitable materials.

In a specific example of control based on catalyst particle size, variations of reactor configuration A with two catalyst particle sizes are used, both with reactor temperature substantially maintained at 30° C., reactor pressure substantially maintained at 100 psi, an interdigitated flow field, substantially pure carbon dioxide gas input at 10 $sccm/cm^2$, and current density substantially maintained at 500 $mA/cm^2$. The first set of catalyst particles have a characteristic size of 4 nm (as in the standard reactor configuration A), resulting in an HCR of 1:1.6 and a voltage of 3.8 V. The second set of catalyst particles have a characteristic size of 20 nm, resulting in an HCR of 1:2.8 and a voltage of 4.2 V.

Characteristics of reactor cell compression can additionally or alternatively be used to affect CCP and/or $H_2$ production. In a specific example of control based on reactor cell compression, reactor configuration A is used with two different gasket thicknesses (resulting in greater compression for a larger gasket thickness), both with reactor temperature substantially maintained at 30° C., reactor pressure substantially maintained at 100 psi, a triple serpentine flow field, substantially pure carbon dioxide gas input at 40 sccm/cm², and current density substantially maintained at 500 mA/cm². The first gasket is 0.012 inches thick, resulting in an HCR of 1:4 and a voltage of 3.6 V. The second gasket is 0.010 inches thick, resulting in an HCR of 1:10.1 and a voltage of 3.8 V.

Characteristics of the flow field can additionally or alternatively be used to affect CCP and/or $H_2$ production. In a first specific example of control based on flow field characteristics, reactor configuration A is used under two different sets of process conditions, both with reactor temperature substantially maintained at 30° C. and reactor pressure substantially maintained at 120 psi. In the first set of conditions, an interdigitated flow field is used, substantially pure carbon dioxide gas is input at 10 sccm/cm², and current density is substantially maintained at 160 mA/cm², resulting in a CO:$H_2$ ratio of 1.6:1. In the second set of conditions, a quadruple serpentine flow field is used, substantially pure carbon dioxide gas is input at 40 sccm/cm², and current density is substantially maintained at 120 mA/cm², resulting in a CO:$H_2$ ratio of 18.5:1.

In a second specific example of control based on flow field characteristics, reactor configuration A is used under two different sets of process conditions, both with reactor temperature substantially maintained at 30° C., reactor pressure substantially maintained at 100 psi, substantially pure carbon dioxide gas input at 40 sccm/cm², and current density is substantially maintained at 500 mA/cm². In the first set of conditions, an interdigitated flow field is used and a voltage of 3.6 V is substantially maintained, resulting in a CO:$H_2$ ratio of 1.6:1. In the second set of conditions, a triple serpentine flow field is used and a voltage of 3.8 V is substantially maintained, resulting in a CO:$H_2$ ratio of 10.1:1.

However, any other suitable flow field can additionally or alternatively be employed to control the reactor outputs, the process conditions can additionally or alternatively include any other suitable reactor conditions, and the method can additionally or alternatively include controlling the reactor output in any suitable manner.

5. Impurity Tolerance

In some embodiments, such as embodiments in which the reactor is run at a high pressure and/or the catalyst is held at low voltage (e.g., negative voltage relative to the anode), the system and/or method may achieve high tolerance to impurities and/or dilute carbon dioxide inputs (e.g., as compared to other carbon dioxide reactors), such as tolerance to poisoning by impurities in the reactor input(s) and/or to inputs diluted by species such as methane, CO, $O_2$, and/or $N_2$. For example, the method can include determining target process conditions (e.g., reactor configuration such as PEM type, high target reactor pressure, etc.) to achieve impurity and/or dilute input tolerance (e.g., always selecting such process conditions; selecting such process conditions in response to a current and/or anticipated state of the reactor input, such as an impure and/or dilute state; etc.). These impurities can include species typically present in reactor input streams (e.g., products of coal and/or natural gas combustion, such as outputs from coal- or natural gas-fired power plants), such as $SO_x$ and/or $NO_x$, and/or can include any other impurities such as ammonia, hydrogen sulfide, and mercury. In one example, the system and/or method are capable of functioning effectively using input streams including up to 4% CO, 6% $O_2$, 10% $N_2$, 800 ppm $NO_x$, and/or 100 ppm $SO_x$, with a sum of CO, $O_2$, and $N_2$ impurities, e.g., no greater than 10%.

In a specific example of dilute input tolerance, reactor configuration A with a single serpentine flow field is used, current density is substantially maintained at 160 mA/cm², reactor pressure is substantially maintained at 110 psi, reactor temperature is substantially maintained at 20° C., and carbon dioxide-containing gasses with various levels of dilution in methane or nitrogen are input at 200 sccm/cm². In this specific example, reactor performance is highly tolerant of methane dilution up to at least 50% methane, wherein methane concentrations of 0%, 25%, and 50% result in CO:$H_2$ ratios between 9.5:1 and 8.5:1 and CO fractional yields greater than 90%. More significant performance reduction is observed using 75% methane, with a reduction in CO fractional yield to approximately 84%. In this specific example, similar tolerance to nitrogen dilution is observed, wherein nitrogen concentrations of 0%, 25%, 50%, and 75% result in CO:$H_2$ ratios between 9:1 and 8:1, and nitrogen concentrations up to 50% result in CO fractional yields greater than 85% (with 75% nitrogen concentration resulting in a CO fractional yield of approximately 81%).

In a specific example of impurity tolerance, reactor configuration A with a single serpentine flow field is used, current density is substantially maintained at 150 mA/cm², reactor pressure is substantially maintained at 100 psi, reactor temperature is substantially maintained between 20° C. and 25° C., and carbon dioxide-containing gasses with various impurities are input at 100 sccm/cm². In this specific example, reactor output metrics (e.g., CO fractional yield) under the various impurity conditions are compared to baseline reactor performance under the same conditions but using a substantially impurity-free carbon dioxide input. In this specific example, reactor performance was shown not to deviate significantly from the baseline performance for CO concentrations of 4% or less, for $NO_x$ concentrations of 800 ppm or less, for $SO_x$ concentrations of 120 ppm or less, or for oxygen concentrations of 6% or less.

However, the system and/or method can additionally or alternatively exhibit any suitable tolerance to impure and/or dilute inputs or exhibit no such tolerance.

In certain embodiments, an impurity or multiple impurities pass through the carbon oxide reduction reactor to an output stream where they are (a) separated upstream of another chemical reactor, and/or (b) passed into another chemical reactor. In embodiments where impurities in an output stream are passed to another chemical reactor, impurities may be used by the other reactor in the chemical manipulation of that process. For example, hydrogen sulfide or other sulfur-containing impurity may be employed by microbial species in a downstream bioreactor.

6. System Configuration Selection

One or more system configurations may be employed based on output HCR considerations, such as based on a desired output HCR (e.g., given a particular set of process conditions and/or a range of acceptable process conditions) and/or HCR range.

In some embodiments, this includes: at a first reactor (e.g., electrolyzer, such as a gas-phase electrolyzer), accepting an input including a carbon oxide and electrochemically producing a first reduction product (e.g., including molecular hydrogen and/or one or more CCPs other than the carbon oxide input at a first HCR) from the input (e.g., under a first set of process conditions). The choice of the first reactor design and its operating conditions may include determining a desired HCR and/or HCR range (e.g., based on downstream reactor metrics, market price metrics, efficiency metrics, and/or any other suitable metrics) and selecting a system configuration (e.g., for a second reactor) based on the first HCR and/or the desired HCR (e.g., such that the second reactor will or can output a reduction product with an HCR closer to the desired HCR relative to the first HCR, optionally substantially under the first set of process conditions but additionally or alternatively under any other suitable process conditions). For example, the configuration for the second reactor can be selected such that the second reactor would, under conditions substantially identical to those of the first reactor (e.g., while accepting the input under the first set of process conditions), produce a second reduction product from the input, wherein the second reduction product includes molecular hydrogen and the same CCSs as the first reduction product (e.g., includes substantially all species present in the first reduction product), wherein the second reduction product defines a second HCR substantially different from the first HCR, wherein the second HCR may be closer to the desired HCR than the first HCR. Substantial difference between the first HCR and second HCR, for this example and/or any other embodiment described herein, can include the second HCR: being closer to the desired HCR than the first HCR; differing from the first HCR (e.g., being greater or lesser than the first HCR) by at least 1%, 5%, 10%, 30%, 40%, 50%, 60%, 70%, 80%, 90%, 0.5-5%, 2-10%, 5-25%, 20-50%, 40-80%, and/or 75-100%; and/or otherwise differing from the first HCR.

In some embodiments, selecting system configurations can include selecting one or more aspects of a PEM, such as to alter the output HCR. Such selection can include selecting membrane compositions (e.g., different polymer species) and/or microstructures, selecting membrane layer thicknesses, and/or selecting any other suitable aspects of the PEM. In some examples, such selection includes selecting a thickness of an anion exchange membrane and/or proton exchange membrane (e.g., wherein a bipolar PEM with more AEM will tend to produce a lower output HCR than one with more proton exchange membrane). In a first specific example, selecting a thinner AEM (e.g., thinner than a reference AEM thickness such as a thickness of the first reactor AEM, thinner than an optimized AEM thickness substantially corresponding to optimal CCP production, etc.) can result in a reactor configured to produce a higher output HCR, whereas selecting a thicker AEM (e.g., thicker than the reference AEM thickness but optionally no thicker than the optimized AEM thickness) can result in a reactor configured to produce a lower output HCR.

Selecting system configurations can additionally or alternatively include selecting one or more aspects of reactor catalyst(s) (e.g., reduction catalyst, oxidation catalyst), such as to alter the output HCR. In some variations, selecting reactor catalyst aspects can include selecting a catalyst layer thickness (e.g., wherein a thicker reduction catalyst will tend to produce a higher HCR). In one example, selecting a thicker reduction catalyst layer (e.g., thicker than a reference reduction catalyst layer thickness such as a thickness of the first reactor reduction catalyst layer, thicker than an optimized reduction catalyst layer thickness substantially corresponding to optimal CCP production, etc.) can result in a reactor configured to produce a higher output HCR, whereas selecting a thinner reduction catalyst layer (e.g., thinner than the reference reduction catalyst layer thickness but optionally no thinner than the optimized reduction catalyst layer thickness) can result in a reactor configured to produce a lower output HCR.

Selecting reactor catalyst aspects can additionally or alternatively include (e.g., in embodiments in which a catalyst layer includes catalyst particles, such as nanoparticles, defining a porous network) selecting a catalyst porosity (e.g., wherein a more porous reduction catalyst network will tend to produce a lower HCR). In one example, selecting a less porous reduction catalyst network (e.g., less porous than a reference reduction catalyst such as a porosity of the first reactor reduction catalyst network, less porous than an optimized reduction catalyst substantially corresponding to optimal CCP production, etc.) can result in a reactor configured to produce a higher output HCR, whereas selecting a more porous reduction catalyst (e.g., more porous than the reference reduction catalyst but optionally no more porous than the optimized reduction catalyst) can result in a reactor configured to produce a lower output HCR.

Selecting reactor catalyst aspects can additionally or alternatively include (e.g., in embodiments in which a catalyst layer includes catalyst particles, such as nanoparticles, and one or more polymer electrolytes, such as wherein the catalyst particles define a porous network that contains the polymer electrolyte and/or are mixed into a medium including the polymer electrolyte) selecting a catalyst-to-polymer electrolyte ratio (CPR) (e.g., wherein a higher reduction catalyst CPR will tend to produce a higher HCR), such as by selecting a degree of polymer electrolyte loading into a porous reduction catalyst network. In one example, selecting a higher reduction catalyst CPR (e.g., higher CPR than a reference reduction catalyst CPR such as a CPR of the first reactor reduction catalyst network, higher CPR than an optimized reduction catalyst substantially corresponding to optimal CCP production, etc.) can result in a reactor configured to produce a higher output HCR, whereas selecting a lower CPR reduction catalyst (e.g., lower CPR than the reference reduction catalyst but optionally no lower than the optimized reduction catalyst CPR) can result in a reactor configured to produce a lower output HCR.

Selecting reactor catalyst aspects can additionally or alternatively include (e.g., in embodiments in which a catalyst layer includes catalyst particles, such as nanoparticles) selecting a characteristic catalyst particle size (e.g., wherein a larger particle size will tend to produce a higher HCR). In one example, selecting a larger reduction catalyst particle size (e.g., larger than the particles of a reference reduction catalyst such as the first reactor reduction catalyst, larger than an optimized reduction catalyst substantially corresponding to optimal CCP production, etc.) can result in a reactor configured to produce a higher output HCR, whereas selecting a smaller reduction catalyst particle size (e.g., smaller than the particles of the reference reduction catalyst but, e.g., no smaller than the particles of the optimized reduction catalyst) can result in a reactor configured to produce a lower output HCR. However, the method can additionally or alternatively include selecting any other suitable reactor catalyst aspects.

The method can additionally or alternatively include selecting a reactor cell compression (e.g., wherein lower compression will tend to result in higher HCR and higher compression will tend to result in lower HCR), a flow field, and/or any other suitable aspects of the system.

U.S. Provisional Application Ser. No. 62/619,996, filed on 22 Jan. 2018, U.S. Provisional Application Ser. No. 62/620, 109, filed on 22 Jan. 2018, and U.S. Provisional Application Ser. No. 62/685,771, filed on 15 Jun. 2018, are each incorporated herein by reference in its entirety.

The electrolyzer design and operating conditions can be tuned for particular applications, and for producing a cathode output having specified compositions. In some implementations, one or more general principles may be applied to operate in a way that produces a required output stream composition.

1. Restrict carbon dioxide reactant availability at the cathode active sites and/or increase current density at the cathode. These operating condition ranges tend to produce the following results: (a) initially, upon decreasing the carbon dioxide reactant availability and/or increasing the current density, the fraction of $CO_2$ converted to CO increases (i.e., $CO:CO_2$ in the output stream increases); (b) at some point, upon further decreasing the carbon dioxide reactant availability and/or increasing the current density, the hydrogen ion reduction reaction becomes more pronounced (i.e., $H_2:CO$ increases). Electrolyzers that can operate with relatively little carbon dioxide input/availability may have flow fields or gas diffusion components that restrict carbon dioxide from reaching active sites on the electrolyzer cathode. In certain embodiments, flow field designs that are not interdigitated, and such flow field designs that have long paths such as serpentine paths between the source of $CO_2$ and the cathode result in higher ratios of $CO:H_2$. Interdigitated flow field forces input gas (carbon oxide) to flow through the gas diffusion layer before exiting at a different location on the flow field. Non-interdigitated designs have long continuous paths for the carbon oxide feed gas to flow into and out of the cathode. Channels on the inlet side are spaced from the channels on the outlet side. In certain embodiments, gas diffusion electrodes that are relatively thick restrict $CO_2$ mass transport to the cathode active sites and therefor tend to increase the ratio of $CO:CO_2$ and/or $H_2:CO$.

2. Make hydrogen ions relatively more available at the cathode. Making hydrogen ions relatively more available at the cathode may produce a cathode product stream with a relatively high ratio of $H_2:CO$. Electrolyzers configured in a way that provide a relatively hydrogen rich product may employ designs that (a) starve the cathode of carbon dioxide reactant (as described in 1), (b) permit a relatively high flux of hydrogen ions to be transported from the anode, where they are generated, to the cathode, and/or (c) operate at a relatively high cell temperature. Electrolyzers that can operate with a relatively high flux of hydrogen ions to the cathode may have MEAs with cation conducting polymers and/or mixed ion conducting polymers at the cathode. Alternatively or additionally, in MEAs including a cathode buffer layer, the layer is designed to be relatively thin and/or have a relatively high hydrogen ion transference number.

3. Make hydrogen ions less available at the cathode. Making hydrogen ions relatively more less at the cathode may produce a cathode product stream with relatively high ratios of $CO:H_2$. Electrolyzers configured in a way that provides a relatively hydrogen poor product may employ designs that (a) provide the cathode with surplus carbon dioxide reactant for a given current density, (b) contain MEA designs that prevent hydrogen ions from reaching the cathode, and/or (c) operate at a relatively low cell temperature.

High $CO_2$ Reduction Product to $CO_2$ Ratio Operating Parameter Regime

In certain embodiments, an electrolyzer is configured to produce, and when operating actually produces, an output stream having a $CO:CO_2$ molar ratio of at least about 1:1 or at least about 1:2 or at least about 1:3. A high CO output stream may alternatively be characterized as having a CO concentration of at least about 25 mole %, or at least about 33 mole %, or at least about 50 mole %.

In certain embodiments, this high carbon monoxide output concentration is obtained by operating a carbon dioxide electrolyzer in a manner that produces any one of or any combination of the following operating conditions:
- a current density of at least about 300 mA/cm2, at the cathode,
- a $CO_2$ stoichiometric flow rate (as described elsewhere herein) of at most about 4, or
- at most about 2.5, or at most about 1.5
- a temperature of at most about 80° C. or at most about 65,
- a pressure range of about 75 to 400 psig,
- an anode water composition of about 0.1 to 50 mM bicarbonate salt, and
- an anode water pH of at least about 1.

In certain embodiments, the electrolyzer may be built to favor high $CO:CO_2$ molar ratios or concentrations, as defined here, by using a carbon dioxide electrolyzer having any one of or any combination of the following properties:
- relatively small nanoparticle cathode catalysts (e.g., having largest dimensions of, on average, about 0.1-15 nm),
- gold as the cathode catalyst material,
- a cathode catalyst layer thickness of about 5-20 um,
- a cathode gas diffusion layer (GDL) with a microporous layer (MPL),
- a cathode GDL with PTFE present at about 1-20 wt %, or about 1-10 wt %, or about 1-5 wt %,
- a GDL that has a thickness of at least about 200 um
- I bipolar MEA having an anion-exchange cathode buffer layer having a thickness of at least about Sum, and
- a cathode flow field having parallel and/or serpentine flow paths.

High Reduction Product (H2+CO) to $CO_2$ Ratio Operating Parameter Regime

In certain embodiments, an electrolyzer is configured to produce, and in operation actually produces, an output stream having a $(H_2+CO):CO_2$ molar ratio of at least about 2:1 or at least about 1:2 or at least about 1:3.

In certain embodiments, this high reduction product output concentration is obtained by operating a carbon dioxide electrolyzer in a manner that produces any one of or any combination of the following operating conditions:
- a current density of at least about 300 mA/cm2,
- a $CO_2$ stoichiometric flow rate of at most about 4, or at most about 2.5, or at most about 1.5
- a temperature of at most about 125° C.,
- a pressure of at most about 800 psi,
- anode water composition of 0 to about 500 mM bicarbonate salt, and
- an anode water pH of about 0-15.

In certain embodiments, the electrolyzer may be built to favor high $(CO+H_2):CO_2$ molar ratios or concentrations, as defined here, by using a carbon dioxide electrolyzer having any one of or any combination of the following properties:
- nanoparticle cathode catalysts (e.g., having a largest dimension, on average, of about 0.1-1000 nm),
- a transition metal as a cathode catalyst material,
- a cathode catalyst layer thickness of about 0.1-100 um,
- a cathode gas diffusion layer with or without a microporous layer (MPL),
- a GDL with about 0-70 wt % PTFE,
- a GDL that is about 10-1000 um thick, and a bipolar MEA having an anion-exchange cathode buffer layer that is about 0-100 um thick.

Hydrogen Rich Product Stream Operating Parameter Regime

In certain embodiments, a carbon dioxide electrolyzer is configured to produce, and when operating actually produces, an output stream having $H_2$:CO in a molar ratio of at least about 1:1.

In certain embodiments, such hydrogen rich output concentration is obtained by operating a carbon dioxide electrolyzer in a manner that produces any one of or any combination of the following operating conditions:
- a current density of at least about 300 mA/cm2,
- a $CO_2$ mass transfer stoichiometric flow rate to the cathode of up to about 2,
- a temperature of at least about 65° C. or at least about 80° C.,
- a pressure range of about 75 to 500 psig,
- an anode water composition of pure water or at least about 50 mM bicarbonate salt, and
- an anode water pH of at most about 1.

In certain embodiments, the electrolyzer may be built to favor hydrogen rich molar ratios or concentrations, as defined here, by using a carbon dioxide electrolyzer having any one of or any combination of the following properties:
- relatively large nanoparticle cathode catalysts (e.g., having a largest dimension of, on average, at least about 80 nm)
- silver, palladium, or zinc as the cathode catalyst material,
- a cathode catalyst layer thickness of at most about 5 um or a thickness of at least about 25 um,
- a cathode gas diffusion layer with no microporous layer (MPL),
- a cathode GDL with no PTFE present or at least about 20 wt % PTFE,
- a cathode GDL having a thickness that is at most about 200 um or at least about 500 um, and
- a bipolar MEA having an anion-exchange cathode buffer layer with a thickness that is about 0-5 um.

High Reduction Product to Hydrogen Product Stream Operating Parameter Regime

In certain embodiments, a carbon dioxide electrolyzer is configured to produce, and when operating actually produces, an output stream having CO:$H_2$ in a molar ratio of at least about 2:1.

In certain embodiments, such product rich output concentration is obtained by operating a carbon dioxide electrolyzer in a manner that produces any one of or any combination of the following operating conditions:
- a current density at the cathode of at least about 300 mA/cm2,
- a $CO_2$ mass transfer stoichiometric flow rate to the cathode of at least about 1.5, or
- at least about 2.5, or at least about 4,
- a temperature of at most about 80° C.,
- a pressure in the range of about 75 to 400 psig,
- an anode water composition of about 0.1 mM to 50 mM bicarbonate salt, and
- an anode water pH of greater than about 1.

In certain embodiments, the electrolyzer may be built to favor product-rich molar ratios or concentrations, as defined here, by using a carbon dioxide electrolyzer having any one of or any combination of the following properties:
- relatively small nanoparticle catalysts (e.g., having largest dimensions of, on average, about 0.1-15 nm),
- gold as the cathode catalyst material,
- a cathode catalyst layer thickness of about 5-20 um,
- a cathode gas diffusion layer with a microporous layer (MPL),
- a cathode GDL with PTFE present at about 1-20 wt %, or about 1-10 wt %, or about 1-5 wt %,
- a cathode GDL that has a thickness of at least about 200 um, and
- a bipolar MEA having an anion-exchange layer with a thickness of at least about 5um.

Stoichiometric Flow Rate

Given that a molar flow rate may be determined, at least in part, by the electrical current delivered to the cell, the molar flow rate may be tied to the current. As an example, the molar flow rate of carbon oxide in the input stream may be defined in terms of flow rate per unit of reaction expected for a given current. Herein, the term "stoichiometric" flow rate refers to a fraction or multiple of the flow rate of reactant carbon oxide required to fully utilize all current at the cathode, assuming that the reduction reaction of carbon oxide is 100% efficient at the cathode to a given reaction. A flow rate of carbon oxide having a stoichiometric value of "1" is the flow rate required to consume all electrons provided at the cathode, and no more than that, in the given reduction reaction at the cathode. Stated another way, the stoichiometric flow rate is the amount of excess (or shortfall) reactant that is present beyond (or below) what could be theoretically reacted if the current efficiency for a given reaction were 100%.

For the carbon dioxide reduction reaction that produces carbon monoxide in an acidic environment ($CO_2+2H^+ + 2e- \rightarrow CO+H_2O$), a carbon dioxide flow rate with a stoichiometric value of 1 provides one mole of carbon dioxide for every two moles of electrons provided by the cell. Stated another way, a cell having a current providing 2 moles of electrons/second and a carbon dioxide flow rate providing 1 mole of carbon dioxide molecules/second would have a stoichiometric flow rate of 1. For the same current and a flow rate of 0.5 carbon dioxide moles/second, the cell would have a stoichiometric flow rate of 0.5. And, again for the same current but with a flow rate of 1.5 carbon dioxide moles/second, the cell would have a stoichiometric flow rate of 1.5. The molar flow rate needed to achieve a stoichiometric flow rate of 1 can be calculated:

Stoichiometric Flow Rate(sccm)=[60(s/min)*Molar gas volume at STP(*mL/mol*)]/[Faraday's constant(*C/mol e-*)*#*e-*'s*/mole $CO_2$]*Amps of current fed to the electrolyzer Total amps of current can be calculated from the current density, the area of the electrolyzer cell and the number of cells in the electrolyzer:

Amps of current=current density*area of the electrolyzer cell*number of cells

In an example, a 100 cm² electrolyzer with a current density of 500 mA/cm² performing the electrochemical reduction of $CO_2$ to CO has a total current of 50 A and the reaction requires 2 moles of e-/mole CO produced, so the stoichiometric flow rate of 1 is:

[60*22,413]/[9,6485*2]*50=348.4 sccm

In this example a stoichiometric flow rate of 0.5 would be:

0.5*348.4=174.2 sccm

And a stoichiometric flow rate of 2 is:

2*348.4=696.8 sccm

In another example of a cell producing ethylene from carbon dioxide, 12 moles of electrons are needed to reduce 2 moles of carbon dioxide to 1 mole of ethylene. The stoichiometric flow rate for a 3 cell 1500 cm2 electrolyzer with a current density of 300 mA/cm2 is:

[60*22,413]/[96,485*6]*1350=3,136 sccm.

The following examples were conducted and illustrate the effects of certain electrolyzer design and operating parameters on the molar ratios of gases in a cathode output stream.

All examples used 20 wt % Au/Vulcan XC-72R with 4 nm Au particles in a cathode catalyst layer. All examples used a 100% $CO_2$ input with no humidification as the input to the cathode of the electrolyzer. All examples used a bipolar MEA with an anion-exchange polymer-electrolyte adjacent to the cathode layer. The anion-exchange polymer had a backbone repeat unit comprised of three aryl groups and a methylene carbon having a CF3 pendant group and an alkyl quaternary ammonium pendant group. The polymer used bicarbonate, carbonate, hydroxide, and/or bromide as the counter ion to the quaternary ammonium group (Orion Polymers and Membrane, Cohoes, NY).

- All use IrOx catalyst at the anode for water oxidation, could also use IrRuOx
- Flow rate of water to the anode ranges from 4 L/min to 40 mL/min
- All are single cells

Example 1

Composition of output stream: 30% CO, 20% $H_2$, 50% $CO_2$ (3:2 CO:$H_2$ ratio)
Current Density: 300 mA/cm2
$CO_2$ input flow rate: 400 sccm
Cell temperature: 50° C.
Cell Area: 100 cm2
Flow field type: Interdigitated
GDL type: Sigracet 29BC
Au metal loading: 0.3 mg/cm2
Catalyst layer thickness: 15 um
AEM layer thickness: 12 um
Membrane type and thickness: Nafion 117, 183 um thick
Applications:
1. Feed directly to a gas fermentation reactor, or $CO_2$ may be removed to increase CO+$H_2$ concentration, or $H_2$ removed or added to change CO:$H_2$ ratio and affect products or combination of these.
2. $H_2$ may be added to make feedstock for F-T, not necessary to remove $CO_2$ for all reactor designs, but could remove $CO_2$ to higher activity in some reactors.

Example 2

Composition of output stream: 50% CO, 5% $H_2$, 45% $CO_2$ (10:1 CO:$H_2$ ratio)
Current Density: 400 mA/cm2
$CO_2$ input flow rate: 110 sccm
Cell temperature: 45° C.
Cell Area: 25 cm2
Flow field type: serpentine
GDL type: Sigracet 39BC
Au metal loading: 0.27 mg/cm2
Catalyst layer thickness: 14 um
AEM layer thickness: 14 um
Membrane type and thickness: Nafion 115, 127 um thick
Applications:
1. Feed directly to a gas fermentation reactor, or $CO_2$ removed to increase CO+$H_2$ concentration, or $H_2$ removed or added to change CO:$H_2$ ratio and affect products or combination of these.
2. $H_2$ may be added to make feedstock for F-T, not necessary to remove $CO_2$ for all reactor designs, but could remove $CO_2$ to higher activity in some reactors.
3. For formate production, may need to remove $CO_2$, but not $H_2$
4. For polycarbonate production, may need to remove $CO_2$+$H_2$ to less than about 2% combined concentration

Example 3

Composition of output stream: 20% CO, 20% $H_2$, 60% $CO_2$ (1:1 CO:$H_2$ ratio)
Current Density: 300 mA/cm2
$CO_2$ input flow rate: 400 sccm
Cell temperature: 50° C.
Cell Area: 100 cm2
Flow field type: interdigitated
GDL type: Sigracet 29BC
Au metal loading: 0.3 mg/cm2
Catalyst layer thickness: 15 um
AEM layer thickness: 12 um
Membrane type and thickness: Nafion 117, 183 um thick
Applications:
1. $H_2$ may be added to make feedstock for F-T, not necessary to remove $CO_2$ for all reactor designs, but could remove $CO_2$ to higher activity in some reactors.

Example 4

Composition of output stream: 35% CO, 35% $H_2$, 30% $CO_2$ (1:1 CO:$H_2$ ratio)
Current Density: 300 mA/cm2
$CO_2$ input flow rate: 60 sccm
Cell temperature: 50° C.
Cell Area: 25 cm2
Flow field type: interdigitated
GDL type: Sigracet 29BC
Au metal loading: 0.32 mg/cm2
Catalyst layer thickness: 15.6 um
AEM layer thickness: 14 um
Membrane type and thickness: Nafion 115, 127 um thick
Applications:
1. Feed directly to a gas fermentation reactor, or $CO_2$ removed to increase CO+$H_2$ concentration, or $H_2$ removed or added to change CO:$H_2$ ratio and affect products or combination of these.
2. $H_2$ may be added to make feedstock for F-T, not necessary to remove $CO_2$ for all reactor designs, but could remove $CO_2$ to higher activity in some reactors.

Example 5

Composition of output stream: 55% CO, 10% $H_2$, 35% $CO_2$ (5.5:1 CO:$H_2$ ratio)
Current Density: 300 mA/cm2
$CO_2$ input flow rate: 60 sccm
Cell temperature: 50° C.
Cell Area: 25 cm2
Flow field type: Serpentine
GDL type: Sigracet 39BC
Au metal loading: 0.24-0.3 mg/cm2
Catalyst layer thickness: 13-15 um
AEM layer thickness: 12-14 um
Membrane type and thickness: Nafion 117, 183 um thick Applications:
1. May be fed directly to a gas fermentation reactor, or $CO_2$ removed to increase $CO+H_2$ concentration, or $H_2$ removed or added to change $CO:H_2$ ratio and affect products or combination of these.
2. $H_2$ may be added to make feedstock for F-T, not necessary to remove $CO_2$ for all reactor designs, but could remove $CO_2$ to higher activity in some reactors.
3. for formate production, need to remove $CO_2$, but not $H_2$
4. For polycarbonate production, need to remove $CO_2+H_2$ to less than about 2% combined concentration Example 6

Composition of output stream: 15% CO, 1% $H_2$, 84% $CO_2$ (15:1 $CO:H_2$ ratio)
Current Density: 600 mA/cm2
$CO_2$ input flow rate: 500 sccm
Cell temperature: 50° C.
Cell Area: 25 cm2
Flow field type: Serpentine
GDL type: Sigracet 39BC
Au metal loading: 0.24-0.3 mg/cm2
Catalyst layer thickness: 13-15 um
AEM layer thickness: 12-14 um
Membrane type and thickness: Nafion 117, 183 um thick
Applications:
1. for formate production, may need to remove $CO_2$, but not $H_2$
2. For polycarbonate production, may need to remove $CO_2+H_2$ to less than about 2% combined concentration In various embodiments, oxygen produced at the anode of a carbon oxide electrolyzer is used in an integrated process. As examples, the electrolyzer-produced oxygen may be used in partial oxidation gasification processes, aerobic fermentation processes, electrolysis processes employing oxygen depolarization electrodes, etc. In one example of an integration scheme, a system having a Fischer Tropsch reactor may employ a carbon dioxide electrolyzer configured to produce syngas as an input to the Fischer Tropsch reactor and to produce oxygen as an input to reactor for gasification of biomass, which also produces syngas for input to the Fischer Tropsch reactor.

7. Integration Schemes

Additional information regarding optional embodiments and/or elements of the system and/or method are provided below.

A product gas from a carbon dioxide reactor of the disclosure can be used in one or more downstream processes. For example, a carbon dioxide reactor of the disclosure configured for syngas production can output a stream of CO, $H_2$, and/or $CO_2$.
Aerobic and Anaerobic Fermentation This output stream can be fed to an input of a bioreactor where microbes (e.g., *Clostridium autoethanogenum, Clostridium carboxidovorans, Clostridium ljungdahlii, Clostridium ragsdalei, Clostridium thermoaceticum, Clostridium thermoautotrophicum, Eubacterium limosum, Peptostreptococcus productus, Butyribacterium methylotrophicum,* acetogens, *E. coli,* etc.) use the energy of CO, $H_2$, and/or some of the carbon contained in CO and $CO_2$ to make one or more bioproducts (e.g., ethanol, acetic acid, butanol, butyric acid, methane, etc.). Unutilized carbon can be released from an output of the downstream bioreactor (e.g., as $CO_2$, optionally along with water vapor and/or other volatile compounds).

$CO_2$ released as an output of a downstream bioreactor can optionally be recycled back to an input of a carbon dioxide reactor of the disclosure (e.g., to increase the carbon efficiency of bioproduct production, to control carbon dioxide reactor operation, etc.). In some embodiments, it may be desirable to process this $CO_2$ before it enters (e.g., re-enters) a carbon dioxide reactor of the disclosure. For example, the water vapor may be removed, any volatile products that will inhibit carbon dioxide reactor function may be removed, and/or the $CO_2$ may be pressurized to the level desired for operation of a carbon dioxide reactor of the disclosure. Carbon dioxide leaving the bioreactor may be near atmospheric pressure and/or have any other suitable pressure, and typical carbon dioxide reactor pressures may be 20 psi to 800 psi, 50 psi to 400 psi, 100 psi to 500 psi, and/or any other suitable range. In some examples, water vapor is removed by a phase separator and/or a desiccant (e.g., a phase separator followed by a desiccant). In some examples, volatile products are removed by oxidation, adsorption onto a suitable adsorbent, and/or condensation. A $CO_2$ compressor can be used to raise the pressure of the $CO_2$ to the pressure suitable for a carbon dioxide reactor. If the carbon dioxide reactor is capable of running on low pressure $CO_2$ and is not inhibited by water vapor or any volatile compounds found in the $CO_2$ stream output from the downstream bioreactor, then the system can be simplified to remove unnecessary purification and compression systems and processes.

For each liter of culture media in the downstream bioreactor, a flow rate in the range of about 1 sccm to 1000 sccm or about 1 sccm to 2000 sccm or about 10 sccm to 500 sccm or any other suitable range of gas from an output of a carbon dioxide reactor can be desirable. For each liter of culture media in the downstream bioreactor, $CO_2$ released can be in the range of about 1 sccm to 2000 sccm or about 10 sccm to 1000 sccm or about 10 sccm to 500 sccm or any other suitable range. For each liter of culture media in the downstream bioreactor, water vapor in an output gas stream exiting the bioreactor may be about 1%-2% of the stream by volume, about 2%-5% of the stream by volume, about 5%-10% of the stream by volume, about 10%-25% of the stream by volume, about 25% to 50% of the stream by volume, about 50% to 90% of the stream by volume, and/or any other suitable amount. Volatile products leaving the downstream bioreactor may make up less than about 0.1%, less than about 0.5% of the stream by volume, less than about 1% of the stream by volume, less than about 4% of the stream by volume, and/or any other suitable amount of the stream.

Some microbial processes can use syngas produced by a carbon dioxide reactor of the disclosure. A syngas output stream of CO, $H_2$, and optionally $CO_2$ may be used as a feedstock for a downstream bioreactor where microbial processes take place to make a range of useful compounds (examples include ethanol, acetic acid, butanol, butyric acid, acetone, methane). The syngas stream itself may not contain all the nutrients needed for the microbes in the downstream bioreactor to grow. The addition of other nutrients to the bioreactor may be required for the microbes to grow and produce products. Examples of suitable microbes include *Clostridium autoethanogenum, Clostridium carboxidovorans, Clostridium ljungdahlii, Clostridium ragsdalei, Clostridium thermoaceticum, Clostridium thermoautotrophicum, Eubacterium limosum, Peptostreptococcus productus, Butyribacterium methylotrophicum,* acetogens, and/or *E. coli.*

One nutrient that can be particularly difficult to introduce to a downstream bioreactor is sulfur. Many microbes require sulfur for certain amino acid syntheses and enzymatic processes. A carbon dioxide reactor of the disclosure that is tolerant to sulfur may simplify the addition of sulfur to a downstream bioreactor (e.g., in addition to providing syngas to the downstream bioreactor). Sulfur in the form of one or more sulfur-containing species (SCSs) such as $H_2S$, $SO_2$, and/or other sulfur oxides ($SO_x$) can be present in the $CO_2$ gas fed to an input of a carbon dioxide reactor of the disclosure. $H_2S$ may pass through a carbon dioxide reactor of the disclosure unchanged and exit with the syngas output stream. The SCSs (e.g., $SO_2$ and/or SON) may pass through unchanged and/or they may be converted to one or more other SCSs (e.g., $H_2S$), and may be output with the syngas output stream. The syngas further comprising sulfur species (e.g., $H_2S$, $SO_2$, and/or SON) can then be fed to an input of a downstream bioreactor (e.g., without the need for additional sulfur nutrients). Sulfur species concentration can be in the range of about 1 ppm-10 ppm, about 5 ppm-50 ppm, about 5 ppm-100 ppm, about 10 ppm to 200 ppm, about 20 ppm to 1000 ppm, and/or any other suitable range.

In some embodiments, the carbon dioxide reactor can be coupled to one or more gas fermentation reactors (e.g., downstream of the carbon dioxide reactor, such as accepting one or more products of the carbon dioxide reactor). The method can optionally include controlling reactor operation based on this coupling, such as to optimize for carbon efficiency and/or energy efficiency. Acetogens are most energy efficient with pure CO as the input, as seen in the energy balances shown in Table 1, and in many cases, exhibit the highest selectivity toward the desired end product as well. However, there are cases where an integrated electrochemical-gas fermentation system may be designed to utilize hydrogen-containing syngas for a number of reasons.

TABLE 1

| | | |
|---|---|---|
| $6CO + 3H_2O \leftrightarrows C_2H_5OH + 4CO_2$ | $\Delta G^{o'} = -217$ kJ/mol | (1) |
| $3CO + 3H_2 \leftrightarrows C_2H_5OH + CO_2$ | $\Delta G^{o'} = -156.9$ kJ/mol | (2) |
| $2CO + 4H_2 \leftrightarrows C_2H_5OH + H_2O$ | $\Delta G^{o'} = -136.8$ kJ/mol | (3) |
| $2CO_2 + 6H_2 \leftrightarrows C_2H_5OH + 3H_2O$ | $\Delta G^{o'} = -96.7$ kJ/mol | (4) |

Using CO for most or all of the electron transfer chemistry in a downstream bioreactor typically results in the production of $CO_2$, which can then be vented in an output stream of the bioreactor. Typically, as the ratio of hydrogen in the syngas is increased, less $CO_2$ is produced, and $CO_2$ byproduct can be eliminated stoichiometrically above a certain ratio of hydrogen to carbon monoxide. In the case of gas fermentation to ethanol, for example, a $CO:H_2$ ratio less than about 1:2 will typically result in the incorporation of all input carbon into the ethanol end product. Hence, tuning the $CO:H_2$ ratio in the output stream of a carbon dioxide reactor of the disclosure could enable an operator to optimize for carbon efficiency (e.g., to minimize $CO_2$ emissions) by shifting toward more $H_2$ production and/or to optimize for energy efficiency by shifting toward higher CO production. Monitoring input costs, such as time of day electricity prices or incentives for carbon utilization, could inform the optimal operating parameters at any time. Tuning production in this manner could also change the outputs, for example by driving toward greater ethanol production (e.g., higher CO) or greater acetate production (e.g., higher $H_2$). Monitoring market prices of outputs could inform the optimal operating parameters at any given time (e.g., wherein the operating parameters are determined based on the market prices, such as to optimize the market price of the products or to optimize total profit from reactor operation).

However, the system and/or method can additionally or alternatively include any other suitable elements.

A system comprised of a $CO_2$ electrolyzer and an aerobic fermentation reactor can be used to generate products such as protein, polyhydroxyalkanoates, acetone, isopropanol, ethanol, and other products. The $CO_2$ electrolyzer takes inputs $CO_2$, water, and electricity and outputs a stream of oxygen and a separate stream containing one or more carbon-based product(s) derived from $CO_2$, hydrogen, unreacted $CO_2$, and water. The carbon-based product can be CO, methane, ethylene, or mixtures of these compounds along with other carbonaceous compounds.

The oxygen and carbon product stream can be fed to an aerobic gas fermentation system containing yeast, *E. coli*, or other microorganisms that can metabolize the compounds in the gas stream to make desired products. Output of the aerobic gas fermentation reactor include a stream containing at least one bioproduct which is typically in the liquid phase and a gas stream containing $CO_2$, water vapor, un-metabolized components of the gas feedstock, and other volatile compounds generated during fermentation such as trace hydrocarbons or $H_2S$. $CO_2$ in this gas stream can be recycled back to the inlet of the $CO_2$ electrolyzer in the same way as anaerobic fermentation processes, but 02 removal may be necessary if the $O_2$ concentration in the stream is greater than about 5%, 1% or 0.25%.

Various microorganism metabolic pathways may be utilized for a gas fermentation reactor configured to receive products of a carbon oxide electrolyzer. The design and operation of the electrolyzer will match the metabolic pathway(s), and hence the required inputs of the pathway(s). One example pathway is the Wood-Ljungdahl Pathway (WLP), which has a set of biochemical reactions that can utilize CO, $CO_2$, formate, methanol, $H_2$, and/or other single-carbon compounds to make acetyl coenzyme A (Acetyl-CoA). Acetyl-CoA is a molecule used as a carbon and energy source for microbes. The Wood-Ljungdahl Pathway is a native metabolic pathway found in acetogenic microbes such as *Clostridium Ljungdahlii*, but other microbes, such as *E. coli*, can be genetically engineered to have this pathway. Acetyl-CoA can be utilized by microbes to build cell mass and/or it can be used as a starting molecule for other biochemical pathways to make other bioproducts such as acetone, ethanol, etc. Biochemical pathways utilizing Acetyl-CoA to make products can be native to an organism or they may be added by genetically engineering so the microbe will make a desired product.

Microbes may utilize multiple metabolic pathways at the same time. For example, sugars (e.g., glucose) may be metabolized by microbes through the glycolysis or nonoxidative glycolysis pathway concurrently with inputs to the WLP. Biomolecules (e.g. ATP/ADP, NADH/NAD+) may be be generated in one metabolic pathway and used in another metabolic pathway.

WLP does not produce ATP. If cells are ATP starved, they will favor acetate production from Acetyl-CoA. To generate ATP, cells can directly utilize $H_2$ through the Flavin-Based Electron Bifurcation Pathway to generate a proton concentration gradient across their cell membranes. This gradient can drive ATP production through ATP Synthase. When cells have ATP available, then Acetyl-CoA can be converted into a range of desired products through either native or genetically engineered biochemical pathways. Ratio of $H_2:CO$ in gas stream can determine availability of ATP and determine the carbon efficiency of the bioprocess.

In some embodiments, an aerobic fermentation process employing methane and carbon dioxide inputs produces 3-hydroxy propanoic acid. In some example systems, a carbon oxide electrolyzer is configured to provide methane and carbon dioxide to a gas fermentation reactor that produces, among other products, 3-hydroxy propanoic acid.

In another example, a carbon dioxide electrolyzer is configured to produce an output of carbon monoxide, carbon dioxide, and hydrogen, which may be processed to have the ratios of these gases adjusted before delivery to a gas fermentation reactor that additionally receives a sugar (e.g., glucose) as an input and reacts these components to produce acetone.

Figure 4:
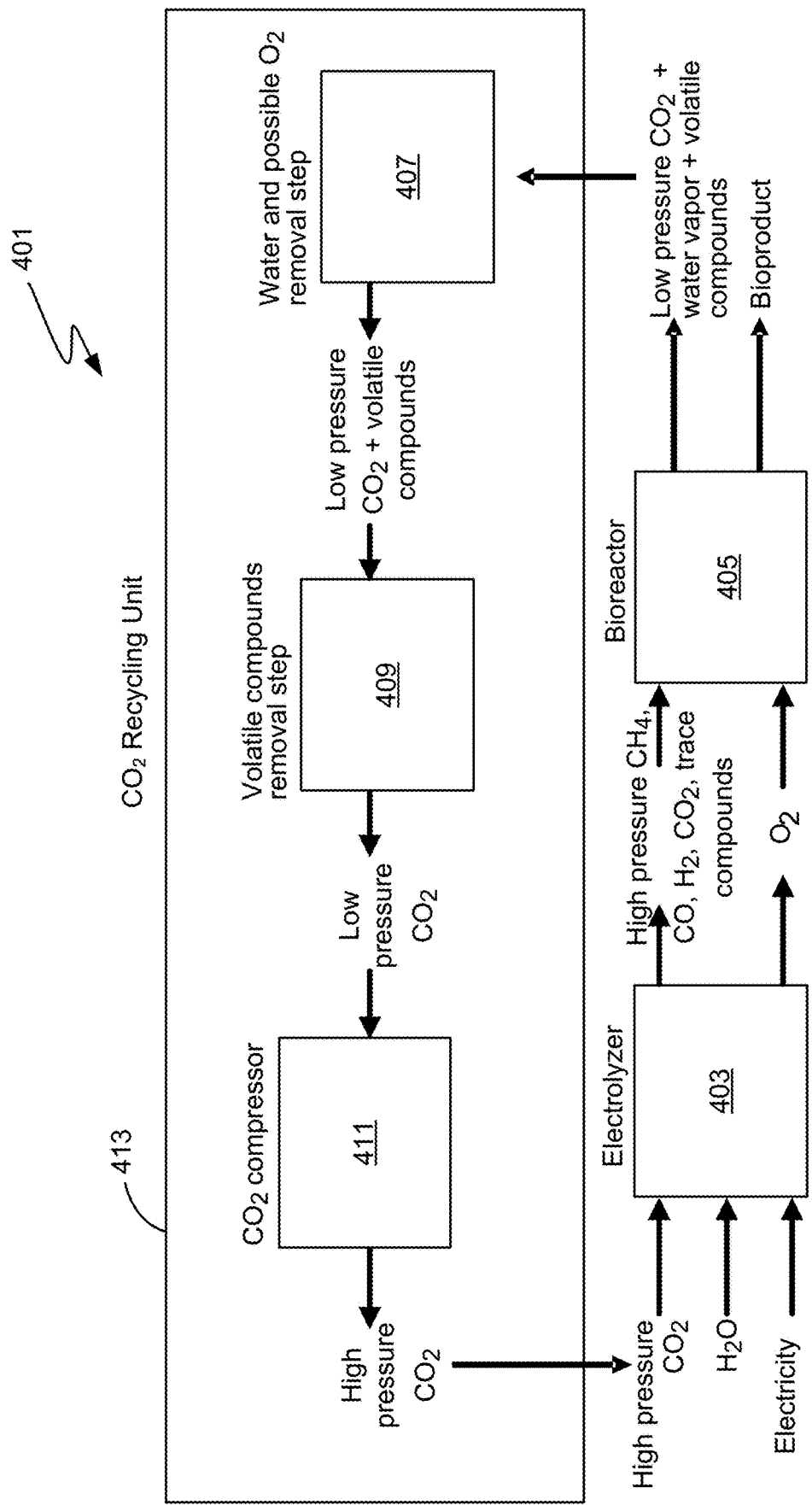
FIG. 4 depicts a gas fermentation system comprising a carbon oxide reduction electrolyzer upstream from a gas fermentation bioreactor.

FIG. 4 depicts a gas fermentation system 401 comprising a carbon oxide reduction electrolyzer 403 upstream from a gas fermentation bioreactor 405, and a recycle unit 413 configured to recycle output of bioreactor 405 to the input of electrolyzer 403.

As shown, electrolyzer 403 is configured to receive water and a carbon oxide (carbon dioxide in this example) as reactants and electricity to drive the anodic and cathodic reactions. The inputs to electrolyzer 403 are provided at a relatively high pressure (at least above atmospheric pressure). The electrolyzer's anodic reaction produces oxygen, which is used as an input to bioreactor 405 only when aerobic fermentation is employed. Outputs from the cathode side of electrolyzer 403 include unreacted carbon dioxide along with hydrogen gas and one or more carbon containing products such as carbon monoxide and/or methane. These outputs are provided at a relatively high pressure.

System 401 is configured to transport the cathode side outputs of electrolyzer 403 along with, optionally, anodically-produced oxygen to bioreactor 405. System 401 is configured to reduce the pressure of some or all the electrolyzer products before or during delivery to bioreactor 405. In certain embodiments, system 401 includes as gas purification unit (not shown) between electrolyzer 403 and bioreactor 405. A gas purification unit is configured to adjust the concentration of the electrolyzer products before they enter bioreactor 405. In some cases, a purification unit reduces the concentration of carbon dioxide in the gas stream. In some cases, a purification unit increases the concentration of carbon monoxide in the gas stream.

Bioreactor 405 is configured to covert the inputs, optionally along with other inputs such as sugar, to desired bioproduct and byproducts. In the depicted example, the biproducts are relatively volatile or otherwise separable from the desired product and can therefore be passed to recycle unit 413. In the depicted embodiment, system 401 is configured to convey carbon dioxide, water vapor, and possibly other volatile compounds from the bioreactor to recycle unit 413 at a low pressure.

Recycle unit 413 comprises one or more separation or removal units and a carbon dioxide compressor. In the depicted embodiment, a recycle unit 413 is configured to initially receive the bioreactor vapor outputs and pass them to a water and optionally oxygen separation unit 407. The output of separation unit 407 may be a mixture of low-pressure carbon dioxide and optionally volatile compounds. Recycle unit 413 is further configured to pass the carbon dioxide and volatiles to a volatile compounds removal unit 409, which removes the volatiles and outputs low pressure carbon dioxide. Recycle unit 413 also includes a carbon dioxide compressor 411 configured to receive the low-pressure carbon dioxide from removal unit 409 and pressurize it a level suitable for input to electrolyzer 403.

In certain embodiments, recycle unit 413 comprises one or more carbon dioxide capture units containing a sorbent for capturing carbon dioxide during a first phase and releasing carbon dioxide during a second phase. Separation unit 409 may be configured to include or work in conjunction with such carbon dioxide capture unit. Examples of such capture units are provided in the description of direct air capture units described herein.

In the depicted embodiment, system 401 is configured to transport pressurized carbon dioxide from recycle unit 413 to a point upstream from a cathode side inlet to electrolyzer 403, where the carbon dioxide mixes with pressurized feedstock carbon dioxide.

In certain embodiments, depending on the bioreaction undertaken, a carbon dioxide electrolyzer located upstream from the bioreactor is configured to operate in (a) a hydrogen rich product stream operating parameter regime as described herein, or (b) a high reduction product to hydrogen product stream operating parameter regime as described herein.

In various embodiments, oxygen produced by the electrolyzer is used in an integrated process such as in gasification processes. For example, a system having a Fischer Tropsch reactor may employ an electrolyzer configured to receive carbon dioxide input from partial oxidation of hydrocarbons or from gasification of biomass, which consume oxygen. The oxygen may come from the anode side of a carbon dioxide electrolyzer and/or from an air separation unit.

Figure 5:
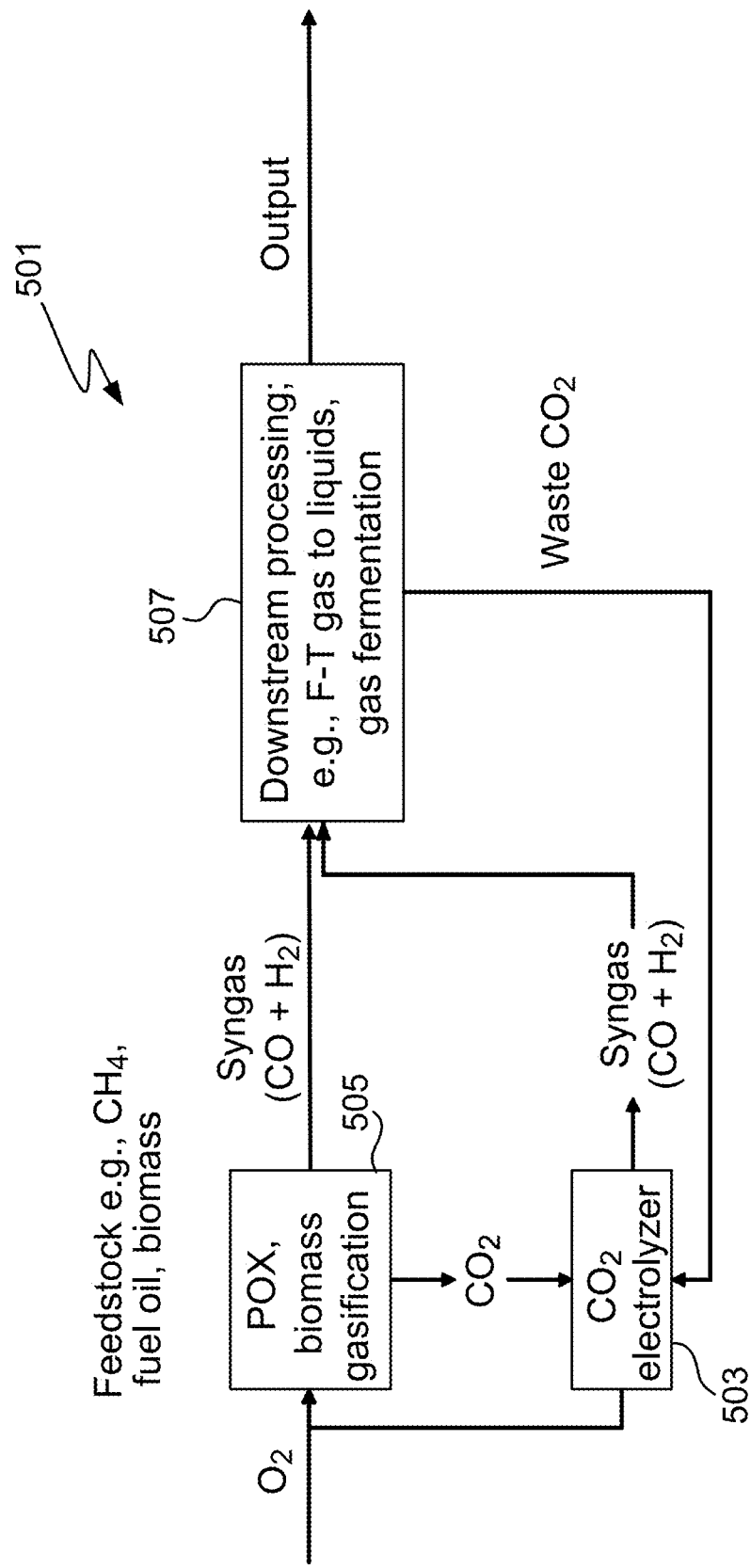
FIG. 5 depicts a system including a carbon dioxide electrolyzer configured to produce syngas.

FIG. 5 depicts a system 501 including a carbon dioxide electrolyzer 503 configured to produce syngas. System 501 also includes an aerobic fermentation reactor 505 configured to produce syngas. System 501 is also configured to deliver oxygen produced at the anode of electrolyzer 503 to reactor 505. This oxygen may replace some of the oxygen normally provided from alternative sources such as air separation and therefore reducing the energy duty and scale of the air separation unit.

System 501 is configured to deliver the syngas produced by electrolyzer 503, the fermentation reactor 505, and potentially other sources to a downstream gasification unit or partial oxidation unit 507. System 501 may be configured to deliver some waste carbon dioxide from unit 507 to the cathode input stream of electrolyzer 503.

Napthas and Fuels

As indicated, Fischer Tropch reactions may be characterized by the following general expression:

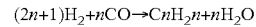

$(2n+1)H_2 + nCO \rightarrow C_nH_{2n} + nH_2O$

While the following discussion focuses on Fisher Tropsch reactions, those of skill in the art appreciate that a class of related reactions may be employed to produce liquid hydrocarbons and mixtures thereof (often generally referred to as naphthas) from input streams that include hydrogen and carbon monoxide. The class of reactions produce various compositions of liquid hydrocarbon mixtures dependent on the composition of the input stream and the reaction conditions. While the term Fischer Tropsch is used herein, it should be understood to cover any of a class of reactions that produce naphtha from a mixture including carbon monoxide and hydrogen. Generally, such reactions or exothermic.

In various embodiments, the input stream to a Fischer Tropsch reactor is about 1:2 molar ratio of $CO:H_2$. To use $CO_2$ as starting point for producing $CO/H_2$ mixture (or other Fischer Tropsch input), some conventional, non-electrolytic processes require two steps. For example, a conventional process employs a first process to produce $CO_2+H_2$ (step 1) and then a reverse water gas shift (RWSG) reaction (step 2) to react $CO_2+H_2$ and produce CO and water to result in a gas having a ratio close to the required 2:1 $CO:H_2$. Thus, in a conventional process, only after obtaining the CO and hydrogen in the correct ratio can a Fischer Tropsch reaction be employed to produce liquid hydrocarbons. Water shift (WSG) reaction and reverse water shift reaction catalysts can produce metal dust that is detrimental to downstream processes. Further, the water shift reactions require a feed of carbon monoxide and/or hydrogen.

Note that a conventional syngas process is sometimes used to directly produce $CO+H_2$ mixture (rather than using a WSG and/or RWSG reaction or a carbon dioxide electrolyzer which my emphasize production of CO). However, syngas production often uses coal.

A Fischer Tropsh system that employs a carbon dioxide electrolyzer as a source of carbon monoxide has various advantages over the WSG or syngas routes. For example, unlike a RWSG reaction, a carbon dioxide electrolyzer does not produce metal dust. Additionally, in comparison to the RWGS reaction, a carbon dioxide electrolyzer provides a higher conversion of $CO_2$ to CO.

However, a carbon dioxide electrolyzer may not produce gas having the required approximately 1:2 molar ratio of $CO:H_2$ for a Fischer Tropsch feed. In some cases, a carbon dioxide electrolyzer produces a CO-rich stream. Therefore, in some embodiments, a Fischer Tropsch system, or any other system that requires a carbon monoxide and hydrogen mixture, may employ a water electrolyzer or other source of hydrogen that optionally works in conjunction with carbon dioxide electrolyzer. The water electrolyzer is configured to make gaseous hydrogen to supplement the CO-rich output of the carbon dioxide electrolyzer. In some embodiments, syngas that is relatively rich in hydrogen can be produced as part of co-electrolysis of carbon dioxide and water. To achieve an approximately: 2 $CO:H_2$ feed concentration for a F-T reaction, the system may include sensors configured to determine the concentration of CO and $H_2$ coming through the gas separation unit from the $CO_2$ electrolyzer. Using the sensed information as feedback, the operating conditions of a water electrolyzer may be adjusted to deliver a hydrogen stream with the quantity of $H_2$ needed to bring the total stream to approximately 1:2 $CO:H_2$ concentration.

Alternatively, a single $CO_2$ electrolyzer can be used to produce a suitable Fischer Tropsch CO and $H_2$ feed blend. This can be accomplished by operating the electrolyzer in a way that biases the output toward hydrogen production and/or by processing the electrolyzer output to adjust its composition prior to delivery to the Fischer Tropsch reactor. In certain embodiments, a carbon dioxide electrolyzer includes an MEA that allows a relatively high proportion of H+ to reach the cathode. One way to promote a relatively high flux of H+ at the cathode is for a bipolar MEA to employ a relatively thin cathode buffer layer and/or to employ cathode and cathode buffer layers having polymers with a relatively high H+ transference number. In another approach, the carbon dioxide electrolyzer is constructed or operated in a way that starves it of carbon dioxide. In certain embodiments, the electrolyzer is operated at a relatively high current density, which tends to produce a higher ratio of hydrogen to carbon monoxide ratio. In some implementations, the electrolyzer employs both a relatively high current density and relatively low carbon dioxide feed to the electrolyzer. Operating at a relatively high current density has the advantage of producing employing a relatively inexpensive electrolyzer for the cost of the equipment.

The output of a $CO_2$ electrolyzer contains product CO, byproduct $H_2$, unreacted $CO_2$, and water vapor. The system may be configured to remove the water vapor and separate the unreacted carbon dioxide. A gas separation unit may be used to separate the $CO_2$ from the CO and $H_2$ and/or otherwise concentrate the CO and $H_2$. The system may include a recycle loop to recycle water to a water inlet of a $CO_2$ or water electrolyzer. The unreacted and separated $CO_2$ is then compressed and returned to the inlet of the $CO_2$ electrolyzer. Examples of gas separation units are presented in FIGS. 19, 20, 23A-D, and the associated description.

A F-T reactor may operate above about 300 psi and between about 150-300° C. If the output of a carbon dioxide electrolyzer and optional water electrolyzer is not at the required pressure, the system may employ a compressor to bring up the feed gas pressure before entering the F-T reactor. In the F-T reactor, the CO—$H_2$ mixture is converted into raw F-T liquid and waxes. A system may include a separator following the F-T reactor to separate water, high melting point F-T liquid, medium melting point F-T liquid, and tail gas, a mixture of volatile hydrocarbons, $CO_2$, CO, and $H_2$. The F-T liquid may be further upgraded via hydrocracking. Distillation and separation of different fractions of the F-T liquid may result in jet fuel, diesel, and gasoline. Water from the F-T reactor can be filtered to remove impurities and fed to a water input of the $CO_2$ and/or optional water electrolyzers.

A F-T system may be designed so that tail gas and/or volatile hydrocarbons (e.g. including methane) are recycled back to the $CO_2$ electrolyzer. The system may be configured to separate the tail gas into $CO_2$, which may be compressed and fed directly to the electrolyzer inlet and volatile hydrocarbons and unreacted CO and $H_2$. The system may be designed or configured such that these products are fed to a combustion reactor to generate heat, energy, and $CO_2$. The $CO_2$ is then fed to the $CO_2$ electrolyzer inlet. The $O_2$ from the electrolyzer may be used as the oxygen source for combustion, resulting in a pure $CO_2$ output stream. The combustion reactor may be run in "rich burn" mode utilizing an excess of fuel to oxygen to minimize the concentration of oxygen in the outlet stream. Water from the combustion reaction may be separated from the gas output and can be fed to the water input of the $CO_2$ electrolyzer or water electrolyzer.

Because a Fischer Tropsch reaction is exothermic, it produces heat that may be used for other purposes in a system. Examples of such other uses include separations (e.g., distillation of light hydrocarbons) and reactions. In conventional systems, such reactions are endothermic reactions for production of syngas such as reforming of fossil fuels, gasification of biomass, or production from carbon dioxide and hydrogen via reverse water gas shift. Hence, in conventional processing, all or a significant portion of the excess heat from a Fischer Tropsch reaction is typically directed to the syngas production. In the present case, however, which produces syngas at a low temperature (e.g. less than about 100° C.) by processes such as carbon dioxide electrolysis optionally along with low temperature water electrolysis, there is more excess heat from the Fischer Tropsch reaction available for other processes such as carbon dioxide capture, thereby reducing the overall external heat requirement of the system and improving carbon and energy efficiency of the carbon dioxide to fuel synthesis pathway.

In some embodiments, tail gas is fed to a reformer where methane or other gaseous hydrocarbon react with water to produce a mixture of hydrogen and carbon monoxide, a form of syngas. This may increase the yield of carbon from carbon dioxide in liquid hydrocarbon product. Depending on the composition of tail gas, the ratio of hydrogen to carbon monoxide may vary. In some embodiments, some amount of carbon dioxide and/or oxygen is present in reformer. In many cases, the reforming reaction is endothermic. In some embodiments, heat to drive the endothermic reaction is provided, at least in part, from excess heat generated during the Fischer Tropsch reaction. In some cases, some heat may be provided by combustion or direct electrical heat. For combustion-derived heat, oxygen (optionally from an electrolyzer) may be fed to the furnace to improve efficiency, and carbon dioxide emissions could be captured and fed to the electrolyzer.

Figure 6A:
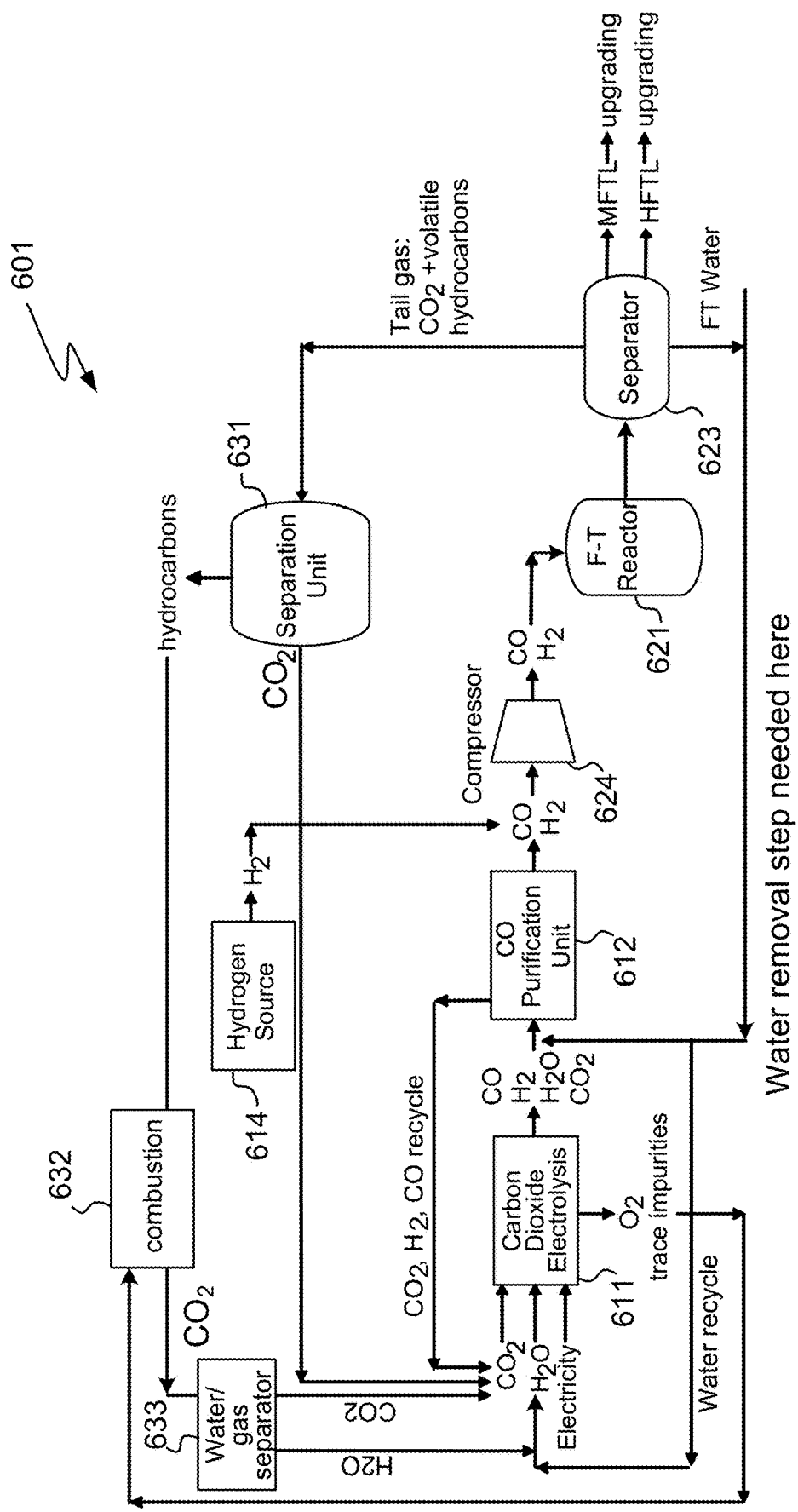
FIG. 6A depicts a Fischer Tropsch system configured to produce liquid hydrocarbons in which a source of carbon is a carbon oxide feedstock such as one containing carbon dioxide and/or carbon monoxide.

FIG. 6A depicts a system 601 configured to produce liquid hydrocarbons in which a primary or exclusive source of carbon is a carbon oxide feedstock such as one containing carbon dioxide and/or carbon monoxide. The system includes two primary reactors: an electrolytic carbon oxide reduction cell or electrolyzer 611 and a Fischer Tropsch reactor 621.

The electrolyzer 611 is connected to a source of electricity and has one or more inlets for receiving reactants such as carbon dioxide and water. The electrolyzer 611 has one or more outlets on the anode side for removing oxygen and possibly trace impurities and one or more outlets on the cathode side for removing reduction products including at least carbon monoxide. Other compounds leaving the cathode side may include hydrogen, water, and carbon dioxide.

The cathode side outlet is connected to a purification unit such as a carbon monoxide purification unit 612 which is designed to separate or purify carbon monoxide from other components. In the depicted embodiment, purification unit 612 has one outlet for providing carbon monoxide and another outlet for providing carbon dioxide, hydrogen, and possibly some carbon monoxide. In certain embodiments, the carbon monoxide purification unit 612 may be a sorbent-based unit such as presented in FIGS. 19, 20, and/or 23A-D and the associated description.

In the system 601, carbon dioxide, possibly along with some hydrogen and carbon monoxide, are recycled from outlet of the CO purification unit 612 back to the inlet streams for the cathode side of electrolyzer 611.

The Fischer Tropsch reactor 621 is configured to receive carbon monoxide and hydrogen in a pressurized feed stream and at a specified composition. In system 601, a compressor 624 compresses the carbon monoxide from the electrolyzer 611 along with hydrogen to an appropriate pressure for the Fischer-Tropsch reaction. A Fischer-Tropsch reaction may take place at a temperature of about 150-300° C. and at a pressure of about one to several tens of atmospheres. The reaction is exothermic, so little or no heat is provided to the reactor 621.

As mentioned, the input to a Fischer Tropsch reactor may have a CO:H ratio of about n:(2n+1), where n is the length in carbon atoms of the desired alkane product of the reaction. Thus, in various embodiments, the molar ratio of hydrogen to carbon monoxide provided to reactor 621 is about (2n+1) to n. To provide the desired inlet composition ratio of hydrogen to carbon monoxide for the Fischer Tropsch reaction, a hydrogen source 614 may be coupled to the outlet of CO purification unit 612 or to the inlet of compressor 624. Alternatively, or in addition, the electrolyzer 611 may be designed or operated in a manner that produces a relatively high ratio of hydrogen to carbon dioxide. Reactor designs and operating conditions for accomplishing this ratio are described elsewhere herein. In some cases, a gas having a relatively high ratio of hydrogen to carbon monoxide is produced from reforming reaction, such as reaction using FT tail gas as an input.

As depicted, system is 601 is configured to provide the output of Fischer Tropsch reactor 621 to a separator 623 configured to separate MFTL and HFTL Fischer Tropsch liquids from water and tail gas. As depicted the Fischer Tropsch water may be recycled back to the input of the CO purification unit 612 and/or the input of electrolyzer 611.

System 601 comprises a main recycle loop having a separation unit 631, a combustion chamber 632, and a water/gas separator 633. Separation unit 631 is configured to receive tail gas from separator 623 and remove carbon dioxide from volatile hydrocarbons. System 601 is configured to recycle carbon dioxide from unit 631 to a carbon dioxide feed stream to electrolyzer 611.

System 601 is configured to transport the volatile hydrocarbons from separation unit 631 to combustion unit 632, which is configured to burn the hydrocarbons using a source of oxygen from electrolyzer 611. System 601 is configured to transport the combustion products from combustion unit 632 to gas/water separator unit 633, which is configured to separate carbon dioxide and water combustion products. System 601 is configured to transport the water to an anode inlet of electrolyzer 611 and transport the carbon dioxide to a cathode inlet of electrolyzer 611.

In certain embodiments, a carbon dioxide electrolyzer located upstream from a Fischer Tropsch reactor is configured to operate in (a) a hydrogen rich product stream operating parameter regime as described herein, and/or (b) a high reduction product to $CO_2$ ratio operating parameter regime as described herein.

In certain embodiments, system 601 comprises one or more carbon dioxide capture units containing a sorbent for capturing carbon dioxide during a first phase and releasing carbon dioxide during a second phase. Separation unit 631 and/or gas/water separator unit 633 may be configured to include or work in conjunction with such carbon dioxide capture unit. Examples Some principles of operation are provided in the description of direct air capture units described herein. In some embodiments, a Fischer Tropsch system is configured to provide waste heat produced from an exothermic Fischer Tropsch reaction to a carbon dioxide capture unit.

Figure 6B:
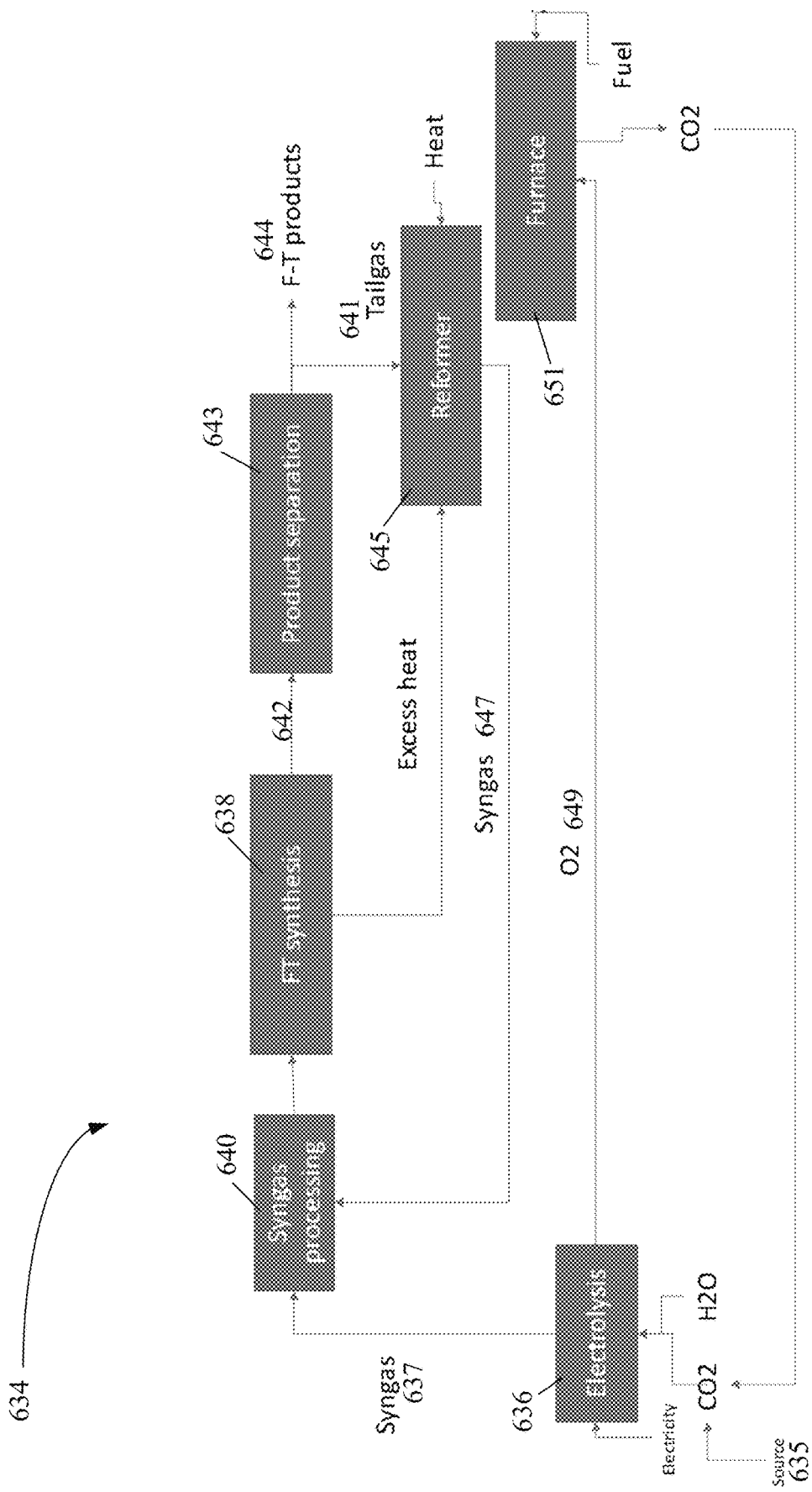
FIG. 6B depicts a Fischer Tropsch system configured to produce liquid hydrocarbons in which a source of carbon is a carbon oxide feedstock and tail gas from the system reformed to produce addition carbon monoxide and hydrogen.

FIG. 6B presents an example system 634 for producing a liquid hydrocarbon mixture from a carbon dioxide input stream 635 by using (a) a carbon dioxide electrolyzer 636 to produce carbon monoxide and hydrogen 637 and (b) a Fischer Tropsch reactor 638 configured to receive carbon monoxide and hydrogen and produce liquid hydrocarbons. Carbon monoxide and hydrogen, at least some produced by electrolyzer 636 is preprocessed in syngas processing element 640 which may purify or otherwise modify the syngas (e.g., removal of unreacted $CO_2$ from the electrolyzer as well as compression and/or heating or cooling of the syngas stream) prior to delivery prior to entering the Fischer Tropsch reactor. System 634 is further configured to provide processed gas from element 640 to Fischer Tropsch reactor 638, which can produce a mixture light hydrocarbons and other components 642, which the system makes available to a product separation subsystem 643, which may include a feature for separating tail gas 641 from one or more liquid hydrocarbon streams 644. In the depicted embodiment, system 634 includes a reformer 645 and is configured to provide tail gas 641 to the reformer. The tail gas contains methane that can react with water (optionally also included in tail gas 641) by a methane reforming reaction to produce a hydrogen-rich mixture 647 of carbon monoxide and hydrogen. System 634 is also configured to deliver mixture 647 to syngas processing element 640, which prepares the gas for introduction to the Fischer Tropsch reactor 638. The methane reforming reaction is endothermic. In some embodiments, excess heat from the reaction in Fischer Tropsch reactor 638 is provided reformer 645.

In the embodiment depicted in FIG. 6B, system 634 is optionally configured to provide oxygen 649 from electrolyzer 636 to a furnace 651, which is configured to burn fuel and produce additional heat for use with system 634 or elsewhere.

Direct Air Capture of $CO_2$

In certain embodiments, an electrolytic carbon dioxide reduction system uses carbon dioxide received directly from air. A system for such embodiments includes a direct air $CO_2$ capture subsystem and a carbon dioxide reduction electrolyzer subsystem. The system is configured so that $CO_2$ from the capture subsystem supplies $CO_2$, directly or indirectly, to the cathode side of the electrolyzer subsystem.

Because air is often the only significant feedstock, an air capture $CO_2$ electrolysis system may be deployed at any location where there is space for the system components. In some deployments, the system occupies a relatively unpopulated area. In some deployments, the system occupies a populated area. In some embodiments, the system is deployed, at least partially, on a vehicle or vessel. For example, an air capture unit may be provided on a vehicle or vessel while a carbon dioxide electrolyzer may be provided at a port or offshore platform. In some cases, the deployment location has a ready supply of energy, e.g., a location where solar and/or wind power is plentiful. In some cases, the deployment location is a desert. In some embodiments, the system is deployed in an extraterrestrial environment having a $CO_2$-containing atmosphere. In some embodiments, the system is deployed on large vessel such as a cargo ship or military vessel such as an aircraft carrier. In some embodiments, the energy source is provided by a solar or windfarm associated with an offshore platform or port, while carbon dioxide capture unit is provided on a ship or other watercraft. A carbon dioxide electrolyzer may be provided on the offshore platform or port.

The system may be designed so that air or other gas is provided under specified conditions to the $CO_2$ capture subsystem. In certain embodiments, fans, vacuum pumps, or simply wind are used to deliver air to a $CO_2$ capture subsystem.

In certain embodiments, the $CO_2$ capture subsystem comprises two stages: a first stage in which air is contacted with a sorbent that removes $CO_2$ from air (phase 1), and second stage in which heat, electricity, pressure, and/or humidity is applied to the sorbent to release $CO_2$ and/or water (phase 2).

In some implementations, the $CO_2$ capture subsystem employs a solid or liquid absorbent or adsorbent to capture the $CO_2$ in phase 1. In various implementations, phase 1 is performed at ambient conditions or near ambient conditions. In phase 2, a temperature, electrical, pressure, and/or moisture swing is applied, causing the absorbed or adsorbed $CO_2$, and optionally water, to be released.

In certain embodiments, the absorbent is heated to release the $CO_2$. As an example, the sorbent is heated from, e.g., ambient temperature (e.g., about 20-40° C.) to a temperature of at least about 75° C. to release $CO_2$ and optionally water. In some cases, the temperature swing is from ambient to about 50 to 1000° C. or from ambient to about 75-200° C. or from ambient to about 600 to 1000° C. As an example, the sorbent is heated for a duration of time sufficient remove a desired fraction of $CO_2$ and optionally water. The duration is a function of the amount of the sorbent to be treated, the fraction of $CO_2$ and/or water to be removed, and the heat transfer to the sorbent.

In certain embodiments, the absorbent is exposed to humidity to release the $CO_2$. As an example, the sorbent is initially exposed to dry air (e.g., air having at most about 50 mole % water, or at most about 30 mole % water, or at most about 5 mole % water) and subsequently exposed to humid vapor (e.g., air having at least about 75 mole % water, or at least about 90 mole % water, or about 100 mole % water.

In some embodiments, a $CO_2$ capture unit employs an electro-swing mechanism for capturing and later releasing $CO_2$. In certain cases, an electro-swing carbon dioxide unit comprises a faradaic adsorption system comprising an electrochemical cell that exploits the reductive addition of $CO_2$ to a redox species such as a quinone (e.g., 2,6-di-tert-butyl-1,4-benzoquinone), 4,4'-bipyridine, or a thiolate, for carbon dioxide capture. These redox agents may be provided in an organic electrolyte. In some cases, an electro-swing adsorption system provides carbon dioxide capture materials on a solid support such as a carbon nanotube support and/or a zeolite support. In some cases, an electro-swing $CO_2$ capture unit releases $CO_2$ by providing heat (e.g., by Joule heating) to an absorbent and/or electrode holding the captured $CO_2$.

Depending on the configuration of the $CO_2$ capture subsystem and its operating conditions, it can produce $CO_2$ from air at a high concentration of, e.g., about 90 mole % or greater. In some cases, the $CO_2$ capture subsystem is configured to produce $CO_2$ at a relatively lower concentration, which is still sufficient for $CO_2$ reduction electrolyzers to operate.

As examples, $CO_2$ capture sorbents and associated subsystem components are available from Climeworks AG of Zurich, Switzerland, Global Thermostat of New York, NY, Carbon Engineering Ltd. of Squamish, B.C., Canada, and Silicon Kingdom Holdings of Dublin, Ireland.

As indicated, captured and subsequently released $CO_2$ is feedstock that is delivered directly or indirectly to the cathode side of the $CO_2$ reduction electrolyzer. In certain embodiments, water captured from the air is also used in the feedstock of the $CO_2$ electrolyzer.

In certain embodiments, an air capture $CO_2$ electrolysis system is configured to operate in a manner that delivers $CO_2$ from direct air capture subsystem in a substantially pure stream of, e.g., about 99 mole % $CO_2$ or greater. In certain embodiments, the system is configured to operate using a lower concentration of $CO_2$ to the electrolyzer, e.g., about 98 mole % $CO_2$ or greater, or about 90 mole % $CO_2$ or greater, or even about 50 mole % $CO_2$ or greater. In some cases, quite low $CO_2$ concentrations are used as the feedstock. Such concentrations are still substantially greater than the atmospheric concentration of carbon dioxide, which is about 0.035 mole %. In certain embodiments, the system is configured to operate using a $CO_2$ concentration of about 5-15 mole %, which is mixed with air or another gas such as nitrogen.

Depending on the type of sorbent used in the process, water may also be captured along with $CO_2$ and released with it. In certain embodiments, the output of the $CO_2$ capture subsystem is humidified $CO_2$ having a water concentration about 0 to 20 mole % water.

In certain embodiments, the output of the $CO_2$ capture subsystem contains only $CO_2$ and other components in air such as nitrogen, oxygen, water, argon, or any combination. In all cases, the $CO_2$ is present at a concentration that is greater than its concentration in air. In certain embodiments, the output of the $CO_2$ capture subsystem contains no sulfur.

A direct air capture unit and $CO_2$ electrolyzer can be integrated in several ways depending on the type of air capture technology. Heat and mass transfer components may be integrated in the overall air capture $CO_2$ electrolysis system.

For example, in some designs, $CO_2$ reduction electrolyzer is configured to receive $CO_2$ from and provide heat and/or humidity to the direct air capture subsystem. The provided heat may release captured $CO_2$ during phase 2 of a direct air capture subsystem employing a temperature swing desorption mechanism. Humidified electrolyzer product gas can be used to release captured $CO_2$ during phase 2 of a direct air capture subsystem employing a moisture swing desorption mechanism.

In certain embodiments, the $CO_2$ electrolyzer is designed or configured to receive dilute $CO_2$ (e.g., no greater than about 50 mole % $CO_2$) as an input.

Direct air capture units can be designed with multiple sorbent vessels. To receive a continuous stream of $CO_2$ (and optionally water) from the air capture subsystem, at least two different vessels are operated to be at a different stage of sorption/desorption during operation of the overall air capture $CO_2$ electrolysis system. For instance, while one sorbent vessel is taking in air to capture $CO_2$, another may be heated to release $CO_2$; as each vessel continues through the sorption/desorption cycle, the sorption vessel that was taking in $CO_2$ will vent $CO_2$ and vice versa. The addition of many vessels at different points in the cycle can deliver a continuous stream of inputs to the $CO_2$ electrolyzer and accept a continuous stream of air containing $CO_2$ and moisture and/or heat and/or vacuum.

Direct air capture units can be sized to deliver the desired volume of $CO_2$ flow for a downstream process, such as a $CO_2$ electrolyzer. This may involve employing multiple sorbent-containing vessels. For example, a direct air capture subsystem may be configured to deliver 750 slpm $CO_2$. Such subsystem may couple to a 200-cell electrochemical stack composed of 1000 cm2 membrane-electrode assemblies operated at 300 mA/cm2 and 3 V/cell to produce 378 slpm CO and 42 slpm hydrogen given 90% $CO_2$ to CO current efficiency of the process. Unreacted $CO_2$ at the outlet of the electrolyzer may be recycled to the inlet to increase carbon efficiency. Operated continuously, the combined air capture and electrolyzer unit may produce approximately 675 kg/day CO. In general, in some designs, an air capture $CO_2$ electrolyzer system is configured to output at least about 100 kg/day CO and/or other $CO_2$ reduction product(s). in some designs, an air capture $CO_2$ electrolyzer system is configured to output at least about 500 kg/day CO and/or other $CO_2$ reduction product(s).

In certain embodiments, systems employing a carbon oxide electrolyzer and optionally a direct air capture of carbon dioxide unit also include a module configured to capture water from air or an atmosphere. In some embodiments, the module configured to capture water form air utilize solar energy from photovoltaics and/or thermal solar along with hygroscopic material. In certain embodiments, the module configured to capture water is an ambient dehumidifier such as a hydropanel (available from, e.g., Zero Mass Water, Inc. of Scottsdale, AZ).

Figure 7A:
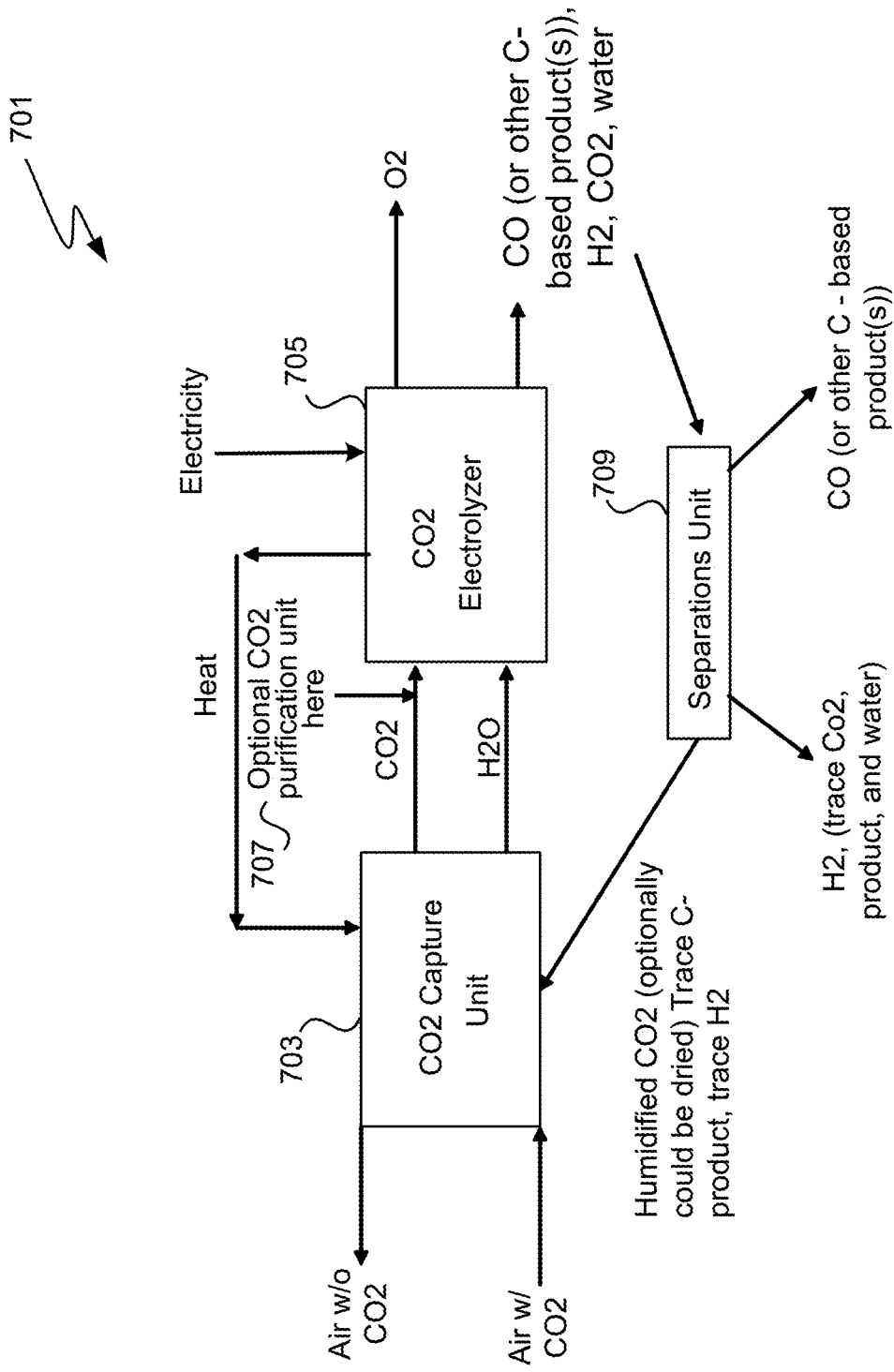
FIG. 7A illustrates an air capture $CO_2$ electrolyzer system comprising a direct air $CO_2$ capture subsystem and an $CO_2$ reduction electrolyzer subsystem.

FIG. 7A illustrates an air capture $CO_2$ electrolyzer system 701 comprising a direct air $CO_2$ capture subsystem 703 and an $CO_2$ reduction electrolyzer subsystem 705. As illustrated direct air $CO_2$ capture subsystem 703 is configured to receive, during sorption phase 1, air containing $CO_2$ under, e.g., atmospheric conditions (about 0.035 mole % $CO_2$) optionally with humidity, and release air with most $CO_2$ removed and optionally with much humidity removed.

Direct air $CO_2$ capture subsystem 703 is configured to release, during phase 2, $CO_2$ and optionally water. At least the $CO_2$, and optionally the water, are provided as inputs to the $CO_2$ electrolyzer 705. The $CO_2$ released from direct air capture subsystem 703 during phase 2 is provided to the cathode side of electrolyzer 705. As depicted, an optional $CO_2$ purification unit 707 is interposed between direct air $CO_2$ capture subsystem 703 and electrolyzer 705. The water optionally provided by direct air $CO_2$ capture subsystem 703 may be directed to the cathode side (as humidity in the $CO_2$ feedstock) or anode side (as reactant) of electrolyzer 705.

In the depicted embodiment, electrolyzer 705 is configured to receive electricity (to drive the $CO_2$ reduction reaction and the anode oxidation reaction). Also, electrolyzer 705 is configured to provide excess heat from the electrolysis reaction to direct air $CO_2$ capture subsystem 703 and drive phase 2 ($CO_2$ release from the sorbent).

$CO_2$ electrolyzer 705 is configured to output oxygen (the anode reaction product when water is the reactant) and one or more $CO_2$ reduction products, which may include CO and/or other carbon-based products as described elsewhere herein. The product stream(s) of $CO_2$ electrolyzer 705 may contain hydrogen, $CO_2$, and/or water. As depicted, system 701 is configured to provide the electrolyzer output to a separations unit 709, configured to separate CO and/or other carbon-based electrolysis products from hydrogen, $CO_2$, water, and/or other components. In the depicted embodiment, system 701 is configured to deliver humidified $CO_2$ from separations unit 709 to direct air $CO_2$ capture subsystem 703.

In certain embodiments, a carbon oxide is captured onboard a vessel or vehicle as fuel is combusted. The fuel may be used, for example, in an internal combustion engine to propel the vessel or vehicle. The fuel may be used for other purposes such as heating, electricity generation etc. The captured carbon oxide is provided to the cathode of a carbon oxide electrolyzer, which produces a reduced product that is directly used, stored, or converted to a different product (e.g., a chemical, polymer, or fuel) by downstream processing. In embodiments, where the electrolyzer and associated downstream components are configured to produce fuel, the resulting fuel may be employed in the original vessel or vehicle, or in one or more other vessels or vehicles. In some implementations, both the carbon oxide capture subsystem and the electrolyzer, as well as an optional downstream processing subsystem, are provided on board, on the vehicle or vessel. In some implementations, only the carbon oxide capture subsystem is provided to the vehicle or vessel. In some cases, the captured carbon oxide is temporarily stored on the vehicle or vessel. For example, carbon dioxide may be stored in one or more tanks, pressurized containers, tanker ships, and the like. In other cases, the captured carbon oxide is stored off the vehicle or vessel such as in underground reservoirs, tanker ships, offshore platforms, and the like. In some cases, stored carbon oxide is offloaded from the vessel or vehicle where it is provided to a carbon oxide electrolyzer. Examples of locations where stored carbon oxide may be offloaded and/or where the electrolyzer is located include chemical plants, ports, and offshore platforms, including some located proximate a source of green energy such as a wind energy or solar energy. Examples of vessels and vehicles include ships, trucks, buses, passenger vehicles, aircraft, and other craft.

Figure 7B:
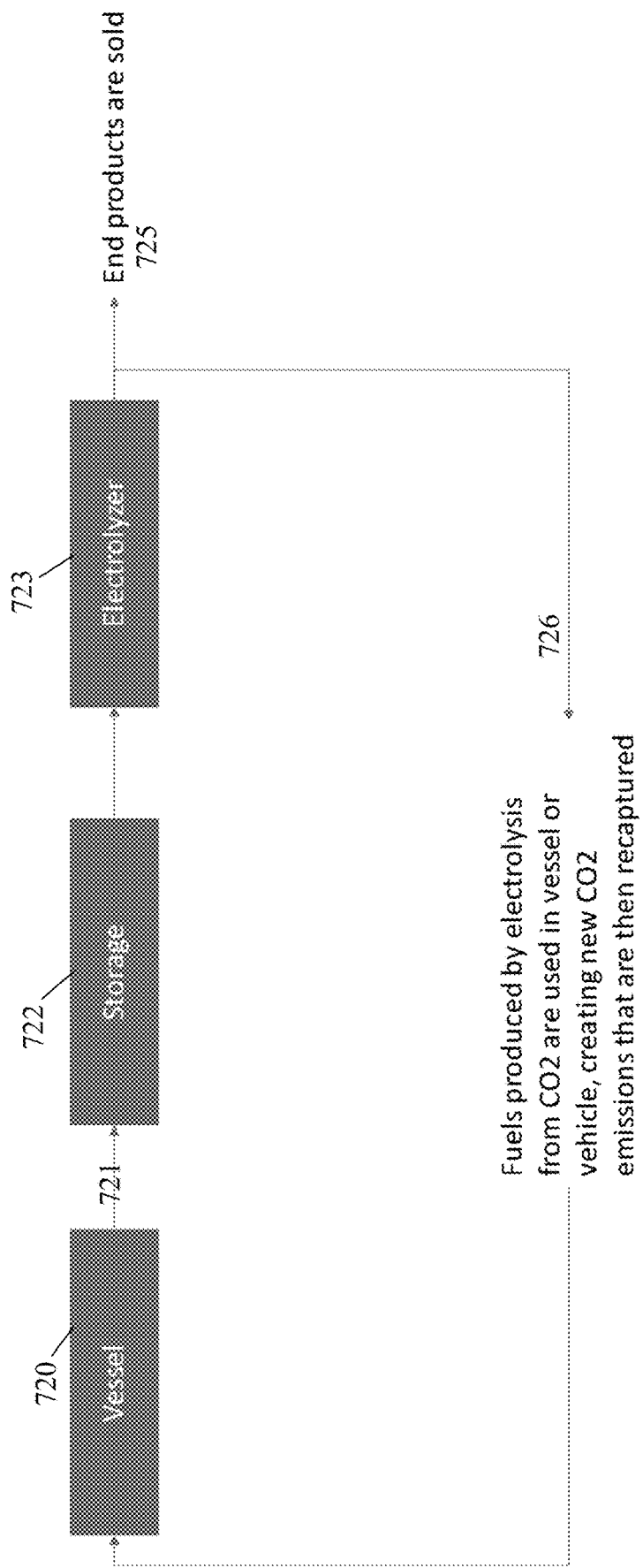
FIG. 7B illustrates an air capture $CO_2$ electrolyzer system comprising a direct air $CO_2$ capture subsystem on a vehicle or vessel.

FIG. 7B depicts an example in which carbon dioxide is captured from fuel combustion products onboard a vessel or vehicle. As illustrated, a vessel 720 produces a carbon oxide 721, which is stored in a storage medium 722 prior to being supplied to a carbon oxide electrolyzer 723. The electrolyzer and associated downstream chemical processing apparatus may produce a chemical product 725 and/or a fuel 726. In the case of a fuel, the fuel may be utilized by the vehicle or vessel.

In certain embodiments, depending on the needs of the system, a carbon dioxide electrolyzer located downstream from a direct air $CO_2$ capture subsystem is configured to operate in (a) a high reduction product to $CO_2$ ratio operating parameter regime as described herein, (b) a hydrogen rich product stream operating parameter regime as described herein, or (c) a high reduction product to hydrogen product stream operating parameter regime as described herein.

Polycarbonates

Certain aspects of this disclosure pertain to polycarbonate production systems that include (a) one or more carbon oxide electrolyzers configured to produce one or more carbon-containing products and (b) one or more polycarbonate synthesis reactors configured to produce polycarbonate polymer from carbon containing compounds derived, directly or indirectly, from the products of the one or more electrolyzers.

In certain embodiments, at least one electrolyzer in a polycarbonate production system includes a membrane electrode assembly (MEA), optionally including a polymer electrolyte membrane (PEM) such as a cation exchange polymer membrane. Unless otherwise specified or clear from context references here to a carbon oxide electrolyzer, including carbon dioxide reduction electrolyzers, encompass MEA-based electrolyzers, of which certain embodiments are described elsewhere herein.

In certain embodiments, a polycarbonate production system includes a carbon dioxide reduction electrolyzer configured to produce carbon monoxide and one or more other subsystems that convert carbon monoxide into one or more intermediates for subsequent reaction to produce a polycarbonate polymer.

In various embodiments, the direct output of the carbon oxide electrolyzer is converted to one or more intermediate compounds, such as a phenol, a ketone, and/or an organic carbonate, which is or are reacted to produce polycarbonate. The conversion to such intermediate compounds may take place by any of various processes. Examples include Fischer Tropsch reactions, gas fermentation reactions, and cracking reactions.

In gas fermentation subsystem embodiments, a carbon dioxide electrolyzer is used to produce carbon monoxide, and optionally hydrogen, that is subsequently used in a downstream gas fermentation process to produce one or more intermediate compounds for producing a polycarbonate polymer. Examples of these intermediate compounds include ketones (e.g., acetone), light hydrocarbons, and phenol.

In Fischer Tropsch subsystems, which may correspond with other embodiments described herein, carbon monoxide and hydrogen from a carbon dioxide electrolyzer are reacted to form naphtha or other light hydrocarbon product.

In certain embodiments, one or more subsystems for producing intermediates produce or are configured to produce a diol compound such as bisphenol A. Other diol polycarbonate intermediates may be produced in alternative embodiments, these include bisphenols other than bisphenol A. In certain embodiments, a subsystem comprises a reactor to produce phosgene from carbon monoxide and chlorine. The carbon monoxide may be produced from the carbon dioxide reduction electrolyzer.

In certain embodiments, a polycarbonate synthesis system employs at least two distinct electrolytic modules that may share some common electrical infrastructure such as a common electrical bus. In certain embodiments, the two distinct electrolytic modules are two distinct electrolytic carbon oxide reduction electrolyzers. As an example, a first carbon oxide reduction electrolyzer is a carbon dioxide electrolyzer designed, configured, or operated in a manner that produces carbon monoxide and optionally hydrogen gas, and a second carbon oxide reduction electrolyzer is a carbon dioxide electrolyzer designed, configured, or operated in a manner that produces at least one product compound having at least two carbon atoms such as ethylene or a ketone such as acetone. In some implementations, the first electrolyzer comprises a cathode with a noble metal catalyst such as gold and the second electrolyzer comprises a cathode with a transition metal catalyst such as copper. As disclosed elsewhere herein, an MEA-based carbon oxide electrolyzer may have various designs or configurations that allow production of distinct products (e.g., CO versus $C_2$ compounds).

In certain embodiments, a first electrolytic module is a carbon oxide reduction module and a second electrolytic module is a chlorine generation module such as a chlor-alkali cell. These two modules may share common electrical infrastructure. In some embodiments, the chlorine generating module is a conventional chlor-alkali module configured to receive a chloride salt and water as inputs and produce chlorine gas and hydrogen gas as outputs. In some embodiments, the chlorine generating module comprises an oxygen reduction chlor-alkali cell configured to receive a chloride salt in the electrolyte and receive oxygen gas at the cathode (an oxygen depolarized cathode) and produce chlorine gas at the anode and water at the cathode. Such oxygen reduction chlor-alkali cells run for efficiently and consume less electrical energy than conventional chlor-alkali cells. However, they require a source of oxygen. In some implementations, the polycarbonate production system is configured so that oxygen gas produced as the anode of a carbon oxide reduction cell is provided to the cathode of a chlorine generating cell configured to reduce oxygen. In some implementations, the polycarbonate production system is configured to provide water produced by an oxygen reduction chlor-alkali cell to the carbon oxide rejection cell, either as anode water or humidification for a carbon oxide feed stream.

Figure 8A:
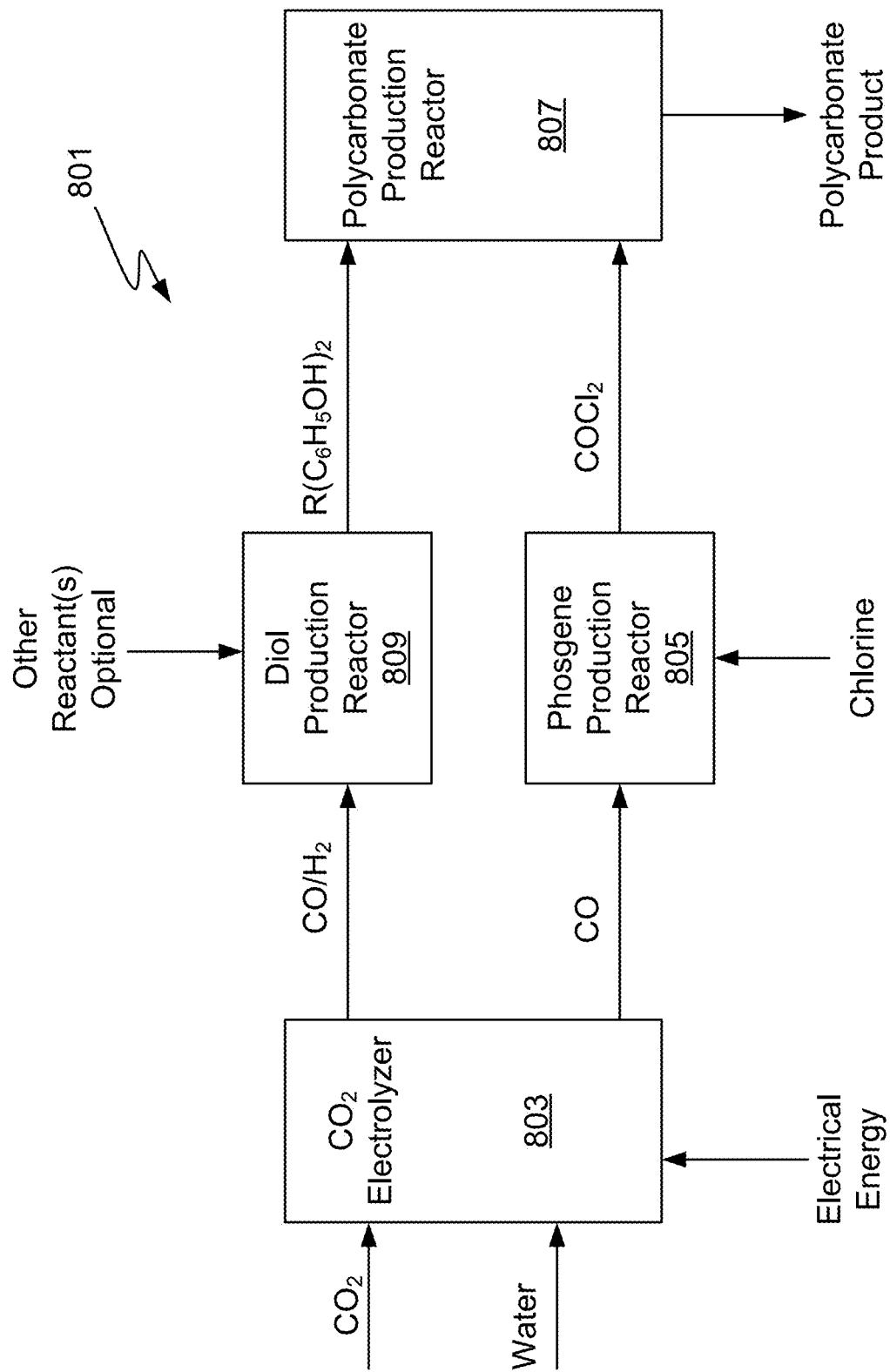
FIG. 8A presents a general representation of a system for producing a polycarbonate polymer using a carbon dioxide reduction electrolyzer.

In certain embodiments as depicted in FIG. 8A, a system 801 includes an electrolytic cell such as chlor-alkali cell for producing chlorine. In some implementations, system 801 is configured to feed the oxygen from the electrolyzer 803 to a cathode of a chlor-alkali cell comprising an oxygen depolarized cathode. In some implementations, system 801 is configured to feed the oxygen from the water electrolyzer to an oxygen depolarized cathode of a chlor-alkali cell. System 801 may be configured to provide hydrogen from the water electrolyzer to a Fischer Tropsch reactor, a gas fermentation reactor, or other reactor used in production of a polyol precursor. Oxygen from electrolyzer 803 or other electrolyzer may be used in lieu of oxygen from other sources such as air separation.

In certain embodiments, the alkaline biproduct of a chlor-alkali cell (e.g., sodium hydroxide) is provided as a feedstock to a complementary chemical production system such as formate production system, including as an example, a formate production system employing a carbon oxide electrolyzer.

In certain embodiments, the polycarbonate employs a bisphenol A linkage in the polymer backbone, and, in fact, most system and method examples presented herein describe bisphenol A as the polycarbonate precursor, along with phosgene. However, for some applications, other diols are used in place of bisphenol A. Examples include other linear and ring unsaturated diols, as well as diphenols and other bisphenols. It should be understood that, in the examples described herein, when reference is made to bisphenol A, it is intended that other biphenols may be employed as appropriate for the desired polycarbonate end product. It should also be understood that appropriate system and method modifications may be employed to replace phenol production modules with modules configured to produce phenol derivatives or analogs, and/or replace acetone production modules with modules configured to produce other ketones.

A polycarbonate synthesis reaction may involve treatment of bisphenol A with sodium hydroxide, which deprotonates the hydroxyl groups of the bisphenol A.

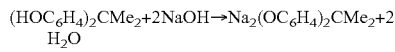

$$(HOC_6H_4)_2CMe_2 + 2NaOH \rightarrow Na_2(OC_6H_4)_2CMe_2 + 2H_2O$$

The diphenoxide ($Na_2(OC_6H_4)_2CMe_2$) reacts with phosgene to give a chloroformate, which subsequently is attacked by another phenoxide. The net reaction from the diphenoxide is:

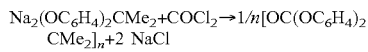

$$Na_2(OC_6H_4)_2CMe_2 + COCl_2 \rightarrow 1/n[OC(OC_6H_4)_2CMe_2]_n + 2\ NaCl$$

In various embodiments, at least one carbon dioxide reduction electrolyzer used in a polycarbonate production system is designed or configured to operate in a manner that produces a significant fraction of hydrogen in addition to carbon monoxide. In certain embodiments, a carbon dioxide electrolyzer located upstream of a diol production reactor is configured to operate in (a) a hydrogen rich product stream operating parameter regime as described herein, and/or (b) a high reduction product to $CO_2$ ratio operating parameter regime as described herein.

Electrolyzers for producing carbon monoxide often employ a cathode catalyst comprising a noble metal such as gold. Such catalysts favor production of carbon monoxide over hydrogen-containing compounds such as methane, ethylene, formic acid, etc. Electrolyzers configured in a way that provides a hydrogen rich product may employ designs that (a) starve the cathode of carbon dioxide reactant, and/or (b) permit a relatively high flux of hydrogen ions to be transported from the anode, where they are generated, to the cathode. Electrolyzers that can operate with relatively little carbon dioxide may input may have flow fields or gas diffusion components that restrict carbon dioxide from reaching active sites on the electrolyzer cathode. Electrolyzers that can operate with a relatively high flux of hydrogen ions to the cathode may have MEAs with cation conducting polymers and/or mixed ion conducting polymers at the cathode and/or a cathode buffer layer, if one is used. In some cases, in which an MEA includes an anion conductive cathode buffer layer, the layer is designed to be relatively thin and/or have a relatively high hydrogen ion transference number.

FIG. 8A depicts a general representation of a system for producing a polycarbonate polymer using a carbon dioxide reduction electrolyzer. As depicted, a polycarbonate production system 801 includes a carbon dioxide reduction electrolyzer 803 configured to receive carbon dioxide and water as reactants and electricity to drive the anodic and cathodic reactions that produce oxygen and one or more carbon dioxide reduction products. In the depicted embodiment, the carbon dioxide reduction reactor 803 is configured to produce at least carbon monoxide as one reduction product. System 801 is specifically configured to deliver the carbon monoxide from electrolyzer 803 to a phosgene production reactor 805. Reactor 805 additionally includes an input for receiving chlorine gas. The chlorine gas and carbon monoxide react in phosgene reactor 805 to produce phosgene as an output. System 801 is further configured to deliver phosgene from phosgene reactor 805 to a polycarbonate synthesis reactor. 807.

In certain embodiments, a carbon dioxide electrolyzer located upstream from a phosgene production reactor is configured to operate in (a) a high reduction product to hydrogen product stream operating parameter regime as described herein, and/or (b) a high reduction product to $CO_2$ ratio operating parameter regime as described herein.

As depicted, polycarbonate synthesis reactor 807 also has an input for receiving a diol input material. The diol input may be produced by a variety of methods including via a reactor not shown in this figure. Alternatively, as depicted here, system 801 includes a diol synthesis reactor or subsystem 809 that is configured to receive carbon dioxide reduction products from electrolyzer 803. In various embodiments, these electrolyzer reaction products include carbon monoxide and hydrogen. In some cases, these electrolyzer products include a $C_2$ or higher product such as acetone or formaldehyde. In certain embodiments, reactor or subsystem 809 is configured to receive and react inputs from sources other than electrolyzer 803. These other inputs may include, for example, phenolic compounds such as bisphenols. System 801 is also configured to transport the diol produced by diol synthesis reactor or subsystem 809 to polycarbonate synthesis reactor 807. Within polycarbonate synthesis reactor 807, the diol and phosgene react to produce polycarbonate polymer. In the depicted embodiment, the polycarbonate final product is available via an outlet from the polycarbonate synthesis reactor. 807.

It should be understood that a polycarbonate production system such as depicted in FIG. 8A may include additional or alternative types of modules not shown in the figure. These include, for example, one or more purification units, such as a carbon monoxide purification modules, heaters, compressors, condensers, and other chemical reactors. Examples of gas purification units for use in the system of 8A or any other polycarbonate production system described herein are presented in FIGS. 19 and 20 and the associated description.

Among the types of reactors that can be used to generate phenolic, ketone, and organic carbonate intermediates include gas fermentation reactors, Fischer Tropsch reactors, and oxidative carbonylation reactors. In some cases, particularly for reaction paths used to form by phenol compounds, the system 801 may include multiple intermediate modules or reactors. In one example, system 801 includes one module for producing simple liquid hydrocarbons, another module for cracking those hydrocarbons to produce aromatics and other unsaturated carbon-containing compounds, and/or one or more additional intermediate reactors for producing for ketones, organic carbonates, and/or phenol derivatives. In various embodiments, these intermediate modules for producing ketones and/or phenols employ a combination of carbon monoxide and excess hydrogen produced by the carbon dioxide reduction electrolyzer 803.

Figure 8B:
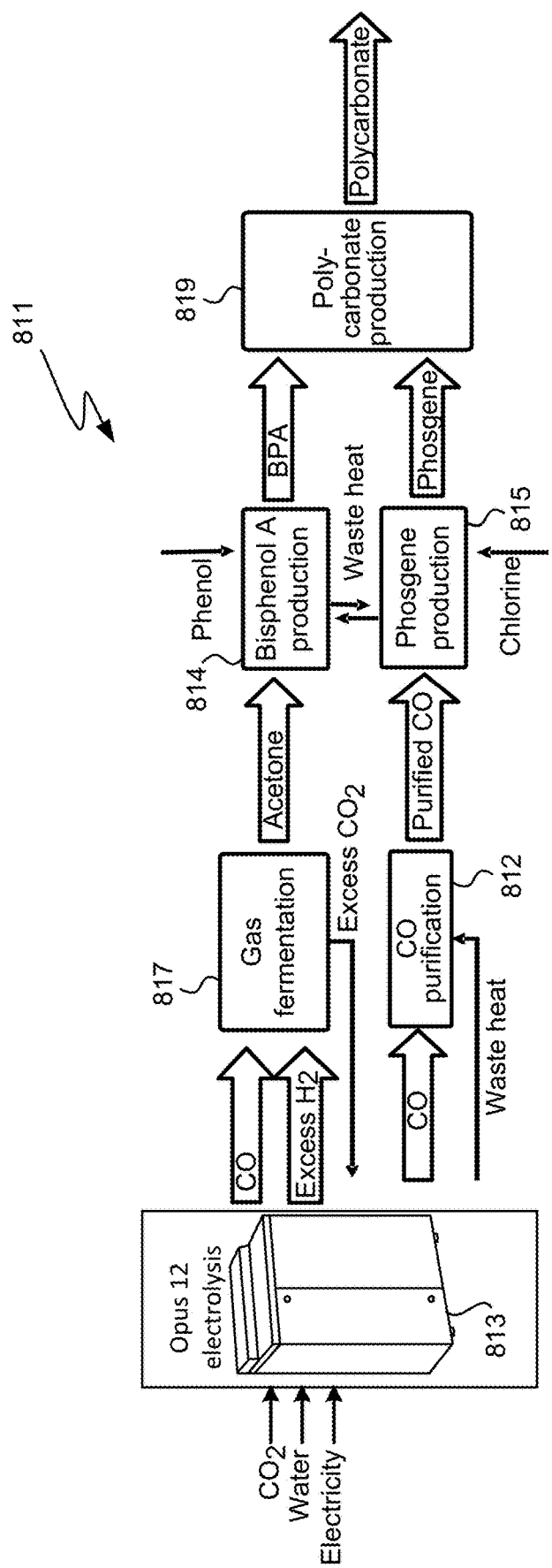
FIG. 8B presents an example of a polycarbonate synthesis system having a carbon dioxide reduction electrolyzer configured to receive carbon dioxide and water as reactant inputs and electricity to drive the electrolysis reactions at the anode and cathode.

FIG. 8B presents an example of a polycarbonate synthesis system 811 having a carbon dioxide reduction electrolyzer 813 configured to receive carbon dioxide and water as reactant inputs and electricity to drive the electrolysis reactions at the anode and cathode. Carbon dioxide electrolyzer 813 is configured to output carbon monoxide. As depicted, system 811 is configured to deliver carbon monoxide output by electrolyzer 813 to a carbon monoxide purification module 812.

In certain embodiments, a carbon monoxide purification unit such as 812 is configured as described above such as in any one of the embodiments described in connection with Fischer Tropsch processes. See for example, the CO purification units in FIGS. 19 and 20.

In certain embodiments, system 811 is configured to provide waste heat from electrolyzer 813 to carbon monoxide purification unit 812 in order to facilitate purification of the carbon monoxide.

System 811 is further configured to deliver purified carbon monoxide from carbon monoxide purification unit 812 to a phosgene production reactor 815. As depicted, phosgene production reactor 815 is configured to receive, in addition to the purified carbon monoxide, chlorine gas. Phosgene production reactor 815 is configured to generate phosgene, which, during operation, is provided via an appropriate transport component to a polycarbonate production reactor 819.

In the depicted embodiment, system 811 includes a gas fermentation subsystem 817 configured to receive carbon monoxide and hydrogen gas, as reactants, from the carbon dioxide electrolyzer 813. In the depicted embodiment, gas fermentation subsystem 817 is configured to react carbon monoxide and hydrogen, and to produce acetone.

Gas fermentation subsystem 817 is also configured to produce carbon dioxide as an output. In certain configurations, system 811 is configured to provide excess carbon dioxide directly from the output of subsystem 817 to electrolyzer 813. In some implementations, system 811 is configured to provide carbon dioxide directly to the feedstock for electrolyzer 813.

As depicted, system 811 is configured to transport acetone from gas fermentation subsystem 817 to a bisphenol A production unit 814. Bisphenol A production unit 814 is configured to react acetone and phenol to produce bisphenol A. The acetone comes, as mentioned, from gas fermentation subsystem 817. The phenol may be provided from any of a variety of sources, including some that use carbon monoxide or other output from electrolyzer 813.

In the depicted embodiment, bisphenol A from reactor 814 is provided, during operation, via an appropriate conveyance component to a polycarbonate production reactor 819. Additionally, phosgene from reactor 815 is provided, during operation, via a conveyance component to reactor 819, which is configured to react phosgene and bisphenol A to produce a polycarbonate as a final output.

In the depicted embodiment, system 811 is configured with heat exchangers and/or other heat transfer components to provide heat, as needed, among the various intermediate reactors and subsystems. For example, bisphenol a synthesis reactor 814 and phosgene reactor 815 may be configured to transfer heat therebetween as necessary during various reaction phases.

Figure 8C:
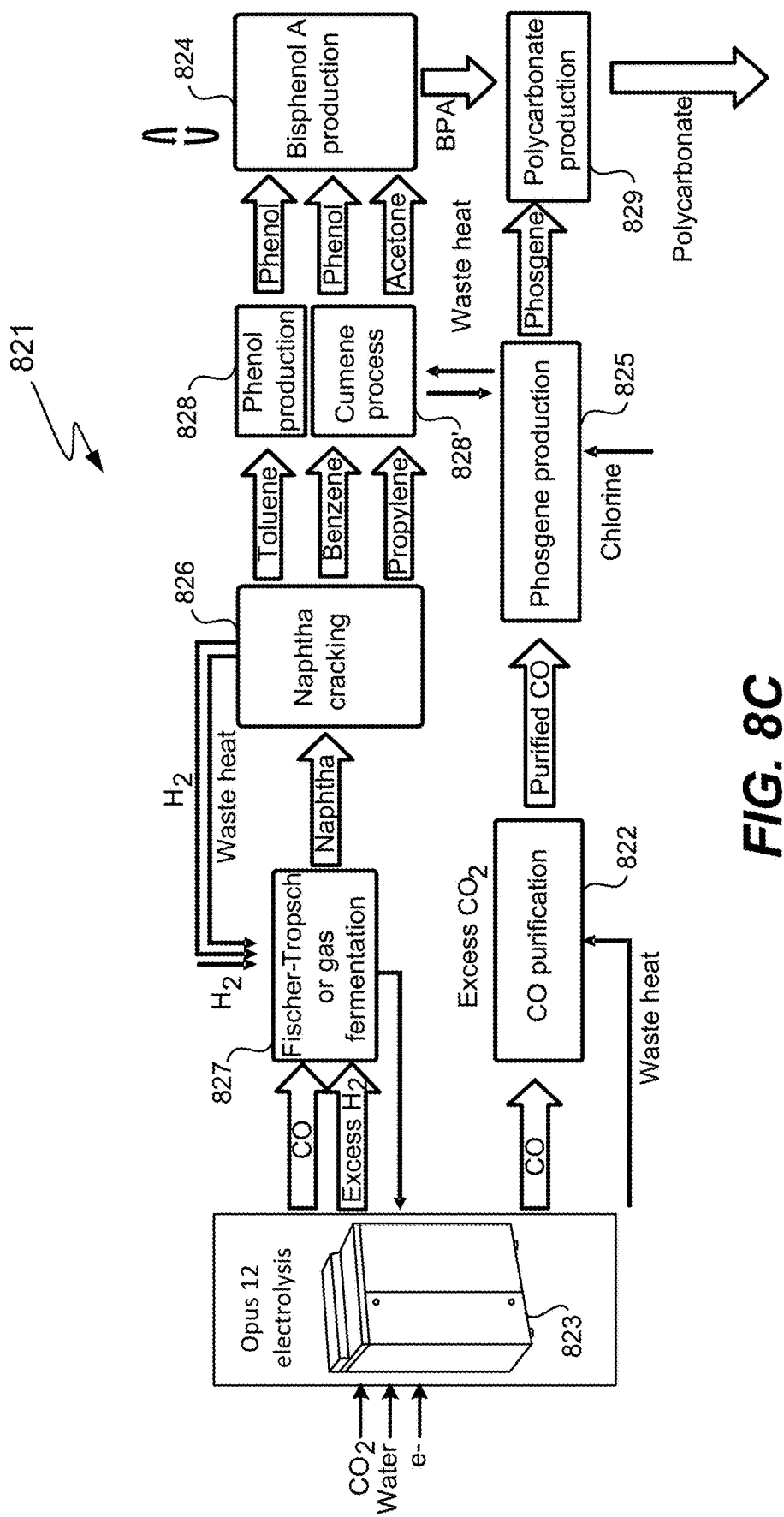
FIG. 8C depicts a polycarbonate production system.

FIG. 8C depicts a polycarbonate production system 821. The depicted system includes a carbon dioxide reduction electrolyzer 823 configured to provide carbon monoxide output to a carbon monoxide purification unit 822, which is, in turn, configured to provide purified carbon monoxide to a phosgene production reactor 825. Phosgene production reactor 825 is configured to produce and output phosgene to a polycarbonate synthesis reactor 829, which produces final polycarbonate polymer. The components of this phosgene production pathway may be generally constructed and operated as described in conjunction with other polycarbonate production embodiments described herein.

In the embodiment depicted in FIG. 8C, bisphenol A is provided via a pathway that receives carbon monoxide and hydrogen gas from electrolyzer 823 and converts these input gases to phenol and acetone via a naphtha production reaction.

In the depicted embodiment, system 821 is configured to transport some fraction of the carbon monoxide produced by electrolyzer 823 along with hydrogen gas produced by electrolyzer 823 to a reactor 827 configured to produce naphtha. Reactor 827 is, in certain embodiments, a Fischer Tropsch reactor. In other embodiments, reactor. 827 is a gas fermentation reactor configured to produce naphtha from carbon monoxide and hydrogen input. Regardless of which choice reactor is used, the output is naphtha. Naphtha is a mixture of various hydrocarbons that may contain straight, branched, and/or cyclic aliphatic hydrocarbons having, e.g., about five to ten carbon atoms. System 821 is further configured to provide excess carbon dioxide optionally produced by reactor 827 to carbon dioxide electrolyzer 823 to combine with input carbon dioxide feedstock to the electrolyzer cathode.

System 821 is configured to deliver naphtha from reactor 827 to a naphtha cracking unit 826 configured to operate in a mode that converts reactant naphtha to various unsaturated hydrocarbons such as toluene, benzene, and propylene. In the depicted embodiment, waste products of the naphtha cracking reaction performed at reactor 826 include hydrogen and waste heat. In the depicted embodiment, system 821 is configured to provide waste heat and hydrogen gas from naphtha cracking unit 826 to Fischer Tropsch or gas fermentation reactor 827.

System 821 is configured to provide the unsaturated hydrocarbon outputs of cracking unit 826 to one or more reactors for converting these unsaturated hydrocarbons to phenol and/or acetone. In the depicted embodiment, system 821 includes a phenol synthesis reactor 828 configured to receive toluene from naphtha cracking reactor 826 and convert the toluene to phenol.

Various processes may be employed to convert toluene to phenol. One of these involves oxidation of toluene with atmospheric oxygen to benzoic acid, which is carried out in the liquid phase at temperatures of about 100-150° C. and an absolute pressure of about 3 bar. A cobalt naphthenate is used as a soluble catalyst at concentrations of 0.1-0.3%. In a second step, the oxidation of benzoic acid with atmospheric oxygen and steam uses molten benzoic acid as the reactant and solvent at a temperature of about 230-240° C. and atmospheric pressure. Copper(II) benzoate is used as a soluble catalyst. Magnesium salts may be added to act as a promoter. In this reaction, copper(II)benzoate decomposes to copper(I) benzoate and benzoylsalicylic acid (2-(benzoyloxy)benzoic acid). The copper(I) benzoate is regenerated to copper(II)benzoate with atmospheric oxygen. The benzoylsalicylic acid is hydrolyzed with steam to benzoic acid and salicylic acid (2-hydroxybenzoic acid). The salicylic acid is decarboxylated rapidly to phenol and carbon dioxide.

Additionally, system 821 is configured with components to transport benzene and propylene from naphtha cracking reactor 826 to a cumene process reactor or subsystem 828' that is configured to react the benzene and propylene to produce phenol and acetone. In some implementations, subsystem 828' is configured to react benzene and propylene, via an alkylation reaction, in the presence of phosphoric acid and catalyst to produce cumene, which may then react in the presence of oxygen and sulfuric acid to produce phenol and acetone (Hock rearrangement).

System 821 further comprises a bisphenol A production reactor 824 configured to receive phenol and acetone from the phenol production reactor 828 and the cumene process reactor/subsystem 828'. Bisphenol A synthesis reactor 824 is configured to produce bisphenol A from the phenol and acetone reactants.

System 821 further comprises the polycarbonate synthesis reactor 829, as previously mentioned. Reactor 829 is configured to receive bisphenol A from reactor 824 and, as mentioned, phosgene from reactor 825 to produce polycarbonate output.

As illustrated, system 821 is configured to transfer heat as needed between various components such as between the cumene process reactor/subsystem 828' and phosgene reactor. 825.

Figure 8D:
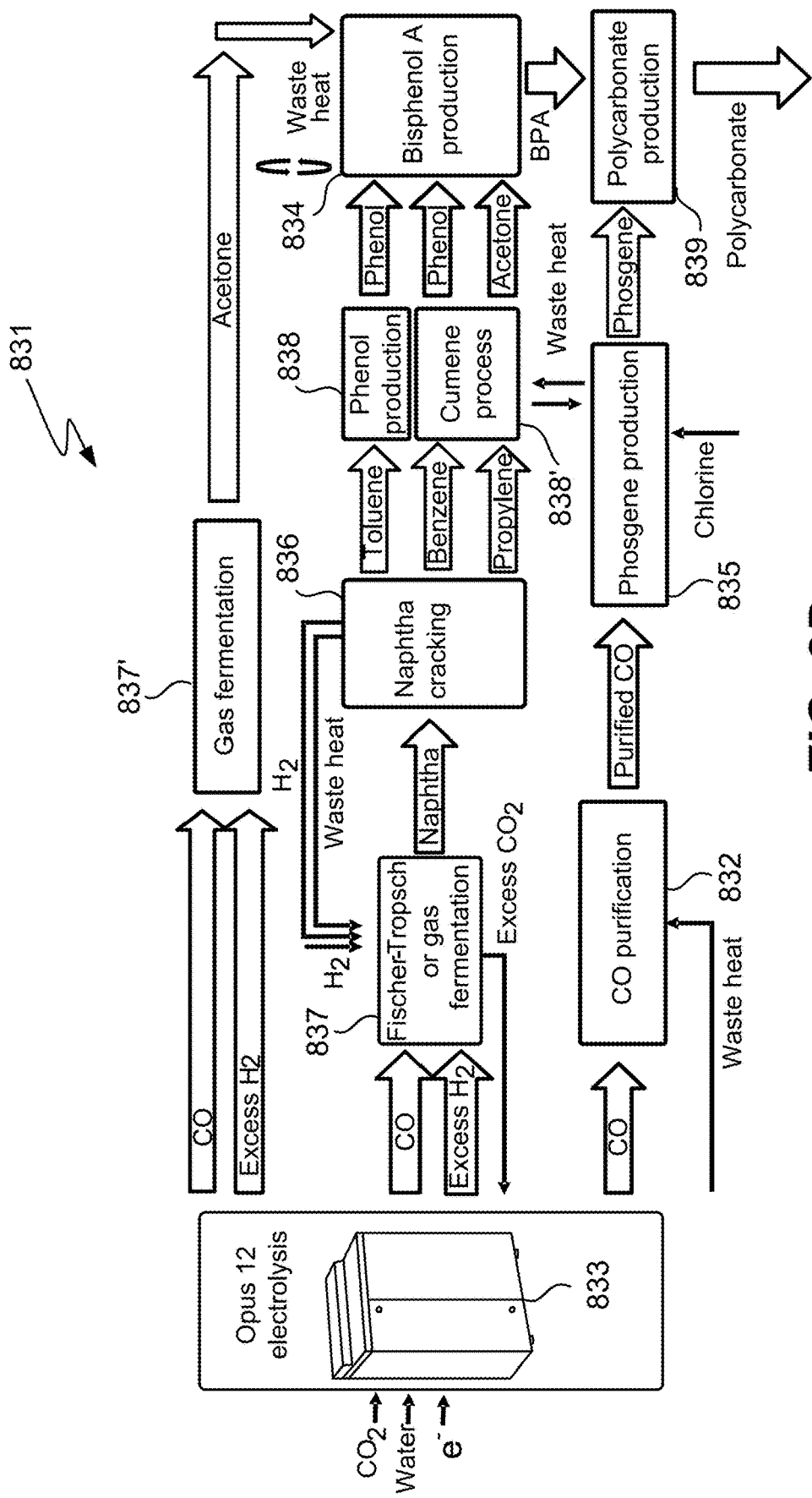
FIG. 8D illustrates a polycarbonate synthesis system, which has a parallel path from a carbon dioxide electrolyzer to a bisphenol A synthesis reactor to deliver acetone input to a reactor.

FIG. 8D illustrates a polycarbonate synthesis system 831, which in some implementations is similar to system 821 of FIG. 8C but with a parallel path from electrolyzer 823 to bisphenol A synthesis reactor 824 to deliver acetone input to reactor 824.

In the embodiment of FIG. 8D, system 831 includes a gas fermentation reactor 837' configured to receive carbon monoxide and hydrogen gas from electrolyzer 833 and, via a biological fermentation reaction, produce acetone. In the depicted embodiment, system 831 is configured to convey acetone from fermentation reactor 837' to a bisphenol A synthesis reactor 834.

System 831 additionally includes a phosgene path configured to receive carbon monoxide produced by a carbon dioxide electrolyzer 833 and output phosgene to a polycarbonate production reactor 839. The phosgene path includes, as depicted, a carbon monoxide purification unit 832 configured to receive the carbon monoxide from electrolyzer 832 and a phosgene production reactor 835 configured to receive purified carbon monoxide from unit 832.

System 831 additionally includes a phenol production path configured to receive carbon monoxide and hydrogen gas produced by carbon dioxide electrolyzer 833 and output phenol to bisphenol A production reactor 834.

In the phenol path, system 831 comprises a reactor gas fermentation or Fischer Tropsch reactor 837 configured to produce naphtha from electrolyzer produced carbon monoxide and hydrogen. System 831 is further configured to provide excess carbon dioxide optionally produced by reactor 837 to carbon dioxide electrolyzer 833.

System 831 further comprises a naphtha cracking unit 836 configured to convert naphtha from reactor 837 to various unsaturated hydrocarbons such as toluene, benzene, and propylene. System 831 is configured to deliver hydrogen and heat produced by the naphtha cracking reaction in reactor 836 to Fischer Tropsch or gas fermentation reactor 837.

System 831 is configured to provide the unsaturated hydrocarbon outputs of cracking unit 836 to one or more reactors configured to convert these unsaturated hydrocarbons to phenol and/or acetone. In the depicted embodiment, system 831 includes a phenol synthesis reactor 838 configured to receive toluene from naphtha cracking reactor 836 and convert the toluene to phenol. Additionally, system 831 comprises a cumene process reactor or subsystem 838' configured to react the benzene a propylene from reactor 836 and produce phenol and acetone.

Phenol and acetone from reactor 838', acetone from gas fermentation reactor 837', phenol from phenol synthesis reactor 838 are provided to bisphenol A synthesis reactor 834. System 831 is configured to provide biphenol A from reactor 834 and phosgene from reactor 835 to polycarbonate production reactor 839, which is configured to act on these inputs and produce polycarbonate polymer.

Figure 8E:
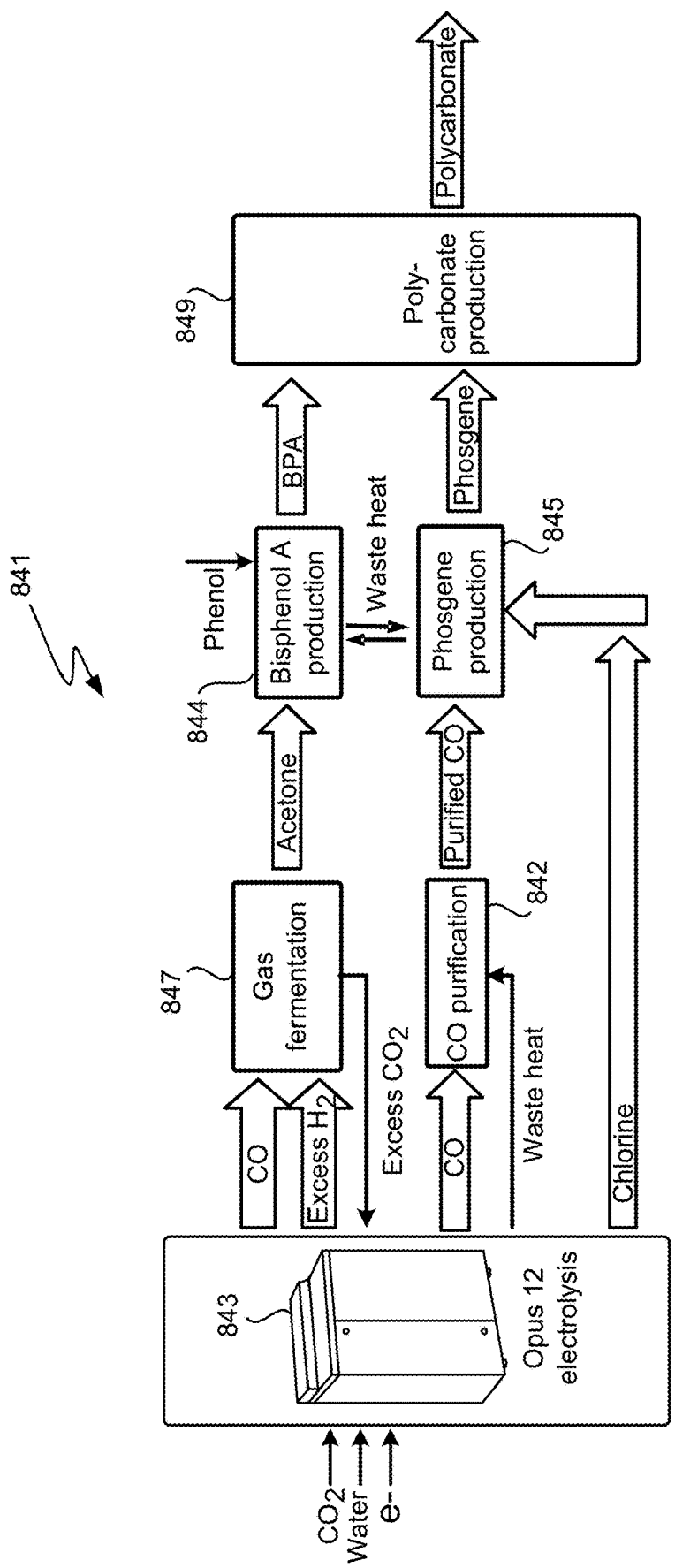
FIG. 8E depicts a polycarbonate production system including a polycarbonate synthesis reactor configured to receive phosgene from electrolyzer-produced carbon monoxide and to receive bisphenol A from a reactor that receives fermentation-produced acetone.

FIG. 8E depicts a polycarbonate production system 841 including a polycarbonate synthesis reactor 849 configured to receive phosgene from electrolyzer-produced carbon monoxide and to receive bisphenol A from a reactor 844 that receives fermentation-produced acetone. Additionally, system 841 includes a chlorine production pathway for providing electrolytically produced chlorine to a phosgene production reactor 845.

In the depicted embodiment, system 841 includes a carbon dioxide reduction electrolyzer, 843 that may operate and be configured in a manner similar to that of the electrolyzers described in other polycarbonate production systems herein. As depicted, system 841 is configured to transport carbon monoxide produced by electrolyzer 843 directly to a carbon monoxide purification unit 842. System 841 is also configured to transport purified carbon monoxide from carbon monoxide purification unit 842 to phosgene production reactor 845. The phosgene production pathway may be configured to operate in a manner similar to that of and employ components similar to that of other polycarbonate production systems described herein. However, in the depicted embodiment, the chlorine used in phosgene production reactor 845 is produced electrolytically in conjunction with operation of the carbon dioxide reduction electrolyzer 842. In certain embodiments, the chlorine is produced by a chlor-alkali cell employing a chloride salt (e.g., NaCl) as a source of chloride ions for electrolytic oxidation to produce chlorine gas.

In the depicted embodiment, system 841 is further configured to provide carbon monoxide and hydrogen gas from electrolyzer 843 to a gas fermentation reactor 847 configured to convert the carbon monoxide, hydrogen gas, via a biological fermentation reaction, to acetone. System 841 is further configured to convey acetone from fermentation reactor 847 to bisphenol A production reactor 844. As illustrated, bisphenol A production reactor 844 is configured to receive phenol in addition to the acetone as inputs, and react them to produce bisphenol A. As illustrated, system 841 is configured to deliver bisphenol A from reactor 844 to polycarbonate production reactor 849. Additionally, system 841 is configured to transfer heat, as appropriate during the course of the polycarbonate production process, between bisphenol A production reactor 844 and phosgene production reactor 845.

Figure 8F:
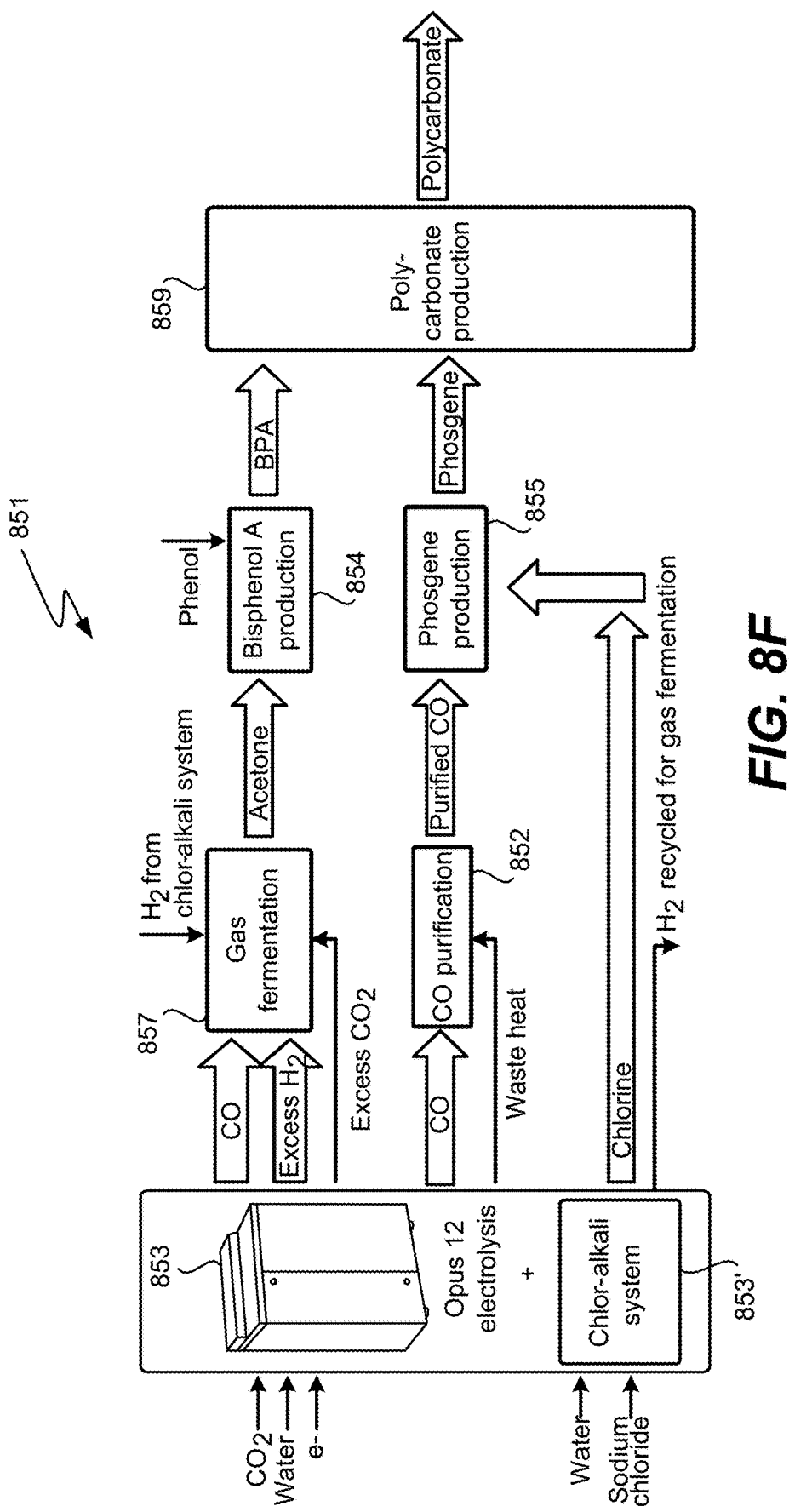
FIG. 8F depicts a polycarbonate production system that includes an electrolysis subsystem comprising a carbon dioxide reduction electrolyzer and a chlor-alkali system.

FIG. 8F depicts a polycarbonate production system 851 that includes an electrolysis subsystem comprising a carbon dioxide reduction electrolyzer 853 and a chlor-alkali system 853'. Chlor-alkali system 853' is configured to receive as inputs water and sodium chloride and produce as outputs chlorine gas and hydrogen gas. System 851 is configured to deliver chlorine produced by chlor-alkali system 53' to a phosgene production reactor 855. System 851 is also configured to deliver hydrogen gas optionally produced by chlor-alkali system 853' to a gas fermentation reactor 857. In certain embodiments, system 851 is configured to feed the oxygen from the electrolyzer 853 to a cathode of chlor-alkali system 853', which comprises an oxygen depolarized cathode. In certain embodiments, system 851 includes a water electrolyzer configured to produce oxygen which may be delivered to an oxygen depolarized cathode of a chlor-alkali cell. System 851 may also be configured to provide hydrogen from the water electrolyzer to a gas fermentation reactor or other reactor used to produce diols.

System 851 is further configured to deliver carbon monoxide and hydrogen gas from carbon dioxide reduction electrolyzer 853 to gas fermentation reactor 857. Thus, gas fermentation reactor 857 is configured to receive hydrogen from both carbon dioxide reduction electrolyzer 853 and from chlor-alkali system 853'. Gas fermentation reactor 857 is configured to conduct biological fermentation on the carbon monoxide and hydrogen gas inputs and produce acetone as an output. Gas fermentation reactor 857 is also configured to produce carbon dioxide as a byproduct. System 851, in the depicted embodiment, is configured to deliver excess carbon dioxide produced by reactor 857 to electrolyzer 853.

System 851 is further configured to transport acetone produced by gas fermentation reactor 857 to a bisphenol A production reactor 854. Bisphenol A production reactor 854 is also configured with an input to receive phenol. The bisphenol A production reactor 854 is configured to react acetone and phenol and produce bisphenol A.

Another pathway in system 851 is a phosgene production pathway that includes a carbon monoxide purification unit 852 configured to receive and purify carbon monoxide produced by carbon dioxide reduction electrolyzer 853. System 851 is further configured to provide purified carbon monoxide from purification unit 852 to phosgene production reactor 855. As mentioned, phosgene production reactor 855 is also configured to receive chlorine from chlor-alkali system 855'.

As depicted, polycarbonate production system 851 additionally comprises a polycarbonate production reactor 859 as well as components for conveying bisphenol A from bisphenol A production reactor 854 and for conveying phosgene from phosgene production reactor 855 to polycarbonate production reactor 859. Reactor 859 is configured to react the bisphenol A and phosgene to produce polycarbonate polymer.

Figure 8G:
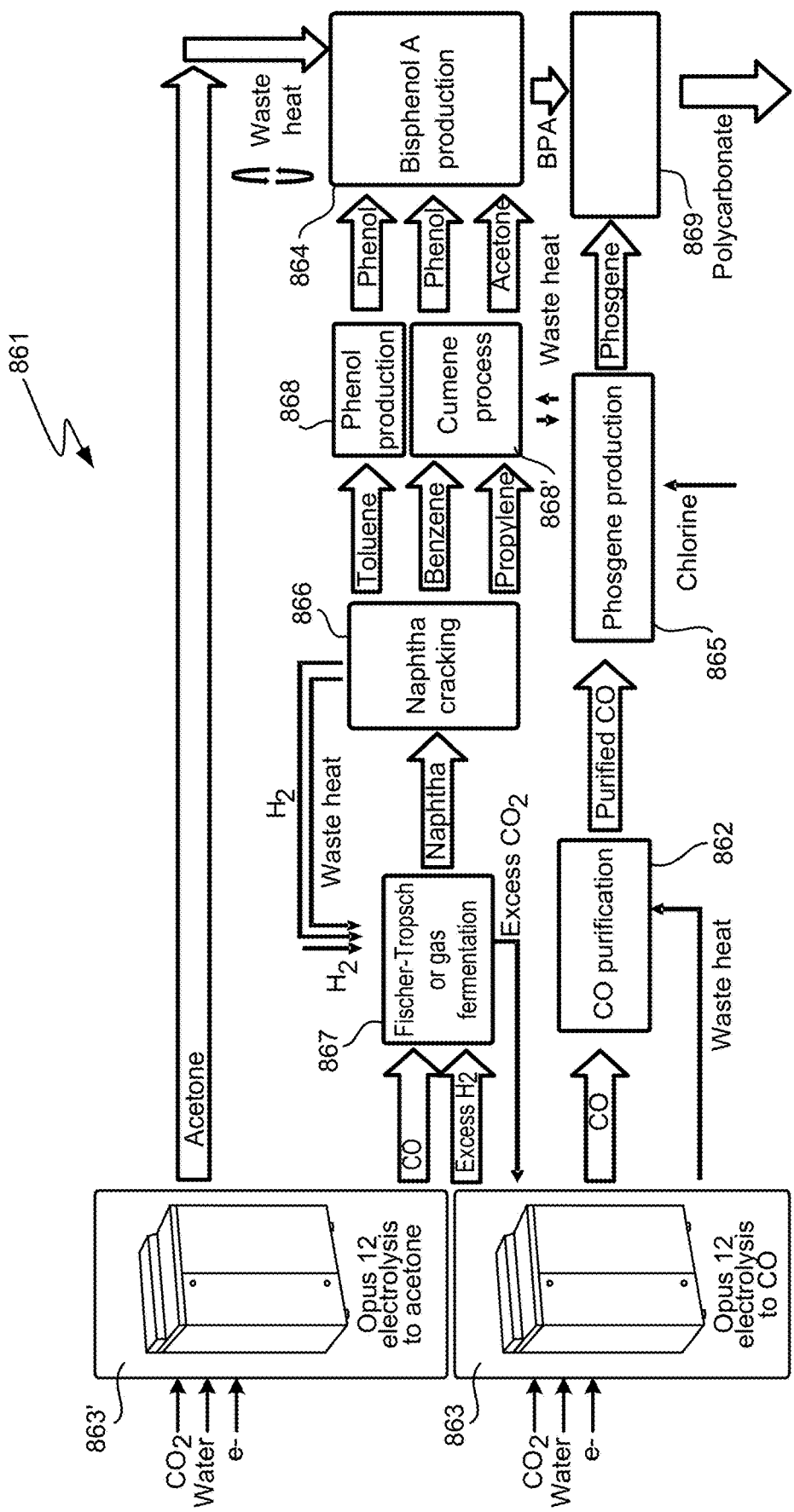
FIG. 8G depicts a polycarbonate production system that employs three separate pathways from a carbon dioxide reduction electrolyzer subsystem.

FIG. 8G depicts a polycarbonate production system 861 that employs three separate pathways from a carbon dioxide reduction electrolyzer subsystem. A first carbon dioxide reduction electrolyzer 863 is configured to (a) produce carbon monoxide and hydrogen for a naphtha path, and (b) produce a carbon monoxide for a phosgene path. A separate carbon dioxide reduction electrolyzer 863' is configured to produce acetone for an acetone path.

The phosgene production path may be similar to that described in other systems for producing polycarbonate. It includes a carbon monoxide purification unit 862 and a phosgene production reactor 865. Carbon monoxide purification unit 862 is configured to receive carbon monoxide and waste heat from electrolyzer 863. It is also configured to provide purified carbon monoxide to phosgene production reactor 865, which has inputs for receiving chlorine gas as well as phosgene.

The acetone pathway includes, as mentioned, a separate carbon dioxide reduction electrolyzer, 863', which is designed and/or operated in a manner distinct from electrolyzer 863. As depicted, system 861 is configured to deliver acetone directly from electrolyzer 863' to a bisphenol A synthesis reactor 864.

Similar to polycarbonate production system 831 depicted in FIG. 8D, the naphtha pathway includes a Fisher Tropsch or gas fermentation reactor 867, a naphtha cracking subsystem 866, a phenol production reactor 868, and a cumene process reactor 868'. The Fisher Tropsch or gas fermentation reactor is configured to receive carbon monoxide and hydrogen gas from carbon dioxide electrolyzer 863 and output naphtha. The Fisher Tropsch or gas fermentation reactor 867 is also configured to receive hydrogen gas from naphtha cracking reactor 866 and to deliver excess carbon dioxide back to electrolyzer 863.

Naphtha cracking subsystem 866 is configured to produce at least propylene, benzene, and toluene. System 861 is configured with conveyance components to deliver the benzene and propylene from the naphtha cracking subsystem 866 to cumene process reactor 868, which is configured to produce phenol and acetone as outputs. System 861 is also configured to convey toluene from naphtha cracking subsystem 866 to phenol production reactor 868 which is configured to produce phenol. System 861 is further configured to deliver the acetone and phenol from cumene process reactor 868' along with phenol produced by phenol production reactor 868 to bisphenol A synthesis reactor 864. As mentioned, system 861 is also configured to deliver acetone from electrolyzer 863' to bisphenol A synthesis reactor 864.

System 861 is additionally configured to deliver bisphenol A produced by reactor 868 along with phosgene produced by reactor 865 to a polycarbonate synthesis reactor 869.

Figure 8H:
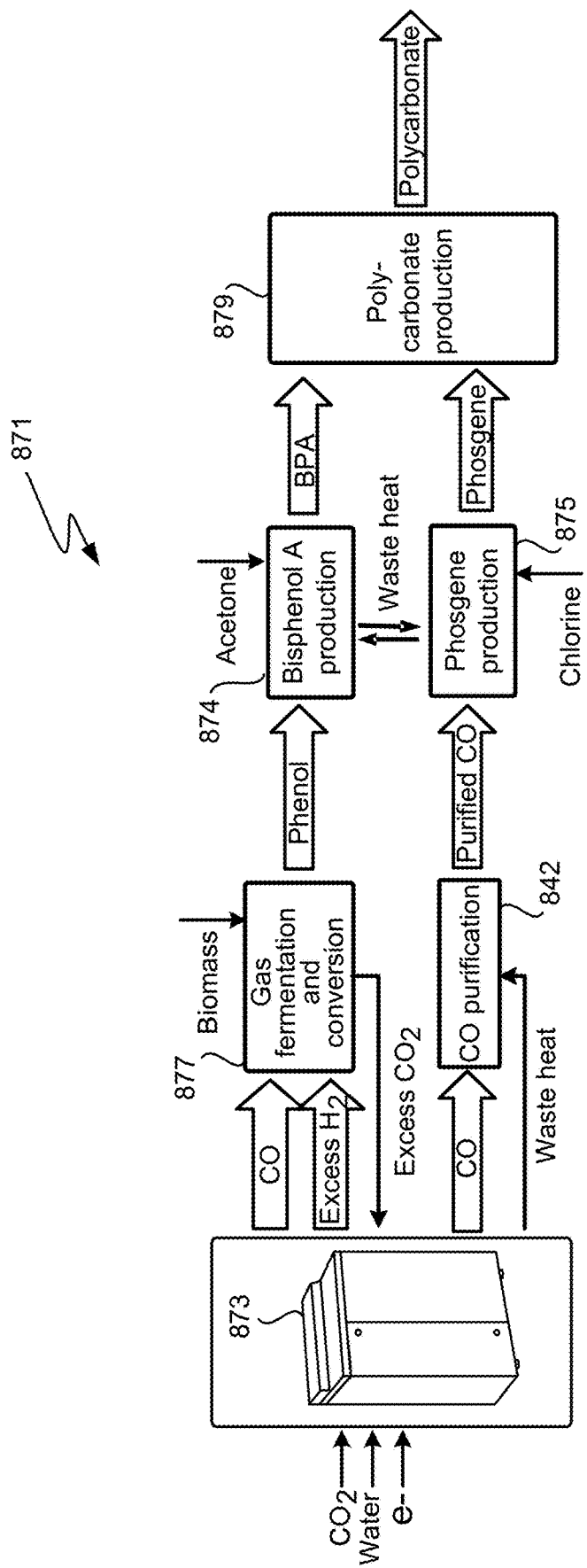
FIG. 8H depicts a polycarbonate polymer production system including a carbon dioxide reduction electrolyzer and components for conveying carbon monoxide and hydrogen gas to a gas fermentation and conversion reactor or subsystem, which is configured to directly produce phenol and excess carbon dioxide.

FIG. 8H depicts another implementation of a polycarbonate polymer production system. This system is denoted as 871. It includes a single carbon dioxide reduction electrolyzer 873 and components for conveying carbon monoxide and hydrogen gas from electrolyzer 873 to a gas fermentation and conversion reactor or subsystem 877, which is configured to directly produce phenol and excess carbon dioxide. System 871 is configured to deliver excess carbon dioxide produced by reactor or subsystem 877 back to the inlet on a cathode side of electrolyzer 873.

Reactor or subsystem 877 may be configured to produce phenol from gas input, alone or in combination with sugar and/or biomass. In some implementations, the gas fermentation reactor produces mevalonic acid or mevalonolactone, which may be converted to phenol by heating in the process a silica catalyst. In certain embodiments, a microorganism used to produce mevalonic acid is a naturally occurring microorganism such as *E. Coli* modified to express a MVL pathway.

System 871 is further configured to deliver phenol from reactor 877 to a bisphenol A synthesis reactor 874, which is also configured to receive acetone and phenol as inputs and produce bisphenol A as an output.

System 871 is also configured to transport carbon monoxide produced by electrolyzer 873 to a carbon monoxide purification unit 872 and to transport purified carbon monoxide from unit 872 to a phosgene production reactor 875, which is configured to receive the purified carbon monoxide along with chlorine and to produce phosgene.

System 871 is further configured to transport phosgene from reactor 875 and bisphenol A from reactor 874 to a polycarbonate synthesis reactor 879, which reacts the bisphenol A and phosgene to produce and output polycarbonate polymer.

In certain embodiments, polycarbonate synthesis is conducted without phosgene but nevertheless using carbon monoxide produced from a carbon dioxide electrolyzer. Polycarbonate synthesis systems may be configured to for various non-phosgene routes to polycarbonate. In some phosgene-free routes, polymerisation relies on the transesterification of DPC (diphenyl carbonate) with bisphenol A. In certain embodiments, non-phosgene systems are configured to produce an intermediate dialkyl carbonate, such as dimethyl carbonate (DMC), as the source of carbonate functionality. These systems may be configured to react phenol with dimethyl carbonate to make, e.g., phenyl methyl carbonate. Various non-phosgene routes employ a method to make the dialkyl carbonates. In certain embodiments, these are made using carbon monoxide from a carbon dioxide electrolyzer. As an example, DMC may be produced using oxidative carbonylation:

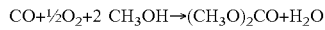

Formates

Alkali metal formates have many uses including as enzyme stabilizers in liquid detergents. The enzymes may be lipases, amylases, proteases, etc. Other formates such as alkali earth metal formates also have many uses. In certain embodiments, a formate production system employs a carbon dioxide reduction electrolyzer to convert carbon dioxide to carbon monoxide, which is processed to produce alkali metal formates. In various embodiments, a metal formate is produced by contacting a metal hydroxide with carbon monoxide. The contact may occur in a liquid (e.g., aqueous) or solid medium.

Figure 9:
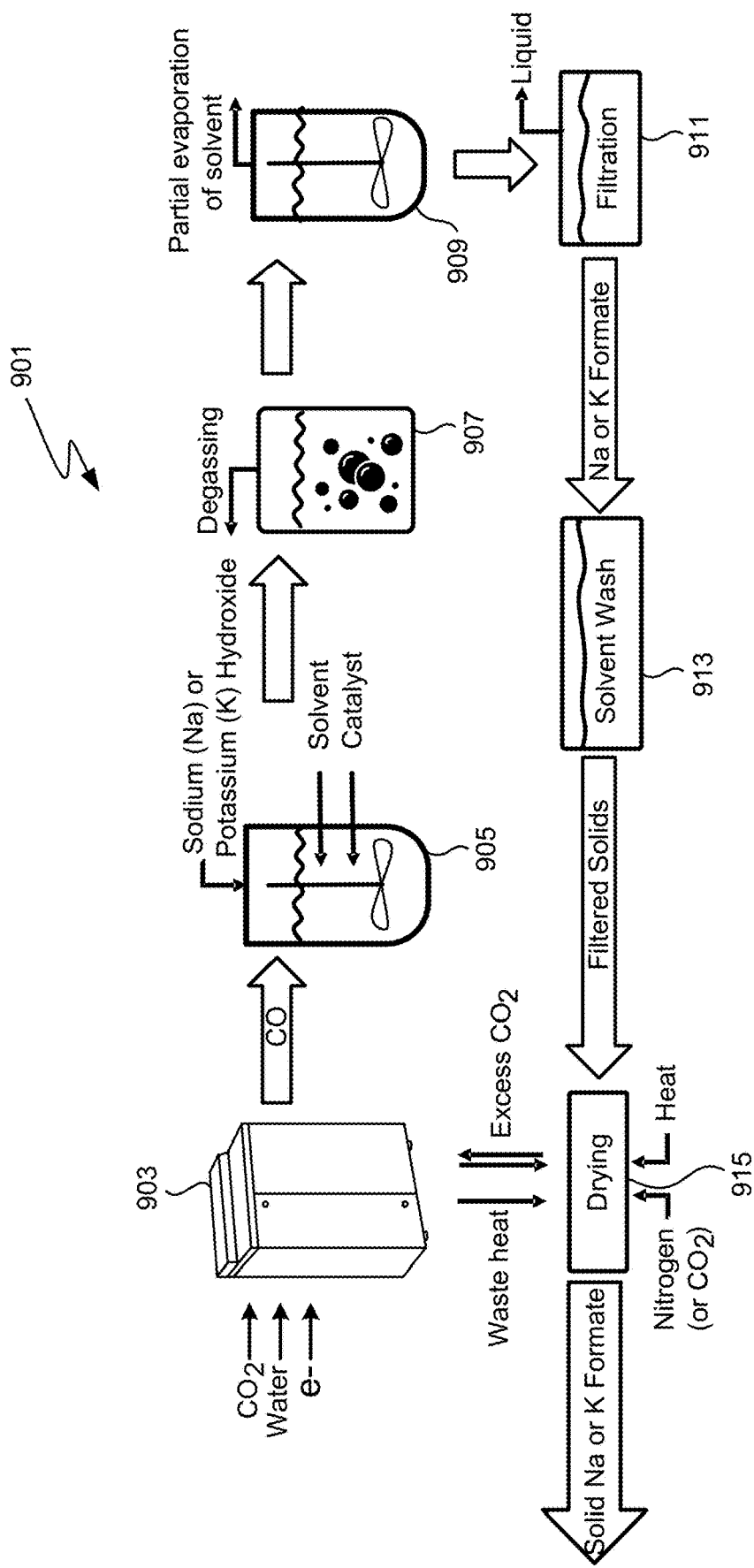
FIG. 9 illustrates an example formate production system comprising a carbon dioxide reduction electrolyzer, a formate production reactor, and various downstream formate recovery units.

FIG. 9 illustrates an example formate production system 901 comprising a carbon dioxide reduction electrolyzer 903, a formate production reactor 905, and various downstream formate recovery units. Electrolyzer 903 is configured to receive oxygen and carbon dioxide as reactants and to receive electricity to drive reduction of carbon dioxide to produce carbon monoxide. System 901 is configured to transport carbon monoxide from electrolyzer 903 to formate production reactor 905 where the carbon monoxide reacts with a hydroxide (e.g., sodium hydroxide, potassium hydroxide, cesium hydroxide, or calcium hydroxide) to produce dissolved metal formate. Reactor 905 is configured to receive not only the carbon monoxide from electrolyzer 903 but metal hydroxide, solvent, and catalyst. Reactor 905 may be a stirred tank reactor.

In certain embodiments, a carbon dioxide electrolyzer located upstream from a metal formate production reactor is configured to operate in (a) a high reduction product to hydrogen product stream operating parameter regime as described herein, and/or (b) a high reduction product to $CO_2$ ratio operating parameter regime as described herein.

System 901 is configured to transport formate-containing solution from reactor 905 to a degassing unit 907, which, during operation, removes gases from the formate solution. Such gases include unreacted carbon monoxide. System 901 is further configured to transport degassed formate solution from unit 907 to an evaporator 909 configured to at least partially evaporate solvent from the formate solution and produce a slurry or other liquid-solid mixture containing precipitated metal formate. System 901 additionally includes a filtration unit 911 configured to receive and filter the output of evaporator 909. The output of filtration unit 911 includes concentrated solid metal formate salt. System 901 additionally comprises a solvent wash unit 913 configured to wash the solid formate-containing output of unit 911 by contacting the formate material with a solvent. System 901 is further configured to transport the filtered and washed solid formate from unit 913 to a drier 915 configured to dry the solid formate and produce the solid metal formate in final form. Drier 915 is configured to receive a drying gas such as nitrogen or carbon dioxide along with heat. In certain embodiments, drier 915 is configured to receive waste heat from electrolyzer 903. In certain embodiments, drier 915 is configured to receive carbon dioxide from electrolyzer 903 or from the inlet stream to electrolyzer 903. In some implementations, externally provided drying carbon dioxide is passed from drier 915 to an input stream for electrolyzer 903.

In some implementations, the formate produced by system 901 is an alkali metal formate such as sodium, potassium, or cesium formate, or an alkali earth formate such as calcium or barium formate. In some cases, system 901 is configured to produce formic acid from metal formate by using a reactor configured to contact the metal formate with an acid such hydrochloric acid.

In some embodiments, a metal formate is produced by contacting carbon monoxide produced by a carbon dioxide electrolyzer with solid or slurry-form metal hydroxide. For example, sodium formate may be produced by contacting solid sodium hydroxide with a carbon monoxide stream. The reaction may be represented as NaOH(s)+CO (g)→NaCOOH (s). Solid hydroxide may be provided in various forms such as a powder. In some cases, to increase surface area of the hydroxide available for reaction, it is milled, pulverized, or otherwise reduced in particle size, optionally during reaction with carbon monoxide. For example, solid hydroxide may be ground in a ball mill autoclave during contact with carbon monoxide. In some cases, optionally during reaction in an autoclave, the solid hydroxide is contacted with carbon monoxide at a temperature of at least about 200° C. (e.g., about 230 to 300° C.) and/or at a pressure of at least about 2 bar (e.g., about 5 to 10 bar). In some embodiments, a formate production reaction in an autoclave has a residence time of at least about 15 to 60 minutes or about 20 to 40 minutes.

In some metal formate syntheses, the carbon monoxide is provided to a reactor (e.g., an autoclave with solid metal hydroxide) in a concentration of at least about 0.5 mole fraction, or at least about 0.8 mole fraction, or at least about 0.9 mole fraction.

Ethylene Glycol

Figure 10A:
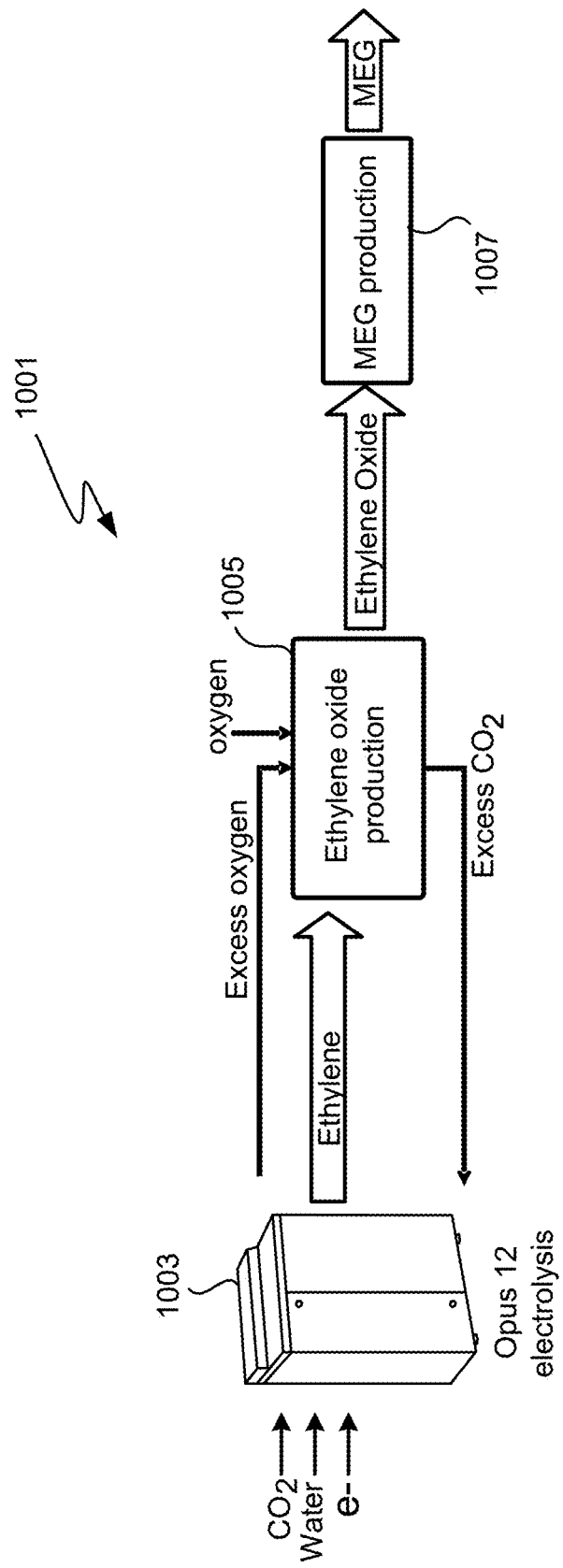
FIG. 10A depicts a monoethylene glycol (MEG) production system including a carbon oxide electrolyzer, an ethylene oxide production reactor, and a MEG production reactor.
Figure 10B:
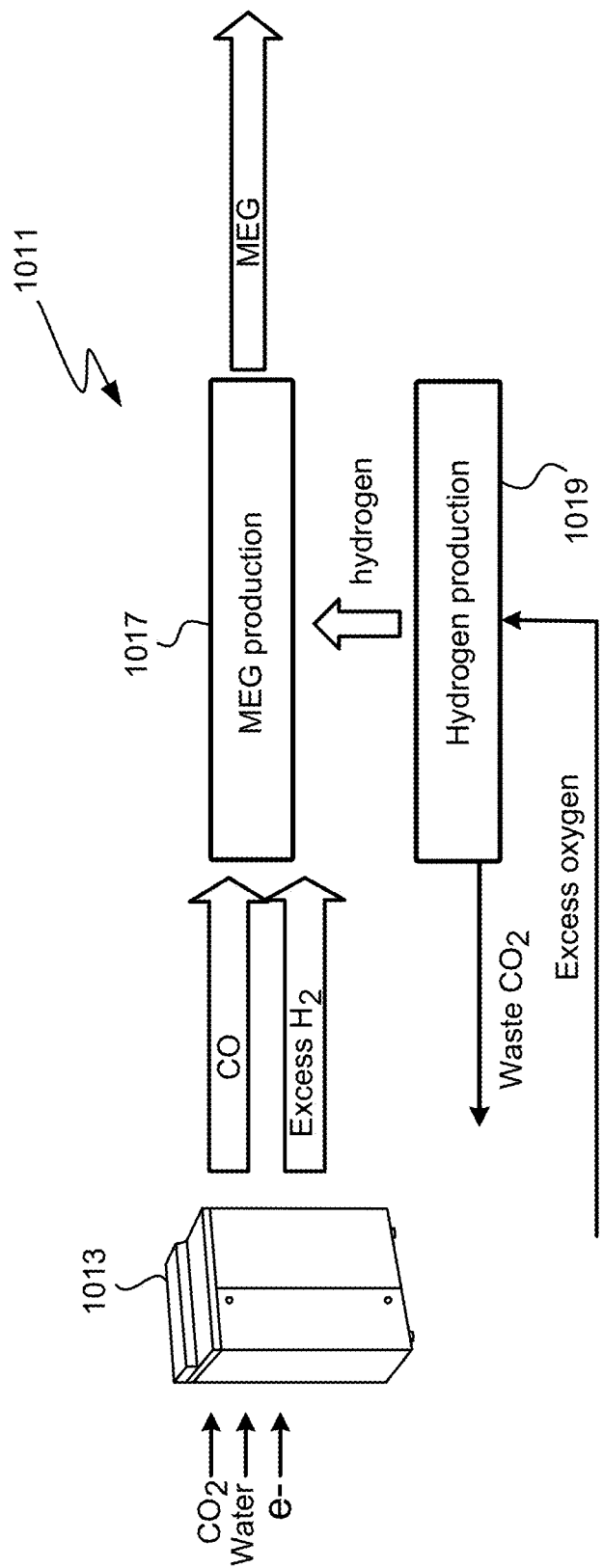
FIG. 10B depicts a MEG production system including a carbon dioxide electrolyzer and an MEG production reactor.

FIGS. 10A and 10B illustrate processes for preparing ethylene glycol (monoethylene glycol or MEG). As depicted in FIG. 10A, an MEG production system 1001 includes a carbon oxide electrolyzer 1003, an ethylene oxide production reactor 1005, and a MEG production reactor 1007. Electrolyzer 1003 is configured to produce ethylene. System 1001 is configured to deliver the ethylene from electrolyzer 1003 to ethylene oxide production reactor 1005. Optionally, system 1001 is additionally configured to deliver oxygen from electrolyzer 1003 to reactor 1005. Regardless of the source of oxygen, reactor 1005 is configured to react ethylene and oxygen to produce ethylene oxide.

In certain embodiments, reactor 1005 is a direct ethylene oxide reactor designed or configured to produce ethylene oxide directly from ethylene and oxygen. In this approach, ethylene and compressed oxygen may be fed to a multi-tubular catalytic reactor (an example of reactor 1005). During operation of such reactor, the mixture is passed over a silver oxide catalyst supported on a porous carrier at about 200-300° C. and about 10-30 bar. The reaction is exothermic, and heat removed can be used elsewhere in the system. System 1001 may be configured to cool gases from the reactor 1005 and pass them through a scrubber where the ethylene oxide is absorbed as a dilute aqueous solution.

The system 1001 may be configured to deliver ethylene oxide from reactor 1005 to ethylene glycol production reactor 1007. Reactor 1007 may be configured to react the ethylene oxide and water to produce ethylene glycol. The reaction may be catalyzed by acid or base, or performed at neutral pH and at elevated temperature. In certain embodiments, system 1001 is configured to provide heat from electrolyzer 1003 and/or ethylene oxide production reactor 1005 to MEG reactor 1007.

As depicted in FIG. 10B, an MEG production system 1011 includes a carbon dioxide electrolyzer 1013 and an MEG production reactor 1017. Electrolyzer 1013 is designed or configured to produce carbon monoxide and hydrogen. System 1011 is configured to deliver these outputs to reactor 1017, along with oxygen (optionally from electrolyzer 1013) where the reactants react to produce ethylene glycol. Reactor 1017 may be configured to produce ethylene glycol from these reactants via a two-step process that produces dimethyl oxalate as intermediate from a reaction pathway involving methanol, dinitrogen trioxide, and carbon monoxide. The production of dimethyl oxalate may employ a palladium catalyst. Reactor 1017 may be configured to perform the second step by reacting the dimethyl oxalate with hydrogen gas using a copper catalyst to produce the ethylene glycol. In this process, only carbon monoxide, hydrogen, and oxygen are consumed. Hydrogen for the reaction may come from any suitable source. A generic hydrogen source is depicted as hydrogen producer 1019 in system 1011. In certain embodiments, hydrogen producer 1019 is a water electrolyzer. In certain embodiments, hydrogen producer 1019 is a reactor configured to perform a water shift reaction. In certain embodiments, hydrogen is produced from a fossil fuel, and carbon dioxide product is optionally recycled to electrolyzer 1013. System 1011 may be configured to provide excess oxygen from electrolyzer 1013 to a combustion reactor.

In certain embodiments, a carbon dioxide electrolyzer located upstream from a MEG production reactor is configured to operate in (a) a hydrogen rich product stream operating parameter regime as described herein, and/or (b) a high reduction product to $CO_2$ ratio operating parameter regime as described herein.

Polyethylene Terephthalate

Figure 11:
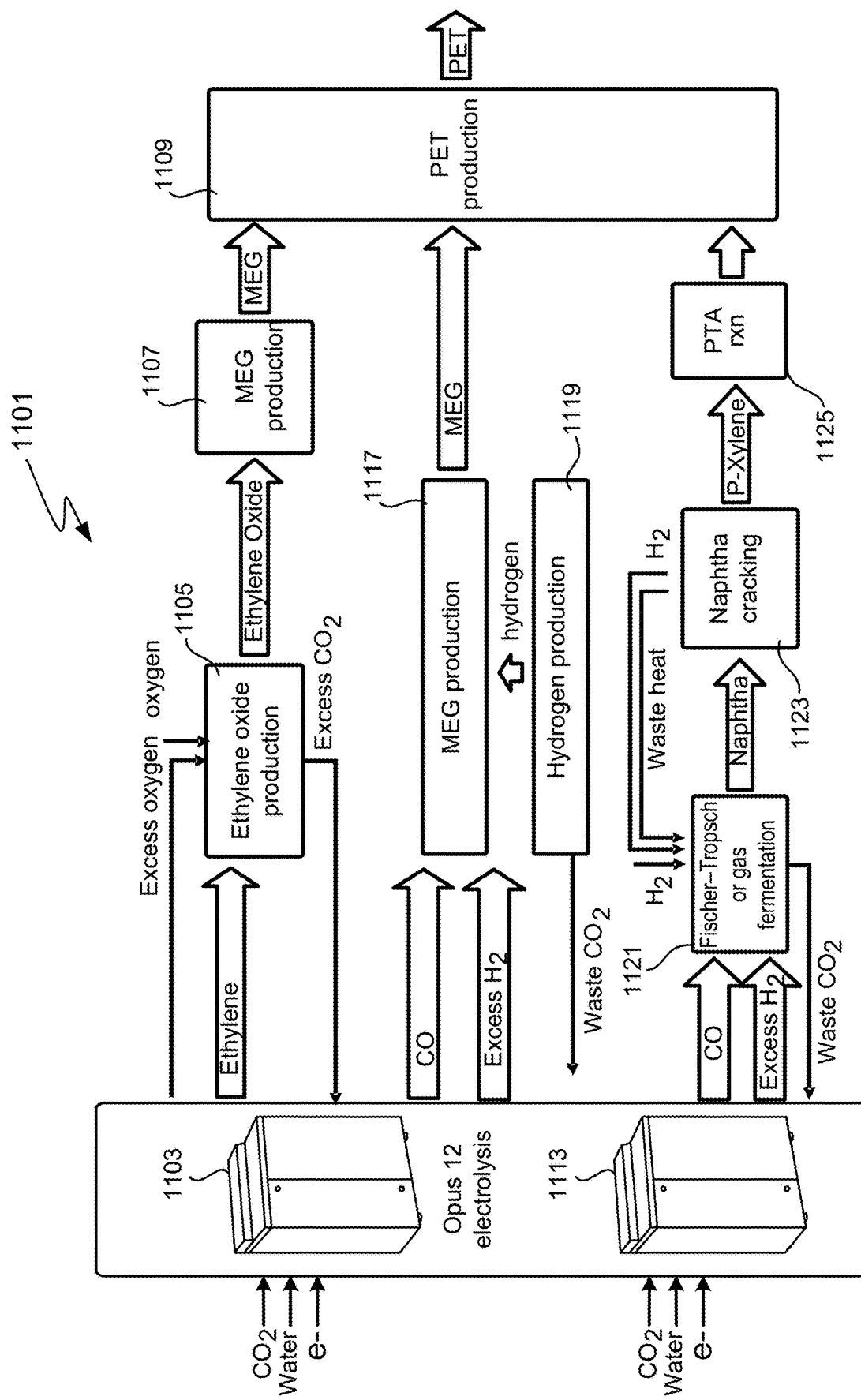
FIG. 11 provides a schematic illustration of systems that may be employed to produce polyethylene terephthalate.

FIG. 11 provides a schematic illustration of systems 1101 that may be employed to produce the polymer polyethylene terephthalate. One process or group of processes employs a carbon oxide electrolyzer 1103 configured to produce ethylene. Another process or group of processes employs a carbon dioxide electrolyzer 1113 configured to produce carbon monoxide and hydrogen.

A system 1101 is configured to implement a PET production pathway including electrolyzer 1103. As depicted, system 1101 additionally includes an ethylene oxide production reactor 1105 and an ethylene glycol production reactor 1107, which may be configured and arranged as in system 1001 of FIG. 10A. System 1101 is configured to deliver ethylene glycol to a PET production reactor 1109, which is configured to react with ethylene glycol with phthalic acid to produce PET polymer.

A version of system 1101 for producing both ethylene glycol and phthalic acid includes an electrolyzer 1113 configured to produce carbon monoxide and hydrogen. The ethylene glycol production pathway is configured to react these products, possibly with the addition of extra hydrogen from a source 1119 in an MEG production reactor 1117. System 1101 is configured to provide MEG from reactor 1117 to PET production reactor 1109. The version of system 1101 employing electrolyzer 1113 optionally does not include components for the MEG pathway employing electrolyzer 1103, ethylene oxide production reactor 1105, and MEG synthesis reactor 1107.

The version of system 1101 employing electrolyzer 1113 may also include reactors for producing terephthalic acid from carbon monoxide and hydrogen produced by electrolyzer 1113. The reactors may produce naphtha and p-xylene as intermediates. In the depicted embodiment, A Fischer Tropsch or gas fermentation reactor 1121 is configured to produce naphtha from the carbon monoxide and hydrogen output by electrolyzer 1113. Reactor 1121 may be designed or configured as described elsewhere herein. A naphtha cracking reactor 1123 is configured to crack the naphtha and produce p-xylene. In certain embodiments, system 1101 is configured to supply excess heat and/or hydrogen produced by cracker 1123 to reactor 1121. A PTA reactor 1125 is configured to convert the p-xylene to terephthalic acid.

In certain embodiments, a carbon dioxide electrolyzer located upstream from a Fischer Tropsch reactor is configured to operate in (a) a hydrogen rich product stream operating parameter regime as described herein, and/or (b) a high reduction product to $CO_2$ ratio operating parameter regime as described herein.

In some versions of system 1101, a carbon oxide reduction electrolyzer is configured to produce ethylene glycol (MEG) directly, by electrolysis. In such versions, the electrolyzer would replace or supplement another MEG production pathway, such as one employing reactor 1107 or reaction 1117. Some versions of system 1101 employ a reactor configured to directly convert carbon monoxide from reactor 1113 along with hydrogen to p-xylene. This version of system 1101 is configured to transport such p-xylene to PTA reactor 1125.

Acetic Acid

Figure 12:
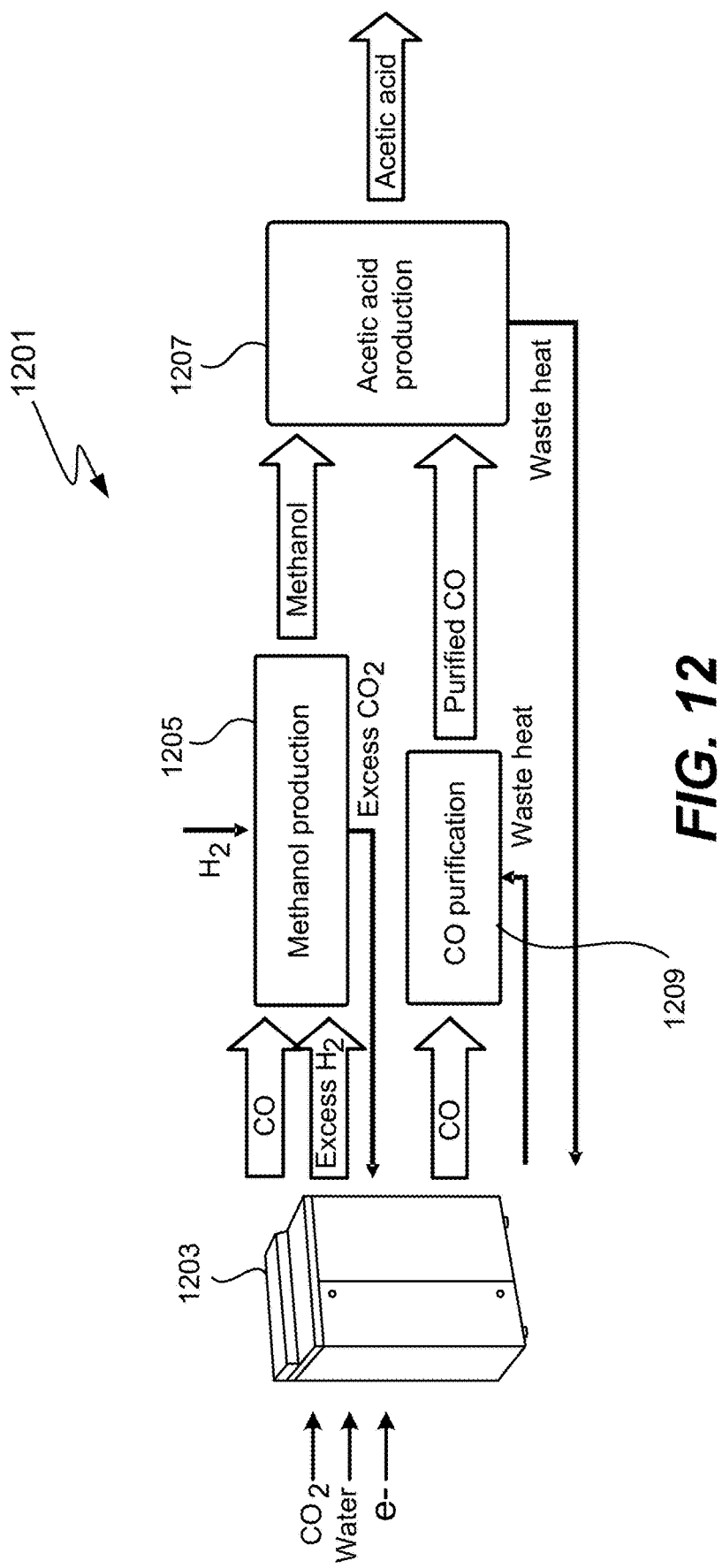
FIG. 12 schematically illustrates a system for producing acetic acid from carbon monoxide and hydrogen produced by a carbon dioxide electrolyzer.

FIG. 12 illustrates schematically a system 1201 for producing acetic acid from carbon monoxide and hydrogen produced by a carbon dioxide electrolyzer 1203. System 1201 comprises a methanol production reactor 1205 configured to react carbon monoxide and hydrogen to produce methanol. Reactor 1205 may be configured in the manner of conventional methanol synthesis reactors that employ syngas.

In certain embodiments, a carbon dioxide electrolyzer located upstream from a methanol production reactor is configured to operate in (a) a hydrogen rich product stream operating parameter regime as described herein, and/or (b) a high reduction product to $CO_2$ ratio operating parameter regime as described herein.

System 1201 also includes an acetic acid production reactor 1207 configured to react the methanol and purified carbon monoxide to produce acetic acid. Reactor 1207 may be configured to perform methanol carbonylation using, e.g., a metal carbonyl catalyst. In certain embodiments, system 1201 includes a carbon monoxide purification unit 1209 configured to produce the purified carbon monoxide. The carbon dioxide purification unit may be designed in a manner described elsewhere herein (e.g., in the manner of the units in FIGS. 19 and 20.

Isocyanates

Figure 13:
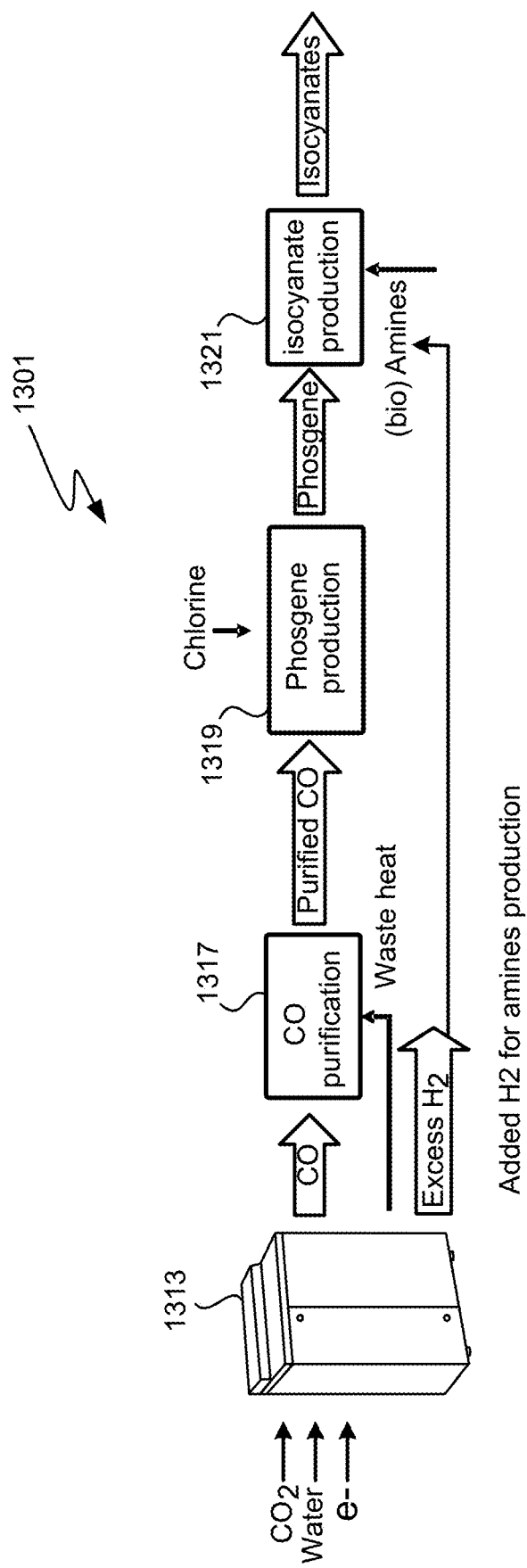
FIG. 13 illustrates schematically a system configured to produce a diisocyanate from electrolytically generated carbon monoxide.

FIG. 13 illustrates schematically a system 1301 configured to produce a diisocyanate from electrolytically generated carbon monoxide.

System 1301 may be configured to transport carbon monoxide produced by a carbon dioxide electrolyzer 1313 to a carbon monoxide purification unit 1317. System 1301 may also be configured to transport purified carbon monoxide from unit 1317 to a phosgene production reactor 1319 configured to react the purified carbon monoxide with chlorine to produce phosgene. In certain embodiments, phosgene production reactor 1319 is designed or configured to operate in a manner similar to other phosgene production reactors described herein, such as in connection with polycarbonate production systems. Examples of carbon monoxide purification units are presented in FIGS. 19 and 20 and the associated description.

In certain embodiments, a carbon dioxide electrolyzer located upstream from a phosgene production reactor is configured to operate in (a) a high reduction product to hydrogen product stream operating parameter regime as described herein, and/or (b) a high reduction product to $CO_2$ ratio operating parameter regime as described herein.

In certain embodiments, system 1301 includes an electrolytic cell such as chlor-alkali cell for producing chlorine. System 1301 may be configured to provide chlorine to phosgene production reactor 1319. In some implementations, system 1301 is configured to feed the oxygen byproduct of electrolyzer 1313 to a cathode of a chlor-alkali cell comprising an oxygen depolarized cathode. Oxygen from electrolyzer 1313 may be used in lieu of oxygen from other sources such as air separation. In some implementations, system 1301 includes a water electrolyzer and system 1301 is configured to feed oxygen produced by the water electrolyzer to an oxygen depolarized cathode of a chlor-alkali cell. System 1301 may be configured to provide hydrogen from a water electrolyzer to an amine production reactor.

In the depicted embodiment, system 1301 is configured to transport phosgene from phosgene production reactor 1319 to an isocyanate production reactor 1321 that is configured to react phosgene and an amine to produce a polyisocyanate, e.g., a diisocynate such as toluene diisocyanate (TDI) or methylene diisocyanate (MDI), depending on the structure of the supplied amine. In some implementations, reactor 1321 is configured to react phosgene and free amine in an inert organic solvent at low temperature. The resulting mixture of carbamoyl chlorides and amine hydrochloride is then reacted at higher temperature to produce the desired polyisocyanate.

In certain embodiments, the amine reactant is produced by a reactor or reaction employing one or more carbon oxide reduction products produced by a carbon oxide electrolyzer as described herein, e.g., via Fischer Tropsch and cracking reactions. In certain embodiments, the amine reactant is produced by a bioreactor such as a gas fermentation reactor. In certain embodiments, system 1301 is configured to provide electrolytically generated hydrogen (optionally from electrolyzer 1313 or a water electrolyzer) to a gas fermentation reactor configured to produce an amine product or an intermediate used in amine production. In some implementations, hydrogen for amine production is provided by a separate source.

Regardless of the amine source, reactor 1321 may be configured to react a polyamine with phosgene by a phosgenation reaction to produce the polyisocyanate such as a diisocyanate. In certain embodiments, the diisocyanate is 2,4-toluene diisocyanate and/or 2,6-toluene diisocyanate. In certain embodiments, the diisocyanate is 4,4'-diphenylmethane diisocyanate.

In various embodiments, substantially pure carbon monoxide is used to produce phosgene, which is then reacted with various amines to produce isocyanates. Some amines may be produced using hydrogen, thus providing an application for byproduct hydrogen from a carbon dioxide electrolyzer or from a co-located water electrolyzer.

As an example, for systems configured to produce toluene diisocyanate (TDI), a carbon dioxide electrolyzer may be configured or operated to produce a hydrogen rich output stream. A high hydrogen content stream (e.g., an approximately 1:1 $H_2$:CO ratio) may be used for the production of the precursors toluene diamine (TDA) and phosgene. The TDA may be produced by hydrogenation of dinitrotoluene. For example, hydrogen may be used to produce nitric acid (described elsewhere), which is used for the nitration of toluene to produce dinitrotoluene.

In certain embodiments, a system comprising a carbon dioxide electrolyzer is configured to produce methylene diisocyanate (MDI) from aniline and phosgene. Aniline may be produced by hydrogenation of nitrobenzene. In some embodiments, a system for producing MDI via aniline is configured to produce a feed gas having a relatively high ratio of hydrogen to carbon monoxide (e.g., in the neighborhood of about 3:1 hydrogen:CO). In some embodiments, a system is configured to produce nitric acid (described elsewhere), which is used for the nitration of benzene to produce nitrobenzene. A system may be configured to employ a separate gas stream containing a relatively lower concentration of hydrogen (e.g., a ratio in the neighborhood about 1:1 hydrogen and CO), which may be used to produce formaldehyde, which is in turn reacted with aniline to produce diamines, which are subsequently phosgenated to produce MDI.

In certain embodiments, a system comprising a carbon dioxide electrolyzer is configured to produce hexamethylene diisocyanate (HDI) using a hydrogen rich gas stream (e.g., a gas stream having a $H_2$:CO ratio of about 4:1) The system may be configured to hydrogenate adiponitrile to produce hexamethylenediamine, which is subsequently phosgenated to produce HDI.

Polyurethane

Figure 14:
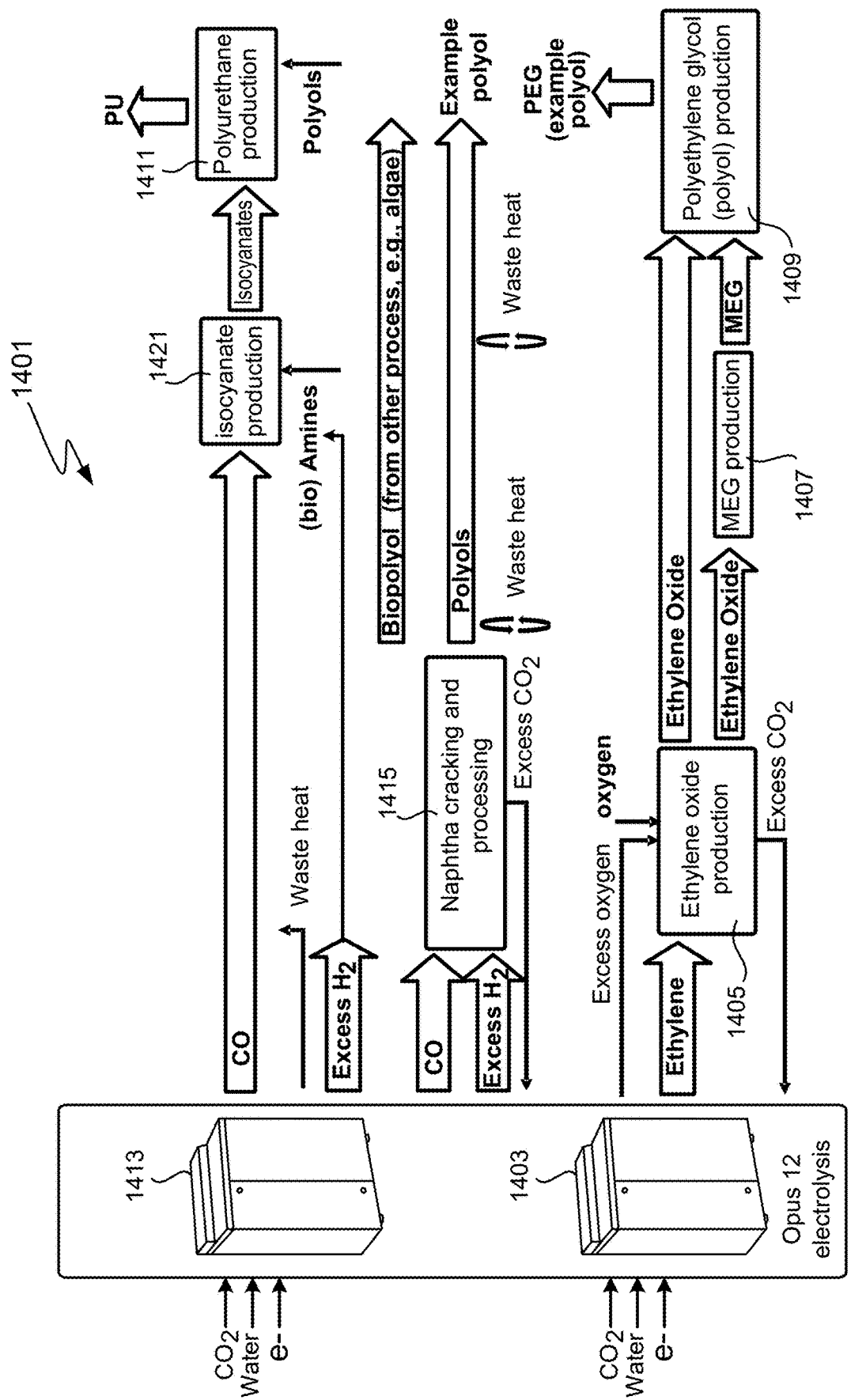
FIG. 14 provides a schematic illustration of systems that may be employed to produce polyurethane.

FIG. 14 provides a schematic illustration of systems 1401 that may be employed to produce the polymer polyurethane. One group of reactors employs a carbon oxide electrolyzer 1403 configured to produce ethylene. Another group of reactors employs a carbon dioxide electrolyzer 1413 configured to produce carbon monoxide and hydrogen. In alternative embodiments, only one of these two groups of reactors is employed, and an alternative source is used to provide the intermediate chemicals that would otherwise be produced by the other of the group of reactors.

In some implementations, system 1401 is configured to transport ethylene and optionally oxygen from electrolyzer 1403 to an ethylene oxide production reactor 1405. System 1401 is also configured to provide ethylene oxide from reactor 1405 to an ethylene glycol production reactor 1407 and/or to a polyethylene glycol production reactor 1409. In certain embodiments, ethylene oxide production reactor 1405 and/or ethylene glycol production reactor 1407 are designed or configured to operate in a manner similar to that of reactors 1005 and 1007 of system 1001.

Polyethylene glycol production reactor 1409 may be configured to produce polyethylene glycol from the interaction of ethylene oxide with water, ethylene glycol, and/or ethylene glycol oligomers. The length of the PEG chain and polydispersity of the product are affected by the choice and ratio of reactants. System 1401 may be configured to transport heat generated by the exothermic PEG production reaction from reactor 1409 to a carbon monoxide purification process (e.g., for phosgene production) or other energy-requiring process. Examples of carbon monoxide purification units are presented in FIGS. 19 and 20 and the associated description.

In some implementations, system 1401 is configured to transport carbon monoxide and optionally hydrogen from electrolyzer 1413 to a reactor or group of reactors 1415 configured to produce one or more polyol (e.g., a polyethylene glycol). Reactor or group of reactors 1415 may be a bioreactor configured to produce polyols by a gas fermentation reaction. In some embodiments, reactor(s) 1415 are configured to produce a polyol using an algae-based reaction. In certain embodiments, reactor or group of reactors 1415 includes Fischer Tropsch reactor and/or a naphtha cracking reactor used to produce hydrocarbons that can be converted to polyols.

In certain embodiments, a carbon dioxide electrolyzer located upstream from a naphtha generating and cracking subsystem is configured to operate in (a) a hydrogen rich product stream operating parameter regime as described herein, and/or (b) a high reduction product to $CO_2$ ratio operating parameter regime as described herein.

System 1401 may be configured to utilize carbon monoxide and optionally hydrogen produced by electrolyzer 1413 to produce a diisocyanate such as MDI or TDI. In certain embodiments, system 1401 is configured to implement diisocyanate production using as a subsystem the system 1301 depicted in FIG. 13. Such subsystem may include a carbon monoxide purification unit and a phosgene production reactor. Regardless of how the diisocyanate precursors such as phosgene and free amines are produced, system 1401 is configured to react them in a diisocyanate production reactor 1421. Depending on the polyurethane to be produced, different types of diisocyanates may be employed. Examples include 2,4-toluene diisocyanate and/or 2,6-toluene diisocyanate. In certain embodiments, the diisocyanate is 4,4'-diphenylmethane diisocyanate.

System 1401 is optionally configured to provide excess carbon monoxide in the outlet stream of ethylene-production electrolyzer 1403 to an phosgene/isocyanate production pathway.

System 1401 includes a polyurethane production reactor 1411 configured to receive a polyol and a diisocyanate, and to react them to produce polyurethane polymer. In certain implementations, the polyol is produced by, e.g., reactor or reactor group 1415 and/or polyethylene glycol production reactor 1409. In some implementation, system 1401 is configured to transport the polyol from one or both of these reactors and/or to transport diisocyanate from reactor 1421 to polyurethane production reactor 1411. In certain embodiments, reactor 1411 is designed or configured to contact and react steams of polyol and diisocyanate. In certain embodiments, the polyol stream includes a catalyst (e.g., and acidic or basic amine), a surfactant, and/or a blowing agent.

Oxalic Acid

In certain embodiments, oxalic acid is produced from carbon monoxide generated by a carbon dioxide electrolyzer. Various pathways may be employed to produce oxalic acid from carbon monoxide. Examples of systems incorporating these pathways are depicted in FIGS. 15 through 18.

In certain embodiments, a carbon dioxide electrolyzer and associated oxalic acid production units are deployed at or near a plant for producing cement. Carbon dioxide produced by the cement plant may be used to feedstock for the carbon dioxide electrolyzer. The oxalic acid produced by the system may be used for curing cement. In certain embodiments, oxalic acid used in cement produces calcium oxalic, which has a very low solubility. Cements produced with oxalic acid may resist degradation due to contact with acids while in use (e.g., after installation or construction).

Figure 15:
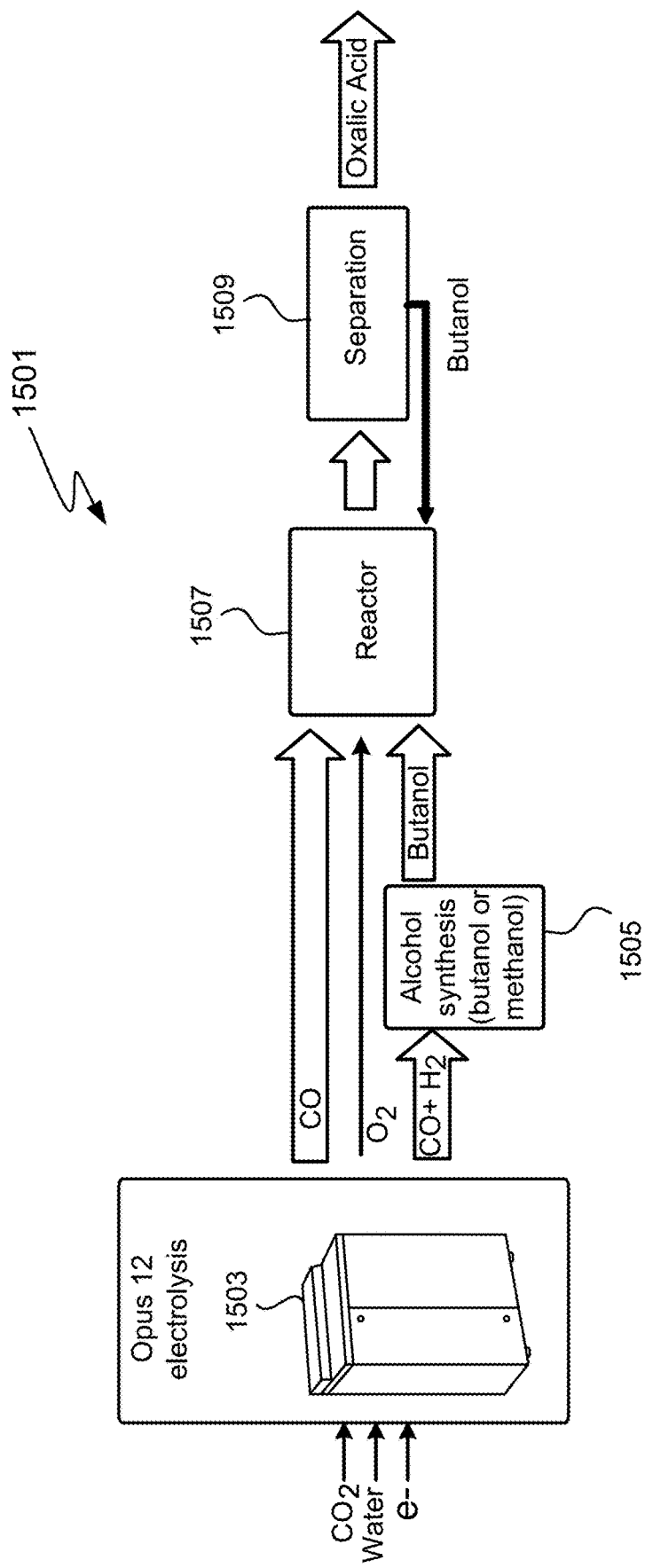
FIG. 15 depicts a system comprising a carbon dioxide electrolyzer configured to produce carbon monoxide and hydrogen for use in producing oxalic acid.

FIG. 15 depicts a system 1501 comprising a carbon dioxide electrolyzer 1503 configured to produce carbon monoxide and hydrogen. System 1501 is configured to transport some of the carbon monoxide and hydrogen, optionally along with some oxygen, produced by electrolyzer 1503 to an alcohol production reactor 1505. Reactor 1505 is configured produce, in certain embodiments, methanol or butanol.

In some implementations, reactor 1505 is a bioreactor employing an organism having a metabolic pathway for converting carbon monoxide to an alcohol such as butanol. Examples of such organisms include autotrophic acetogens such as *Clostridium carboxidivorans. Butyribacterium methylotrophicum*. In some embodiments, reactor 1505 is configured to produce methanol by a catalytic reaction of carbon monoxide and hydrogen at elevated temperature and pressure. In some embodiments, the catalyst is a mixture of copper and zinc oxides supported on alumina. In some embodiments, system 1501 is configured to provide additional hydrogen, beyond that produced by electrolyzer 1503, to alcohol reactor 1505.

In certain embodiments, a carbon dioxide electrolyzer located upstream from an alcohol production reactor is configured to operate in (a) a hydrogen rich product stream operating parameter regime as described herein, and/or (b) a high reduction product to $CO_2$ ratio operating parameter regime as described herein.

System 1501 is further configured to transport alcohol produced by reactor 1505 to an oxalic acid production reactor 1507. In certain embodiments, reactor 1507 is configured to react the alcohol with carbon monoxide and oxygen to produce an oxalic acid diester, which is subsequently hydrolyzed to produce free oxalic acid.

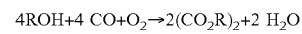

$$4ROH + 4\ CO + O_2 \rightarrow 2(CO_2R)_2 + 2\ H_2O$$

The carbon monoxide provided to reactor 1507 may be provided directly from electrolyzer 1503. In some embodiments, the carbon monoxide from electrolyzer 1503 is purified before delivery to reactor 1507.

Reactor 1507 may produce oxalic acid in an impure form. Therefore, system 1501 may be further configured to provide the oxalic acid product to a separator 1509, which may be configured to purify the oxalic acid and return unreacted alcohol to reactor 1507. In certain embodiments, separator 1509 is configured to perform an azeotropic distillation on the oxalic acid product from reactor 1507.

Figure 16:
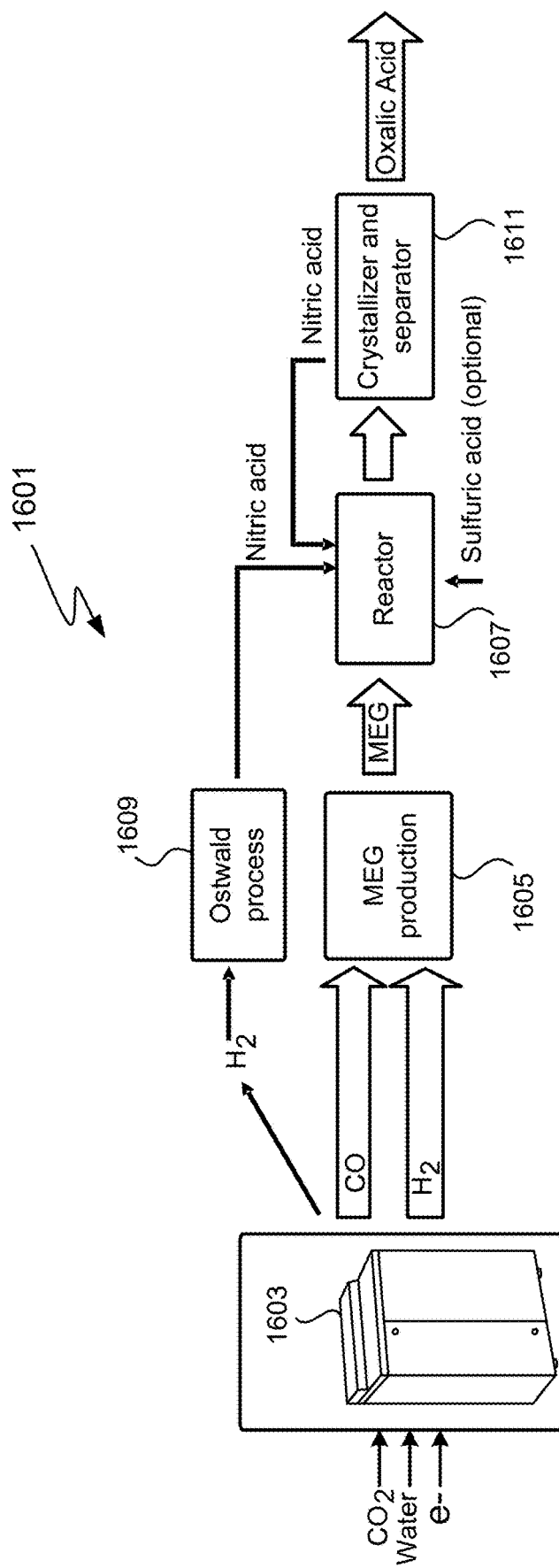
FIG. 16 illustrates a system configured to produce oxalic acid from carbon monoxide produced by an electrolyzer.

FIG. 16 illustrates a system 1601 configured to produce oxalic acid from carbon monoxide produced by an electrolyzer 1603. As depicted, system 1601 is configured to transport carbon monoxide and hydrogen produced by electrolyzer 1603 to an ethylene glycol production reactor 1605. Reactor 1605 may be designed or configured to produce ethylene glycol in a fashion similar to that described above with reference to system 1011 (see reactor 1017) of FIG. 10A.

In certain embodiments, a carbon dioxide electrolyzer located upstream from an MEG production reactor is configured to operate in (a) a hydrogen rich product stream operating parameter regime as described herein, and/or (b) a high reduction product to $CO_2$ ratio operating parameter regime as described herein.

System 1601 is configured to transport ethylene glycol produced by reactor 1605 to an oxalic acid production reactor 1607 configured to oxidize ethylene glycol and produce oxalic acid. In certain embodiments, reactor 1607 is configured to utilize oxidants such as nitric acid and/or air to produce the oxalic acid from ethylene glycol. In certain embodiments, reactor 1607 is configured to react an alcohol (MEG) in the presence of an oxidizing agent such as air or nitric acid using a catalyst such as vanadium pentoxide to produce oxalic acid.

In certain embodiments, system 1601 includes a reactor 1609 for producing nitric acid. In certain embodiments, reactor 1609 is designed of configured to implement the Ostwald process. In certain embodiments, system 1601 additionally includes a reactor for implementing the Haber process to produce ammonia. System 1601 may be configured to provide the ammonia to Ostwald reactor 1609. In some implementations, a Haber reactor and Ostwald reactor 1609 are provided as a subsystem that takes hydrogen and nitrogen as reactants and produces nitric acid as a product. System 1601 may be configured to direct hydrogen produced by electrolyzer 1603 to a subsystem for producing nitric acid (e.g., a subsystem that first generates ammonia from hydrogen and nitrogen). In some embodiments, nitric acid is supplied from an external source. It should be understood that in other embodiments that require nitric acid, e.g., other systems for producing oxalic acid, nitric acid can be produced from a Haber process subsystem that receives hydrogen from a carbon oxide electrolyzer.

In the depicted embodiment, reactor 1607 receives nitric acid from reactor 1609 and produces oxalic acid. In certain embodiments, reactor 1609 produces relatively impure oxalic acid, such as oxalic acid that contains some amount of nitric acid. In the depicted embodiment, system 1601 is configured to deliver impure oxalic acid to a crystallizer and separator unit 1611 that is configured to purify the oxalic acid and return nitric acid to reactor 1607.

Figure 17A:
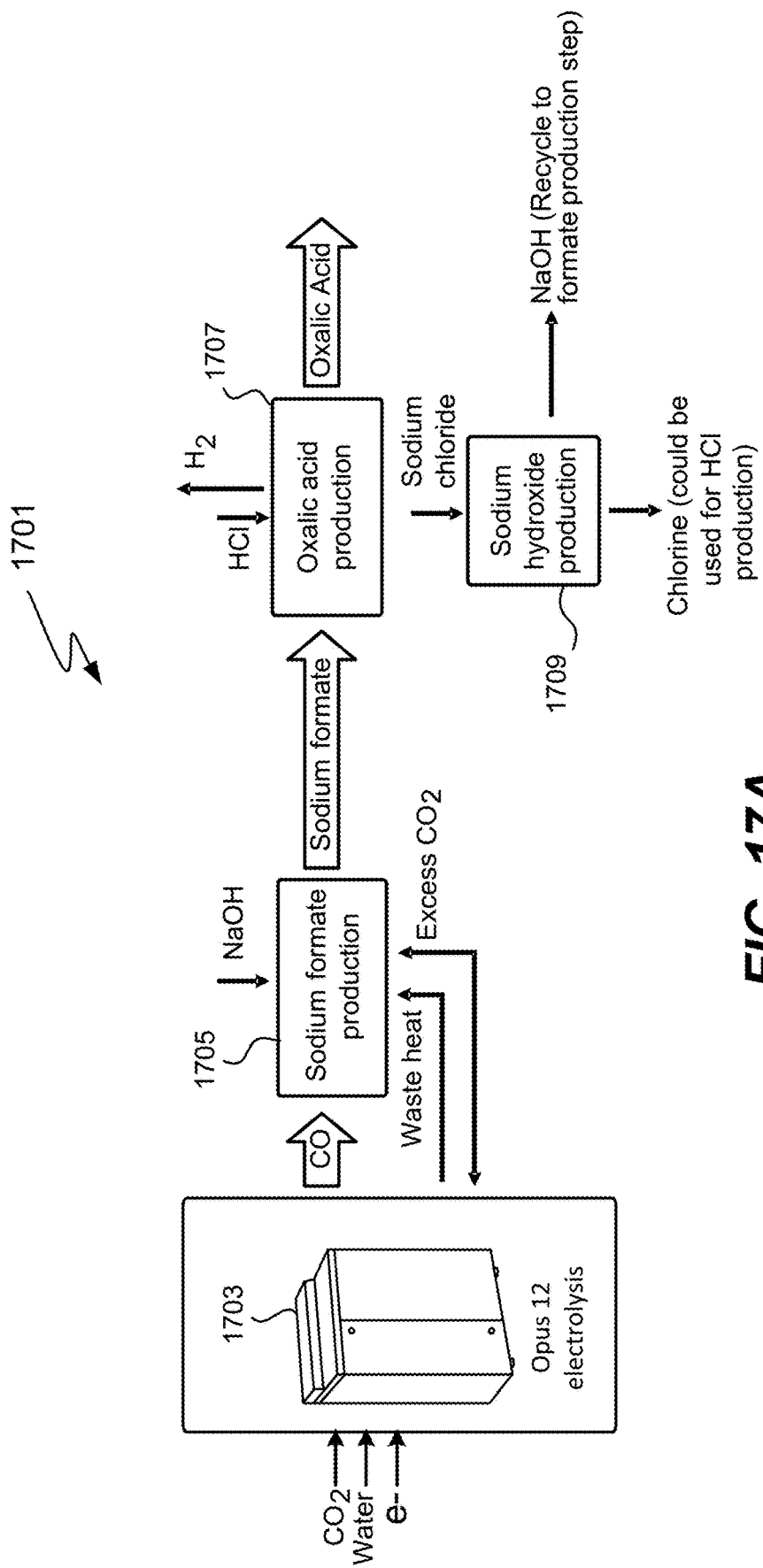
FIG. 17A depicts a system comprising a carbon dioxide electrolyzer, a metal formate production reactor, and an oxalic acid formation reactor.

FIG. 17A depicts a system 1701 comprising a carbon dioxide electrolyzer 1703, a metal formate production reactor 1705, and an oxalic acid formation reactor 1707. System 1701 is configured to deliver carbon monoxide produced by electrolyzer 1703 to formate production reactor 1705. During operation, a metal hydroxide along with heat—optionally, waste heat from electrolyzer 1703—is provided to reactor 1705 which produces the metal formate. The production and purification and/or extraction of the formate may proceed as described above with reference to FIG. 9. In some implementations, the formate is an alkali metal formate such as sodium, potassium, or cesium formate, or an alkali earth formate such as calcium or barium formate. In certain embodiments, the formate is sodium formate. In certain embodiments, the formate is potassium formate.

Regardless of how the metal formate is produced and optionally extracted, system 1701 is configured to transport the formate to oxalic acid production reactor 1707. Reactor 1707 may be configured to convert formate to oxalate via a pyrolysis reaction. Reactor 1707 may also be configured to convert metal oxalate to oxalic acid through contact with acid. In certain embodiments, oxalic acid formation reactor 1707 is configured to receive an acid, such as hydrochloric acid to, for example, to drive the reaction. In certain embodiments, a halide byproduct (e.g., NaCl) of the oxalic production reaction (in reactor 1707) is provided to a chlor-alkali electrolyzer or other system 1709 configured to produce chlorine gas and metal hydroxide. In some implementations, system 1701 is configured to utilize the chlorine to produce hydrogen chloride or hydrochloric acid, which may be delivered to oxalic acid production reactor 1707. In some implementations, system 1701 is configured to utilize hydroxide from reactor 1709 in formate production reactor 1705.

As indicated, oxalic acid may be produced from a metal formate by conversion to a metal oxalate and subsequent acidification. In some implementations, a process may include the following operations: (1) produce a metal formate from carbon monoxide produced by a carbon dioxide electrolyzer (2) produce a metal oxalate from the metal formate by, e.g., pyrolysis, and (3) produce oxalic acid by exposing the metal oxalate to acid. The overall process can be conducted as a batch process. In some cases, at least the metal formate production operation and the metal oxalate production operation are performed in the same vessel. In some examples, a formate and/or oxalate production vessel may be a pressure vessel such as an autoclave. In some cases, a metal formate production vessel and/or a metal oxalate production vessel includes mechanism for reducing the particle size of a solid reactant such as a metal hydroxide. In some examples, the production vessel includes a ball mill.

In some embodiments, optionally during reaction in an autoclave, a formate production reaction (e.g., a reaction between carbon monoxide and solid sodium hydroxide) has a residence time of at least about 15 to 60 minutes or about 20 to 40 minutes. In some cases the solid hydroxide is contacted with carbon monoxide at a temperature of at least about 200° C. (e.g., about 230 to 300° C.) and/or at a pressure of at least about 2 bar (e.g., about 5 to 10 bar).

The operation of converting a metal formate to a metal oxalate may be accomplished by pyrolysis, optionally in the same reaction in which metal formate was produced. In certain embodiments, the chemical reaction is NaCOOH+ CO→$Na_2C_2O_4$. The reaction may be conducted in the presence of heat and sodium carbonate. In batch processes in which a single reactor is used to produce metal formate and metal oxalate, a metal carbonate (e.g., sodium carbonate) may be the only input added to the reactor prior to the oxalate reaction.

In some embodiments, the metal oxalate production reaction is conducted at a pressure of about 0.5 to 5 bar (e.g., substantially atmospheric pressure). In some embodiments, the metal oxalate production reaction is conducted at a temperature of at least about 200° C., or at least about 300° C., or about 300 to 400° C. In some embodiments the residence time of the metal oxylate production reaction about 10 to 100 minutes, or about 20 to 40 minutes.

In some implementations, at the beginning the metal oxalate production reaction, the reactor pressure is reduced to a low pressure (e.g., about 1 bar), while the reactor heats until reaching a temperature of at least about 300° C. (e.g., about 360° C.). During the pyrolysis operation, the metal hydroxide residue may continue to react with carbon monoxide, and this increases the overall conversion of this reaction.

A solid metal carbonate may serve as a catalyst. Further, it may inhibit the thermal decomposition of metal oxalate to metal carbonate and carbon monoxide. In some implementations, the reactor pressure is reduced to a low pressure (e.g., about 1 bar), while the reactor heats until reaching a temperature of at least about 300° C. (e.g., about 360° C. During the pyrolysis operation, the metal hydroxide residue may continue to react with carbon monoxide, and this increases the overall conversion of this reaction.

In certain embodiments, oxalic acid is formed from metal oxalate and an acid such as a hydrohalic acid. In certain embodiments, the acid is hydrochloric acid having a concentration of about 0.05 to 0.2 M. In some implementations, an oxalic acid formation reaction is conducted in a crystallizer such as a batch crystallizer. In some embodiments, the reactor is configured to produce a recirculation stream to increase the efficiency of oxalic acid crystals separation.

In some embodiments, oxalic acid is produced at a temperature of about 20 to 100° C., or about 50 to 100° C. In some embodiments, the newly produced oxalic acid is cooled (e.g., to about 30° C. or lower) for about 10 to 60 minutes. In some embodiments, the pressure employed during the oxalic acid formation reaction is about 0.5 to 2 bar (e.g., approximately atmospheric pressure). In certain embodiments, a reaction solution containing metal oxalate is brought to a low pH, e.g., about 1 to 3 or simply about 1.

In some implementations, the mass of water added to metal oxalate is sufficient to complete dissolution of the metal oxalate at an initial temperature. The dissolution process may occur while the temperature in the batch is about 80° C., for example. The crystallization process may occur when the temperature of the solution in the batch decreased, e.g., rapidly decreases. This operation may be enabled by the using a by-pass stream of water that was initially used to dissolve the metal oxalate. Namely, when oxalic acid is completely dissolved, the water stream may avoid passage through a heater and flow directly to a heat exchanger placed in the batch. A process for forming and crystallizing oxalic acid may be accomplished using a crystallizer such as crystallizer 1731 depicted in FIG. 17B.

Crystallized oxalic acid is optionally filtered and/or dried. In some embodiments, oxalic acid is filtered using a pusher centrifuge. In some embodiments, oxalic acid is dried using a fluidized bed drier. In some implementation, filtered oxalic acid has a moisture content of about 20-30% by mass.

Figure 17B:
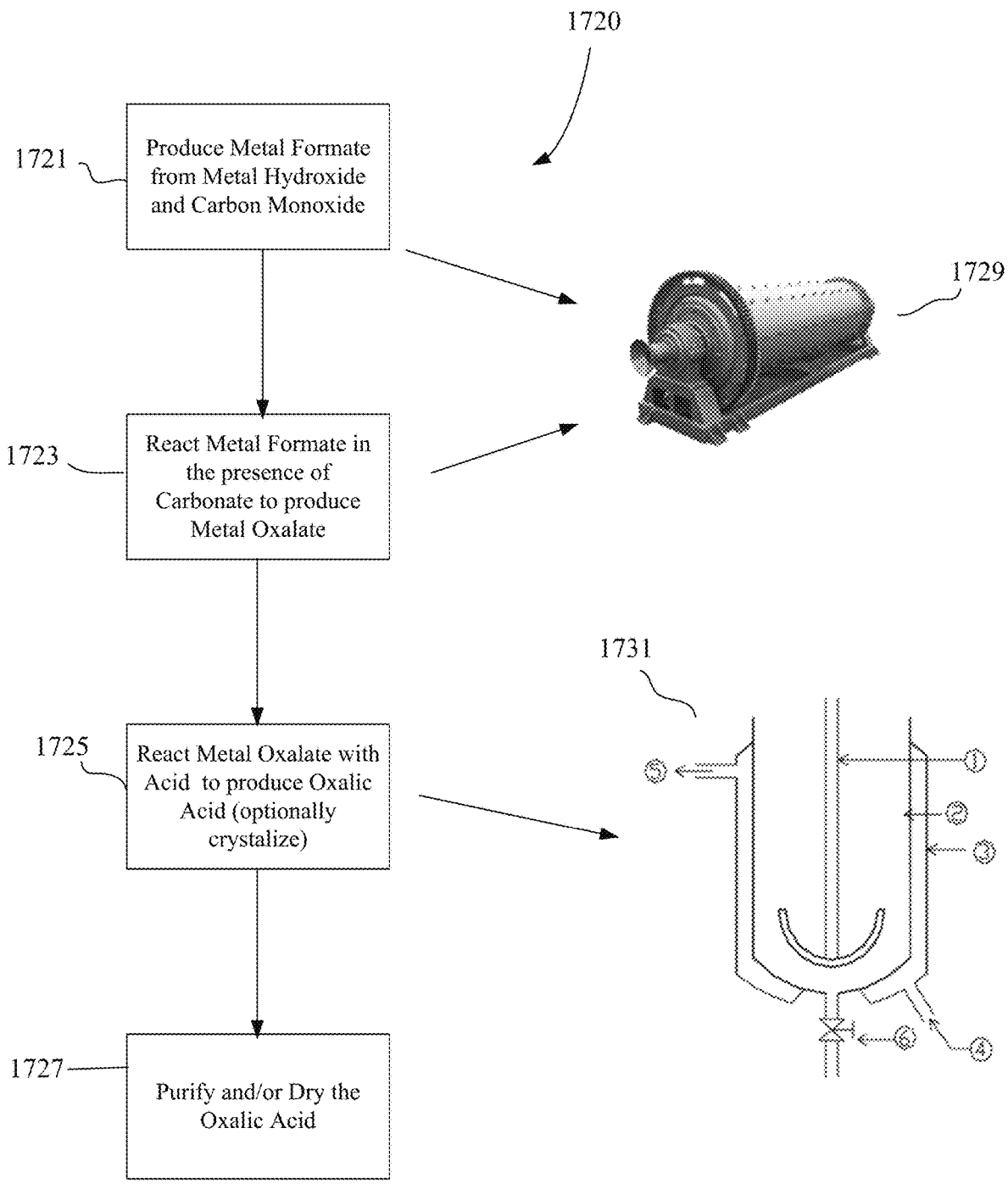
FIG. 17B depicts a process and some associated components for producing oxalic acid using carbon monoxide from a carbon dioxide electrolyzer.

FIG. 17B depicts a process 1720 of forming oxalic acid from solid metal formate. As shown, process 1720 begins with formation of a metal formate at an operation 1721. This process involves reaction of carbon monoxide from a carbon dioxide electrolyzer with a metal hydroxide. Any suitable process of creating metal formate may be employed. Examples include all processes disclosed herein for producing metal formate, including those processes described in association with FIG. 9. After the metal formate is produced, it is converted to a metal oxalate in an operation 1723. In the depicted operation, the formate to oxalate conversion reaction is performed in the presence of a metal carbonate such as sodium carbonate. In certain embodiments, one or both of operations 1721 and 1723 are performed in a ball mill autoclave such as autoclave 1729 depicted in the figure.

After the metal oxalate is formed in operation 1723, the metal oxalate is reacted with an acid such as a hydrohalic acid (e.g., hydrochloric acid) to form oxalic acid. See operation 1725. In some embodiments, the reaction may take place in a crystallizer such as a batch cooling crystallizer 1731 depicted in the figure. The batch cooling crystallizer includes (1) an agitator, (2) baffles, (3) a cooling jacket, (4) a jacket fluid inlet, (5) a jacket fluid outlet, and (6) an outlet valve. This arrangement facilitates both formation and crystallization of oxalic acid.

After the oxalic acid is formed and optionally crystallized in operation 1723, it is optionally purified and/or dried. In one example, purification is accomplished by filtering. In one example, drying is accomplished in a fluidized bed.

Figure 18:
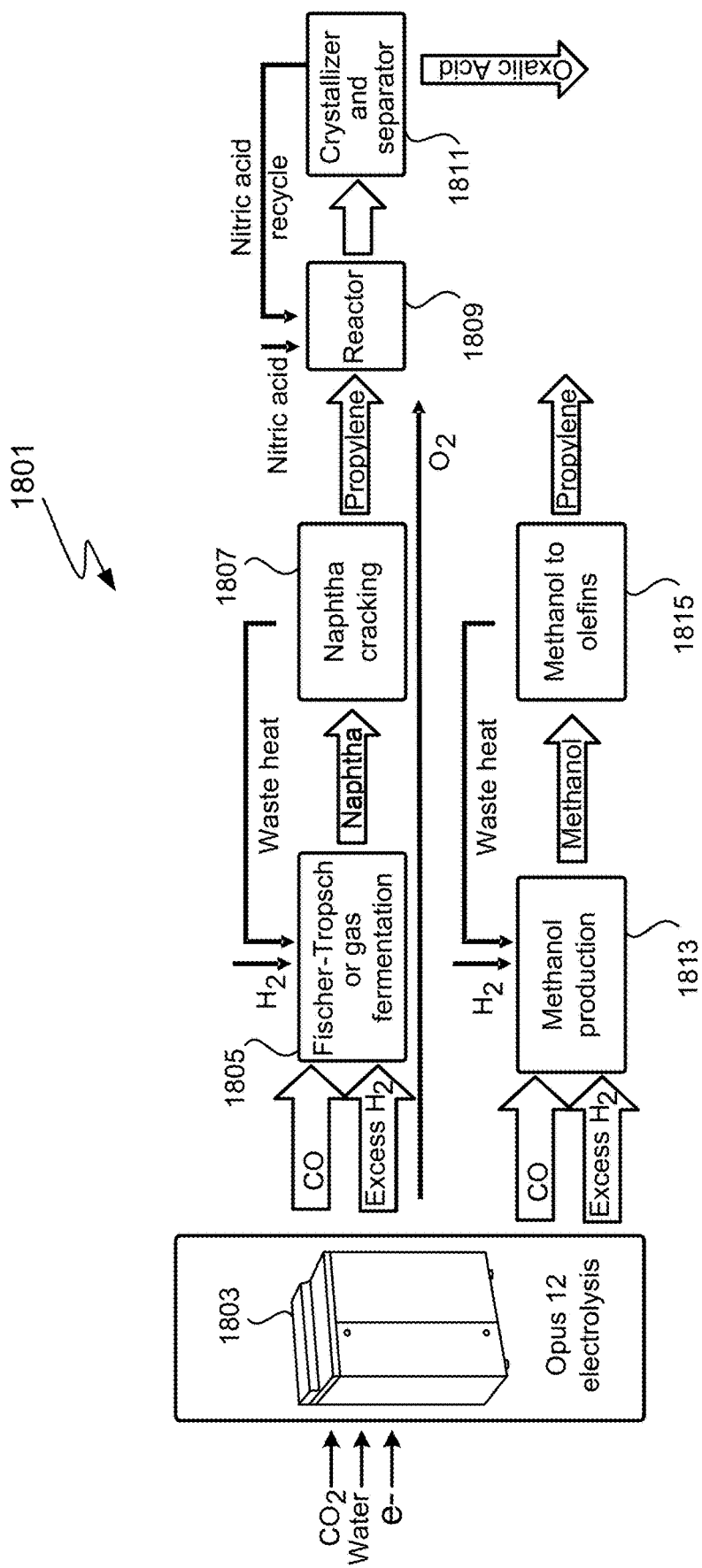
FIG. 18 depicts a system comprising a carbon dioxide electrolyzer configured to produce carbon monoxide and hydrogen for use in producing oxalic acid.

FIG. 18 depicts a system 1801 comprising a carbon dioxide electrolyzer 1803 configured to produce carbon monoxide and hydrogen. System 1801 is configured to provide the carbon monoxide and hydrogen produced by electrolyzer 1803 to a Fischer Tropsch reactor or a gas fermentation reactor, either generically illustrated by block 1805. Depending upon the content of the products produced by electrolyzer 1803 and the reaction taking place in reactor 1805, additional hydrogen may be needed to promote the reaction of reactor 1805. To this end, reactor 1805 may be configured with an inlet for externally produced hydrogen gas. Reactor 1805 is configured to produce naphtha, and system 1801 is configured to transfer the naphtha from reactor 1805 to a naphtha cracking reactor 1807. Naphtha cracking reactor 1807 is configured to crack naphtha in a manner that produces at least some propylene.

In certain embodiments, a carbon dioxide electrolyzer located upstream from an propylene production reactor is configured to operate in (a) a hydrogen rich product stream operating parameter regime as described herein, and/or (b) a high reduction product to $CO_2$ ratio operating parameter regime as described herein.

System 1801 is configured to deliver the propylene to an oxalic acid production reactor 1809 that is configured to receive nitric acid and optionally oxygen, in addition to the propylene. In some implementations, system 1801 is configured to deliver excess oxygen from electrolyzer 1803 to reactor 1809. In certain embodiments, reactor 1809 is configured to absorb propylene into nitric acid and to heat the resulting mixture while adding oxygen and removing nitrogen oxides. The resulting process produces oxalic acid, which system 1801 is configured to deliver to a separation unit such as a crystallizer and separator unit 1811. In certain embodiments, unit 1811 is configured to produce pure oxalic acid. System 1801 may be configured to return nitric acid from unit 1811 to reactor 1809.

In a version of system 1801, propylene is generated from electrolyzer-produced carbon monoxide and hydrogen by a different route. In this version, system 1801 is configured to deliver carbon monoxide and hydrogen from carbon dioxide electrolyzer 1803 to an alcohol synthesis reactor 1813 that is configured to produce methanol or other alcohol. In certain embodiments, reactor 1813 is configured to receive additional hydrogen from a source apart from electrolyzer 1803. In some implementations, reactor 1813 is configured to produce alcohol in a manner similar to that of the methanol synthesis reactor 1205 in FIG. 12.

Reactor 1801 is configured to transport alcohol produced by alcohol synthesis reactor 1813 to a methanol to olefins reactor 1815 configured to convert the alcohol to one or more olefins including propylene. System 1801 is configured to transport propylene produced by reactor 1815 to oxalic acid synthesis reactor 1809. Methanol to olefins reactor 1815 may be configured to convert alcohol (e.g., methanol) to olefins by a reaction involving a network of chemical reactions in the presence of an acidic zeolite catalyst such as H-SAPO-34. The temperature and other parameters of the reactions may be tuned to produce a desired product, which is propylene in system 1801. In certain embodiments, system 1801 is configured to operate reactor 1815 at a temperature of about 600 to 650° C.

In various embodiments, a system employing a carbon dioxide electrolyzer to produce carbon monoxide and hydrogen is configured to produce methanol from the carbon monoxide and hydrogen by a method such as the methanol synthesis reactor 1205 in FIG. 12. The associated system is configured to provide the resulting methanol to a formate synthesis reactor, which may be configured to perform the BASF and/or Kemira-Leonard processes to produce methyl formate.

Purification Units

Various types of purification units may be employed for purifying or otherwise concentrating carbon monoxide produced by a carbon dioxide electrolyzer. Examples include amine absorption units (used with, e.g., gas streams having about $CO_2$ concentrations of about 20% by volume or lower), $CO_2$ adsorption units that take advantage of $CO_2$'s acidity, CO adsorption units (using, e.g., copper compounds), $CO/CO_2$ separation compositions such as molecular sieves and metal organic frameworks, cryogenic system (e.g., flash distillation systems), and membrane permeation units. In certain embodiments, a CO purification unit is configured to operate at a pressure of about 100 to 400 psia. An amine-based $CO_2$ absorption unit may employ an aqueous solution of an ethanol amine such as methyl diethanolamine MDEA, optionally with piperazine to enhance absorption kinetics. The amine absorbent may be regenerated by application of heat. An example unit employs a water solution of about 30% (weight) MDEA and 1% (weight) piperazine.

Cryogenic systems work by cooling the gas mixture and then passing through a fractionation column to separate gases by boiling point. Multiple fractionation columns may be used in a single process to separate and deliver purified components of gas mixtures.

A membrane purification process uses membranes that retain the desired product gas but are highly permeable to the impurities in the gas stream. Membranes are packaged into modules where a high-pressure gas mixture is input at the inlet. The membrane retains the desired product gas at high pressure and allows the undesired impurity gases to leave in a separate low-pressure stream. For CO purification, the membrane retains CO, but allows $H_2$ and $CO_2$ to pass through. Pure CO will exit in the product stream. $H_2$, $CO_2$, and a small volume of CO will leave in the waste stream. The low-pressure waste stream can be repressurized by a compressor and passed through another membrane stage to increase the recovery of CO product. Greater than 99% pure CO can result from a membrane-based separation process.

A sorption process for removing CO may be employed. Sorption processes may employ pressure swing, temperature swing, vacuum swing, or changes in other operating conditions (e.g. humidity swing). Sorbents are typically solids or liquids with a high affinity for the desired gas molecule under one operating condition extreme and a low affinity for the gas molecule under the other extreme of operating condition. For example, sorbents for CO under high pressure conditions (e.g., about 300 kPa, and about 40-60° C.) can capture CO (about 60-70 mol %) from a mixture of $CO_2$ and $H_2$. A system with 4 adsorption towers containing 8 L each of sorbent results in a flow rate of about 5-10 Nm3 of 99-99.9% pure product CO. Use of larger towers or additional stages allows for about 20-30% CO-containing gas mixtures to be upgraded to about 99% or greater purity. Sorbents for CO adsorption have been developed by Kobe steel using copper dopants in a solid matrix such as carbon, alumina, or silica.

Figure 19:
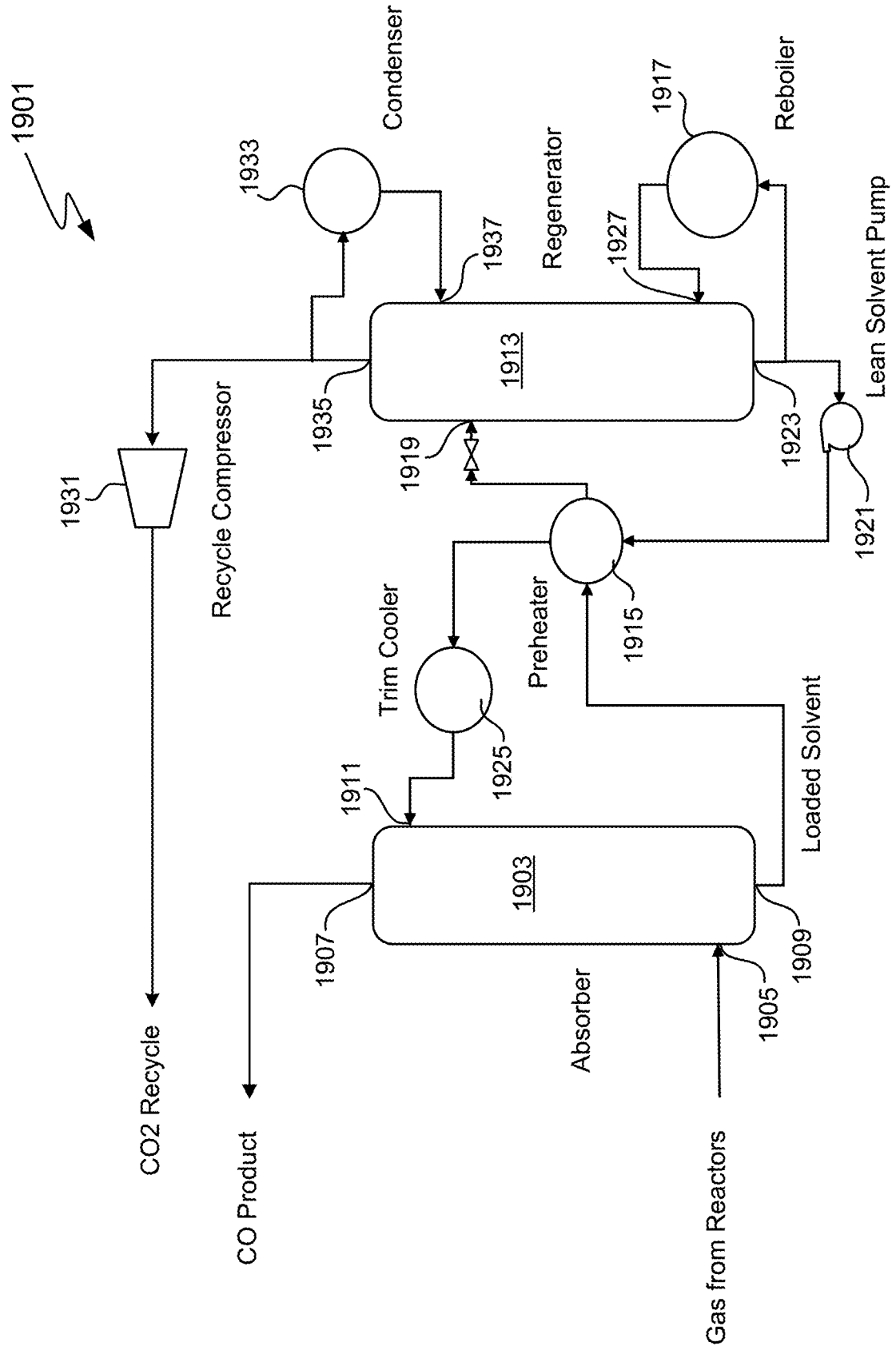
FIG. 19 depicts a system for verifying a carbon monoxide stream containing carbon dioxide and possibly other components such as hydrogen.

FIG. 19 depicts a system 1901 for verifying a carbon monoxide stream containing carbon dioxide and possibly other components such as hydrogen. As depicted, system 1901 includes an absorber 1903 configured to selectively remove carbon dioxide by contacting the carbon dioxide containing gas with absorbent material such as an ethanolamine. Absorber 1903 includes a gas inlet 1905 for receiving an inlet gas stream such as a gas stream from a carbon dioxide electrolyzer (not shown). Absorber 1903 also includes a gas outlet 1907 for releasing purified carbon monoxide.

Also, as depicted, absorber 1903 includes an inlet 1911 for receiving purified sorbent and an outlet 1909 for expelling loaded sorbent, e.g., sorbent containing higher concentrations of carbon dioxide than the sorbent entering the absorber 1903.

System 1901 also includes a regenerator 1913 configured to remove carbon dioxide expelled by absorber 1903 and thereby produce a regenerated sorbent material for reuse in the absorber 1903. In the depicted embodiment, the sorbent is regenerated by heating, which releases carbon dioxide. Heating occurs using a pre-heater 1915, and a reboiler 1917. Preheater 1915 is configured to receive loaded sorbent from the outlet 1909 of absorber 1903 and deliver the preheated sorbent to an inlet 1919 of regenerator 1913. Preheater 1915 receives some heat from lean sorbent on its way to absorber 1903 from regenerator 1913.

System 1901 is configured to transport lean sorbent from an outlet 1923 of regenerator 1913, using a lean solvent pump 1921, to preheater 1915, where the sorbent loses some of its heat. System 1901 is also configured to transport lean sorbent from preheater 1915 to absorber inlet 1911 via a trim cooler 1925. Trim cooler 1925 is configured to further cool the sorbent to a temperature where it can effectively do its job of removing $CO_2$ in absorber 1903. The trim cooler may be a water-cooled module.

As indicated, reboiler 1917 is configured to provide heat for regenerator 1913 to release carbon dioxide from loaded sorbent. As illustrated, reboiler 1917 is included in a recirculation loop that receives a fraction of the lean sorbent from regenerator outlet 1923 and returns heated lean sorbent to regenerator 1913 via an inlet 1927.

Additionally, system 1901 includes a recycle compressor 1931 configured to compress the carbon dioxide to, e.g., a pressure suitable for entering the carbon dioxide electrolyzer that produces the inlet carbon monoxide-containing stream.

System 1901 also includes a subsystem associated with regenerator 1913 that employs a condenser 1933 to condense some of the sorbent that may be included in the released carbon dioxide that exits regenerator 1913 through a gas outlet 1935. Note that condenser 1933 is configured to condense the sorbent and deliver it back to regenerator 1913 at a sorbent inlet 1937.

In some cases, a CO purifier is a hybrid system having two different purification subsystems connected in series. For example, a CO purifier may have a cryogenic subsystem upstream from sorbent subsystem. Hybrid systems may be used, for example, in systems where the input CO stream has a relatively low concentration carbon monoxide such as below about 70% molar.

Figure 20:
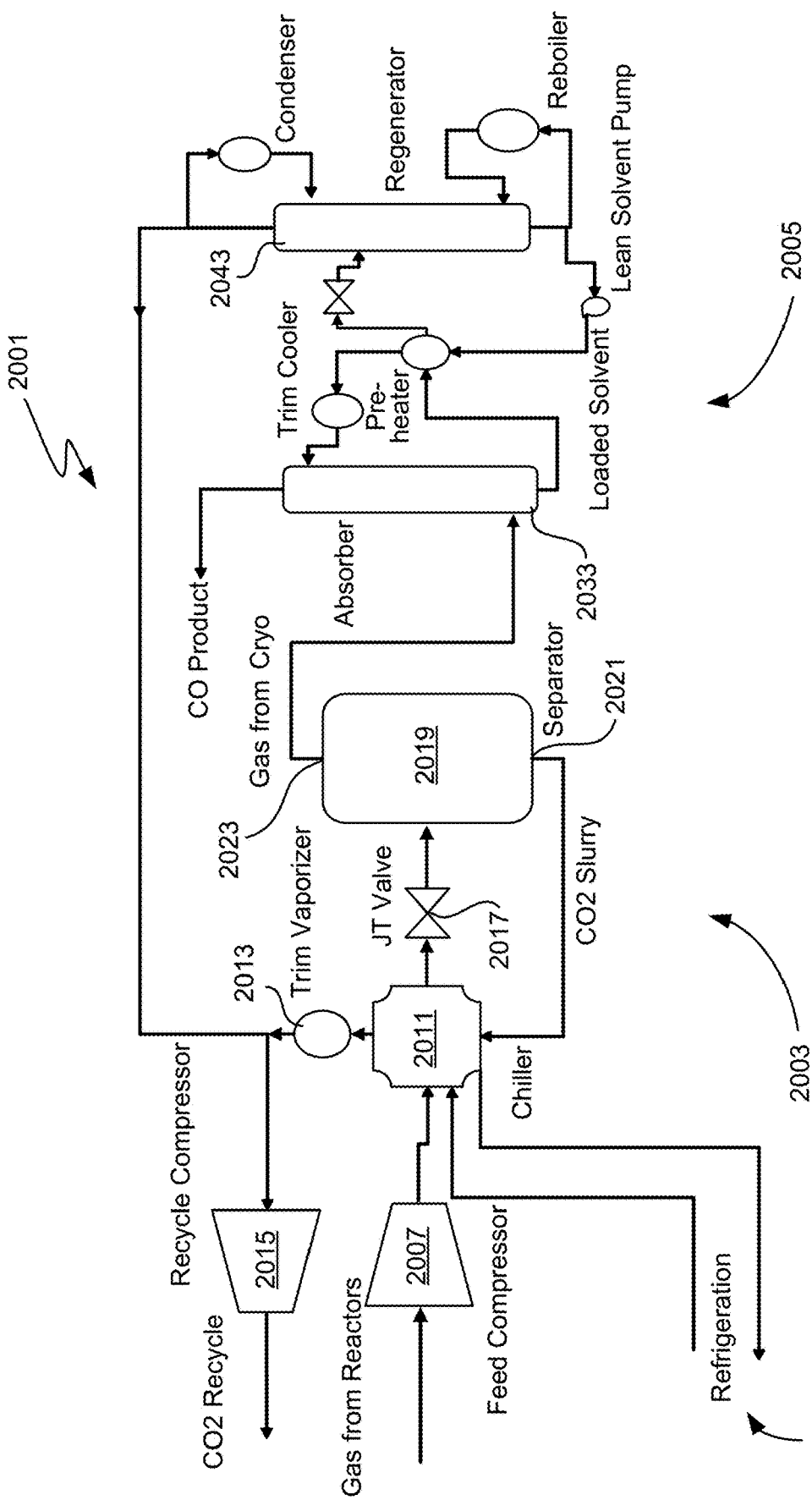
FIG. 20 illustrates a hybrid carbon monoxide purification system having a cryogenic preprocessing subsystem and a sorbent postprocessing subsystem.

FIG. 20 illustrates a hybrid carbon monoxide purification system 2001 having a cryogenic preprocessing subsystem 2003 and a sorbent postprocessing subsystem 2005. The first phase of the system 2001 is the cryogenic subsystem 2003, which is configured to partially concentrate the carbon monoxide. In certain embodiments, the cryogenic subsystem is configured to concentrate carbon monoxide to a level of at least about 70% by volume.

As depicted, cryogenic preprocessing subsystem 2003 is configured to feed product gas from, e.g., a carbon dioxide electrolyzer (not shown) to a compressor 2007 which is configured to compress the gas to a defined pressure or density. System 2001 is configured to transport the compressed gas from compressor 2007 to a chiller 2011 configured to reduce the temperature of the compressed gas. Chiller 2011 is coupled to a refrigeration system 2009, configured to remove sufficient heat from Chiller 2011 to maintain the compressed gas at or below a desired temperature.

Chiller 2011 is configured to chill the compressed gas to a reduced temperature. Chiller 2011 is also configured to receive a $CO_2$ slurry (which provides a reduced temperature) from a separator 2019 and release the $CO_2$ to a trim vaporizer 2013 configured to release vaporized carbon dioxide. The vaporized carbon dioxide from trim vaporizer 2013 may be transported by system 2001 to a recycle compressor 2015, configured to provide pressurized carbon dioxide suitable for feed to the cathode side of the carbon dioxide electrolyzer.

In the depicted embodiment, cryogenic subsystem 2003 is configured to provide chilled and compressed from an output of chiller 2011 to a Joule Thompson valve 2017 configured to rapidly expand the compressed gas and thereby further cool the gas. This action may sufficiently cool the gas to convert some of the gaseous $CO_2$ into liquid or solid or slurry. Regardless, the cold gas is provided to separator 2019 connected to the Joule Thompson valve 2017 and having a carbon dioxide slurry outlet 2021 and a partially purified carbon monoxide gas stream outlet 2023. In certain embodiments, the partially purified carbon monoxide stream has a concentration of at least about 50% molar or at least about 70% molar.

In the depicted embodiment, system 2001 is configured to provide the partially purified carbon monoxide gas stream from outlet 2023 to the sorbent postprocessing subsystem 2005, which in the depicted embodiment is configured similarly to the entire sorbent system 1901. As depicted, subsystem 2005 has an absorber 2033 configured to absorb carbon dioxide from the partially purified CO stream and output purified CO gas. Subsystem 2005 also has sorbent regenerator 2043. Other components of subsystem 2005 include a sorbent trim cooler, a sorbent preheater, a lean sorbent pump, a sorbent reboiler, and a sorbent condenser.

While the discussion of FIGS. 19 and 20, as well as the other discussion of carbon monoxide purifiers describes cases that involve removal of carbon dioxide, carbon monoxide purifiers may additionally or alternatively be configured to remove other impurity gases such as sulfur containing gases (e.g., sulfur oxides).

Supplemental Hydrogen Sources

In certain embodiments, an integrated system employing a carbon oxide electrolyzer includes an additional source of hydrogen (beyond that generated from the electrolyzer) or are configured to receive additional hydrogen from an external source. Examples of integrated systems that may employ additional sources of hydrogen include Fischer Tropsch systems, polycarbonate production systems, ethylene glycol production systems, polyethylene terephthalate production systems, methanol, butanol, and/or other alcohol production systems, acetic acid production systems, isocyanate production systems, polyurethane production systems, and oxalic production systems. In certain embodiments, the additional source of hydrogen is a water electrolyzer such a proton exchange membrane water electrolyzer. In some implementation, a water electrolyzer shares electrical infrastructure with a carbon oxide reduction electrolyzer. In certain embodiments, the additional source of hydrogen is or comprises units configured to perform (a) steam reforming, thermal cracking, and/or partial oxidation of methane, fuel oil, petroleum coke, and/or other fossil fuels, coal gasification, (b) steam methane reforming, (c) gasification, pyrolysis, and/or other high temperature conversion of biomass, municipal solid waste, and/or other waste sources, (d) pressure swing adsorption of refinery waste streams, (e) separation of hydrogen byproduct from industrial reactions such as molten salt chlorine production, and/or (f) dissociation of water by, e.g., solar/thermal energy. In certain embodiments, methane or other simple hydrocarbon used in one or more these units is derived from biogas.

Recovery of Carbon Dioxide from Electrolyzer Output

In many implementations, the product gas exiting the cathode of a carbon dioxide electrolyzer includes a significant fraction of unreacted carbon dioxide. For example, the product gas may contain between about 10 and 70% molar carbon dioxide. In certain embodiments, a system includes carbon dioxide recovery unit arranged to receive product gas from a carbon dioxide electrolyzer and produce a concentrated carbon dioxide product, which may optionally be recycled to the electrolyzer. In one example, carbon dioxide recovery unit comprises a direct air carbon dioxide recovery module such as described elsewhere herein. It should be understood that the product gas from a carbon dioxide electrolyzer may contain a much higher concentration of carbon dioxide than air. Therefore, a direct air capture unit used with an electrolyzer may have a modified configuration compared to a corresponding unit used for direct air capture. As examples, the direct air capture unit may employ temperature swing absorption, pressure swing absorption, or electro-swing absorption.

Figure 21A:
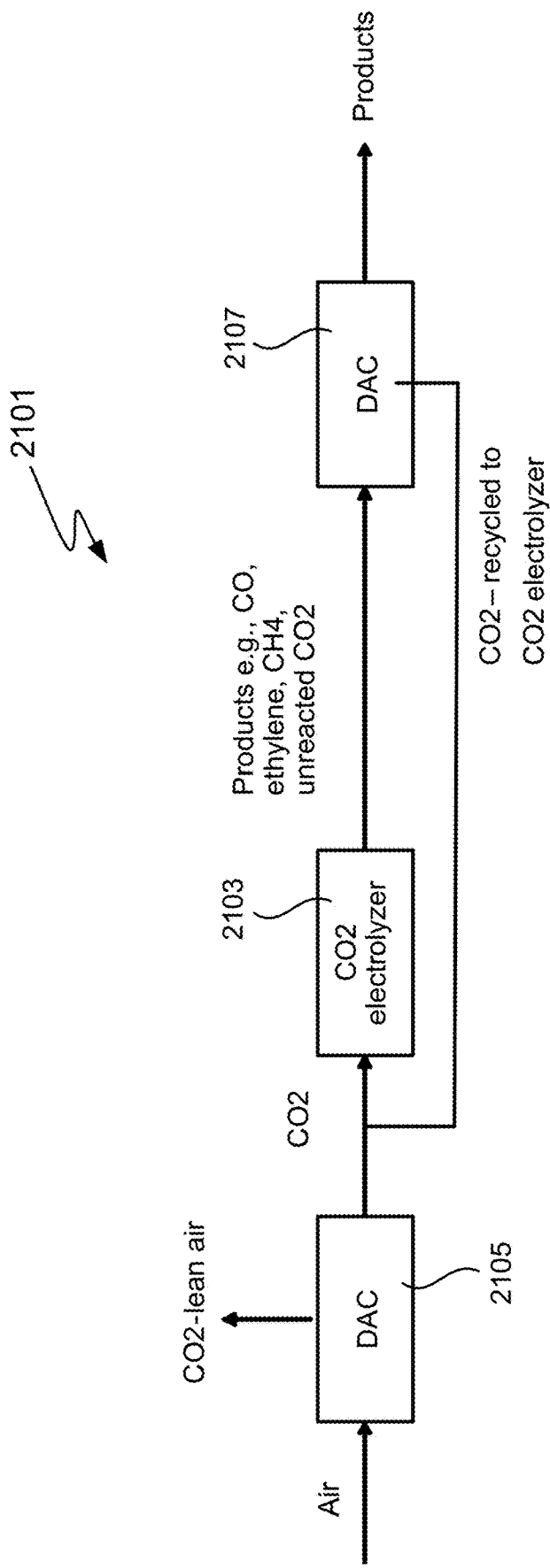
FIG. 21A illustrates a system having an upstream DAC unit configured concentrate carbon dioxide from air, and a downstream DAC unit configured to remove unreacted $CO_2$ from product gas of a carbon dioxide electrolyzer.

FIG. 21A illustrates a system 2101 having an upstream DAC unit 2105 configured concentrate carbon dioxide from air, and a downstream DAC unit 2107 configured to remove unreacted $CO_2$ from product gas of a carbon dioxide electrolyzer 2103. System 2101 is configured to combine the purified unreacted carbon dioxide with fresh carbon dioxide from the upstream DAC unit 2105 and introduce it to the electrolyzer 2103. The downstream DAC unit 2107 may be designed differently from the upstream DAC unit 2105 (e.g., amount of solvent, dimensions of contactor) in order to address the significantly different concentrations of carbon dioxide in air versus in the product gas.

Figure 21B:
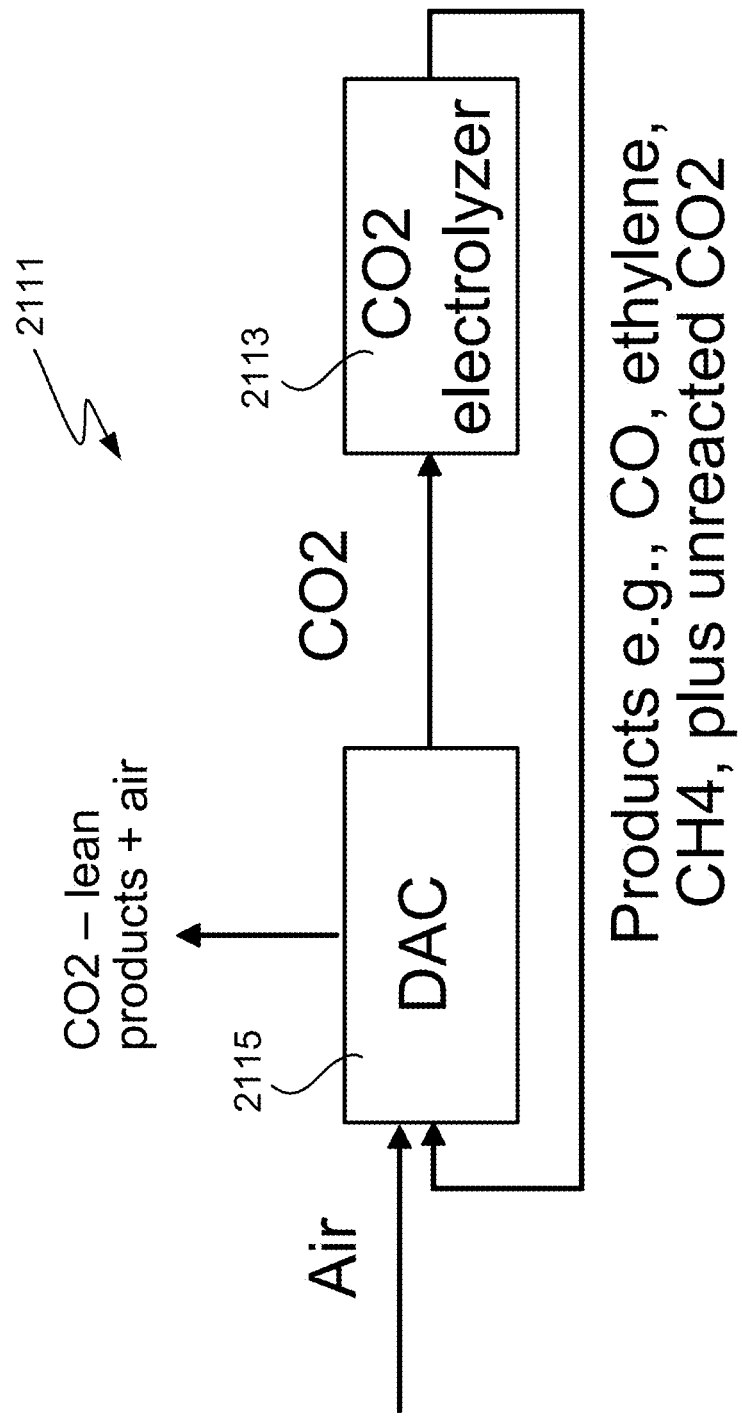
FIG. 21B illustrates a system having a DAC unit configured to capture carbon dioxide from air and separate unreacted carbon dioxide from product gas of an electrolyzer.

FIG. 21B illustrates a system 2111 having a DAC unit 2115 configured to capture carbon dioxide from air and separate unreacted carbon dioxide from product gas of an electrolyzer 2113. System 2111 is configured to feed the separated carbon dioxide into the electrolyzer 2113. The carbon dioxide-lean products and carbon dioxide-lean air leave DAC unit 2115 for downstream processing.

Integration with the Electrical Grid

When the source of electrical energy for a grid is not directly controllable in response to demand, various problems may arise. Solar, wind, and certain other non-combustion-based sources of electrical energy are examples of sources where the energy generation is decoupled from energy demand.

When a renewable energy source is connected to an electrical grid, fluctuations in wind speed or sunlight intensity may lower the amount of power available on the grid to a point where the demand exceeds supply. This may lower the frequency of the grid, which can damage some electrical equipment and/or cause a brown out or black out.

To prevent this, a flexible power generator and consumer may be used in conjunction with a renewable power source. Such component may facilitate electrical grid load leveling system and be configured to draw a flexible load from the grid, reducing power demand when necessary to prevent demand from approaching the supply. This can provide frequency stabilization to the grid to allow it to operate with high amounts of renewable electricity.

Various approaches have been proposed to store the excess energy generated when supply outstrips demand. Examples include water reservoirs, batteries, and water electrolyzers. Using batteries, as an example, to store excess energy on a grid requires a large number of high capacity batteries to provide sufficient capacity to store the maximum excess energy that energy sources on the grid may produce.

By comparison, a carbon oxide electrolyzer may store excess energy in the form of a liquid or a gas, which is relatively easy to store. And, compared to water electrolyzers, a carbon oxide reduction cell can be operated in a manner that produces liquid products rather than gaseous products. Liquid products may be easier to store, particularly given their relatively higher density.

The products of a carbon oxide electrolyzer can be used as fuel for generating electrical energy to put on the grid in periods where demand may exceed supply. The electrolyzer products may be combusted in a turbine or other mechanical source of electrical power and/or electrochemically consumed in a fuel cell to directly produce electrical power. In certain embodiments, a carbon oxide electrolyzer output such as carbon monoxide or methanol is stored for later use in a fuel cell to directly inject electrical energy back into the grid. In certain embodiments, the fuel cell is a fuel cell configured to oxidize carbon-containing reactants (e.g., natural gas) such as a solid oxide fuel cell from Bloom Energy of Sunnyvale, CA.

$CO_2$ electrolysis products can be gas (e.g. CO, methane, ethylene) or liquid phase (e.g. ethanol, methanol, ethylene glycol). Liquid products have the advantage of being easy to store for extended periods of time. Gas phase products can be converted to liquid-phase chemical compounds through a range of downstream processes, such as gas fermentation or thermochemical reactions. Gas and liquid phase products can also be used to make solid materials. For example, CO is one of the inputs needed to make polycarbonate or can react with potassium hydroxide to make potassium formate.

Figure 22A:
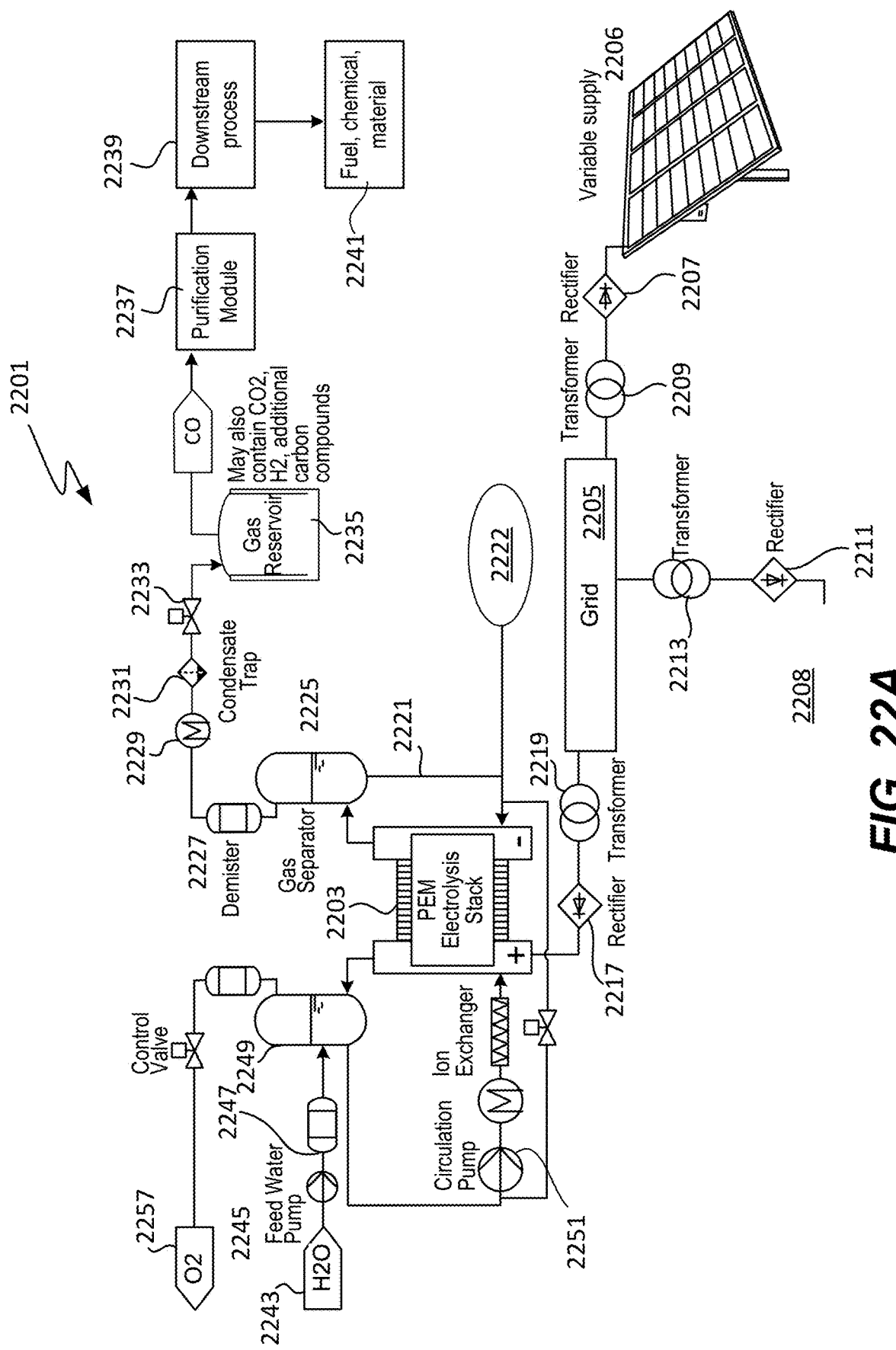
FIG. 22A depicts a system that couples a carbon oxide reduction electrolyzer to an electrical grid or other source of electrical energy.

FIG. 22A depicts a system 2201 that couples a carbon oxide reduction electrolyzer 2203 to an electrical grid 2205 or other source of electrical energy. This system 2201 may be configured to operate in a manner that stores excess energy generated by the electrical system when the energy being produced exceeds the demand for electrical energy.

In system 2201, a variable electrical energy source 2206 generates electrical energy that is optionally provided to an electrical grid 2205. In the depicted embodiment energy source 2206 is coupled to the grid 2205 via an electrical line having a rectifier 2207 and a transformer 2209. These and/or other electrical elements may be employed to provide the electrical energy from the variable source 2206 to the grid 2205 at an appropriate voltage and waveform, In the depicted embodiment, the grid 2205 is connected to a demand for electrical energy that is approximately constant, at least compared to the variability of the electrical energy supply 2206. In the depicted embodiment, the demand is illustrated by element 2208, which generically represents one or more electrical energy consumers such as residential and/or industrial consumers. For many applications, the energy consumers require electrical energy at a voltage and electrical waveform that can be produced by a rectifier 2211 and a transformer 2213. As shown, these elements are provided between the grid 2205 and the demand 2208.

As indicated, the depicted embodiment provides an electrolytic carbon oxide reduction cell or stack 2203, which is configured to consume excess electrical energy from the grid or other electrical energy system by converting the excess energy to chemical products of electrolytic carbon oxide reduction. If this cell or stack 2203 receives electrical energy directly from a grid, it may require that the electrical energy be rectified and transformed such as by a rectifier 2217, a transformer 2219, and/or other electrical components.

A cathode side of the electrolyzer 2203 receives a carbon oxide reactant (carbon dioxide and/or carbon monoxide) via an inlet line. The carbon oxide may be provided by any one or more of many possible sources or feedstocks 2222 such as those described elsewhere herein.

The cathode is configured to produce a product such as a gaseous or liquid C1 compound (e.g., carbon monoxide, methane, formaldehyde, or formic acid) or a gaseous or liquid higher carbon compound such as ethylene. Such product along with other components are removed from the electrolyzer 2203 via an outlet line. In certain embodiments, the outlet gas, which may be humidified, is provided to a gas separator 2225. Which condenses water and/or one or more liquid products. Unreacted carbon oxide and/or water may be provided back to the carbon oxide electrolyzer 2203 via a line 2221. In certain embodiments, carbon oxide supplied to the electrolyzer is humidified to facilitate the reduction reaction.

In the depicted embodiment, various optional components are provided downstream from the cathode side of the electrolyzer 2203. These include a demister 2227, a mass flow meter or controller 2229, a condensate trap 2231, a valve 2233, a gas reservoir 2235, a purification module 2237, and a product conversion system/reactor 2239. A resulting fuel, chemical, or other material 2241 is appropriately stored or used. As mentioned, the chemical products of electrolyzer 2203 store the excess energy produced by the variable energy source. That energy may be recovered by converting the chemical energy stored in the products to thermal or electrical energy by combustion, fuel cell operation, etc. Alternatively, the energy is not recovered, at least not in the near term, and the electrochemical reduction products are converted to another useful commodity such as a plastic.

The electrolyzer 2203 also contains an anode that receives an anode reactant such as water that is electrolytically oxidized at the anode. In the depicted embodiment, a source of water 2243 is provided to the anode of cell 2203 via one or more optional components such as a feed water pump 2245, a demister 2247, a gas separation unit 2249—which also has an inlet for receiving product from the anode, which product may include water vapor and oxygen—a circulation pump 2251, a mass flow meter or controller, and an ion exchanger configured to remove ions or other components of the anode water that could be deleterious to the operation of the electrolyzer 2203. In certain embodiments system 2201 contains a line connecting the anode water recirculation loop to the carbon oxide inlet line 2221 to humidify the carbon oxide delivered to the cathode side of electrolyzer 2203.

The system 2201 may also have one or more components for removing oxygen or other product of the electrolyzer 2203. The anode side of electrolyzer 2203 includes an outlet line 22057 configured to remove oxygen or other product from the electrolyzer. Outlet line 2207 connects with separation unit 2249. The oxygen and water in the anode product stream may be separated from one another in unit 2249, so that the water can be recycle back to the anode via the circulation pump 2251.

System 2201 may be configured with components for removing oxygen or other gaseous product of the anode. In the depicted embodiment, these components are a demister 2259 and a control valve 2261.

In these examples and throughout the disclosure, the described systems may be provided in a facility, a plant, or a complex of buildings. In some embodiments, all or many reactors and units and/or modules of a system are provided in a common factory, plant, or complex. For example, a system for producing a particular material such as a polycarbonate polymer or transportation fuel may comprise a carbon oxide electrolyzer and one or more other reactors that utilize a product of the electrolyzer and/or provide a reactant to the electrolyzer, and the electrolyzer and other reactors are provided in a single building or plant. In some cases, one or more system components is provided in the exterior environment. For example, a direct air capture unit may be provided outside, while a carbon dioxide electrolyzer is located inside a building, even though the system is configured to provide carbon dioxide from the direct air capture unit to the electrolyzer.

Figure 22B:
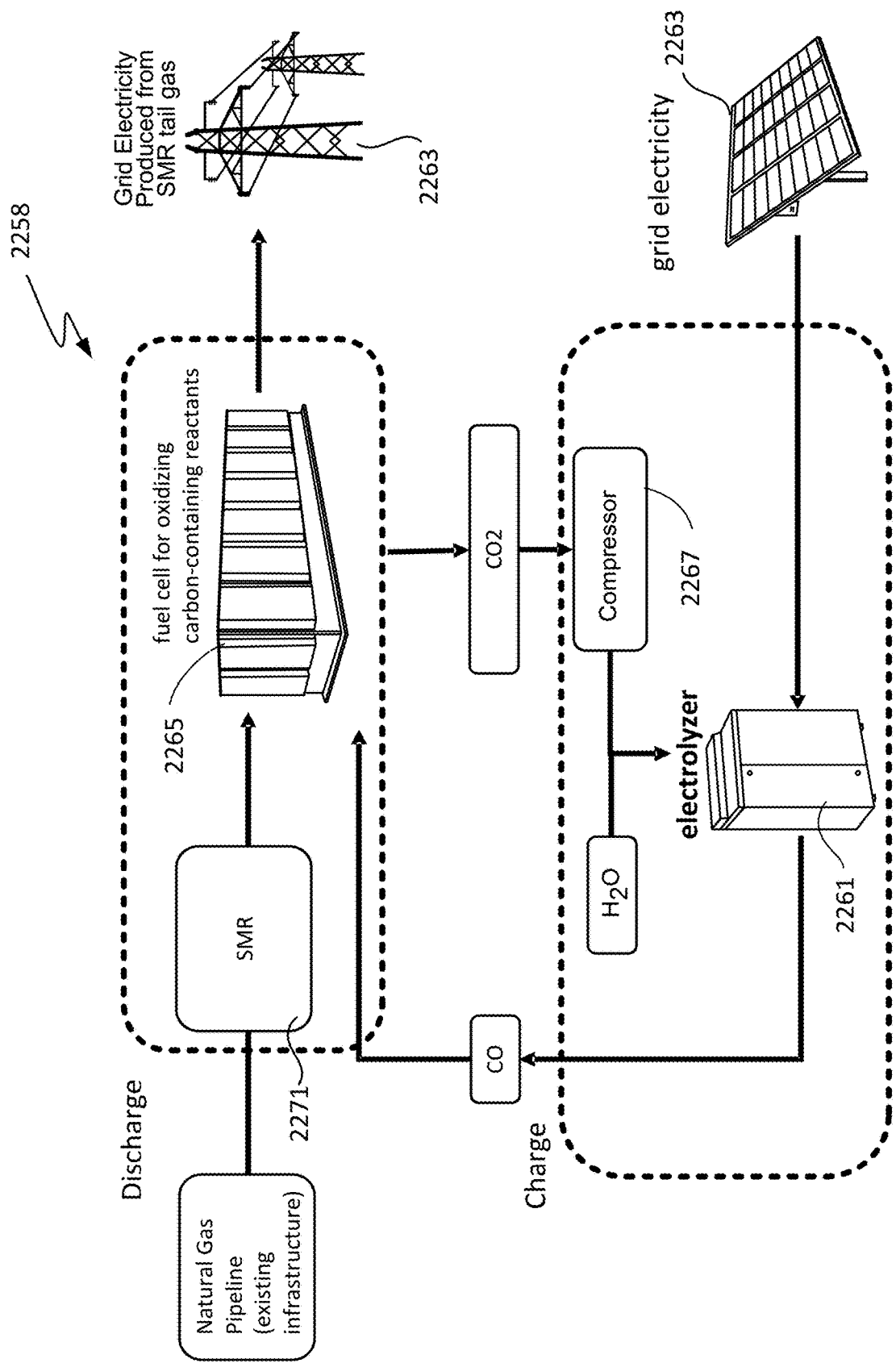
FIGS. 22B and 22C depict further examples of grid management systems employing carbon oxide electrolyzers.
Figure 22C:
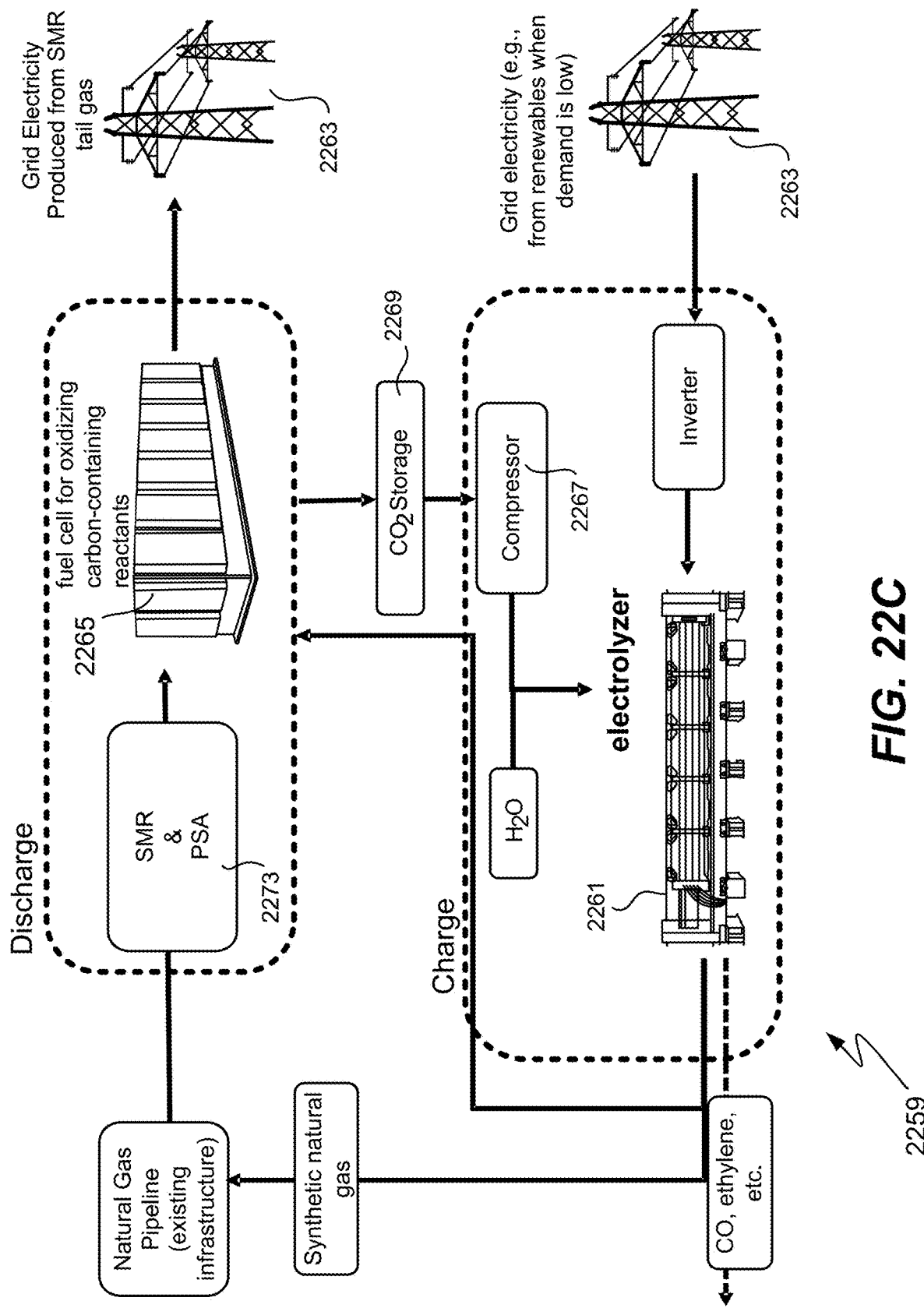

Further examples of grid management systems employing electrolyzers are depicted in FIGS. 22B and 22C. As depicted, systems 2258 and 2259 employ fuel cells configured to oxidize carbon containing reactants (e.g., methane or natural gas) such as solid oxide fuel cells from Bloom Energy as mentioned above. In the depicted embodiments, a carbon oxide electrolyzer 2261 is coupled to a grid or other source of electrical energy 2263 such as a device configured to generate electricity from wind, solar, or other renewable energy source. In addition to electrical energy, electrolyzer 2261 receives carbon dioxide and water as inputs. In certain embodiments, the carbon dioxide input is received, at least in part, from output of a fuel cell 2265. A compressor 2267 may be provided to compress such carbon dioxide before delivery to electrolyzer 2261.

As depicted in the embodiment of FIG. 22B, electrolyzer 2261 is configured to output carbon monoxide, and system 2258 is configured to deliver the carbon monoxide to fuel cell 2265. System 2258 may be further configured to provide natural gas or other input to fuel cell 2265, which is in turn configured to generate electricity that may be provide to grid 2263. In some implementations, system 2258 includes a steam methane reformer unit 2271 configured to produce hydrogen for input to the fuel cell 2265.

As depicted in the embodiment of FIG. 22C, electrolyzer 2261 is configured to output any one or more of various compounds including carbon monoxide, ethylene, methane, and the like. In certain embodiments, one or more of these compounds is removed from system 2259 for purposes potentially unrelated to electrical load leveling. For example, one or more of the compounds may be used as a feed stock for synthesizing a compound or polymer such as described elsewhere herein.

In the depicted embodiment, system 2259 is configured to deliver at least some of the output of electrolyzer 2261 to fuel cell 2265, optionally together with natural gas or other fuel from an external source. In certain embodiments, output from electrolyzer 2261 is provided as a synthetic natural gas or is converted to form such gas. System 2259 is configured to supply the synthetic natural gas alone or with other natural gas to fuel cell 2265. In certain embodiments, system 2259 is configured to provide carbon monoxide and/or other output of electrolyzer 2261 directly to fuel cell 2265. In some implementations, system 2259 includes a steam methane reformer and/or a pressure swing absorption unit 2273 or other purification unit configured to process gas before it is input fuel cell 2265. A steam methane reformer may convert methane from a natural gas source and/or the electrolyzer to hydrogen for delivery to the fuel cell 2265. A pressure swing absorption unit may be used to remove some carbon dioxide or other impurity from the inlet stream to the fuel cell 2265. In some embodiments, another type of impurity removal unit is employed.

In certain embodiments such as those depicted in FIG. 22B and/or FIG. 22C, a pressure swing absorber or other gas purification unit is configured to separate a pure hydrogen stream from the gas mixture exiting a steam methane reformer. The tail gas from the reformer may include CO, $CO_2$, unreacted $CH_4$, and some $H_2$. The tail gas is fed to the fuel cell, which, in turn, produces a stream of relatively pure $CO_2$ (and water) which is then fed to the $CO_2$ electrolyzer. Some steam methane reformers are configured to make a product having a relatively high concentration of hydrogen by employing a water gas shift reaction after the reforming reaction. The water gas shift reaction converts carbon monoxide and water (reactants) into carbon dioxide and hydrogen. In some implementations, steam methane reformers are configured to make a syngas mixture and may not implement the water gas shift step.

In some implementations such as those depicted in FIG. 22B and/or FIG. 22C, a steam methane reformer produces two $CO_2$-containing streams: (1) the tail gas, as described above, which comes from the reactor, and (2) flue gas, which comes from the furnaces that are used to heat the reactor tubes and generate steam for the reaction. The tail gas may contain fairly high concentrations of carbon dioxide (e.g., about 15% before separation and then about 50% after separation). The flue gas has a relatively lower concentration of carbon dioxide (e.g., only about 3-5% $CO_2$ concentration). In various implementations, about two thirds of the carbon dioxide emissions are from the tail gas, and about one-third are from the flue gas. In certain embodiments, the system is configured to capture emissions from (a) the tail gas before the purification (e.g., with a pressure swing absorber), (b) the tail gas after the purification, (c) the flue gas, or (d) a combined stream from flue gas and the tail gas. In some implementations, a system is configured to feed oxygen from a carbon oxide electrolyzer into one or more furnaces of a steam methane reformer. In some implementations, this provides higher efficiency and/or yields a higher carbon dioxide concentration in the flue gas, thereby simplifying carbon dioxide capture.

Fuel cell 2265 is configured to output electricity that may be delivered to grid 2263. In certain embodiments, system 2259 comprises a carbon dioxide storage unit 2269 configured to store carbon dioxide output from fuel cell 2265 prior to use by electrolyzer 2261.

Syngas Preparation

Embodiments described in this section and/or illustrated in FIGS. 23A-D pertain to making mixtures of carbon monoxide and hydrogen. Some of these mixtures may be referred to as syngas. The embodiments described here concern methods and systems configured to receive a mixture of carbon monoxide, carbon dioxide, and hydrogen and modify the mixture to produce a mixture of carbon monoxide and hydrogen having a particular composition. In some cases, the input is a gaseous mixture obtained from a carbon oxide electrolyzer such as one of the carbon oxide electrolyzers described herein.

A carbon monoxide and hydrogen mixture produced as described here may have various applications. It can be used to produce a naphtha or other liquid hydrocarbon composition such as may be produced by a Fischer Tropsch process (see e.g., the discussion of FIGS. 6A and 6B). It can also be used as an input to a gas fermentation reactor (see e.g., FIGS. 4 and 5). It can also be sued to produce any of various chemicals such as alcohols (see e.g., FIGS. 15 and 18) and/or polyols (see e.g., FIGS. 14 and 16).

Various embodiments for producing a mixture of carbon monoxide and hydrogen may employ carbon oxide separator system such as described in relation to FIGS. 19 and 20.

A mixture of carbon monoxide and hydrogen may be produced by directly removing either CO or $CO_2$ from an input stream. In embodiments that produce the mixture by directly separating CO from the input stream, hydrogen may be added to a purified CO stream downstream from a CO purification operation. For example, purified hydrogen may be prepared by separating it from $CO_2$ in an operation that is downstream from the CO separation operation.

Figure 23A:
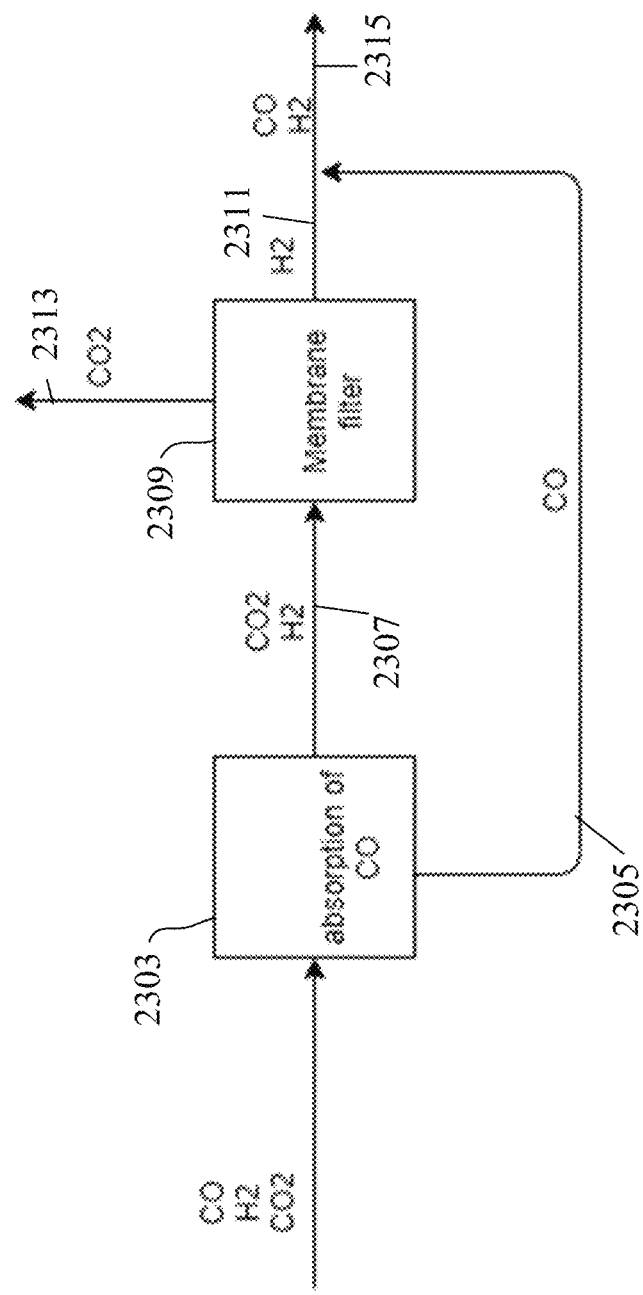
FIG. 23A depicts a system for producing a mixture of hydrogen and carbon monoxide by processing carbon dioxide electrolyzer output to first remove carbon monoxide and then remove hydrogen from a carbon dioxide-containing stream.

FIG. 23A depicts a general scheme for producing a mixture of carbon monoxide and hydrogen in a process that separates carbon monoxide directly from the input stream. The input stream, which may be provided from the cathode outlet of a carbon dioxide electrolyzer, contains carbon dioxide, carbon monoxide, hydrogen, and optionally other components such as small amounts of water and/or hydrocarbon(s). The input stream is fed to one or more separation elements 2303 configured to produce one stream 2305 containing purified carbon monoxide and another stream 2307 containing a mixture of carbon dioxide and hydrogen. Element(s) 2303 may include, for example, a CO absorption element and/or a CO absorption and stripping subsystem such as a pressure swing or temperature swing subsystem. Steam 2307 is fed to one or more elements 2309 configured to separate hydrogen from carbon dioxide. In some embodiments, element(s) 2309 contain a membrane separator that, e.g., blocks passage of carbon dioxide while allowing passage of hydrogen. In operation, element(s) 2309 produce a hydrogen stream 2311 and a carbon dioxide stream 2313. Hydrogen stream 2311 may be combined with carbon monoxide stream 2305 to produce a stream 2315 containing a mixture of carbon monoxide and hydrogen. Carbon dioxide stream 2313 may be, optionally, recycled to a carbon oxide electrolyzer.

In some embodiments, a process of making a mixture of hydrogen and carbon monoxide may be characterized by the following operations:
1. Separation of CO from the mixture by, e.g., ionic liquid absorption in a pressure swing absorption process
2. Separate $H_2$ from $CO_2$ via, e.g., a membrane
3. Mix $H_2$ and CO In certain embodiments for producing purified carbon monoxide directly from the input stream, an ionic liquid is used to strip the carbon monoxide from an input gas stream. During the separation, the ionic liquid contacts the input gas and selectively absorbs the carbon monoxide while allowing most of the hydrogen and carbon dioxide to pass (undissolved or unabsorbed). In some embodiments, the input stream contacts ionic liquid in an absorption column. After contacting, the input stream, a carbon monoxide rich stream of ionic liquid is fed to a stripper which operates under conditions that strip carbon monoxide from the ionic liquid. A resulting lean stream of ionic liquid may be recycled back to the component(s) that selectively absorb carbon monoxide.

Suitable ionic liquids for separating carbon monoxide preferentially absorb carbon monoxide without substantially absorbing carbon dioxide and/or hydrogen. Other characteristics may include low cost, low vapor pressure (e.g., no production of volatile organic compounds during use), low kinematic viscosity (e.g., below about 150 cSt), moderate absorption conditions (e.g., temperature of about 0° C. to 20° C.; pressure of about 25 bar or lower (e.g., about 17 bar)), moderate stripping conditions (e.g., temperature of about 0-100° C. or lower; pressure of about 5 bar or lower), and/or low toxicity. Examples of such ionic liquids include 1-hexyl-3-methylimidazolium chloride (with cuprous chloride).

In some embodiments, a mixture of carbon monoxide and hydrogen is produced by directly removing carbon dioxide from an input stream containing carbon monoxide, hydrogen, and carbon dioxide. In such embodiments, one output stream of the separation includes a desired mixture of hydrogen and carbon monoxide.

Figure 23B:
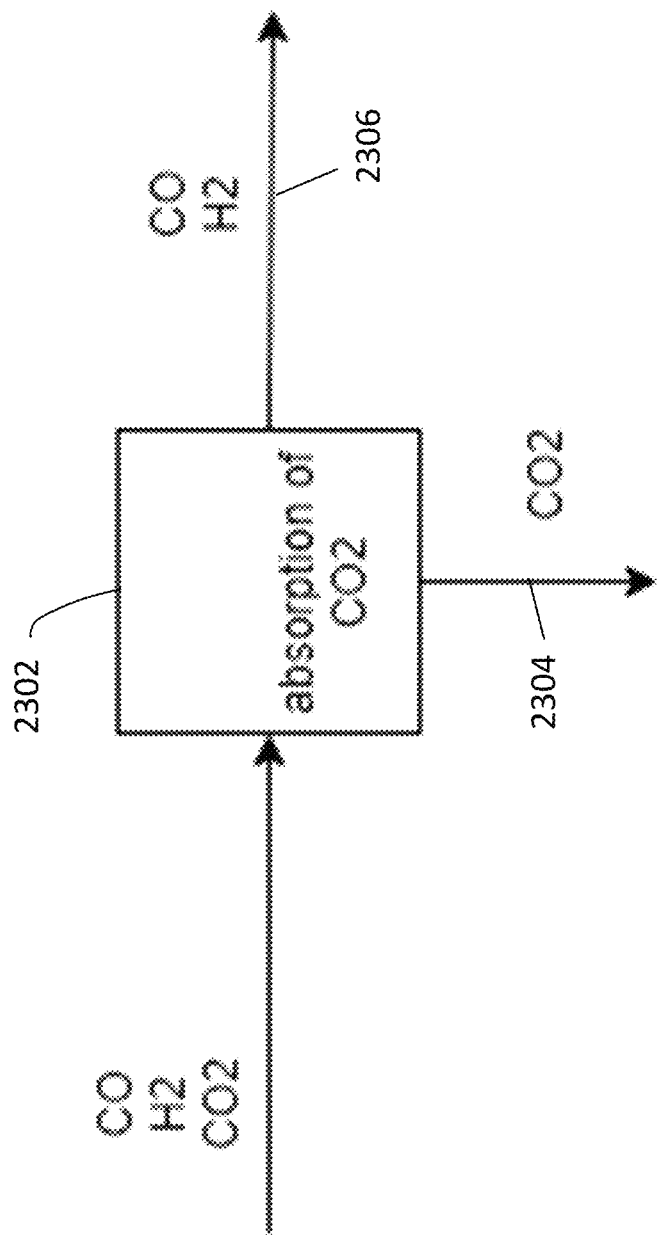
FIG. 23B depicts a system for producing a mixture of hydrogen and carbon monoxide by processing carbon dioxide electrolyzer output to directly remove carbon dioxide.

FIG. 23B depicts a general scheme for producing a mixture of carbon monoxide and hydrogen in a process that separates carbon dioxide directly from the input stream. The input stream, which may be provided from the cathode outlet of a carbon dioxide electrolyzer, contains carbon dioxide, carbon monoxide, hydrogen, and optionally other components such as small amounts of water and/or hydrocarbon(s). The input stream is fed to one or more elements 2302 configured to produce a carbon dioxide stream 2304 containing purified carbon dioxide and another stream 2306 containing a mixture of carbon monoxide and hydrogen. Element(s) 2302 may include, for example, a carbon dioxide absorption element or a subsystem containing carbon dioxide absorption and stripping elements such as a pressure swing or temperature swing subsystem. Carbon dioxide stream may be, optionally, recycled to a carbon oxide electrolyzer.

In certain embodiments for removing carbon dioxide directly from the input stream, an ionic liquid is used to strip the carbon dioxide from an input gas stream. The ionic liquid contacts the input gas and selectively absorbs the carbon dioxide while allowing most of the hydrogen and carbon monoxide to pass. In some embodiments, the input stream contacts ionic liquid in an absorption column. After contacting, the input stream, a carbon dioxide rich stream of ionic liquid is fed to a stripper which operates under conditions that strip carbon dioxide from the ionic liquid. A resulting lean stream of ionic liquid may be recycled back to the component(s) that selectively absorb carbon dioxide.

Suitable ionic liquids for separating carbon dioxide preferentially absorb carbon dioxide without substantially absorbing carbon monoxide and/or hydrogen. Other characteristics may include low cost, low vapor pressure (e.g., no production of volatile organic compounds during use), low kinematic viscosity (e.g., below about 150 cSt), moderate absorption conditions (e.g., temperature of about 15° C. or higher; pressure of about 50 bar or lower), moderate stripping conditions (e.g., temperature of about 0-100° C. or lower; pressure of about 5 bar or lower), and/or low toxicity. Examples of such ionic liquids include 1-Butyl-3-methylimidazolium hexafluorophosphate [bmim][PF6].

In some implementations, a system configured to produce a mixture of carbon monoxide and hydrogen contains no components configured to cool an input or outstream below about 30° C. or below about 20° C. or below about 10° C. For example, the system does not include a compressor to chill the inlet gas below about 20° C.

CO Separation Example

As explained, carbon monoxide and hydrogen are included in output from a carbon dioxide electrolyzer. This electrolyzer output gas serves as an input to separation system that produces a mixture of carbon monoxide and hydrogen. In some embodiments, the carbon monoxide is recovered from the gas stream by a pressure swing absorption process using an ionic liquid such as 1-hexyl-3-methylimidazolium chloride (CuCl).

A pressurized inlet gas stream enters at the bottom of the absorption column, while absorbent is sprayed from the column's top. A packed bed may enhance the contact between the gas and liquid phase and facilitate carbon monoxide absorption. The remaining gas compounds ($CO_2$, $H_2$, and minor leftover CO) leave from the column's top while CO enriched liquid phase leaves from the column's bottom.

In certain embodiments, the absorbent includes a mixture of CuCl and the ionic liquid (e.g., about 50% mol CuCl and 50% mol ionic liquid 1-hexyl-3-methylimidazolium chloride). The inlet molar amount of CuCl may be about 1.5 to 2.5 times (e.g., about 1.9 times) larger than the amount of carbon monoxide to be absorbed.

The CO enriched liquid phase is heated in a heat exchanger and then enters a stripping column. The stripping column's pressure may be less than 2 bar (e.g., approximately atmospheric), while temperature may be relatively low at the top (e.g., about 30° C.) to relatively high at the bottom (e.g., about 60° C.). Under these conditions, most of the CO may evaporate. The liquid phase flows to the bottom of the column, where some fraction (e.g., about 15%) is recirculated back to the column using, e.g., a total reboiler, while the remaining (e.g., about 85%) flows back to the absorption column. In certain embodiments, boiled liquid coming from a reboiler transfers heat to the incoming stream.

Figure 23C:
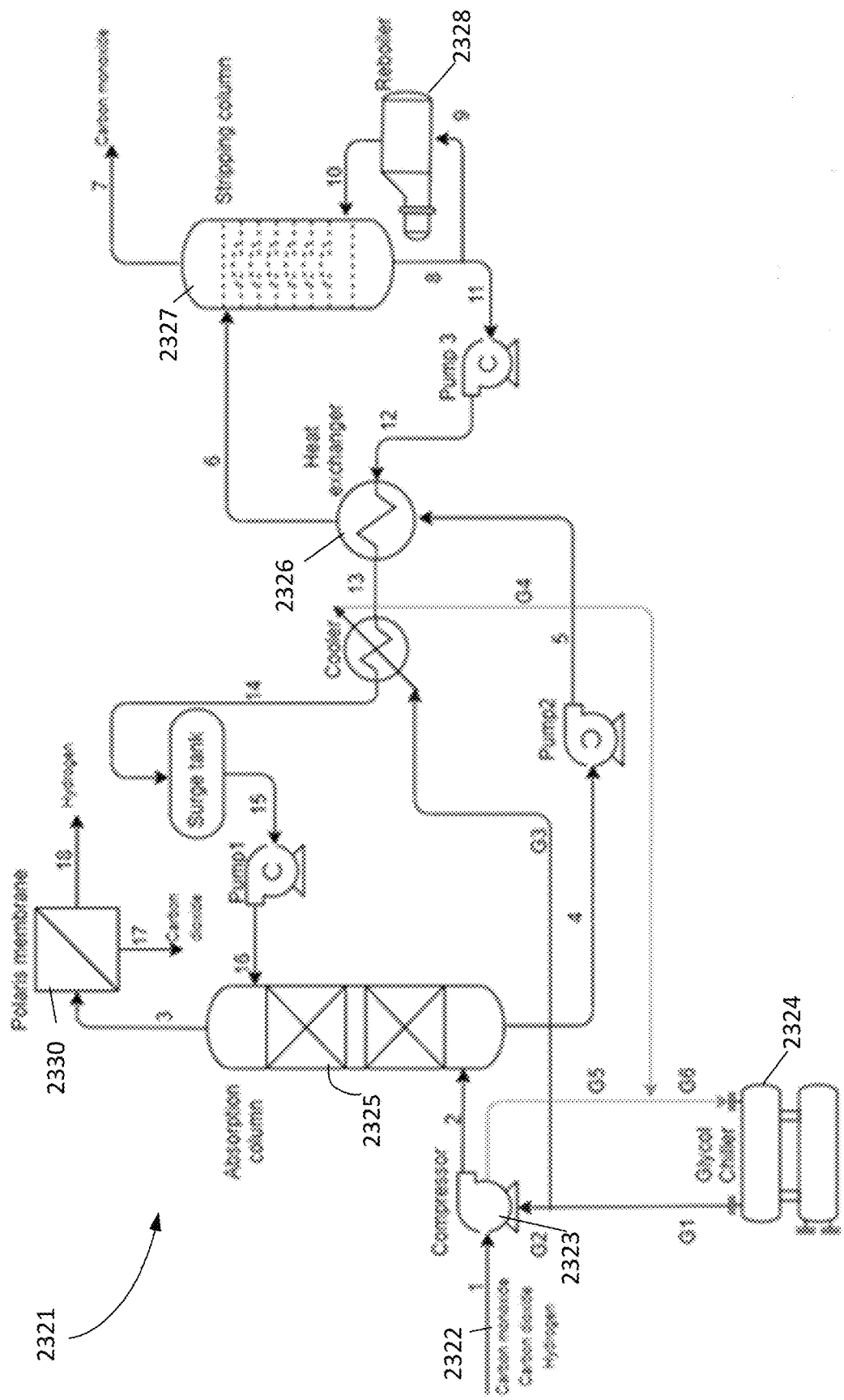
FIG. 23C depicts a system for producing a mixture of hydrogen and carbon monoxide by processing carbon dioxide electrolyzer output to first remove carbon monoxide and then remove hydrogen from a carbon dioxide-containing stream.

See the following CO absorption-stripping components of system 2321 shown in FIG. 23C: An inlet stream 2322 is compressed and chilled by a compressor 2323 working in conjunction with a chiller 2324. Compressed and chilled inlet gas enters the bottom of an absorption column 2325 where CO in the inlet stream is selectively absorbed by a liquid. A CO-enriched liquid phase is heated in the heat exchanger 2326 (stream 5) and then enters the stripping column 2327 (stream 6). The stripping column's pressure may be atmospheric, while temperature may, for example, range from 30° C. at the top to 60° C. at the bottom. The CO's solubility in the absorbent at these operating parameters is low, causing most CO to evaporate. The liquid phase flows to column's 2327 bottom (stream 8), where around, e.g., 15% is recirculated back to column 2327 using a reboiler 2328 (stream 9/10), while the remaining, e.g., 85% flows back to absorption column 2325 (stream 11-16).

A gas stream of $CO_2$ and $H_2$ exits the top of absorption column 2325. The $CO_2$ and $H_2$ may be separated by various techniques. In some embodiments, they are separated using a membrane filter 2330. In some embodiments, the membrane filter is a Polaris™ filter from Membrane Technology and Research Corporation Inc. of Newark, CA Such membrane may have a high permeability of $CO_2$ compared to $H_2$, which is obtained as a retentate. In some example, a membrane filter operates at a pressure of about 5 to 15 bar (e.g., about 9 bar pressure) and/or at a temperature of about 0-20° C. (e.g., about 5° C.).

$CO_2$ Separation Example

As in the CO absorption embodiments, carbon monoxide and hydrogen are included in output from a carbon dioxide electrolyzer. This electrolyzer output gas serves as an input to a separation system that produces a mixture of carbon monoxide and hydrogen. In certain implementations, $CO_2$ is absorbed directly from the input stream using an ionic liquid such as [bmim][PF6]. The absorption may be conducted at any of various pressures (e.g., about 10-60 bar). In some implementations, the inlet gas stream's pressure may be about 8 to 16 bar. To this end, the system may employ additional compression by a compressor.

In some embodiments, a $CO_2$ absorption column is operated at a relatively high pressure such as about 20 to 60 bar or about 40-50 bar (e.g., about 44 bar). At this pressure and 25° C., the solubility of $CO_2$ is about 0.2 moles in 1 mole of ionic liquid. In some embodiments, a $CO_2$ absorption column is operated at a relatively low pressure such as about 1 to 20 bar. In certain embodiments, the absorption column is operated at temperature of about 20 to 80° C., or about 20-30° C., or about 40 to 60° C.

Figure 23D:
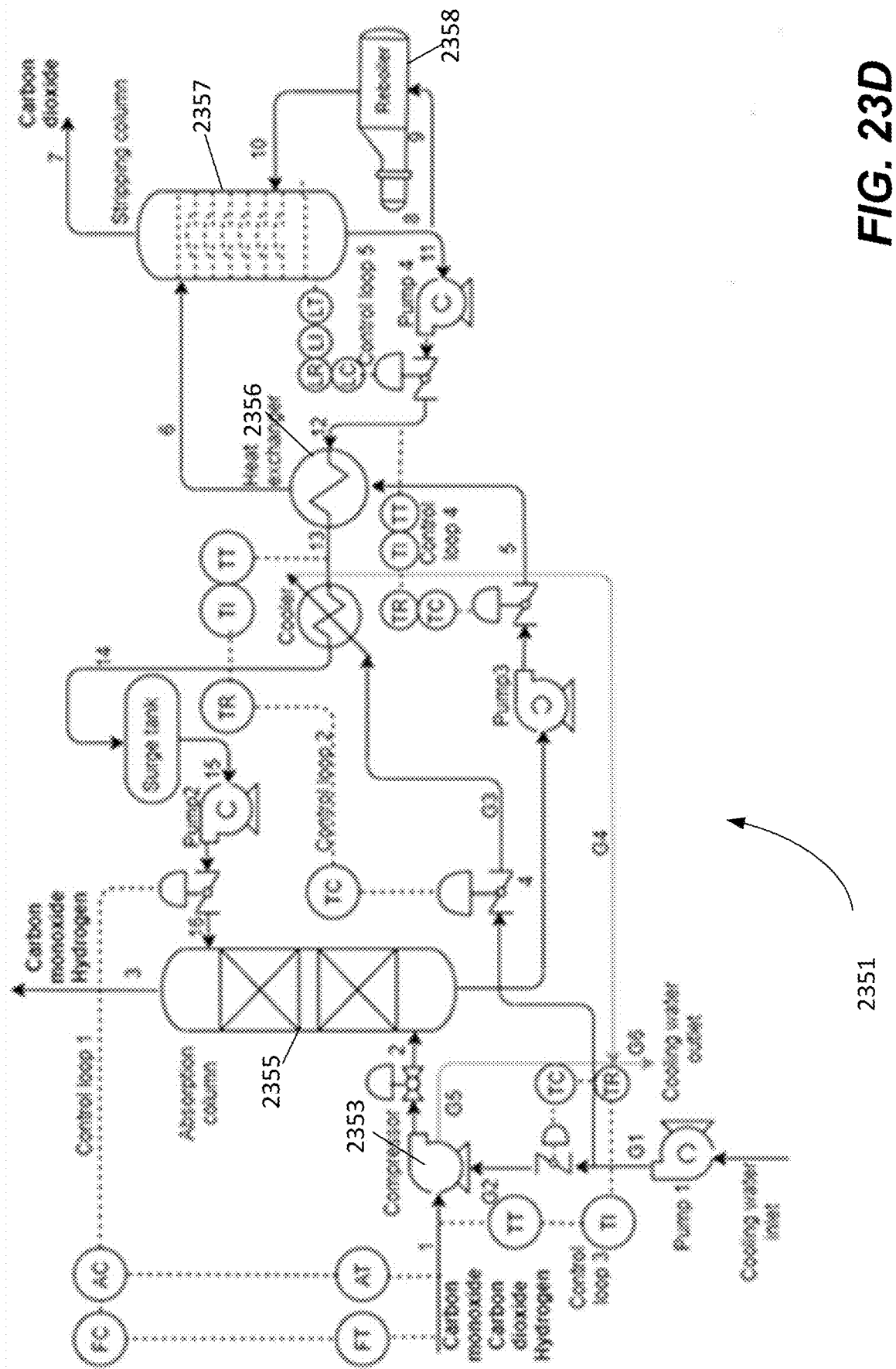
FIG. 23D depicts a system for producing a mixture of hydrogen and carbon monoxide by processing carbon dioxide electrolyzer output to directly remove carbon dioxide.

FIG. 23D illustrates an example $CO_2$ absorption-stripping system 2351 for processing a carbon oxide electrolyzer's output to produce a mixture of carbon monoxide and hydrogen. An inlet stream is compressed by a compressor 2353. Compressed inlet gas (stream (2)) enters the bottom of an absorption column 2355 where $CO_2$ in the inlet stream is selectively absorbed by a liquid (e.g., an ionic liquid). The flow rate of absorbent liquid may be adjusted or controlled by monitoring the molar flow rate of carbon dioxide in inlet stream. The absorbent liquid in the column may be maintained at particular level. Because the absorbent recirculates through the system, it may not accumulate in the column's bottom. A controller may be employed to sense the amount of absorbent in the column bottom and adjust or maintain the absorbent level to a desired level within the column.

In certain embodiments, a $CO_2$ absorption column operates under the following conditions:

The partial pressure of $CO_2$: 13 bars
Temperature: 28.1° C.
Liquid phase viscosity: 110 cP
Gaseous phase viscosity: 0.017 cP
Diffusivity of the $CO_2$ in the absorbent: 500 mm$^2$/s
Column diameter: 0.5 m
Column height: 12.4 m
Pressure drop: 0.012 bar
Cf (packing constant): 170
Packing total specific area: 108 m$^2$/m$^3$
Nominal packing diameter: 0.005 m A gas stream of CO and $H_2$ (stream (3)) exits the top of absorption column 2355. This stream may be employed as a syngas.

A $CO_2$-enriched liquid phase from the absorption column 2355 is heated in a heat exchanger 2356 (stream 5) and then enters a stripping column 2357 (stream 6). The $CO_2$'s solubility in the absorbent at operating parameters in the stripper is low, causing most $CO_2$ to evaporate. A liquid phase flows to stripping column's 2357 bottom (stream 8), where a fraction of it is recirculated back to column 2357 using a reboiler 2358 (stream 9/10), while the remaining liquid flows back to absorption column 2355 (stream 11-16). In certain embodiments, around 4 to 5% of the bottom liquid at the bottom of the absorption column is recirculated back to the column using, e.g., a reboiler.

In certain embodiments, a $CO_2$ stripping column is operated at a pressure of approximately 0.5 to 5 bar (e.g., about 1 bar), with the inlet $CO_2$-rich absorbent stream having a temperature of about 40 to 60° C., and the column's bottom having a temperature of about 60 to 80° C.

Ethylene Purification

Embodiments described in this section pertain to making ethylene. The embodiments described here concern methods and systems configured to receive a mixture containing ethylene and modifying the mixture to produce purified ethylene. In some cases, the input is a gaseous mixture obtained from a carbon oxide electrolyzer such as one of the carbon oxide electrolyzers described herein.

In some implementations, an ethylene purification system is configured to produce relatively pure ethylene, without necessarily producing a relatively pure stream of any other components produced by the electrolyzer. In some implementations, an ethylene purification system is configured to produce relatively pure ethylene along with a relatively pure stream of one or more other components such as hydrogen, carbon monoxide, carbon dioxide, methane, ethanol, or any combination thereof.

In various embodiments, an ethylene purification system includes one or more components or subsystems for (a) absorbing and separating carbon dioxide, (b) separating ethylene from one or more other components by membrane filtration, (c) fractional distillation to separate ethylene and methane, (d) chemically converting methane to ethylene, and (e) any combination of (a)-(d). In some embodiments, an amine or ionic liquid is used to absorb carbon dioxide. In some embodiments, a membrane filtration component is configured to separate carbon monoxide and hydrogen from ethylene (optionally along with methane).

Ethylene produced as described here may have various applications. For example, it can be used to produce ethylene oxide (see e.g., the discussion of FIGS. 10A, 11, and 14) and, in some cases, reaction products of ethylene oxide such as monoethylene glycol and polyethylene glycol.

In certain embodiments described in this section, the input gas includes ethylene and typically some methane and unreacted carbon dioxide. Other components that may be present include hydrogen, carbon monoxide water, ethanol, and any combination thereof.

As an example, an inlet stream to an ethylene purification system may have a composition of the follow mol %: hydrogen (4.75%), methane (23.72%), carbon monoxide (0%), carbon dioxide (50.73%), ethylene (9.49%), ethyl alcohol (4.75%), and water (6.57%). A composition such as this may be produced by a carbon dioxide electrolyzer.

Pathway 1: Cryogenic Distillation for Ethylene Separation

In some embodiments, ethylene is separated from other components by a pathway including absorption of carbon dioxide and subsequent fractional distillation to remove hydrogen, carbon monoxide, and/or methane to produce purified ethylene. As an example, the process may include the following sequence of operations:

Operation 1: Condensation of liquid products to remove ethanol and water
Operation 2: $CO_2$ removal
Operation 3: Distillation—removal of hydrogen, CO and methane
Operation 3 (alternate or optional): Methane conversion to ethylene by oxidative coupling of methane The separation process to remove water and ethanol from an input stream may be implemented in various ways. In some embodiments, it is implemented in a two-step process of condensation and then a molecular sieve absorption process to further remove the water and ethanol. In some embodiments, the condensation of water and ethyl alcohol is accomplished using compression of the input stream. In some embodiments, the condensation of water and ethyl alcohol is accomplished using an absorption column, e.g., a countercurrent column with water as on stream. The column optionally includes a catalyst. In some implementations, thermal equilibrium is reached in the column and both outlet streams have the same temperature (e.g., about 25 to 50° C.).

In some cases, carbon dioxide is removed from a gas stream using an amine such as diethanolamine, monoethanolamine, dimethylamine, piperazine, 2-aminopropanol, diisopropanolamine, aminoethoxyethanol, and/or methyl diethanolamine, or by an ionic liquid. In some implementations, the concentration of a chosen amine is at least about 10 times greater than the concentration of carbon dioxide. In some embodiments, the amine-containing liquid has about 50-80 mole percent amine in an aqueous solution.

Example working conditions for an amine-based carbon dioxide removal process:
Absorber: about 35 to 50° C. and about 5 to 205 atm of absolute pressure;
Regenerator: about 100 to 126° C. and about 1.4 to 1.7 atm of absolute pressure at a tower bottom.

In some implementations, a temperature difference of about 5° C. or more is maintained between the lean amine and sour gas. If the temperature difference is closer, the condensation of hydrocarbons may occur.

Various approaches may be employed to demethanizing an ethylene and methane containing stream. In some embodiments, a cryogenic distillation process is performed. See e.g., U.S. Pat. No. 3,902,329 (King III, et al.), which is incorporated herein by reference in its entirety. In some embodiments, cryogenic distillation is conducted at a temperature of about −90° C. or lower.

In some implementations, an ethylene/methane gas mixture is pressurized in the compressor (e.g., to a pressure of about 100 bar and an outlet temperature of about 15° C.). The gas mixture is cooled with the chilled water. Then, by, e.g., throttling the compressed gas mixture with a throttle valve, the outlet gas may be substantially cooled (e.g., to a temperature of about −100° C.).

Below is presented an example process for separation of methane from the ethylene by cryogenic distillation:
20-30 plates or more
Temperature: −90° C. to −105° C. on the plate at which the condensate is returned to the column.
Pressure: 25 to 40 bar or higher
98% Efficiency In some examples, a cryogenic distillation column has the following design parameters:
Diameter: 0.085 m
Height: 6.8 m
Stages: 17
Stage efficiency: 80%
Reflux ratio: 1.129
Vapor linear velocity: 3 m/s
Separation efficiency: 98%

In some embodiments, the process removes hydrogen from ethylene (and optionally other components) via membrane separation.

In some embodiments, the process employs oxidative coupling of methane (OCM) to ethylene. OCM may be performed on a methane-containing steam after the separation of methane and ethylene. This process can produce ethane, CO, $H_2$, and $CO_2$ as unwanted byproducts. Besides the temperature of the reaction, an important parameter is the amount of oxygen that reacts with the methane.

OCM may include some of or all the below-presented reactions. See e.g., Bhatia, Subhash & Thien, Chua & Mohamed, Abdul. (2009). Oxidative coupling of methane (OCM) in a catalytic membrane reactor and comparison of its performance with other catalytic reactors. Chemical Engineering Journal—CHEM ENG J. 148. 525-532. 10.1016/j.cej.2009.01.008, which is incorporated herein by reference in its entirety.

Step 1: $CH_4 + 2O_2 \rightarrow CO_2 + H_2O_2$
Step 2: $2CH_4 + 0.5O_2 \rightarrow C_2H_6 + H_2O$
Step 3: $CH_4 + O_2 \rightarrow CO + H_2O + H_2$
Step 4: $CO + 0.5O_2 \rightarrow CO_2$
Step 5: $C_2H_6 + 0.5O_2 \rightarrow C_2H_4 + H_2O$
Step 6: $C_2H_4 + 2O_2 \rightarrow 2CO + 2H_2O_2$
Step 7: $C_2H_6 \rightarrow C_2H_4 + H_2$
Step 8: $C_2H_4 + 2H_2O \rightarrow 2CO + 4H_2$
Step 9: $CO + H_2O \rightarrow CO_2H_2$ Step 10: $CO_2 + H_2 \rightarrow CO + H_2O$ The yield of this process is dependent on reaction conditions and the oxygen ratio. The amounts of methane and oxygen may be chosen to promote reactions in, e.g., steps 2 and 5. In certain embodiments, this process occurs in the catalyst membrane reactor consisting of disk-shaped planar BSCF membranes.

Examples of OCM reactor designs and operation are presented in the following table taken from X. Tan, K. Li, in Handbook of Membrane Reactors: Reactor Types and Industrial Applications, 2013, which is incorporated herein by reference in its entirety.

| Material | T (° C.) | Geometry | Catalyst | $S_{C2}$ (%) | $Y_{C2}$ (%) | References |
|---|---|---|---|---|---|---|
| $Bi_{1.5}Y_{0.3}Sm_{0.2}O_{3-\delta}$ | 900 | Tubular | — | 54 | 35 | Akin and Lin, 2002 |
| BSCF | 850 | Tubular | La-Sr/CaO | 66 | 15 | Wang et al., 2005 |
| BSCF | 900 | Disk | La-Sr/CaO | 65 | 18 | Olivier et al., 2009 |
| LSCF | 950 | Hollow fiber | — | 43.8 | 15.3 | Tan and Li, 2006 |
| LSCF | 975 | Hollow fiber | $SrTi_{0.9}Li_{0.1}O_3$ | 40 | 21 | Tan et al., 2007 |
| LSCF | 900 | Hollow fiber | $Bi_{1.5}Y_{0.3}Sm_{0.2}O_{3-\delta}$ | 79 | 39 | Othman et al., 2015 |
| BCFZ | 800 | Hollow fiber | $Mn-Na_2WO_4/SiO_2$ | 50 | 17 | Czuprat et al., 2010 |
| BCGCF | 850 | Tubular | Na-W-Mn | 67.4 | 34.7 | Bhatia et al., 2009 |

In various embodiments, the OCM temperature is in a range for the steam cracking of ethane to produce ethylene. The analysis shows that operating at a temperature range of 850° C.-950° C. and steam to hydrocarbon ratio of 0.3-0.5 produces good ethylene yield while minimizing byproducts. In some embodiments, the OCM-cracking reaction is conducted in a tubular reactor and at elevated pressure (e.g., about 2 to 2.5 bar).

In certain embodiments, about 0.3 of the methane is converted to ethylene (molar), which may be about the amount of ethylene present in a typical inlet feed. Therefore, by utilization of the above process, the produced amount of ethylene is almost doubled.

In some embodiments, a process includes an operation of separating steam and hydrogen from the formed ethylene. An absorption counter flow column may be employed for this operation. As an example, process conditions may include a pressure of about 5 to 50 bar (e.g., about 10 bar) and a temperature of about 150 to 500° C. (e.g., about 300° C.). In some embodiments, an absorption column with an adequate volume flow of the water separates nearly 100% of water and hydrogen from the gas.

Pathway 2: Usage of the Membranes for Ethylene Separation

In some embodiments, ethylene is separated from other components by a pathway including membrane separation of gas streams to produce an ethylene-rich stream. As an example, such process may include the following sequence of operations:

Operation 1: Condensation of liquid products to remove ethanol and water
Operation 2: $CO_2$ removal with amine treatment
Operation 3: $CO + H_2$ Removal with membrane separation
Operation 4: Ethylene separation from methane with membrane separation.

In some implementations, operations 1 and 2 are performed in the same manner as in the above-described pathway that employed cryogenic distillation. Operations 3 and 4 are performed using membranes designed or configured to separate gaseous components from one another. In certain embodiments, suitable membranes are provided by Membrane Technology & Research, Inc. of Newark, CA.

The design may include a compression stage that removes ethanol and water prior to membrane separation.

Membrane Stage to Remove Non-Hydrocarbons

A first membrane may separate nearly 100% of $H_2$, $CO_2$, ethanol, and water. It may not significantly separate $CH_4$ from $C_2H_4$.

As an example, starting from an initial gas mixture of 50.7 mol % $CO_2$, 23.7 mol % $CH_4$, and 9.5 mol % $C_2H_4$, the resulting product stream contains 64.7 mol % $CH_4$ and 30.5 mol % $C_2H_4$, with most of the remaining gas being $CO_2$ (3.7%). To reduce loss of the $CH_4/C_2H_4$ mixture in a permeate stream, a two-stage separation design may be employed.

The pressure is 10 bar, and the inlet stream is at 30° C. temperature. The cooling process occurs in the membrane, and the temperature of the residue is −2.1° C. The 10% percent loss is satisfying from my point of view.

In some embodiments, the membrane is a hollow fiber membrane comprising polypropylene (PP), polyethylene (PE), polytetrafluoroethylene (PTFE), PVDF, polysulfone (PS), polyetherimide (PEI), or any combination thereof. In some embodiments, the membrane has a porosity of about 50-70% (e.g., about 60%). In some embodiments, the membrane has a mean pore size of about 2 to 3 μm.

Ethylene/Methane Separation

In certain embodiments, a methane-ethylene separation membrane includes a metal-organic membrane for separation at the room temperature. In certain embodiments, a methane-ethylene membrane separation, has an adsorption selectivity of 12 to 20 at 296 K. An adsorption selectivity=20 represents the 95% separation process efficiency.

The membrane may include a microporous metal-organic framework $Zn_4$ L(DMA)$_4$ (UTSA-33, H8L=1,2,4,5-tetra (5-isophthalic acid)benzene, DMA=N,N'-dimethylacetamide) with small pores of about 4.8 to 6.5 A (He, Yabing, et al. "A microporous metal-organic framework for highly selective separation of acetylene, ethylene, and ethane from methane at room temperature." Chemistry-A European Journal 18.2 (2012): 613, which is incorporated herein by reference in its entirety).

In some implementations, after the methane separation, the methane is subjected to OCM to increase the yield of ethylene.

Pathway 3: Usage of Filtration Membranes and Cryogenic Distillation for Ethylene Separation In certain embodiments, a membrane filter is employed to separate methane and ethylene from other components such as hydrogen, carbon monoxide, and carbon dioxide. In some embodiments, a methane—ethylene mixture is subsequently separated by cryogenic distillation into relatively pure streams of ethylene and methane. In some implementations, a separate membrane filter is employed to separate hydrogen from carbon monoxide, carbon dioxide, and optionally other components.

In some implementations, a process may include the following operations:

Operation 1: Compression of gas stream to enable condensation of ethyl alcohol and water Operation 2: Removal of water and ethyl alcohol in countercurrent absorption column with catalyst Operation 3: Membrane filtration to separate methane and ethylene from other gases such as carbon dioxide, carbon monoxide, and hydrogen Operation 4 (optional): Membrane filtration to separation hydrogen from carbon monoxide and carbon dioxide.

Operation 5: Cryogenic distillation to separate methane and ethane (optionally use the cooled methane output stream as a cooling utility)

Oxygen Production

A carbon oxide electrolyzer anode may produce oxygen from water. The oxygen may be employed in any of various integration schemes for the electrolyzer. In some cases, oxygen can be used in a combustion reaction with a fuel. In some cases, oxygen can be compressed and stored for later use. In certain embodiments, compressed oxygen is cooled and then passed through a throttle valve causing the oxygen to liquefy. Cooling may be accomplished using a Freon-type cooler. In some cases, an oxygen stream is first cooled using a brine cooler (e.g., employing $CaCl_2$ brine). For example, at 40 bars and −120° C., oxygen becomes liquid. In some implementations, the oxygen stream is cooled to about −70° C. or lower.

Controller Embodiments

In embodiments employing a controller or other logic for controlling operation of one or more reactors, pumps, separators, and/or other components of a system the controller or logic may employ program instructions such as executable instructions on computer-readable medium. The instructions may be executed by computer-executable components such as those integrated with a communication system. The computer-readable medium may be stored on any suitable computer readable media such as RAMs, ROMs, flash memory, EEPROMs, optical devices (CD or DVD), hard drives, floppy drives, or any suitable device. The computer-executable component is optionally a processor, but the instructions may alternatively or additionally be executed by any suitable dedicated hardware device.

Although omitted for conciseness, embodiments of the system and/or method can include every combination and permutation of the various system components and the various method processes, wherein one or more instances of the method and/or processes described herein can be performed asynchronously (e.g., sequentially), concurrently (e.g., in parallel), or in any other suitable order by and/or using one or more instances of the systems, elements, and/or entities described herein.

The Figures illustrate the architecture, functionality and operation of possible implementations of systems, methods and computer program products according to disclosed embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the disclosed embodiments of the disclosure without departing from the scope of this disclosure defined in the following claims.

What is claimed is:

1. A system for producing one or more chemical compounds, the system comprising:
   (a) a carbon oxide reduction electrolyzer comprising a membrane electrode assembly, which comprises one or more ion conductive polymer layers and a cathode catalyst layer comprising (i) an ion-conducting polymer, and (ii) a cathode catalyst in the ion-conducting polymer, wherein cathode catalyst is configured to facilitate chemical reduction of carbon oxide to a carbon-containing reaction product, wherein the cathode catalyst layer contacts at least one of the one or more ion conductive polymer layers; and
   (b) a gas fermentation reactor configured to receive the carbon-containing reaction product produced by the carbon oxide reduction electrolyzer and produce the one or more chemical compounds,
   wherein the gas fermentation reactor is configured to perform aerobic fermentation, and the system is configured to provide oxygen from an anode of the carbon oxide reduction electrolyzer to the gas fermentation reactor.

2. The system of claim 1, wherein the carbon oxide reduction electrolyzer is configured to produce methane, and wherein the system is configured to transport the methane to the gas fermentation reactor.

3. The system of claim 1, wherein the carbon oxide reduction electrolyzer is configured to produce carbon monoxide and hydrogen, and wherein the system is configured to transport the carbon monoxide and the hydrogen to the gas fermentation reactor.

4. The system of claim 3, wherein the gas fermentation reactor is configured to produce ethanol, acetic acid, butanol, butyric acid, or methane.

5. The system of claim 3, wherein the gas fermentation reactor is configured to produce a ketone, a light hydrocarbon, or phenol, and wherein the system further comprises one or more reactors for converting the ketone, the light hydrocarbon, or phenol to a diol.

6. The system of claim 5, wherein the gas fermentation reactor is configured to produce the ketone and the ketone is acetone and wherein the diol is bisphenol A.

7. The system of claim 3, wherein the gas fermentation reactor is configured to produce naphtha.

8. The system of claim 7, wherein the system further comprises one or more reactors for converting the naphtha to terephthalic acid.

9. The system of claim 1, wherein the carbon-containing reaction product comprises a ketone, an alkane, and/or an aromatic compound.

10. The system of claim 1, wherein the gas fermentation reactor is configured to produce protein, a polyhydroxyalkanoate, acetone, isopropanol, or ethanol.

11. The system of claim 1, wherein the gas fermentation reactor is configured to produce carbon dioxide and wherein the system is configured to transport carbon dioxide from the gas fermentation reactor to the carbon oxide reduction electrolyzer.

12. The system of claim 1, wherein the carbon oxide reduction electrolyzer and the gas fermentation reactor are located in a single plant.

13. The system of claim 1, wherein the system is configured to recycle carbon dioxide from the gas fermentation reactor to the membrane electrode assembly.

14. The system of claim 13, further comprising one or more carbon dioxide capture units comprising a sorbent for capturing carbon dioxide during a first phase of recycling and releasing carbon dioxide during a second phase of recycling.

15. The system of claim 13, wherein the system is configured to remove oxygen from carbon dioxide recycled from the gas fermentation reactor to the membrane electrode assembly.

16. The system of claim 1, wherein the gas fermentation reactor is configured to perform biochemical reactions in the Wood-Ljungdahl Pathway (WLP).

17. The system of claim 1, wherein the membrane electrode assembly is configured to receive a carbon oxide input at a pressure above atmospheric pressure.

18. The system of claim 1, wherein the gas fermentation reactor is configured to produce an amine, and wherein the system further comprises one or more reactors for converting the amine to a polyisocyanate.

19. A method for producing one or more chemical compounds, the method comprising:
chemically reducing a carbon oxide to a carbon-containing reaction product via the carbon oxide reduction electrolyzer comprising a membrane electrode assembly of the system of claim 1; and
in the gas fermentation reactor of the system of claim 1, receiving oxygen from the carbon oxide reduction electrolyzer and performing aerobic fermentation to produce the one or more chemical compounds from the carbon-containing reaction product.

20. The method of claim 19, wherein the carbon-containing reaction product comprises methane, and further comprising transporting the methane to the gas fermentation reactor.

21. The method of claim 19, wherein the carbon-containing reaction product comprises carbon monoxide and hydrogen, and further comprising transporting the carbon monoxide and the hydrogen to the gas fermentation reactor.

22. The method of claim 19, wherein the one or more chemical compounds comprise ethanol, acetic acid, butanol, butyric acid, and/or methane.

23. The method of claim 19, wherein the one or more chemical compounds comprise a ketone, an alkane, and/or an aromatic compound.

24. The method of claim 19, wherein the one or more chemical compounds comprise a protein, a polyhydroxyalkanoate, acetone, isopropanol, or ethanol.

25. The method of claim 19, wherein the one or more chemical compounds comprise an amine, and further comprising converting the amine to a polyisocyanate.

26. The method of claim 19, wherein producing the one or more chemical compounds in the gas fermentation reactor comprises performing aerobic fermentation, and
further comprising providing oxygen from an anode of the carbon oxide reduction electrolyzer to the gas fermentation reactor.

27. The method of claim 19, further comprising transporting carbon dioxide produced by the gas fermentation reactor to the membrane electrode assembly.

28. The method of claim 19, further comprising providing the carbon oxide to the membrane electrode assembly at a pressure above atmospheric pressure.

29. A system for producing one or more chemical compounds, the system comprising:
(a) a source of biogas comprising carbon dioxide;
(b) a carbon oxide reduction electrolyzer for receiving the carbon dioxide from the biogas, wherein the carbon oxide reduction electrolyzer comprises a membrane electrode assembly, the membrane electrode assembly comprising one or more ion conductive polymer layers and a cathode catalyst for facilitating chemical reduction of the carbon dioxide to a carbon-containing reaction product; and
(c) a gas fermentation reactor configured to receive the carbon-containing reaction product produced by the carbon oxide reduction electrolyzer and produce the one or more chemical compounds,
wherein the gas fermentation reactor is configured to perform aerobic fermentation, and the system is configured to provide oxygen from an anode of the carbon oxide reduction electrolyzer to the gas fermentation reactor.

30. A system for producing one or more chemical compounds, the system comprising:
(a) a carbon oxide reduction electrolyzer comprising (i) a membrane electrode assembly, which comprises one or more ion conductive polymer layers and a cathode catalyst for facilitating chemical reduction of carbon oxide to a carbon-containing reaction product, (ii) an anode configured to receive a feed stream comprising water, and (iii) an inlet for receiving the feed stream and providing the feed stream to the anode; and
(b) a gas fermentation reactor configured to receive the carbon-containing reaction product produced by the carbon oxide reduction electrolyzer and produce the one or more chemical compounds,
wherein the gas fermentation reactor is configured to perform aerobic fermentation, and the system is configured to provide oxygen from the anode of the carbon oxide reduction electrolyzer to the gas fermentation reactor.

31. The system of claim 30, wherein the carbon oxide reduction electrolyzer is configured to produce methane, and wherein the system is configured to transport the methane to the gas fermentation reactor.

32. The system of claim 30, wherein the carbon oxide reduction electrolyzer is configured to produce carbon monoxide and hydrogen, and wherein the system is configured to transport the carbon monoxide and the hydrogen to the gas fermentation reactor.

* * * * *